US012173290B2

(12) United States Patent
Takeuchi et al.

(10) Patent No.: US 12,173,290 B2
(45) **Date of Patent: *Dec. 24, 2024**

(54) MATERIALS AND METHODS FOR CONTROLLING GENE EDITING

(71) Applicants: CRISPR THERAPEUTICS AG, Zug (CH); BAYER HEALTHCARE LLC, Whippany, NJ (US)

(72) Inventors: Ryo Takeuchi, Cambridge, MA (US); Abraham Scaria, Cambridge, MA (US)

(73) Assignees: CRISPR THERAPEUTICS AG, Zug (CH); BAYER HEALTHCARE LLC, Whippany, NJ (US)

( * ) Notice: Subject to any disclaimer, the term of this patent is extended or adjusted under 35 U.S.C. 154(b) by 902 days.

This patent is subject to a terminal disclaimer.

(21) Appl. No.: 16/912,999

(22) Filed: Jun. 26, 2020

(65) Prior Publication Data

US 2020/0407729 A1 Dec. 31, 2020

Related U.S. Application Data

(60) Provisional application No. 62/868,209, filed on Jun. 28, 2019.

(51) Int. Cl.

| | |
|---|---|
| ***C12N 15/11*** | (2006.01) |
| ***C12N 9/22*** | (2006.01) |
| ***C12N 15/64*** | (2006.01) |
| ***C12N 15/86*** | (2006.01) |

(52) U.S. Cl.

CPC ............... *C12N 15/64* (2013.01); *C12N 9/22* (2013.01); *C12N 15/86* (2013.01); *C12N 2310/122* (2013.01); *C12N 2310/20* (2017.05); *C12N 2750/14143* (2013.01); *C12N 2750/14151* (2013.01); *C12N 2800/22* (2013.01)

(58) Field of Classification Search

CPC ...... C12N 9/22; C12N 2310/20; C12N 15/86; C12N 15/113; C12N 15/11

See application file for complete search history.

(56) References Cited

U.S. PATENT DOCUMENTS

| | | | | |
|---|---|---|---|---|
| 2014/0377809 | A1 | 12/2014 | Court et al. | |
| 2019/0153441 | A1* | 5/2019 | Kantardzhieva ... | A61K 31/7088 |
| 2019/0338309 | A1* | 11/2019 | Vallier ..................... | C12N 9/22 |

FOREIGN PATENT DOCUMENTS

| | | | | |
|---|---|---|---|---|
| WO | 2018/009534 A1 | 1/2018 | | |
| WO | 2018/069474 A1 | 4/2018 | | |
| WO | 2018/106693 A1 | 6/2018 | | |
| WO | 2019/046341 A2 | 3/2019 | | |
| WO | 2019/081935 A1 | 5/2019 | | |
| WO | 2019/092507 A2 | 5/2019 | | |
| WO | WO-2019092505 A1 * | 5/2019 | ........... | C12N 15/102 |
| WO | 2019/118935 A1 | 6/2019 | | |
| WO | WO-2019183150 A1 * | 9/2019 | ........... | C12N 15/113 |
| WO | 2020/112908 A2 | 6/2020 | | |

OTHER PUBLICATIONS

De Solis, C. et al., "The Development of a Viral Mediated CRISPR/Cas9 System with Doxycycline, Dependent gRNA Expression for Inducible In vitro and In vivo Genome Editing," Frontiers in Molecular Neuroscience, vol. 9:52-63 (2016).

Invitation to Pay Additional Fees and, Where Applicable, Protest Fee, PCT/US2020/039754, dated Oct. 5, 2020, 17 pages.

* cited by examiner

*Primary Examiner* — Dana H Shin

(74) *Attorney, Agent, or Firm* — Casimir Jones, S.C.; J. Mitchell Jones

(57) ABSTRACT

The present application provides a CRISPR/Cas system comprising a nuclease segment that encodes a Cas9 nuclease or variant thereof, a guide RNA segment comprising a nucleotide sequence that encodes a gRNA or sgRNA, and a promoter segment comprising a nucleotide sequence that encodes a first promoter comprising one or more tetracycline operator sequence, wherein the gRNA segment is operably linked to the promoter segment. The present application also provides materials and methods for controlling transcriptional expression of guide RNAs and/or post-transcriptional expression of Cas nuclease.

28 Claims, 21 Drawing Sheets

Specification includes a Sequence Listing.

pSIA187

| Plasmid from which AAV vector was produced | Lane number of gel | TetR encoded on plasmid | shRNA encoded on plasmid |
|---|---|---|---|
| pSIA185 | 1 | Yes | No |
| pSIA186 | 2 | No | Yes |
| pSIA187 | 3 | Yes | Yes |
| pSIA036 | 4 | No | No |
| NONE (pSIA036 used as PCR template) | 5 | No | No |

| Plasmid from which AAV Vector was produced | Lane number of gel | TetR gene encoded on plasmid | shRNA gene encoded on plasmid | SIN sites encoded on plasmid |
|---|---|---|---|---|
| pSIA069 | 1 | No | No | Yes |
| pSIA071 | 2 | No | No | No |
| pSIA188 | 3 | Yes | No | Yes |
| pSIA189 | 4 | No | Yes | Yes |
| pSIA190 | 5 | Yes | Yes | Yes |

SEQUENCE LISTING

```
<160> NUMBER OF SEQ ID NOS: 69

<210> SEQ ID NO 1
<211> LENGTH: 115
<212> TYPE: RNA
<213> ORGANISM: Artificial Sequence
<220> FEATURE:
<223> OTHER INFORMATION: sgRNA sequence

<400> SEQUENCE: 1

gacgggugug guacgcagcc acuguuuaag uacucugugc uggaaacagc acagaaucua     60

cuuaaacaag gcaaaaugcc guguuuaucu cgucaacuug uuggcgagau uuuuu         115


<210> SEQ ID NO 2
<211> LENGTH: 112
<212> TYPE: RNA
<213> ORGANISM: Artificial Sequence
<220> FEATURE:
<223> OTHER INFORMATION: sgRNA sequence

<400> SEQUENCE: 2

gggugguggua cgcagccacu guuuaaguac ucugugcugg aaacagcaca gaaucuacuu     60

aaacaaggca aaaugccgug uuuaucucgu caacuuguug gcgagauuuu uu            112


<210> SEQ ID NO 3
<211> LENGTH: 223
<212> TYPE: DNA
<213> ORGANISM: Artificial Sequence
<220> FEATURE:
<223> OTHER INFORMATION: Truncated  H1 promoter comprising 2 TetO sites

<400> SEQUENCE: 3

gaacgctgac gtcatcaacc cgctccaagg aatcgcgggc ccagtgtcac taggcgggaa     60

cacccagcgc gcgtgcgccc tggcaggaag atggctgtga gggacagggg agtggcgccc    120

tgcaatattt gcatgtcgct atgtgttctg ggaaatcacc ataaacgtga aatccctatc    180

agtgatagag acttataagt tccctatcag tgatagagac acc                      223


<210> SEQ ID NO 4
<211> LENGTH: 19
<212> TYPE: DNA
<213> ORGANISM: Artificial Sequence
<220> FEATURE:
<223> OTHER INFORMATION: TetO site sequence

<400> SEQUENCE: 4

tccctatcag tgatagaga                                                  19


<210> SEQ ID NO 5
```

<211> LENGTH: 6805
<212> TYPE: DNA
<213> ORGANISM: Artificial Sequence
<220> FEATURE:
<223> OTHER INFORMATION: Plasmid

<400> SEQUENCE: 5
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgctccg gtgcccgtca gtgggcagag cgcacatcgc 180
ccacagtccc cgagaagttg gggggagggg tcggcaattg aaccggtgcc tagagaaggt 240
ggcgcggggt aaactgggaa agtgatgtcg tgtactggct ccgccttttt cccgagggtg 300
ggggagaacc gtatataagt gcagtagtcg ccgtgaacgt tctttttcgc aacgctagct 360
aactaccggt gccaccatgg ccccaaagaa gaagcggaag gtcggatcca agcggaacta 420
tatcctggga ctggacatcg gaattacctc cgtgggatac ggcatcatcg attacgagac 480
tagggacgtg attgacgccg gcgtgagact ctttaaggag gccaacgtgg aaaacaacga 540
aggtcgcaga tccaagcggg gtgcaagacg cctgaagcgc cggaggagac atcggataca 600
gcgcgtgaag aagctccttt tcgactacaa cctcctcact gaccactcgg aattgtccgg 660
tatcaacccc tacgaagccc gcgtgaaagg cctgagccag aagctgtccg aagaggagtt 720
tagcgcagcc ctgctgcacc tggctaagcg aagggggggtg cacaacgtga acgaggtgga 780
ggaggacact ggcaacgaac tgtccaccaa ggagcagatt tcacggaact cgaaggcgct 840
ggaagagaaa tatgtggccg agctgcagct ggagaggctc aagaaggatg gcgaagtccg 900
ggggagcatc aatcgcttca agacctcgga ctacgtgaag gaagccaaac agctgttgaa 960
ggtgcagaag gcctaccacc aactggacca atcattcatt gacacttaca tcgatctgct 1020
tgaaaccagg cgcacctact acgagggtcc tggagaaggc agccctttcg gatggaagga 1080
catcaaggag tggtatgaga tgctgatggg tcattgcacc tactttccgg aagaactgcg 1140
ctcagtgaag tacgcgtaca acgctgacct ctacaacgct ctcaacgatc tgaacaacct 1200
cgtgatcacc cgggacgaga acgaaaagct ggagtactac gaaaagttcc agattatcga 1260
aaacgtgttc aagcagaaga agaagcccac cctgaagcag attgcaaagg agatccttgt 1320
gaacgaggag gatattaagg gctaccgggt cacctccacc gggaaaccag agttcactaa 1380
tctcaaggtg taccatgaca ttaaggacat tactgcccgc aaggagatca ttgaaaacgc 1440
ggaactgctg gaccaaatcg cgaagatcct gaccatctat cagagctccg aggatatcca 1500
ggaggaactt actaacctca attccgagct gacgcaggaa gaaatcgagc aaattagcaa 1560
cctgaagggt tacactggaa cccacaacct cagcttgaaa gcgattaacc ttattttgga 1620
tgaactttgg cacactaatg acaatcagat cgccattttc aaccggctga aactggtgcc 1680
gaagaaggtg gacctgagcc aacagaagga aatcccgacc acccttgtgg acgatttcat 1740
cctgtcacct gtggtgaaga ggagcttcat ccagtcgatc aaggtcatca acgccatcat 1800
aaagaagtac ggccttccca acgacatcat catcgaactg gcccgcgaga agaactccaa 1860
agatgcccag aagatgatca acgagatgca gaagcgaaac cggcagacga acgaacggat 1920
cgaggagatc atccggacca ccgggaagga aaacgcgaag tacctgatcg agaaaatcaa 1980
gctgcatgat atgcaggaag ggaagtgtct ctactccctg gaggccattc cgctggagga 2040
tttgctgaac aacccctttca actacgaagt cgatcatatc attcctcgct ccgtgtcctt 2100
cgataactcc ttcaacaata aggtcctcgt gaagcaggag gagaagtaag tatcaaggtt 2160

```
acaagacagg tttaaggaga ccaatagaaa ctgggctcga gcttgtcgag acagagaaga   2220
ctcttgcgtt tctgataggc acctattggt cttactgaca tccactttgc ctttctctcc   2280
acagctcgaa gaagggcaac agaaccccgt tccagtacct ctcgtcgtcc gactccaaga   2340
tcagctacga aactttcaag aagcacattc tgaacctggc caagggcaaa gggagaatta   2400
gcaagaccaa gaaggaatac ctcctggaag agagagacat caaccgcttc tcggtgcaaa   2460
aggatttcat caaccgcaac ctggtcgata ccagatacgc caccagggga ctgatgaacc   2520
tcctgcggtc ctacttccgg gtcaacaatc tggacgtgaa ggtcaaatcc atcaacgggg   2580
gctttacttc tttcctgcgc cggaagtgga agttcaagaa ggaacggaac aagggataca   2640
agcaccacgc tgaagatgcc ctgattattg ccaacgccga cttcatcttt aaggaatgga   2700
aaaagctgga caaggctaag aaggtcatgg agaaccagat gttcgaagaa aagcaggccg   2760
agtccatgcc cgaaatcgaa accgagcagg aatacaagga gatcttcatc acaccgcacc   2820
aaatcaagca catcaaggac ttcaaggatt acaagtacag ccaccgggtg gacaagaagc   2880
ctaacagaga gcttatcaac gacaccctgt actccacgcg caaggacgac aagggaaaca   2940
cattgatcgt gaacaacctg aacggactgt atgacaagga caatgacaaa ctgaagaagc   3000
tgatcaacaa atcgccggaa aagctcctga tgtaccatca cgaccctcaa acctaccaga   3060
aactgaagct catcatggag cagtacggcg acgaaaagaa tcccctgtac aaatactacg   3120
aggagactgg aaattacctg actaagtact ccaagaagga taacggcccc gtgatcaaga   3180
agattaagta ctacggaaac aaactgaacg cacatctcga catcaccgat gattatccaa   3240
actcccgcaa caaagtcgtg aagctctccc tcaaaccgta ccgcttcgac gtgtacctgg   3300
ataatggggt gtacaagttc gtgaccgtga agaacctgga cgtcattaag aaggaaaact   3360
actacgaagt gaactcaaag tgctacgagg aagccaagaa gctcaagaag atcagcaacc   3420
aggccgagtt catcgcatcg ttttacaaca atgacctcat taagattaat ggagaactgt   3480
acagagtgat cggcgtgaac aacgacctcc tgaaccggat tgaagtgaac atgatcgata   3540
ttacctaccg ggagtatctg gagaacatga acgacaagcg cccaccgaga atcatcaaaa   3600
ctattgcctc caagacccaa tccattaaga aatactccac cgacatcctg ggcaacctgt   3660
acgaggtcaa gtcgaagaag cacccccaga ttatcaagaa gggaaaaagg ccggcggcca   3720
cgaaaaaggc cggccaggca aaaaagaaaa aggcttaaga attcctagag ctcgctgatc   3780
agcctcgaaa cttgtttatt gcagcttata atggttacaa ataaagcaat agcatcacaa   3840
atttcacaaa taaagcattt ttttcactgc attctagttg tggtttgtcc aaactcatca   3900
atgtatctta tcatgtctgt ataccagcag gctttcctag gttcgaacgc tgacgtcatc   3960
aacccgctcc aaggaatcgc gggcccagtg tcactaggcg ggaacaccca gcgcgcgtgc   4020
gccctggcag gaagatggct gtgagggaca ggggagtggc gccctgcaat atttgcatgt   4080
cgctatgtgt tctgggaaat caccataaac gtgaaatccc tatcagtgat agagacttat   4140
aagttcccta tcagtgatag agacaccgac gggtgtggta cgcagccact gtttaagtac   4200
tctgtgctgg aaacagcaca gaatctactt aaacaaggca aaatgccgtg tttatctcgt   4260
caacttgttg gcgagatttt ttcacgtgcg gaccgaggct gcagcgtcgt cctccctagg   4320
aacccctagt gatggagttg gccactccct ctctgcgcgc tcgctcgctc actgaggccg   4380
ggcgaccaaa ggtcgcccga cgcccgggct ttgcccgggc ggcctcagtg agcgagcgag   4440
cgcgcagctg cctgcagggg cgcctgatgc ggtattttct ccttacgcat ctgtgcggta   4500
```

-continued

```
tttcacaccg catacgtcaa agcaaccata gtacgcgccc tgtagcggcg cattaagcgc   4560
ggcgggtgtg gtggttacgc gcagcgtgac cgctacactt gccagcgccc tagcgcccgc   4620
tcctttcgct ttcttccctt cctttctcgc cacgttcgcc ggctttcccc gtcaagctct   4680
aaatcggggg ctccctttag ggttccgatt tagtgcttta cggcacctcg accccaaaaa   4740
acttgatttg ggtgatggtt cacgtagtgg gccatcgccc tgatagacgg tttttcgccc   4800
tttgacgttg gagtccacgt tctttaatag tggactcttg ttccaaactg gaacaacact   4860
caaccctatc tcgggctatt cttttgattt ataagggatt ttgccgattt cggcctattg   4920
gttaaaaaat gagctgattt aacaaaaatt taacgcgaat tttaacaaaa tattaacgtt   4980
tacaatttta tggtgcactc tcagtacaat ctgctctgat gccgcatagt taagccagcc   5040
ccgacacccg ccaacacccg ctgacgcgcc ctgacgggct tgtctgctcc cggcatccgc   5100
ttacagacaa gctgtgaccg tctccgggag ctgcatgtgt cagaggtttt caccgtcatc   5160
accgaaacgc gcgagacgaa agggcctcgt gatacgccta tttttatagg ttaatgtcat   5220
gaacaataaa actgtctgct tacataaaca gtaatacaag gggtgttatg agccatattc   5280
aacgggaaac gtcgaggccg cgattaaatt ccaacatgga tgctgattta tatgggtata   5340
aatgggctcg cgataatgtc gggcaatcag gtgcgacaat ctatcgcttg tatgggaagc   5400
ccgatgcgcc agagttgttt ctgaaacatg gcaaaggtag cgttgccaat gatgttacag   5460
atgagatggt cagactaaac tggctgacgg aatttatgcc tcttccgacc atcaagcatt   5520
ttatccgtac tcctgatgat gcatggttac tcaccactgc gatccccgga aaaacagcat   5580
tccaggtatt agaagaatat cctgattcag gtgaaaatat tgttgatgcg ctggcagtgt   5640
tcctgcgccg gttgcattcg attcctgttt gtaattgtcc ttttaacagc gatcgcgtat   5700
ttcgtctcgc tcaggcgcaa tcacgaatga ataacggttt ggttgatgcg agtgattttg   5760
atgacgagcg taatggctgg cctgttgaac aagtctggaa agaaatgcat aaacttttgc   5820
cattctcacc ggattcagtc gtcactcatg gtgatttctc acttgataac cttatttttg   5880
acgaggggaa attaataggt tgtattgatg ttggacgagt cggaatcgca gaccgatacc   5940
aggatcttgc catcctatgg aactgcctcg gtgagttttc tccttcatta cagaaacggc   6000
tttttcaaaa atatggtatt gataatcctg atatgaataa attgcagttt catttgatgc   6060
tcgatgagtt tttctaatct catgaccaaa atcccttaac gtgagttttc gttccactga   6120
gcgtcagacc ccgtagaaaa gatcaaagga tcttcttgag atcctttttt tctgcgcgta   6180
atctgctgct tgcaaacaaa aaaaccaccg ctaccagcgg tggtttgttt gccggatcaa   6240
gagctaccaa ctctttttcc gaaggtaact ggcttcagca gagcgcagat accaaatact   6300
gtccttctag tgtagccgta gttaggccac cacttcaaga actctgtagc accgcctaca   6360
tacctcgctc tgctaatcct gttaccagtg gctgctgcca gtggcgataa gtcgtgtctt   6420
accgggttgg actcaagacg atagttaccg gataaggcgc agcggtcggg ctgaacgggg   6480
ggttcgtgca cacagcccag cttggagcga acgacctaca ccgaactgag atacctacag   6540
cgtgagctat gagaaagcgc cacgcttccc gaagggagaa aggcggacag gtatccggta   6600
agcggcaggg tcggaacagg agagcgcacg agggagcttc cagggggaaa cgcctggtat   6660
ctttatagtc ctgtcgggtt tcgccacctc tgacttgagc gtcgattttt gtgatgctcg   6720
tcaggggggc ggagcctatg gaaaaacgcc agcaacgcgg cctttttacg gttcctggcc   6780
ttttgctggc cttttgctca catgt                                         6805
```

<210> SEQ ID NO 6
<211> LENGTH: 8353
<212> TYPE: DNA
<213> ORGANISM: Artificial Sequence
<220> FEATURE:
<223> OTHER INFORMATION: Plasmid

<400> SEQUENCE: 6
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgctccg gtgcccgtca gtgggcagag cgcacatcgc 180
ccacagtccc cgagaagttg gggggagggg tcggcaattg aaccggtgcc tagagaaggt 240
ggcgcggggt aaactgggaa agtgatgtcg tgtactggct ccgccttttt cccgagggtg 300
ggggagaacc gtatataagt gcagtagtcg ccgtgaacgt tctttttcgc aacgctagct 360
aactaccggt gccaccatgg ccccaaagaa gaagcggaag gtcggatcca agcggaacta 420
tatcctggga ctggacatcg gaattacctc cgtgggatac ggcatcatcg attacgagac 480
tagggacgtg attgacgccg gcgtgagact ctttaaggag gccaacgtgg aaaacaacga 540
aggtcgcaga tccaagcggg gtgcaagacg cctgaagcgc cggaggagac atcggataca 600
gcgcgtgaag aagctccttt tcgactacaa cctcctcact gaccactcgg aattgtccgg 660
tatcaacccc tacgaagccc gcgtgaaagg cctgagccag aagctgtccg aagaggagtt 720
tagcgcagcc ctgctgcacc tggctaagcg aagggggggtg cacaacgtga acgaggtgga 780
ggaggacact ggcaacgaac tgtccaccaa ggagcagatt tcacggaact cgaaggcgct 840
ggaagagaaa tatgtggccg agctgcagct ggagaggctc aagaaggatg gcgaagtccg 900
ggggagcatc aatcgcttca agacctcgga ctacgtgaag gaagccaaac agctgttgaa 960
ggtgcagaag gcctaccacc aactggacca atcattcatt gacacttaca tcgatctgct 1020
tgaaaccagg cgcacctact acgagggtcc tggagaaggc agccctttcg gatggaagga 1080
catcaaggag tggtatgaga tgctgatggg tcattgcacc tactttccgg aagaactgcg 1140
ctcagtgaag tacgcgtaca acgctgacct ctacaacgct ctcaacgatc tgaacaacct 1200
cgtgatcacc cgggacgaga acgaaaagct ggagtactac gaaaagttcc agattatcga 1260
aaacgtgttc aagcagaaga agaagcccac cctgaagcag attgcaaagg agatccttgt 1320
gaacgaggag gatattaagg gctaccgggt cacctccacc gggaaaccag agttcactaa 1380
tctcaaggtg taccatgaca ttaaggacat tactgcccgc aaggagatca ttgaaaacgc 1440
ggaactgctg gaccaaatcg cgaagatcct gaccatctat cagagctccg aggatatcca 1500
ggaggaactt actaacctca attccgagct gacgcaggaa gaaatcgagc aaattagcaa 1560
cctgaagggt tacactggaa cccacaacct cagcttgaaa gcgattaacc ttattttgga 1620
tgaactttgg cacactaatg acaatcagat cgccattttc aaccggctga aactggtgcc 1680
gaagaaggtg gacctgagcc aacagaagga aatcccgacc acccttgtgg acgatttcat 1740
cctgtcacct gtggtgaaga ggagcttcat ccagtcgatc aaggtcatca acgccatcat 1800
aaagaagtac ggccttccca acgacatcat catcgaactg gcccgcgaga agaactccaa 1860
agatgcccag aagatgatca acgagatgca gaagcgaaac cggcagacga acgaacggat 1920
cgaggagatc atccggacca ccgggaagga aaacgcgaag tacctgatcg agaaaatcaa 1980
gctgcatgat atgcaggaag ggaagtgtct ctactccctg gaggccattc cgctggagga 2040
tttgctgaac aacccttca actacgaagt cgatcatatc attcctcgct ccgtgtcctt 2100

-continued

```
cgataactcc ttcaacaata aggtcctcgt gaagcaggag gagaagtaag tatcaaggtt   2160

acaagacagg tttaaggaga ccaatagaaa ctgggctcga gcttgtcgag acagagaaga   2220

ctcttgcgtt tctgataggc acctattggt cttactgaca tccactttgc ctttctctcc   2280

acagctcgaa gaagggcaac agaaccccgt tccagtacct ctcgtcgtcc gactccaaga   2340

tcagctacga aactttcaag aagcacattc tgaacctggc caagggcaaa gggagaatta   2400

gcaagaccaa gaaggaatac ctcctggaag agagagacat caaccgcttc tcggtgcaaa   2460

aggatttcat caaccgcaac ctggtcgata ccagatacgc caccagggga ctgatgaacc   2520

tcctgcggtc ctacttccgg gtcaacaatc tggacgtgaa ggtcaaatcc atcaacgggg   2580

gctttacttc tttcctgcgc cggaagtgga agttcaagaa ggaacggaac aagggataca   2640

agcaccacgc tgaagatgcc ctgattattg ccaacgccga cttcatcttt aaggaatgga   2700

aaaagctgga caaggctaag aaggtcatgg agaaccagat gttcgaagaa aagcaggccg   2760

agtccatgcc cgaaatcgaa accgagcagg aatacaagga gatcttcatc acaccgcacc   2820

aaatcaagca catcaaggac ttcaaggatt acaagtacag ccaccgggtg gacaagaagc   2880

ctaacagaga gcttatcaac gacaccctgt actccacgcg caaggacgac aagggaaaca   2940

cattgatcgt gaacaacctg aacggactgt atgacaagga caatgacaaa ctgaagaagc   3000

tgatcaacaa atcgccggaa aagctcctga tgtaccatca cgaccctcaa acctaccaga   3060

aactgaagct catcatggag cagtacggcg acgaaaagaa tcccctgtac aaatactacg   3120

aggagactgg aaattacctg actaagtact ccaagaagga taacggcccc gtgatcaaga   3180

agattaagta ctacggaaac aaactgaacg cacatctcga catcaccgat gattatccaa   3240

actcccgcaa caaagtcgtg aagctctccc tcaaaccgta ccgcttcgac gtgtacctgg   3300

ataatggggt gtacaagttc gtgaccgtga agaacctgga cgtcattaag aaggaaaact   3360

actacgaagt gaactcaaag tgctacgagg aagccaagaa gctcaagaag atcagcaacc   3420

aggccgagtt catcgcatcg ttttacaaca atgacctcat taagattaat ggagaactgt   3480

acagagtgat cggcgtgaac aacgacctcc tgaaccggat tgaagtgaac atgatcgata   3540

ttacctaccg ggagtatctg gagaacatga acgacaagcg cccaccgaga atcatcaaaa   3600

ctattgcctc caagacccaa tccattaaga aatactccac cgacatcctg ggcaacctgt   3660

acgaggtcaa gtcgaagaag cacccccaga ttatcaagaa gggaaaaagg ccggcggcca   3720

cgaaaaaggc cggccaggca aaaaagaaaa aggcttaaga attcctagag ctcgctgatc   3780

agcctcgaaa cttgtttatt gcagcttata atggttacaa ataaagcaat agcatcacaa   3840

atttcacaaa taaagcattt ttttcactgc attctagttg tggtttgtcc aaactcatca   3900

atgtatctta tcatgtctgt ataccagcag gctttcctag gttcgaacgc tgacgtcatc   3960

aacccgctcc aaggaatcgc gggcccagtg tcactaggcg ggaacaccca gcgcgcgtgc   4020

gccctggcag gaagatggct gtgagggaca ggggagtggc gccctgcaat atttgcatgt   4080

cgctatgtgt tctgggaaat caccataaac gtgaaatccc tatcagtgat agagacttat   4140

aagttcccta tcagtgatag agacaccgac gggtgtggta cgcagccact gtttaagtac   4200

tctgtgctgg aaacagcaca gaatctactt aaacaaggca aaatgccgtg tttatctcgt   4260

caacttgttg gcgagatttt ttcacgtgcg gaccgaggct gcagcgtcgt cctccctagg   4320

aacccctagt gatggagttg gccactccct ctctgcgcgc tcgctcgctc actgaggccg   4380

ggcgaccaaa ggtcgcccga cgcccgggct ttgcccgggc ggcctcagtg agcgagcgag   4440

cgcgcagctg cctgcagggg cgcctgatgc ggtattttct ccttacgcat ctgtgcggta   4500
```

-continued

```
tttcacaccg catacgtcaa agcaaccata gtacgcgccc tgtagcggcg cattaagcgc   4560
ggcgggtgtg gtggttacgc gcagcgtgac cgctacactt gccagcgccc tagcgcccgc   4620
tcctttcgct ttcttccctt cctttctcgc cacgttcgcc ggctttcccc gtcaagctct   4680
aaatcggggg ctccctttag ggttccgatt tagtgcttta cggcacctcg accccaaaaa   4740
acttgatttg ggtgatggtt cacgtagtgg gccatcgccc tgatagacgg tttttcgccc   4800
tttgacgttg gagtccacgt tctttaatag tggactcttg ttccaaactg gaacaacact   4860
caaccctatc tcgggctatt cttttgattt ataagggatt ttgccgattt cggcctattg   4920
gttaaaaaat gagctgattt aacaaaaatt taacgcgaat tttaacaaaa tattaacgtt   4980
gacattgatt attgactagt tattaatagt aatcaattac ggggtcatta gttcatagcc   5040
catatatgga gttccgcgtt acataactta cggtaaatgg cccgcctggc tgaccgccca   5100
acgacccccg cccattgacg tcaataatga cgtatgttcc catagtaacg ccaataggga   5160
ctttccattg acgtcaatgg gtggagtatt tacggtaaac tgcccacttg gcagtacatc   5220
aagtgtatca tatgccaagt acgcccccta ttgacgtcaa tgacggtaaa tggcccgcct   5280
ggcattatgc ccagtacatg accttatggg actttcctac ttggcagtac atctacgtat   5340
tagtcatcgc tattaccatg gtgatgcggt tttggcagta catcaatggg cgtggatagc   5400
ggtttgactc acggggattt ccaagtctcc accccattga cgtcaatggg agtttgtttt   5460
ggcaccaaaa tcaacgggac tttccaaaat gtcgtaacaa ctccgcccca ttgacgcaaa   5520
tgggcggtag gcgtgtacgg tgggaggtct atataagcag agctctctgg ctaactagag   5580
aacccactgc ttactggctt atcgttaatt aaccggtgcc accatgatgt cccgccttga   5640
taaatcaaaa gtaataaaca gtgctcttga gcttctcaat gaagttggta tagaagggtt   5700
gacgactcgg aaattggcgc aaaaactcgg tgttgagcag ccaaccttgt attggcatgt   5760
taaaaacaaa cgagcactcc tcgacgcttt ggcgatagag atgctggaca ggcaccacac   5820
gcatttctgt cccctcgaag gagagtcatg gcaggatttc cttagaaata acgcaaagtc   5880
cttcagatgt gcgctgctta gtcaccgcga cggcgcaaaa gttcatctcg gcactaggcc   5940
aaccgagaaa cagtacgaga ctctggagaa ccaactggcg tttttgtgtc aacagggttt   6000
tagtctcgaa aatgcgctct atgctctctc tgcggttggc catttcaccc tcggatgcgt   6060
actggaagat caggagcacc aagtggccaa agaagaacgg gaaacgccga ctacggacag   6120
catgcctccg ttgctccggc aagctataga gctcttcgat caccaaggcg ctgagccagc   6180
tttcttgttc ggattggaac ttattatatg cgggctcgaa aagcagctta aatgcgagtc   6240
aggttaagcg gccgctcgag tctagagggc ccgtttaaac ccgctgatca gcctcgactg   6300
tgccttctag ttgccagcca tctgttgttt gcccctcccc cgtgccttcc ttgaccctgg   6360
aaggtgccac tcccactgtc ctttcctaat aaaatgagga aattgcatcg cattgtctga   6420
gtaggtgtca ttctattctg gggggtgggg tggggcagga cagcaagggg gaggattggg   6480
aagacaatag caggcatgct ggggatgcgg tgggctctat ggaacgttta caattttatg   6540
gtgcactctc agtacaatct gctctgatgc cgcatagtta agccagcccc gacacccgcc   6600
aacacccgct gacgcgccct gacgggcttg tctgctcccg gcatccgctt acagacaagc   6660
tgtgaccgtc tccgggagct gcatgtgtca gaggttttca ccgtcatcac cgaaacgcgc   6720
gagacgaaag ggcctcgtga tacgcctatt tttataggtt aatgtcatga acaataaaac   6780
tgtctgctta cataaacagt aatacaaggg gtgttatgag ccatattcaa cgggaaacgt   6840
```

cgaggccgcg attaaattcc aacatggatg ctgatttata tgggtataaa tgggctcgcg 6900
ataatgtcgg gcaatcaggt gcgacaatct atcgcttgta tgggaagccc gatgcgccag 6960
agttgtttct gaaacatggc aaaggtagcg ttgccaatga tgttacagat gagatggtca 7020
gactaaactg gctgacggaa tttatgcctc ttccgaccat caagcatttt atccgtactc 7080
ctgatgatgc atggttactc accactgcga tccccggaaa aacagcattc caggtattag 7140
aagaatatcc tgattcaggt gaaaatattg ttgatgcgct ggcagtgttc ctgcgccggt 7200
tgcattcgat tcctgtttgt aattgtcctt ttaacagcga tcgcgtattt cgtctcgctc 7260
aggcgcaatc acgaatgaat aacggtttgg ttgatgcgag tgattttgat gacgagcgta 7320
atggctggcc tgttgaacaa gtctggaaag aaatgcataa acttttgcca ttctcaccgg 7380
attcagtcgt cactcatggt gatttctcac ttgataacct tatttttgac gaggggaaat 7440
taataggttg tattgatgtt ggacgagtcg gaatcgcaga ccgataccag gatcttgcca 7500
tcctatggaa ctgcctcggt gagttttctc cttcattaca gaaacggctt tttcaaaaat 7560
atggtattga taatcctgat atgaataaat tgcagtttca tttgatgctc gatgagtttt 7620
tctaatctca tgaccaaaat cccttaacgt gagttttcgt tccactgagc gtcagacccc 7680
gtagaaaaga tcaaaggatc ttcttgagat cctttttttc tgcgcgtaat ctgctgcttg 7740
caaacaaaaa aaccaccgct accagcggtg gtttgtttgc cggatcaaga gctaccaact 7800
ctttttccga aggtaactgg cttcagcaga gcgcagatac caaatactgt ccttctagtg 7860
tagccgtagt taggccacca cttcaagaac tctgtagcac cgcctacata cctcgctctg 7920
ctaatcctgt taccagtggc tgctgccagt ggcgataagt cgtgtcttac cgggttggac 7980
tcaagacgat agttaccgga taaggcgcag cggtcgggct gaacgggggg ttcgtgcaca 8040
cagcccagct tggagcgaac gacctacacc gaactgagat acctacagcg tgagctatga 8100
gaaagcgcca cgcttcccga agggagaaag gcggacaggt atccggtaag cggcagggtc 8160
ggaacaggag agcgcacgag ggagcttcca gggggaaacg cctggtatct ttatagtcct 8220
gtcgggtttc gccacctctg acttgagcgt cgatttttgt gatgctcgtc aggggggcgg 8280
agcctatgga aaaacgccag caacgcggcc tttttacggt tcctggcctt ttgctggcct 8340
tttgctcaca tgt 8353

<210> SEQ ID NO 7
<211> LENGTH: 6802
<212> TYPE: DNA
<213> ORGANISM: Artificial Sequence
<220> FEATURE:
<223> OTHER INFORMATION: Plasmid

<400> SEQUENCE: 7
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgctccg gtgcccgtca gtgggcagag cgcacatcgc 180
ccacagtccc cgagaagttg gggggagggg tcggcaattg aaccggtgcc tagagaaggt 240
ggcgcggggt aaactgggaa agtgatgtcg tgtactggct ccgccttttt cccgagggtg 300
ggggagaacc gtatataagt gcagtagtcg ccgtgaacgt tctttttcgc aacgctagct 360
aactaccggt gccaccatgg ccccaaagaa gaagcggaag gtcggatcca agcggaacta 420
tatcctggga ctggacatcg gaattacctc cgtgggatac ggcatcatcg attacgagac 480
tagggacgtg attgacgccg gcgtgagact ctttaaggag gccaacgtgg aaaacaacga 540

```
aggtcgcaga tccaagcggg gtgcaagacg cctgaagcgc cggaggagac atcggataca    600
gcgcgtgaag aagctccttt tcgactacaa cctcctcact gaccactcgg aattgtccgg    660
tatcaacccc tacgaagccc gcgtgaaagg cctgagccag aagctgtccg aagaggagtt    720
tagcgcagcc ctgctgcacc tggctaagcg aaggggggtg cacaacgtga acgaggtgga    780
ggaggacact ggcaacgaac tgtccaccaa ggagcagatt tcacggaact cgaaggcgct    840
ggaagagaaa tatgtggccg agctgcagct ggagaggctc aagaaggatg gcgaagtccg    900
ggggagcatc aatcgcttca agacctcgga ctacgtgaag gaagccaaac agctgttgaa    960
ggtgcagaag gcctaccacc aactggacca atcattcatt gacacttaca tcgatctgct   1020
tgaaaccagg cgcacctact acgagggtcc tggagaaggc agccctttcg gatggaagga   1080
catcaaggag tggtatgaga tgctgatggg tcattgcacc tactttccgg aagaactgcg   1140
ctcagtgaag tacgcgtaca acgctgacct ctacaacgct ctcaacgatc tgaacaacct   1200
cgtgatcacc cgggacgaga acgaaaagct ggagtactac gaaaagttcc agattatcga   1260
aaacgtgttc aagcagaaga agaagcccac cctgaagcag attgcaaagg agatccttgt   1320
gaacgaggag gatattaagg gctaccgggt cacctccacc gggaaaccag agttcactaa   1380
tctcaaggtg taccatgaca ttaaggacat tactgcccgc aaggagatca ttgaaaacgc   1440
ggaactgctg gaccaaatcg cgaagatcct gaccatctat cagagctccg aggatatcca   1500
ggaggaactt actaacctca attccgagct gacgcaggaa gaaatcgagc aaattagcaa   1560
cctgaagggt tacactggaa cccacaacct cagcttgaaa gcgattaacc ttattttgga   1620
tgaactttgg cacactaatg acaatcagat cgccattttc aaccggctga aactggtgcc   1680
gaagaaggtg gacctgagcc aacagaagga aatcccgacc acccttgtgg acgatttcat   1740
cctgtcacct gtggtgaaga ggagcttcat ccagtcgatc aaggtcatca acgccatcat   1800
aaagaagtac ggccttccca acgacatcat catcgaactg gcccgcgaga agaactccaa   1860
agatgcccag aagatgatca acgagatgca gaagcgaaac cggcagacga acgaacggat   1920
cgaggagatc atccggacca ccgggaagga aaacgcgaag tacctgatcg agaaaatcaa   1980
gctgcatgat atgcaggaag ggaagtgtct ctactccctg gaggccattc cgctggagga   2040
tttgctgaac aaccctttca actacgaagt cgatcatatc attcctcgct ccgtgtcctt   2100
cgataactcc ttcaacaata aggtcctcgt gaagcaggag gagaagtaag tatcaaggtt   2160
acaagacagg tttaaggaga ccaatagaaa ctgggctcga gcttgtcgag acagagaaga   2220
ctcttgcgtt tctgataggc acctattggt cttactgaca tccactttgc ctttctctcc   2280
acagctcgaa gaagggcaac agaaccccgt tccagtacct ctcgtcgtcc gactccaaga   2340
tcagctacga aactttcaag aagcacattc tgaacctggc caagggcaaa gggagaatta   2400
gcaagaccaa gaaggaatac ctcctggaag agagagacat caaccgcttc tcggtgcaaa   2460
aggatttcat caaccgcaac ctggtcgata ccagatacgc caccagggga ctgatgaacc   2520
tcctgcggtc ctacttccgg gtcaacaatc tggacgtgaa ggtcaaatcc atcaacgggg   2580
gctttacttc tttcctgcgc cggaagtgga agttcaagaa ggaacggaac aagggataca   2640
agcaccacgc tgaagatgcc ctgattattg ccaacgccga cttcatcttt aaggaatgga   2700
aaaagctgga caaggctaag aaggtcatgg agaaccagat gttcgaagaa aagcaggccg   2760
agtccatgcc cgaaatcgaa accgagcagg aatacaagga gatcttcatc acaccgcacc   2820
aaatcaagca catcaaggac ttcaaggatt acaagtacag ccaccgggtg gacaagaagc   2880
```

-continued

```
ctaacagaga gcttatcaac gacaccctgt actccacgcg caaggacgac aagggaaaca   2940
cattgatcgt gaacaacctg aacggactgt atgacaagga caatgacaaa ctgaagaagc   3000
tgatcaacaa atcgccggaa aagctcctga tgtaccatca cgaccctcaa acctaccaga   3060
aactgaagct catcatggag cagtacggcg acgaaaagaa tcccctgtac aaatactacg   3120
aggagactgg aaattacctg actaagtact ccaagaagga taacggcccc gtgatcaaga   3180
agattaagta ctacggaaac aaactgaacg cacatctcga catcaccgat gattatccaa   3240
actcccgcaa caaagtcgtg aagctctccc tcaaaccgta ccgcttcgac gtgtacctgg   3300
ataatggggt gtacaagttc gtgaccgtga agaacctgga cgtcattaag aaggaaaact   3360
actacgaagt gaactcaaag tgctacgagg aagccaagaa gctcaagaag atcagcaacc   3420
aggccgagtt catcgcatcg ttttacaaca atgacctcat taagattaat ggagaactgt   3480
acagagtgat cggcgtgaac aacgacctcc tgaaccggat tgaagtgaac atgatcgata   3540
ttacctaccg ggagtatctg gagaacatga acgacaagcg cccaccgaga atcatcaaaa   3600
ctattgcctc caagacccaa tccattaaga aatactccac cgacatcctg ggcaacctgt   3660
acgaggtcaa gtcgaagaag cacccccaga ttatcaagaa gggaaaaagg ccggcggcca   3720
cgaaaaaggc cggccaggca aaaaagaaaa aggcttaaga attcctagag ctcgctgatc   3780
agcctcgaaa cttgtttatt gcagcttata atggttacaa ataaagcaat agcatcacaa   3840
atttcacaaa taaagcattt ttttcactgc attctagttg tggtttgtcc aaactcatca   3900
atgtatctta tcatgtctgt ataccagcag gctttcctag gttcgaacgc tgacgtcatc   3960
aacccgctcc aaggaatcgc gggcccagtg tcactaggcg ggaacaccca gcgcgcgtgc   4020
gccctggcag gaagatggct gtgagggaca ggggagtggc gccctgcaat atttgcatgt   4080
cgctatgtgt tctgggaaat caccataaac gtgaaatccc tatcagtgat agagacttat   4140
aagttcccta tcagtgatag agacaccggg tgtggtacgc agccactgtt taagtactct   4200
gtgctggaaa cagcacagaa tctacttaaa caaggcaaaa tgccgtgttt atctcgtcaa   4260
cttgttggcg agattttttc acgtgcggac cgaggctgca gcgtcgtcct ccctaggaac   4320
ccctagtgat ggagttggcc actccctctc tgcgcgctcg ctcgctcact gaggccgggc   4380
gaccaaaggt cgcccgacgc ccgggctttg cccgggcggc ctcagtgagc gagcgagcgc   4440
gcagctgcct gcaggggcgc ctgatgcggt attttctcct tacgcatctg tgcggtattt   4500
cacaccgcat acgtcaaagc aaccatagta cgcgccctgt agcggcgcat taagcgcggc   4560
gggtgtggtg gttacgcgca gcgtgaccgc tacacttgcc agcgccctag cgcccgctcc   4620
tttcgctttc ttcccttcct ttctcgccac gttcgccggc tttccccgtc aagctctaaa   4680
tcgggggctc cctttagggt tccgatttag tgctttacgg cacctcgacc ccaaaaaact   4740
tgatttgggt gatggttcac gtagtgggcc atcgccctga tagacggttt ttcgcccttt   4800
gacgttggag tccacgttct ttaatagtgg actcttgttc caaactggaa caacactcaa   4860
ccctatctcg ggctattctt ttgatttata agggattttg ccgatttcgg cctattggtt   4920
aaaaaatgag ctgatttaac aaaaatttaa cgcgaatttt aacaaaatat taacgtttac   4980
aattttatgg tgcactctca gtacaatctg ctctgatgcc gcatagttaa gccagccccg   5040
acacccgcca acacccgctg acgcgccctg acgggcttgt ctgctcccgg catccgctta   5100
cagacaagct gtgaccgtct ccgggagctg catgtgtcag aggttttcac cgtcatcacc   5160
gaaacgcgcg agacgaaagg gcctcgtgat acgcctattt ttataggtta atgtcatgaa   5220
caataaaact gtctgcttac ataaacagta atacaagggg tgttatgagc catattcaac   5280
```

```
gggaaacgtc gaggccgcga ttaaattcca acatggatgc tgatttatat gggtataaat   5340

gggctcgcga taatgtcggg caatcaggtg cgacaatcta tcgcttgtat gggaagcccg   5400

atgcgccaga gttgtttctg aaacatggca aaggtagcgt tgccaatgat gttacagatg   5460

agatggtcag actaaactgg ctgacggaat ttatgcctct tccgaccatc aagcatttta   5520

tccgtactcc tgatgatgca tggttactca ccactgcgat ccccggaaaa acagcattcc   5580

aggtattaga agaatatcct gattcaggtg aaaatattgt tgatgcgctg gcagtgttcc   5640

tgcgccggtt gcattcgatt cctgtttgta attgtccttt taacagcgat cgcgtatttc   5700

gtctcgctca ggcgcaatca cgaatgaata acggtttggt tgatgcgagt gattttgatg   5760

acgagcgtaa tggctggcct gttgaacaag tctggaaaga aatgcataaa cttttgccat   5820

tctcaccgga ttcagtcgtc actcatggtg atttctcact tgataacctt atttttgacg   5880

aggggaaatt aataggttgt attgatgttg gacgagtcgg aatcgcagac cgataccagg   5940

atcttgccat cctatggaac tgcctcggtg agttttctcc ttcattacag aaacggcttt   6000

ttcaaaaata tggtattgat aatcctgata tgaataaatt gcagtttcat ttgatgctcg   6060

atgagttttt ctaatctcat gaccaaaatc ccttaacgtg agttttcgtt ccactgagcg   6120

tcagaccccg tagaaaagat caaaggatct tcttgagatc cttttttct gcgcgtaatc   6180

tgctgcttgc aaacaaaaaa accaccgcta ccagcggtgg tttgtttgcc ggatcaagag   6240

ctaccaactc tttttccgaa ggtaactggc ttcagcagag cgcagatacc aaatactgtc   6300

cttctagtgt agccgtagtt aggccaccac ttcaagaact ctgtagcacc gcctacatac   6360

ctcgctctgc taatcctgtt accagtggct gctgccagtg gcgataagtc gtgtcttacc   6420

gggttggact caagacgata gttaccggat aaggcgcagc ggtcgggctg aacggggggt   6480

tcgtgcacac agcccagctt ggagcgaacg acctacaccg aactgagata cctacagcgt   6540

gagctatgag aaagcgccac gcttcccgaa gggagaaagg cggacaggta tccggtaagc   6600

ggcagggtcg gaacaggaga gcgcacgagg gagcttccag ggggaaacgc ctggtatctt   6660

tatagtcctg tcgggtttcg ccacctctga cttgagcgtc gatttttgtg atgctcgtca   6720

gggggcgga gcctatggaa aaacgccagc aacgcggcct ttttacggtt cctggccttt   6780

tgctggcctt ttgctcacat gt                                           6802

<210> SEQ ID NO 8
<211> LENGTH: 6828
<212> TYPE: DNA
<213> ORGANISM: Artificial Sequence
<220> FEATURE:
<223> OTHER INFORMATION: Plasmid

<400> SEQUENCE: 8

cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccgcac gcgtgctccg gtgcccgtca gtgggcagag cgcacatcgc    180

ccacagtccc cgagaagttg gggggagggg tcggcaattg aaccggtgcc tagagaaggt    240

ggcgcggggt aaactgggaa agtgatgtcg tgtactggct ccgccttttt cccgagggtg    300

ggggagaacc gtatataagt gcagtagtcg ccgtgaacgt tctttttcgc aacgctagct    360

aactaccggt gccaccatgg ccccaaagaa gaagcggaag gtcggatcca agcggaacta    420

tatcctggga ctggacatcg gaattacctc cgtgggatac ggcatcatcg attacgagac    480
```

-continued

```
tagggacgtg attgacgccg gcgtgagact ctttaaggag gccaacgtgg aaaacaacga    540
aggtcgcaga tccaagcggg gtgcaagacg cctgaagcgc cggaggagac atcggataca    600
gcgcgtgaag aagctccttt tcgactacaa cctcctcact gaccactcgg aattgtccgg    660
tatcaacccc tacgaagccc gcgtgaaagg cctgagccag aagctgtccg aagaggagtt    720
tagcgcagcc ctgctgcacc tggctaagcg aaggggggtg cacaacgtga acgaggtgga    780
ggaggacact ggcaacgaac tgtccaccaa ggagcagatt tcacggaact cgaaggcgct    840
ggaagagaaa tatgtggccg agctgcagct ggagaggctc aagaaggatg gcgaagtccg    900
ggggagcatc aatcgcttca agacctcgga ctacgtgaag gaagccaaac agctgttgaa    960
ggtgcagaag gcctaccacc aactggacca atcattcatt gacacttaca tcgatctgct   1020
tgaaaccagg cgcacctact acgagggtcc tggagaaggc agccctttcg gatggaagga   1080
catcaaggag tggtatgaga tgctgatggg tcattgcacc tactttccgg aagaactgcg   1140
ctcagtgaag tacgcgtaca acgctgacct ctacaacgct ctcaacgatc tgaacaacct   1200
cgtgatcacc cgggacgaga acgaaaagct ggagtactac gaaaagttcc agattatcga   1260
aaacgtgttc aagcagaaga agaagcccac cctgaagcag attgcaaagg agatccttgt   1320
gaacgaggag gatattaagg gctaccgggt cacctccacc gggaaaccag agttcactaa   1380
tctcaaggtg taccatgaca ttaaggacat tactgcccgc aaggagatca ttgaaaacgc   1440
ggaactgctg gaccaaatcg cgaagatcct gaccatctat cagagctccg aggatatcca   1500
ggaggaactt actaacctca attccgagct gacgcaggaa gaaatcgagc aaattagcaa   1560
cctgaagggt tacactggaa cccacaacct cagcttgaaa gcgattaacc ttattttgga   1620
tgaactttgg cacactaatg acaatcagat cgccattttc aaccggctga aactggtgcc   1680
gaagaaggtg gacctgagcc aacagaagga aatcccgacc acccttgtgg acgatttcat   1740
cctgtcacct gtggtgaaga ggagcttcat ccagtcgatc aaggtcatca acgccatcat   1800
aaagaagtac ggccttccca acgacatcat catcgaactg gcccgcgaga agaactccaa   1860
agatgcccag aagatgatca acgagatgca gaagcgaaac cggcagacga acgaacggat   1920
cgaggagatc atccggacca ccgggaagga aaacgcgaag tacctgatcg agaaaatcaa   1980
gctgcatgat atgcaggaag ggaagtgtct ctactccctg gaggccattc cgctggagga   2040
tttgctgaac aaccctttca actacgaagt cgatcatatc attcctcgct ccgtgtcctt   2100
cgataactcc ttcaacaata aggtcctcgt gaagcaggag gagaagtaag tatcaaggtt   2160
acaagacagg tttaaggaga ccaatagaaa ctgggctcga gcttgtcgag acagagaaga   2220
ctcttgcgtt tctgataggc acctattggt cttactgaca tccactttgc ctttctctcc   2280
acagctcgaa gaagggcaac agaaccccgt tccagtacct ctcgtcgtcc gactccaaga   2340
tcagctacga aactttcaag aagcacattc tgaacctggc caagggcaaa gggagaatta   2400
gcaagaccaa gaaggaatac ctcctggaag agagagacat caaccgcttc tcggtgcaaa   2460
aggatttcat caaccgcaac ctggtcgata ccagatacgc caccagggga ctgatgaacc   2520
tcctgcggtc ctacttccgg gtcaacaatc tggacgtgaa ggtcaaatcc atcaacgggg   2580
gctttacttc tttcctgcgc cggaagtgga agttcaagaa ggaacggaac aagggataca   2640
agcaccacgc tgaagatgcc ctgattattg ccaacgccga cttcatcttt aaggaatgga   2700
aaaagctgga caaggctaag aaggtcatgg agaaccagat gttcgaagaa aagcaggccg   2760
agtccatgcc cgaaatcgaa accgagcagg aatacaagga gatcttcatc acaccgcacc   2820
aaatcaagca catcaaggac ttcaaggatt acaagtacag ccaccgggtg gacaagaagc   2880
```

-continued

```
ctaacagaga gcttatcaac gacaccctgt actccacgcg caaggacgac aagggaaaca   2940
cattgatcgt gaacaacctg aacggactgt atgacaagga caatgacaaa ctgaagaagc   3000
tgatcaacaa atcgccggaa aagctcctga tgtaccatca cgaccctcaa acctaccaga   3060
aactgaagct catcatggag cagtacggcg acgaaaagaa tcccctgtac aaatactacg   3120
aggagactgg aaattacctg actaagtact ccaagaagga taacggcccc gtgatcaaga   3180
agattaagta ctacggaaac aaactgaacg cacatctcga catcaccgat gattatccaa   3240
actcccgcaa caaagtcgtg aagctctccc tcaaaccgta ccgcttcgac gtgtacctgg   3300
ataatggggt gtacaagttc gtgaccgtga agaacctgga cgtcattaag aaggaaaact   3360
actacgaagt gaactcaaag tgctacgagg aagccaagaa gctcaagaag atcagcaacc   3420
aggccgagtt catcgcatcg ttttacaaca atgacctcat taagattaat ggagaactgt   3480
acagagtgat cggcgtgaac aacgacctcc tgaaccggat tgaagtgaac atgatcgata   3540
ttacctaccg ggagtatctg gagaacatga acgacaagcg cccaccgaga atcatcaaaa   3600
ctattgcctc caagacccaa tccattaaga aatactccac cgacatcctg ggcaacctgt   3660
acgaggtcaa gtcgaagaag cacccccaga ttatcaagaa gggaaaaagg ccggcggcca   3720
cgaaaaaggc cggccaggca aaaaagaaaa aggcttaaga attcctagag ctcgctgatc   3780
agcctcgaaa cttgtttatt gcagcttata atggttacaa ataaagcaat agcatcacaa   3840
atttcacaaa taaagcattt ttttcactgc attctagttg tggtttgtcc aaactcatca   3900
atgtatctta tcatgtctgt ataccagcag gctttcctag gttcgagggc ctatttccca   3960
tgattccttc atatttgcat atacgataca aggctgttag agagataatt ggaattaatt   4020
tgactgtaaa cacaaagata ttagtacaaa atacgtgacg tagaaagtaa taatttcttg   4080
ggtagtttgc agttttaaaa ttatgtttta aaatggacta tcatatgctt accgtaactt   4140
gaaagtattt cgatttcttg gctttatata tcttgtggaa aggacgaaac accgggtgtg   4200
gtacgcagcc actgtttaag tactctgtgc tggaaacagc acagaatcta cttaaacaag   4260
gcaaaatgcc gtgtttatct cgtcaacttg ttggcgagat tttttcacgt gcggaccgag   4320
gctgcagcgt cgtcctccct aggaacccct agtgatggag ttggccactc cctctctgcg   4380
cgctcgctcg ctcactgagg ccgggcgacc aaaggtcgcc cgacgcccgg gctttgcccg   4440
ggcggcctca gtgagcgagc gagcgcgcag ctgcctgcag gggcgcctga tgcggtattt   4500
tctccttacg catctgtgcg gtatttcaca ccgcatacgt caaagcaacc atagtacgcg   4560
ccctgtagcg gcgcattaag cgcggcgggt gtggtggtta cgcgcagcgt gaccgctaca   4620
cttgccagcg ccctagcgcc cgctcctttc gctttcttcc cttcctttct cgccacgttc   4680
gccggctttc cccgtcaagc tctaaatcgg gggctccctt tagggttccg atttagtgct   4740
ttacggcacc tcgaccccaa aaaacttgat ttgggtgatg gttcacgtag tgggccatcg   4800
ccctgataga cggtttttcg ccctttgacg ttggagtcca cgttctttaa tagtggactc   4860
ttgttccaaa ctggaacaac actcaaccct atctcgggct attcttttga tttataaggg   4920
attttgccga tttcggccta ttggttaaaa aatgagctga tttaacaaaa atttaacgcg   4980
aattttaaca aaatattaac gtttacaatt ttatggtgca ctctcagtac aatctgctct   5040
gatgccgcat agttaagcca gccccgacac ccgccaacac ccgctgacgc gccctgacgg   5100
gcttgtctgc tcccggcatc cgcttacaga caagctgtga ccgtctccgg gagctgcatg   5160
tgtcagaggt tttcaccgtc atcaccgaaa cgcgcgagac gaaagggcct cgtgatacgc   5220
```

ctatttttat aggttaatgt catgaacaat aaaactgtct gcttacataa acagtaatac 5280
aaggggtgtt atgagccata ttcaacggga aacgtcgagg ccgcgattaa attccaacat 5340
ggatgctgat ttatatgggt ataaatgggc tcgcgataat gtcgggcaat caggtgcgac 5400
aatctatcgc ttgtatggga agcccgatgc gccagagttg tttctgaaac atggcaaagg 5460
tagcgttgcc aatgatgtta cagatgagat ggtcagacta aactggctga cggaatttat 5520
gcctcttccg accatcaagc attttatccg tactcctgat gatgcatggt tactcaccac 5580
tgcgatcccc ggaaaaacag cattccaggt attagaagaa tatcctgatt caggtgaaaa 5640
tattgttgat gcgctggcag tgttcctgcg ccggttgcat tcgattcctg tttgtaattg 5700
tccttttaac agcgatcgcg tatttcgtct cgctcaggcg caatcacgaa tgaataacgg 5760
tttggttgat gcgagtgatt ttgatgacga gcgtaatggc tggcctgttg aacaagtctg 5820
gaaagaaatg cataaacttt tgccattctc accggattca gtcgtcactc atggtgattt 5880
ctcacttgat aaccttattt ttgacgaggg gaaattaata ggttgtattg atgttggacg 5940
agtcggaatc gcagaccgat accaggatct tgccatccta tggaactgcc tcggtgagtt 6000
ttctccttca ttacagaaac ggctttttca aaaatatggt attgataatc ctgatatgaa 6060
taaattgcag tttcatttga tgctcgatga gtttttctaa tctcatgacc aaaatccctt 6120
aacgtgagtt ttcgttccac tgagcgtcag accccgtaga aaagatcaaa ggatcttctt 6180
gagatccttt ttttctgcgc gtaatctgct gcttgcaaac aaaaaaacca ccgctaccag 6240
cggtggtttg tttgccggat caagagctac caactctttt tccgaaggta actggcttca 6300
gcagagcgca gataccaaat actgtccttc tagtgtagcc gtagttaggc caccacttca 6360
agaactctgt agcaccgcct acatacctcg ctctgctaat cctgttacca gtggctgctg 6420
ccagtggcga taagtcgtgt cttaccgggt tggactcaag acgatagtta ccggataagg 6480
cgcagcggtc gggctgaacg gggggttcgt gcacacagcc cagcttggag cgaacgacct 6540
acaccgaact gagataccta cagcgtgagc tatgagaaag cgccacgctt cccgaaggga 6600
gaaaggcgga caggtatccg gtaagcggca gggtcggaac aggagagcgc acgagggagc 6660
ttccaggggg aaacgcctgg tatctttata gtcctgtcgg gtttcgccac ctctgacttg 6720
agcgtcgatt tttgtgatgc tcgtcagggg ggcggagcct atggaaaaac gccagcaacg 6780
cggccttttt acggttcctg gccttttgct ggccttttgc tcacatgt 6828

<210> SEQ ID NO 9
<211> LENGTH: 52
<212> TYPE: RNA
<213> ORGANISM: Artificial Sequence
<220> FEATURE:
<223> OTHER INFORMATION: Short hairpin RNA (shRNA)

<400> SEQUENCE: 9
ggaauuaccu ccgugggaua ccgaaguauc ccacggaggu aauuccuuuu uu 52

<210> SEQ ID NO 10
<211> LENGTH: 52
<212> TYPE: RNA
<213> ORGANISM: Artificial Sequence
<220> FEATURE:
<223> OTHER INFORMATION: Short hairpin RNA (shRNA)

<400> SEQUENCE: 10
ggauauccag gaggaacuua ccgaaguaag uuccuccugg auauccuuuu uu 52

<210> SEQ ID NO 11
<211> LENGTH: 52
<212> TYPE: RNA
<213> ORGANISM: Artificial Sequence
<220> FEATURE:
<223> OTHER INFORMATION: Short hairpin RNA (shRNA)

<400> SEQUENCE: 11
ggagcuucau ccagucgauc acgaaugauc gacuggauga agcuccuuuu uu 52

<210> SEQ ID NO 12
<211> LENGTH: 6785
<212> TYPE: DNA
<213> ORGANISM: Artificial Sequence
<220> FEATURE:
<223> OTHER INFORMATION: Plasmid

<400> SEQUENCE: 12
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgctccg gtgcccgtca gtgggcagag cgcacatcgc 180
ccacagtccc cgagaagttg gggggagggg tcggcaattg aaccggtgcc tagagaaggt 240
ggcgcggggt aaactgggaa agtgatgtcg tgtactggct ccgccttttt cccgagggtg 300
ggggagaacc gtatataagt gcagtagtcg ccgtgaacgt tctttttcgc aacgctagct 360
aactaccggt gccaccatgg attacaaaga ccacgacgga gactacaagg atcacgacat 420
tgattacaag gatgatgatg ataaggcccc aaagaagaag cggaaggtcg gtatccacgg 480
agtcccagca gccggatccg ccatgaagcg gaactatatc ctgggactgg acatcggaat 540
tacctccgtg ggatacggca tcatcgatta cgagactagg gacgtgattg acgccggcgt 600
gagactcttt aaggaggcca acgtggaaaa caacgaaggt cgcagatcca agcggggtgc 660
aagacgcctg aagcgccgga ggagacatcg gatacagcgc gtgaagaagc tcctttttcga 720 ctacaacctc ctcactgacc actcggaatt gtccggtatc aacccctacg aagcccgcgt 780
gaaaggcctg agccagaagc tgtccgaaga ggagtttagc gcagccctgc tgcacctggc 840
taagcgaagg ggggtgcaca acgtgaacga ggtggaggag gacactggca acgaactgtc 900
caccaaggag cagatttcac ggaactcgaa ggcgctggaa gagaaatatg tggccgagct 960
gcagctggag aggctcaaga aggatggcga agtccggggg agcatcaatc gcttcaagac 1020
ctcggactac gtgaaggaag ccaaacagct gttgaaggtg cagaaggcct accaccaact 1080
ggaccaatca ttcattgaca cttacatcga tctgcttgaa accaggcgca cctactacga 1140
gggtcctgga gaaggcagcc ctttcggatg gaaggacatc aaggagtggt atgagatgct 1200
gatgggtcat tgcacctact ttccggaaga actgcgctca gtgaagtacg cgtacaacgc 1260
tgacctctac aacgctctca acgatctgaa caacctcgtg atcacccggg acgagaacga 1320
aaagctggag tactacgaaa agttccagat tatcgaaaac gtgttcaagc agaagaagaa 1380
gcccaccctg aagcagattg caaaggagat ccttgtgaac gaggaggata ttaagggcta 1440
ccgggtcacc tccaccggga aaccagagtt cactaatctc aaggtgtacc atgacattaa 1500
ggacattact gcccgcaagg agatcattga aaacgcggaa ctgctggacc aaatcgcgaa 1560
gatcctgacc atctatcaga gctccgagga tatccaggag gaacttacta acctcaattc 1620
cgagctgacg caggaagaaa tcgagcaaat tagcaacctg aagggttaca ctggaaccca 1680
caacctcagc ttgaaagcga ttaaccttat tttggatgaa ctttggcaca ctaatgacaa 1740

```
tcagatcgcc attttcaacc ggctgaaact ggtgccgaag aaggtggacc tgagccaaca   1800
gaaggaaatc ccgaccaccc ttgtggacga tttcatcctg tcacctgtgg tgaagaggag   1860
cttcatccag tcgatcaagg tcatcaacgc catcataaag aagtacggcc ttcccaacga   1920
catcatcatc gaactggccc gcgagaagaa ctccaaagat gcccagaaga tgatcaacga   1980
gatgcagaag cgaaaccggc agacgaacga acggatcgag gagatcatcc ggaccaccgg   2040
gaaggaaaac gcgaagtacc tgatcgagaa aatcaagctg catgatatgc aggaagggaa   2100
gtgtctctac tccctggagg ccattccgct ggaggatttg ctgaacaacc ctttcaacta   2160
cgaagtcgat catatcattc ctcgctccgt gtccttcgat aactccttca acaataaggt   2220
cctcgtgaag caggaggaga actcgaagaa gggcaacaga accccgttcc agtacctctc   2280
gtcgtccgac tccaagatca gctacgaaac tttcaagaag cacattctga acctggccaa   2340
gggcaaaggg agaattagca agaccaagaa ggaatacctc ctggaagaga gagacatcaa   2400
ccgcttctcg gtgcaaaagg atttcatcaa ccgcaacctg gtcgatacca gatacgccac   2460
caggggactg atgaacctcc tgcggtccta cttccgggtc aacaatctgg acgtgaaggt   2520
caaatccatc aacgggggct ttacttcttt cctgcgccgg aagtggaagt tcaagaagga   2580
acggaacaag ggatacaagc accacgctga agatgccctg attattgcca acgccgactt   2640
catctttaag gaatggaaaa agctggacaa ggctaagaag gtcatggaga accagatgtt   2700
cgaagaaaag caggccgagt ccatgcccga aatcgaaacc gagcaggaat acaaggagat   2760
cttcatcaca ccgcaccaaa tcaagcacat caaggacttc aaggattaca agtacagcca   2820
ccgggtggac aagaagccta acagagagct tatcaacgac accctgtact ccacgcgcaa   2880
ggacgacaag ggaaacacat tgatcgtgaa caacctgaac ggactgtatg acaaggacaa   2940
tgacaaactg aagaagctga tcaacaaatc gccggaaaag ctcctgatgt accatcacga   3000
ccctcaaacc taccagaaac tgaagctcat catggagcag tacggcgacg aaaagaatcc   3060
cctgtacaaa tactacgagg agactggaaa ttacctgact aagtactcca agaaggataa   3120
cggccccgtg atcaagaaga ttaagtacta cggaaacaaa ctgaacgcac atctcgacat   3180
caccgatgat tatccaaact cccgcaacaa agtcgtgaag ctctccctca aaccgtaccg   3240
cttcgacgtg tacctggata atggggtgta caagttcgtg accgtgaaga acctggacgt   3300
cattaagaag gaaaactact acgaagtgaa ctcaaagtgc tacgaggaag ccaagaagct   3360
caagaagatc agcaaccagg ccgagttcat cgcatcgttt tacaacaatg acctcattaa   3420
gattaatgga gaactgtaca gagtgatcgg cgtgaacaac gacctcctga accggattga   3480
agtgaacatg atcgatatta cctaccggga gtatctggag aacatgaacg acaagcgccc   3540
accgagaatc atcaaaacta ttgcctccaa gacccaatcc attaagaaat actccaccga   3600
catcctgggc aacctgtacg aggtcaagtc gaagaagcac ccccagatta tcaagaaggg   3660
aaaaaggccg gcggccacga aaaaggccgg ccaggcaaaa aagaaaaagg cttaagaatt   3720
cctagagctc gctgatcagc ctcgaaactt gtttattgca gcttataatg gttacaaata   3780
aagcaatagc atcacaaatt tcacaaataa agcatttttt tcactgcatt ctagttgtgg   3840
tttgtccaaa ctcatcaatg tatcttatca tgtctgtata ccagcaggct ttcctaggtt   3900
cgagggccta tttcccatga ttccttcata tttgcatata cgatacaagg ctgttagaga   3960
gataattgga attaatttga ctgtaaacac aaagatatta gtacaaaata cgtgacgtag   4020
aaagtaataa tttcttgggt agtttgcagt tttaaaatta tgttttaaaa tggactatca   4080
tatgcttacc gtaacttgaa agtatttcga tttcttggct ttatatatct tgtggaaagg   4140
```

-continued

```
acgaaacacc gggtgtggta cgcagccact gtttaagtac tctgtgctgg aaacagcaca   4200
gaatctactt aaacaaggca aaatgccgtg tttatctcgt caacttgttg gcgagatttt   4260
ttcacgtgcg gaccgaggct gcagcgtcgt cctccctagg aaccccctagt gatggagttg   4320
gccactccct ctctgcgcgc tcgctcgctc actgaggccg ggcgaccaaa ggtcgcccga   4380
cgcccgggct ttgcccgggc ggcctcagtg agcgagcgag cgcgcagctg cctgcagggg   4440
cgcctgatgc ggtattttct ccttacgcat ctgtgcggta tttcacaccg catacgtcaa   4500
agcaaccata gtacgcgccc tgtagcggcg cattaagcgc ggcgggtgtg gtggttacgc   4560
gcagcgtgac cgctacactt gccagcgccc tagcgcccgc tcctttcgct ttcttccctt   4620
cctttctcgc cacgttcgcc ggctttcccc gtcaagctct aaatcggggg ctccctttag   4680
ggttccgatt tagtgcttta cggcacctcg accccaaaaa acttgatttg ggtgatggtt   4740
cacgtagtgg gccatcgccc tgatagacgg tttttcgccc tttgacgttg gagtccacgt   4800
tctttaatag tggactcttg ttccaaactg gaacaacact caaccctatc tcgggctatt   4860
cttttgattt ataagggatt ttgccgattt cggcctattg gttaaaaaat gagctgattt   4920
aacaaaaatt taacgcgaat tttaacaaaa tattaacgtt tacaatttta tggtgcactc   4980
tcagtacaat ctgctctgat gccgcatagt taagccagcc ccgacacccg ccaacacccg   5040
ctgacgcgcc ctgacgggct tgtctgctcc cggcatccgc ttacagacaa gctgtgaccg   5100
tctccgggag ctgcatgtgt cagaggtttt caccgtcatc accgaaacgc gcgagacgaa   5160
agggcctcgt gatacgccta tttttatagg ttaatgtcat gaacaataaa actgtctgct   5220
tacataaaca gtaatacaag gggtgttatg agccatattc aacgggaaac gtcgaggccg   5280
cgattaaatt ccaacatgga tgctgattta tatgggtata aatgggctcg cgataatgtc   5340
gggcaatcag gtgcgacaat ctatcgcttg tatgggaagc ccgatgcgcc agagttgttt   5400
ctgaaacatg gcaaaggtag cgttgccaat gatgttacag atgagatggt cagactaaac   5460
tggctgacgg aatttatgcc tcttccgacc atcaagcatt ttatccgtac tcctgatgat   5520
gcatggttac tcaccactgc gatccccgga aaaacagcat tccaggtatt agaagaatat   5580
cctgattcag gtgaaaatat tgttgatgcg ctggcagtgt tcctgcgccg gttgcattcg   5640
attcctgttt gtaattgtcc ttttaacagc gatcgcgtat ttcgtctcgc tcaggcgcaa   5700
tcacgaatga ataacggttt ggttgatgcg agtgattttg atgacgagcg taatggctgg   5760
cctgttgaac aagtctggaa agaaatgcat aaacttttgc cattctcacc ggattcagtc   5820
gtcactcatg gtgatttctc acttgataac cttatttttg acgaggggaa attaataggt   5880
tgtattgatg ttggacgagt cggaatcgca gaccgatacc aggatcttgc catcctatgg   5940
aactgcctcg gtgagttttc tccttcatta cagaaacggc tttttcaaaa atatggtatt   6000
gataatcctg atatgaataa attgcagttt catttgatgc tcgatgagtt tttctaatct   6060
catgaccaaa atcccttaac gtgagttttc gttccactga gcgtcagacc ccgtagaaaa   6120
gatcaaagga tcttcttgag atcctttttt tctgcgcgta atctgctgct tgcaaacaaa   6180
aaaaccaccg ctaccagcgg tggtttgttt gccggatcaa gagctaccaa ctctttttcc   6240
gaaggtaact ggcttcagca gagcgcagat accaaatact gtccttctag tgtagccgta   6300
gttaggccac cacttcaaga actctgtagc accgcctaca tacctcgctc tgctaatcct   6360
gttaccagtg gctgctgcca gtggcgataa gtcgtgtctt accgggttgg actcaagacg   6420
atagttaccg gataaggcgc agcggtcggg ctgaacgggg ggttcgtgca cacagcccag   6480
```

-continued

```
cttggagcga acgacctaca ccgaactgag atacctacag cgtgagctat gagaaagcgc   6540

cacgcttccc gaagggagaa aggcggacag gtatccggta agcggcaggg tcggaacagg   6600

agagcgcacg agggagcttc cagggggaaa cgcctggtat ctttatagtc ctgtcgggtt   6660

tcgccacctc tgacttgagc gtcgattttt gtgatgctcg tcaggggggc ggagcctatg   6720

gaaaaacgcc agcaacgcgg cctttttacg gttcctggcc ttttgctggc cttttgctca   6780

catgt                                                               6785
```

<210> SEQ ID NO 13
<211> LENGTH: 6228
<212> TYPE: DNA
<213> ORGANISM: Artificial Sequence
<220> FEATURE:
<223> OTHER INFORMATION: Plasmid

<400> SEQUENCE: 13

```
gacggatcgg gagatctgag ggcctatttc ccatgattcc ttcatatttg catatacgat     60

acaaggctgt tagagagata attggaatta atttgactgt aaacacaaag atattagtac    120

aaaatacgtg acgtagaaag taataatttc ttgggtagtt tgcagtttta aaattatgtt    180

ttaaaatgga ctatcatatg cttaccgtaa cttgaaagta tttcgatttc ttggctttat    240

atatcttgtg gaaaggacga aacaccggag acgacggcac gtctcatttt ttacccgatc    300

ccctatggtg cactctcagt acaatctgct ctgatgccgc atagttaagc cagtatctgc    360

tccctgcttg tgtgttggag gtcgctgagt agtgcgcgag caaaatttaa gctacaacaa    420

ggcaaggctt gaccgacaat tgcatgaaga atctgcttag ggttaggcgt tttgcgctgc    480

ttcgcgatgt acgggccaga tatacgcgtt gacattgatt attgactagt tattaatagt    540

aatcaattac ggggtcatta gttcatagcc catatatgga gttccgcgtt acataactta    600

cggtaaatgg cccgcctggc tgaccgccca acgacccccg cccattgacg tcaataatga    660

cgtatgttcc catagtaacg ccaataggga ctttccattg acgtcaatgg gtggagtatt    720

tacggtaaac tgcccacttg gcagtacatc aagtgtatca tatgccaagt acgcccccta    780

ttgacgtcaa tgacggtaaa tggcccgcct ggcattatgc ccagtacatg accttatggg    840

actttcctac ttggcagtac atctacgtat tagtcatcgc tattaccatg gtgatgcggt    900

tttggcagta catcaatggg cgtggatagc ggtttgactc acggggattt ccaagtctcc    960

accccattga cgtcaatggg agtttgtttt ggcaccaaaa tcaacgggac tttccaaaat   1020

gtcgtaacaa ctccgcccca ttgacgcaaa tgggcggtag gcgtgtacgg tgggaggtct   1080

atataagcag agctctctgg ctaactagag aacccactgc ttactggctt atcgttaatt   1140

aaccggtgcc accatgatgt cccgccttga taaatcaaaa gtaataaaca gtgctcttga   1200

gcttctcaat gaagttggta tagaagggtt gacgactcgg aaattggcgc aaaaactcgg   1260

tgttgagcag ccaaccttgt attggcatgt taaaaacaaa cgagcactcc tcgacgcttt   1320

ggcgatagag atgctggaca ggcaccacac gcatttctgt cccctcgaag gagagtcatg   1380

gcaggatttc cttagaaata acgcaaagtc cttcagatgt gcgctgctta gtcaccgcga   1440

cggcgcaaaa gttcatctcg gcactaggcc aaccgagaaa cagtacgaga ctctggagaa   1500

ccaactggcg tttttgtgtc aacagggttt tagtctcgaa aatgcgctct atgctctctc   1560

tgcggttggc catttcaccc tcggatgcgt actggaagat caggagcacc aagtggccaa   1620

agaagaacgg gaaacgccga ctacggacag catgcctccg ttgctccggc aagctataga   1680

gctcttcgat caccaaggcg ctgagccagc tttcttgttc ggattggaac ttattatatg   1740
```

-continued

```
cgggctcgaa aagcagctta aatgcgagtc aggttaagcg gccgctcgag tctagagggc   1800
ccgtttaaac ccgctgatca gcctcgactg tgccttctag ttgccagcca tctgttgttt   1860
gcccctcccc cgtgccttcc ttgaccctgg aaggtgccac tcccactgtc ctttcctaat   1920
aaaatgagga aattgcatcg cattgtctga gtaggtgtca ttctattctg gggggtgggg   1980
tggggcagga cagcaagggg gaggattggg aagacaatag caggcatgct ggggatgcgg   2040
tgggctctat ggcttctgag gcggaaagaa ccagctgggg ctctaggggg tatccccacg   2100
cgccctgtag cggcgcatta agcgcggcgg gtgtggtggt tacgcgcagc gtgaccgcta   2160
cacttgccag cgccctagcg cccgctcctt tcgctttctt cccttccttt ctcgccacgt   2220
tcgccggctt tccccgtcaa gctctaaatc gggggctccc tttagggttc cgatttagtg   2280
ctttacggca cctcgacccc aaaaaacttg attagggtga tggttcacgt agtgggccat   2340
cgccctgata gacggttttt cgccctttga cgttggagtc cacgttcttt aatagtggac   2400
tcttgttcca aactggaaca acactcaacc ctatctcggt ctattctttt gatttataag   2460
ggattttgcc gatttcggcc tattggttaa aaaatgagct gatttaacaa aaatttaacg   2520
cgaattaatt ctgtggaatg tgtgtcagtt agggtgtgga aagtccccag gctccccagc   2580
aggcagaagt atgcaaagca tgcatctcaa ttagtcagca accaggtgtg gaaagtcccc   2640
aggctcccca gcaggcagaa gtatgcaaag catgcatctc aattagtcag caaccatagt   2700
cccgccccta actccgccca tcccgcccct aactccgccc agttccgccc attctccgcc   2760
ccatggctga ctaatttttt ttatttatgc agaggccgag gccgcctctg cctctgagct   2820
attccagaag tagtgaggag gcttttttgg aggcctaggc ttttgcaaaa agctcccggg   2880
agcttgtata tccattttcg gatctgatca agagacagga tgaggatcgt ttcgcatgat   2940
tgaacaagat ggattgcacg caggttctcc ggccgcttgg gtggagaggc tattcggcta   3000
tgactgggca caacagacaa tcggctgctc tgatgccgcc gtgttccggc tgtcagcgca   3060
ggggcgcccg gttctttttg tcaagaccga cctgtccggt gccctgaatg aactgcagga   3120
cgaggcagcg cggctatcgt ggctggccac gacgggcgtt ccttgcgcag ctgtgctcga   3180
cgttgtcact gaagcgggaa gggactggct gctattgggc gaagtgccgg ggcaggatct   3240
cctgtcatct caccttgctc ctgccgagaa agtatccatc atggctgatg caatgcggcg   3300
gctgcatacg cttgatccgg ctacctgccc attcgaccac caagcgaaac atcgcatcga   3360
gcgagcacgt actcggatgg aagccggtct tgtcgatcag gatgatctgg acgaagagca   3420
tcaggggctc gcgccagccg aactgttcgc caggctcaag gcgcgcatgc ccgacggcga   3480
ggatctcgtc gtgacccatg gcgatgcctg cttgccgaat atcatggtgg aaaatggccg   3540
cttttctgga ttcatcgact gtggccggct gggtgtggcg gaccgctatc aggacatagc   3600
gttggctacc cgtgatattg ctgaagagct tggcggcgaa tgggctgacc gcttcctcgt   3660
gctttacggt atcgccgctc ccgattcgca gcgcatcgcc ttctatcgcc ttcttgacga   3720
gttcttctga gcgggactct ggggttcgaa atgaccgacc aagcgacgcc caacctgcca   3780
tcacgagatt tcgattccac cgccgccttc tatgaaaggt tgggcttcgg aatcgttttc   3840
cgggacgccg gctggatgat cctccagcgc ggggatctca tgctggagtt cttcgcccac   3900
cccaacttgt ttattgcagc ttataatggt tacaaataaa gcaatagcat cacaaatttc   3960
acaaataaag catttttttc actgcattct agttgtggtt tgtccaaact catcaatgta   4020
tcttatcatg tctgtatacc gtcgacctct agctagagct tggcgtaatc atggtcatag   4080
```

-continued

```
ctgtttcctg tgtgaaattg ttatccgctc acaattccac acaacatacg agccggaagc   4140
ataaagtgta aagcctgggg tgcctaatga gtgagctaac tcacattaat tgcgttgcgc   4200
tcactgcccg ctttccagtc gggaaacctg tcgtgccagc tgcattaatg aatcggccaa   4260
cgcgcgggga gaggcggttt gcgtattggg cgctcttccg cttcctcgct cactgactcg   4320
ctgcgctcgg tcgttcggct gcggcgagcg gtatcagctc actcaaaggc ggtaatacgg   4380
ttatccacag aatcagggga taacgcagga aagaacatgt gagcaaaagg ccagcaaaag   4440
gccaggaacc gtaaaaaggc cgcgttgctg gcgtttttcc ataggctccg cccccctgac   4500
gagcatcaca aaaatcgacg ctcaagtcag aggtggcgaa acccgacagg actataaaga   4560
taccaggcgt ttccccctgg aagctccctc gtgcgctctc ctgttccgac cctgccgctt   4620
accggatacc tgtccgcctt tctcccttcg ggaagcgtgg cgctttctca tagctcacgc   4680
tgtaggtatc tcagttcggt gtaggtcgtt cgctccaagc tgggctgtgt gcacgaaccc   4740
cccgttcagc ccgaccgctg cgccttatcc ggtaactatc gtcttgagtc caacccggta   4800
agacacgact tatcgccact ggcagcagcc actggtaaca ggattagcag agcgaggtat   4860
gtaggcggtg ctacagagtt cttgaagtgg tggcctaact acggctacac tagaagaaca   4920
gtatttggta tctgcgctct gctgaagcca gttaccttcg gaaaaagagt tggtagctct   4980
tgatccggca aacaaaccac cgctggtagc ggtttttttg tttgcaagca gcagattacg   5040
cgcagaaaaa aaggatctca agaagatcct ttgatctttt ctacggggtc tgacgctcag   5100
tggaacgaaa actcacgtta agggattttg gtcatgagat tatcaaaaag gatcttcacc   5160
tagatccttt taaattaaaa atgaagtttt aaatcaatct aaagtatata tgagtaaact   5220
tggtctgaca gttaccaatg cttaatcagt gaggcaccta tctcagcgat ctgtctattt   5280
cgttcatcca tagttgcctg actccccgtc gtgtagataa ctacgatacg ggagggctta   5340
ccatctggcc ccagtgctgc aatgataccg cgagacccac gctcaccggc tccagattta   5400
tcagcaataa accagccagc cggaagggcc gagcgcagaa gtggtcctgc aactttatcc   5460
gcctccatcc agtctattaa ttgttgccgg gaagctagag taagtagttc gccagttaat   5520
agtttgcgca acgttgttgc cattgctaca ggcatcgtgg tgtcacgctc gtcgtttggt   5580
atggcttcat tcagctccgg ttcccaacga tcaaggcgag ttacatgatc ccccatgttg   5640
tgcaaaaaag cggttagctc cttcggtcct ccgatcgttg tcagaagtaa gttggccgca   5700
gtgttatcac tcatggttat ggcagcactg cataattctc ttactgtcat gccatccgta   5760
agatgctttt ctgtgactgg tgagtactca accaagtcat tctgagaata gtgtatgcgg   5820
cgaccgagtt gctcttgccc ggcgtcaata cgggataata ccgcgccaca tagcagaact   5880
ttaaaagtgc tcatcattgg aaaacgttct tcggggcgaa aactctcaag gatcttaccg   5940
ctgttgagat ccagttcgat gtaacccact cgtgcaccca actgatcttc agcatctttt   6000
actttcacca gcgtttctgg gtgagcaaaa acaggaaggc aaaatgccgc aaaaaaggga   6060
ataagggcga cacggaaatg ttgaatactc atactcttcc tttttcaata ttattgaagc   6120
atttatcagg gttattgtct catgagcgga tacatatttg aatgtattta gaaaaataaa   6180
caaatagggg ttccgcgcac atttccccga aaagtgccac ctgacgtc                6228
```

<210> SEQ ID NO 14
<211> LENGTH: 6254
<212> TYPE: DNA
<213> ORGANISM: Artificial Sequence
<220> FEATURE:
<223> OTHER INFORMATION: Plasmid -continued

<400> SEQUENCE: 14
gacggatcgg gagatctgag ggcctatttc ccatgattcc ttcatatttg catatacgat 60
acaaggctgt tagagagata attggaatta atttgactgt aaacacaaag atattagtac 120
aaaatacgtg acgtagaaag taataatttc ttgggtagtt tgcagtttta aaattatgtt 180
ttaaaatgga ctatcatatg cttaccgtaa cttgaaagta tttcgatttc ttggctttat 240
atatcttgtg gaaaggacga aacaccggaa ttacctccgt gggataccga agtatcccac 300
ggaggtaatt cctttttttac ccgatcccct atggtgcact ctcagtacaa tctgctctga 360
tgccgcatag ttaagccagt atctgctccc tgcttgtgtg ttggaggtcg ctgagtagtg 420
cgcgagcaaa atttaagcta caacaaggca aggcttgacc gacaattgca tgaagaatct 480
gcttagggtt aggcgttttg cgctgcttcg cgatgtacgg gccagatata cgcgttgaca 540
ttgattattg actagttatt aatagtaatc aattacgggg tcattagttc atagcccata 600
tatggagttc cgcgttacat aacttacggt aaatggcccg cctggctgac cgcccaacga 660
cccccgccca ttgacgtcaa taatgacgta tgttcccata gtaacgccaa tagggacttt 720
ccattgacgt caatgggtgg agtatttacg gtaaactgcc cacttggcag tacatcaagt 780
gtatcatatg ccaagtacgc cccctattga cgtcaatgac ggtaaatggc ccgcctggca 840
ttatgcccag tacatgacct tatgggactt tcctacttgg cagtacatct acgtattagt 900
catcgctatt accatggtga tgcggttttg gcagtacatc aatgggcgtg gatagcggtt 960
tgactcacgg ggatttccaa gtctccaccc cattgacgtc aatgggagtt tgttttggca 1020
ccaaaatcaa cgggactttc caaaatgtcg taacaactcc gccccattga cgcaaatggg 1080
cggtaggcgt gtacggtggg aggtctatat aagcagagct ctctggctaa ctagagaacc 1140
cactgcttac tggcttatcg ttaattaacc ggtgccacca tgatgtcccg ccttgataaa 1200
tcaaaagtaa taaacagtgc tcttgagctt ctcaatgaag ttggtataga agggttgacg 1260
actcggaaat tggcgcaaaa actcggtgtt gagcagccaa ccttgtattg gcatgttaaa 1320
aacaaacgag cactcctcga cgctttggcg atagagatgc tggacaggca ccacacgcat 1380
ttctgtcccc tcgaaggaga gtcatggcag gatttcctta gaaataacgc aaagtccttc 1440
agatgtgcgc tgcttagtca ccgcgacggc gcaaaagttc atctcggcac taggccaacc 1500
gagaaacagt acgagactct ggagaaccaa ctggcgtttt tgtgtcaaca gggttttagt 1560
ctcgaaaatg cgctctatgc tctctctgcg gttggccatt tcaccctcgg atgcgtactg 1620
gaagatcagg agcaccaagt ggccaaagaa gaacgggaaa cgccgactac ggacagcatg 1680
cctccgttgc tccggcaagc tatagagctc ttcgatcacc aaggcgctga gccagctttc 1740
ttgttcggat tggaacttat tatatgcggg ctcgaaaagc agcttaaatg cgagtcaggt 1800
taagcggccg ctcgagtcta gagggcccgt ttaaacccgc tgatcagcct cgactgtgcc 1860
ttctagttgc cagccatctg ttgtttgccc ctcccccgtg ccttccttga ccctggaagg 1920
tgccactccc actgtccttt cctaataaaa tgaggaaatt gcatcgcatt gtctgagtag 1980
gtgtcattct attctggggg gtggggtggg gcaggacagc aagggggagg attgggaaga 2040
caatagcagg catgctgggg atgcggtggg ctctatggct tctgaggcgg aaagaaccag 2100
ctggggctct agggggtatc cccacgcgcc ctgtagcggc gcattaagcg cggcgggtgt 2160
ggtggttacg cgcagcgtga ccgctacact tgccagcgcc ctagcgcccg ctcctttcgc 2220
tttcttccct tcctttctcg ccacgttcgc cggctttccc cgtcaagctc taaatcgggg 2280

-continued

```
gctcccttta gggttccgat ttagtgcttt acggcacctc gaccccaaaa aacttgatta   2340
gggtgatggt tcacgtagtg ggccatcgcc ctgatagacg gtttttcgcc ctttgacgtt   2400
ggagtccacg ttctttaata gtggactctt gttccaaact ggaacaacac tcaaccctat   2460
ctcggtctat tcttttgatt tataagggat tttgccgatt tcggcctatt ggttaaaaaa   2520
tgagctgatt taacaaaaat ttaacgcgaa ttaattctgt ggaatgtgtg tcagttaggg   2580
tgtggaaagt ccccaggctc cccagcaggc agaagtatgc aaagcatgca tctcaattag   2640
tcagcaacca ggtgtggaaa gtccccaggc tccccagcag gcagaagtat gcaaagcatg   2700
catctcaatt agtcagcaac catagtcccg cccctaactc cgcccatccc gcccctaact   2760
ccgcccagtt ccgcccattc tccgccccat ggctgactaa ttttttttat ttatgcagag   2820
gccgaggccg cctctgcctc tgagctattc cagaagtagt gaggaggctt ttttggaggc   2880
ctaggctttt gcaaaaagct cccgggagct tgtatatcca ttttcggatc tgatcaagag   2940
acaggatgag gatcgtttcg catgattgaa caagatggat tgcacgcagg ttctccggcc   3000
gcttgggtgg agaggctatt cggctatgac tgggcacaac agacaatcgg ctgctctgat   3060
gccgccgtgt tccggctgtc agcgcagggg cgcccggttc tttttgtcaa gaccgacctg   3120
tccggtgccc tgaatgaact gcaggacgag gcagcgcggc tatcgtggct ggccacgacg   3180
ggcgttcctt gcgcagctgt gctcgacgtt gtcactgaag cgggaaggga ctggctgcta   3240
ttgggcgaag tgccggggca ggatctcctg tcatctcacc ttgctcctgc cgagaaagta   3300
tccatcatgg ctgatgcaat gcggcggctg catacgcttg atccggctac ctgcccattc   3360
gaccaccaag cgaaacatcg catcgagcga gcacgtactc ggatggaagc cggtcttgtc   3420
gatcaggatg atctggacga agagcatcag gggctcgcgc cagccgaact gttcgccagg   3480
ctcaaggcgc gcatgcccga cggcgaggat ctcgtcgtga cccatggcga tgcctgcttg   3540
ccgaatatca tggtggaaaa tggccgcttt tctggattca tcgactgtgg ccggctgggt   3600
gtggcggacc gctatcagga catagcgttg gctacccgtg atattgctga agagcttggc   3660
ggcgaatggg ctgaccgctt cctcgtgctt tacggtatcg ccgctcccga ttcgcagcgc   3720
atcgccttct atcgccttct tgacgagttc ttctgagcgg gactctgggg ttcgaaatga   3780
ccgaccaagc gacgcccaac ctgccatcac gagatttcga ttccaccgcc gccttctatg   3840
aaaggttggg cttcggaatc gttttccggg acgccggctg gatgatcctc cagcgcgggg   3900
atctcatgct ggagttcttc gcccacccca acttgtttat tgcagcttat aatggttaca   3960
aataaagcaa tagcatcaca aatttcacaa ataaagcatt tttttcactg cattctagtt   4020
gtggtttgtc caaactcatc aatgtatctt atcatgtctg tataccgtcg acctctagct   4080
agagcttggc gtaatcatgg tcatagctgt ttcctgtgtg aaattgttat ccgctcacaa   4140
ttccacacaa catacgagcc ggaagcataa agtgtaaagc ctggggtgcc taatgagtga   4200
gctaactcac attaattgcg ttgcgctcac tgcccgcttt ccagtcggga aacctgtcgt   4260
gccagctgca ttaatgaatc ggccaacgcg cggggagagg cggtttgcgt attgggcgct   4320
cttccgcttc ctcgctcact gactcgctgc gctcggtcgt tcggctgcgg cgagcggtat   4380
cagctcactc aaaggcggta atacggttat ccacagaatc aggggataac gcaggaaaga   4440
acatgtgagc aaaaggccag caaaaggcca ggaaccgtaa aaaggccgcg ttgctggcgt   4500
ttttccatag gctccgcccc cctgacgagc atcacaaaaa tcgacgctca agtcagaggt   4560
ggcgaaaccc gacaggacta taaagatacc aggcgtttcc ccctggaagc tccctcgtgc   4620
gctctcctgt tccgaccctg ccgcttaccg gatacctgtc cgcctttctc ccttcgggaa   4680
```

```
gcgtggcgct ttctcatagc tcacgctgta ggtatctcag ttcggtgtag gtcgttcgct   4740
ccaagctggg ctgtgtgcac gaaccccccg ttcagcccga ccgctgcgcc ttatccggta   4800
actatcgtct tgagtccaac ccggtaagac acgacttatc gccactggca gcagccactg   4860
gtaacaggat tagcagagcg aggtatgtag gcggtgctac agagttcttg aagtggtggc   4920
ctaactacgg ctacactaga agaacagtat ttggtatctg cgctctgctg aagccagtta   4980
ccttcggaaa aagagttggt agctcttgat ccggcaaaca aaccaccgct ggtagcggtt   5040
tttttgtttg caagcagcag attacgcgca gaaaaaaagg atctcaagaa gatcctttga   5100
tcttttctac ggggtctgac gctcagtgga acgaaaactc acgttaaggg attttggtca   5160
tgagattatc aaaaaggatc ttcacctaga tccttttaaa ttaaaaatga agttttaaat   5220
caatctaaag tatatatgag taaacttggt ctgacagtta ccaatgctta atcagtgagg   5280
cacctatctc agcgatctgt ctatttcgtt catccatagt tgcctgactc cccgtcgtgt   5340
agataactac gatacgggag ggcttaccat ctggccccag tgctgcaatg ataccgcgag   5400
acccacgctc accggctcca gatttatcag caataaacca gccagccgga agggccgagc   5460
gcagaagtgg tcctgcaact ttatccgcct ccatccagtc tattaattgt tgccgggaag   5520
ctagagtaag tagttcgcca gttaatagtt tgcgcaacgt tgttgccatt gctacaggca   5580
tcgtggtgtc acgctcgtcg tttggtatgg cttcattcag ctccggttcc caacgatcaa   5640
ggcgagttac atgatccccc atgttgtgca aaaaagcggt tagctccttc ggtcctccga   5700
tcgttgtcag aagtaagttg gccgcagtgt tatcactcat ggttatggca gcactgcata   5760
attctcttac tgtcatgcca tccgtaagat gcttttctgt gactggtgag tactcaacca   5820
agtcattctg agaatagtgt atgcggcgac cgagttgctc ttgcccggcg tcaatacggg   5880
ataataccgc gccacatagc agaactttaa aagtgctcat cattggaaaa cgttcttcgg   5940
ggcgaaaact ctcaaggatc ttaccgctgt tgagatccag ttcgatgtaa cccactcgtg   6000
cacccaactg atcttcagca tcttttactt tcaccagcgt ttctgggtga gcaaaaacag   6060
gaaggcaaaa tgccgcaaaa aagggaataa gggcgacacg gaaatgttga atactcatac   6120
tcttcctttt tcaatattat tgaagcattt atcagggtta ttgtctcatg agcggataca   6180
tatttgaatg tatttagaaa aataaacaaa taggggttcc gcgcacattt ccccgaaaag   6240
tgccacctga cgtc                                                    6254
```

<210> SEQ ID NO 15
<211> LENGTH: 6254
<212> TYPE: DNA
<213> ORGANISM: Artificial Sequence
<220> FEATURE:
<223> OTHER INFORMATION: Plasmid

<400> SEQUENCE: 15

```
gacggatcgg gagatctgag ggcctatttc ccatgattcc ttcatatttg catatacgat     60
acaaggctgt tagagagata attggaatta atttgactgt aaacacaaag atattagtac    120
aaaatacgtg acgtagaaag taataatttc ttgggtagtt tgcagtttta aaattatgtt    180
ttaaaatgga ctatcatatg cttaccgtaa cttgaaagta tttcgatttc ttggctttat    240
atatcttgtg gaaaggacga aacaccggat atccaggagg aacttaccga agtaagttcc    300
tcctggatat ccttttttac ccgatcccct atggtgcact ctcagtacaa tctgctctga    360
tgccgcatag ttaagccagt atctgctccc tgcttgtgtg ttggaggtcg ctgagtagtg    420
```

-continued

```
cgcgagcaaa atttaagcta caacaaggca aggcttgacc gacaattgca tgaagaatct    480
gcttagggtt aggcgttttg cgctgcttcg cgatgtacgg gccagatata cgcgttgaca    540
ttgattattg actagttatt aatagtaatc aattacgggg tcattagttc atagcccata    600
tatggagttc cgcgttacat aacttacggt aaatggcccg cctggctgac cgcccaacga    660
cccccgccca ttgacgtcaa taatgacgta tgttcccata gtaacgccaa tagggacttt    720
ccattgacgt caatgggtgg agtatttacg gtaaactgcc cacttggcag tacatcaagt    780
gtatcatatg ccaagtacgc cccctattga cgtcaatgac ggtaaatggc ccgcctggca    840
ttatgcccag tacatgacct tatgggactt tcctacttgg cagtacatct acgtattagt    900
catcgctatt accatggtga tgcggttttg gcagtacatc aatgggcgtg gatagcggtt    960
tgactcacgg ggatttccaa gtctccaccc cattgacgtc aatgggagtt tgttttggca   1020
ccaaaatcaa cgggactttc caaaatgtcg taacaactcc gccccattga cgcaaatggg   1080
cggtaggcgt gtacggtggg aggtctatat aagcagagct ctctggctaa ctagagaacc   1140
cactgcttac tggcttatcg ttaattaacc ggtgccacca tgatgtcccg ccttgataaa   1200
tcaaaagtaa taaacagtgc tcttgagctt ctcaatgaag ttggtataga agggttgacg   1260
actcggaaat tggcgcaaaa actcggtgtt gagcagccaa ccttgtattg gcatgttaaa   1320
aacaaacgag cactcctcga cgctttggcg atagagatgc tggacaggca ccacacgcat   1380
ttctgtcccc tcgaaggaga gtcatggcag gatttcctta gaaataacgc aaagtccttc   1440
agatgtgcgc tgcttagtca ccgcgacggc gcaaaagttc atctcggcac taggccaacc   1500
gagaaacagt acgagactct ggagaaccaa ctggcgtttt tgtgtcaaca gggttttagt   1560
ctcgaaaatg cgctctatgc tctctctgcg gttggccatt tcaccctcgg atgcgtactg   1620
gaagatcagg agcaccaagt ggccaaagaa gaacgggaaa cgccgactac ggacagcatg   1680
cctccgttgc tccggcaagc tatagagctc ttcgatcacc aaggcgctga gccagctttc   1740
ttgttcggat tggaacttat tatatgcggg ctcgaaaagc agcttaaatg cgagtcaggt   1800
taagcggccg ctcgagtcta gagggcccgt ttaaacccgc tgatcagcct cgactgtgcc   1860
ttctagttgc cagccatctg ttgtttgccc ctcccccgtg ccttccttga ccctggaagg   1920
tgccactccc actgtccttt cctaataaaa tgaggaaatt gcatcgcatt gtctgagtag   1980
gtgtcattct attctggggg gtggggtggg gcaggacagc aagggggagg attgggaaga   2040
caatagcagg catgctgggg atgcggtggg ctctatggct tctgaggcgg aaagaaccag   2100
ctggggctct agggggtatc cccacgcgcc ctgtagcggc gcattaagcg cggcgggtgt   2160
ggtggttacg cgcagcgtga ccgctacact tgccagcgcc ctagcgcccg ctcctttcgc   2220
tttcttccct tcctttctcg ccacgttcgc cggctttccc cgtcaagctc taaatcgggg   2280
gctcccttta gggttccgat ttagtgcttt acggcacctc gaccccaaaa aacttgatta   2340
gggtgatggt tcacgtagtg ggccatcgcc ctgatagacg gtttttcgcc ctttgacgtt   2400
ggagtccacg ttctttaata gtggactctt gttccaaact ggaacaacac tcaaccctat   2460
ctcggtctat tcttttgatt tataagggat tttgccgatt tcggcctatt ggttaaaaaa   2520
tgagctgatt taacaaaaat ttaacgcgaa ttaattctgt ggaatgtgtg tcagttaggg   2580
tgtggaaagt ccccaggctc cccagcaggc agaagtatgc aaagcatgca tctcaattag   2640
tcagcaacca ggtgtggaaa gtccccaggc tccccagcag gcagaagtat gcaaagcatg   2700
catctcaatt agtcagcaac catagtcccg cccctaactc cgcccatccc gcccctaact   2760
ccgcccagtt ccgcccattc tccgccccat ggctgactaa ttttttttat ttatgcagag   2820
```

gccgaggccg cctctgcctc tgagctattc cagaagtagt gaggaggctt ttttggaggc 2880
ctaggctttt gcaaaaagct cccgggagct tgtatatcca ttttcggatc tgatcaagag 2940
acaggatgag gatcgtttcg catgattgaa caagatggat tgcacgcagg ttctccggcc 3000
gcttgggtgg agaggctatt cggctatgac tgggcacaac agacaatcgg ctgctctgat 3060
gccgccgtgt tccggctgtc agcgcagggg cgcccggttc tttttgtcaa gaccgacctg 3120
tccggtgccc tgaatgaact gcaggacgag gcagcgcggc tatcgtggct ggccacgacg 3180
ggcgttcctt gcgcagctgt gctcgacgtt gtcactgaag cgggaaggga ctggctgcta 3240
ttgggcgaag tgccggggca ggatctcctg tcatctcacc ttgctcctgc cgagaaagta 3300
tccatcatgg ctgatgcaat gcggcggctg catacgcttg atccggctac ctgcccattc 3360
gaccaccaag cgaaacatcg catcgagcga gcacgtactc ggatggaagc cggtcttgtc 3420
gatcaggatg atctggacga agagcatcag gggctcgcgc cagccgaact gttcgccagg 3480
ctcaaggcgc gcatgcccga cggcgaggat ctcgtcgtga cccatggcga tgcctgcttg 3540
ccgaatatca tggtggaaaa tggccgcttt tctggattca tcgactgtgg ccggctgggt 3600
gtggcggacc gctatcagga catagcgttg gctacccgtg atattgctga agagcttggc 3660
ggcgaatggg ctgaccgctt cctcgtgctt tacggtatcg ccgctcccga ttcgcagcgc 3720
atcgccttct atcgccttct tgacgagttc ttctgagcgg gactctgggg ttcgaaatga 3780
ccgaccaagc gacgcccaac ctgccatcac gagatttcga ttccaccgcc gccttctatg 3840
aaaggttggg cttcggaatc gttttccggg acgccggctg gatgatcctc cagcgcgggg 3900
atctcatgct ggagttcttc gcccacccca acttgtttat tgcagcttat aatggttaca 3960
aataaagcaa tagcatcaca aatttcacaa ataaagcatt tttttcactg cattctagtt 4020
gtggtttgtc caaactcatc aatgtatctt atcatgtctg tataccgtcg acctctagct 4080
agagcttggc gtaatcatgg tcatagctgt ttcctgtgtg aaattgttat ccgctcacaa 4140
ttccacacaa catacgagcc ggaagcataa agtgtaaagc ctggggtgcc taatgagtga 4200
gctaactcac attaattgcg ttgcgctcac tgcccgcttt ccagtcggga aacctgtcgt 4260
gccagctgca ttaatgaatc ggccaacgcg cggggagagg cggtttgcgt attgggcgct 4320
cttccgcttc ctcgctcact gactcgctgc gctcggtcgt tcggctgcgg cgagcggtat 4380
cagctcactc aaaggcggta atacggttat ccacagaatc aggggataac gcaggaaaga 4440
acatgtgagc aaaaggccag caaaaggcca ggaaccgtaa aaaggccgcg ttgctggcgt 4500
ttttccatag gctccgcccc cctgacgagc atcacaaaaa tcgacgctca agtcagaggt 4560
ggcgaaaccc gacaggacta taaagatacc aggcgtttcc ccctggaagc tccctcgtgc 4620
gctctcctgt tccgaccctg ccgcttaccg gatacctgtc cgcctttctc ccttcgggaa 4680
gcgtggcgct ttctcatagc tcacgctgta ggtatctcag ttcggtgtag gtcgttcgct 4740
ccaagctggg ctgtgtgcac gaaccccccg ttcagcccga ccgctgcgcc ttatccggta 4800
actatcgtct tgagtccaac ccggtaagac acgacttatc gccactggca gcagccactg 4860
gtaacaggat tagcagagcg aggtatgtag gcggtgctac agagttcttg aagtggtggc 4920
ctaactacgg ctacactaga agaacagtat ttggtatctg cgctctgctg aagccagtta 4980
ccttcggaaa aagagttggt agctcttgat ccggcaaaca aaccaccgct ggtagcggtt 5040
tttttgtttg caagcagcag attacgcgca gaaaaaaagg atctcaagaa gatcctttga 5100
tcttttctac ggggtctgac gctcagtgga acgaaaactc acgttaaggg attttggtca 5160

```
tgagattatc aaaaaggatc ttcacctaga tccttttaaa ttaaaaatga agttttaaat   5220
caatctaaag tatatatgag taaacttggt ctgacagtta ccaatgctta atcagtgagg   5280
cacctatctc agcgatctgt ctatttcgtt catccatagt tgcctgactc cccgtcgtgt   5340
agataactac gatacgggag ggcttaccat ctggccccag tgctgcaatg ataccgcgag   5400
acccacgctc accggctcca gatttatcag caataaacca gccagccgga agggccgagc   5460
gcagaagtgg tcctgcaact ttatccgcct ccatccagtc tattaattgt tgccgggaag   5520
ctagagtaag tagttcgcca gttaatagtt tgcgcaacgt tgttgccatt gctacaggca   5580
tcgtggtgtc acgctcgtcg tttggtatgg cttcattcag ctccggttcc caacgatcaa   5640
ggcgagttac atgatccccc atgttgtgca aaaaagcggt tagctccttc ggtcctccga   5700
tcgttgtcag aagtaagttg gccgcagtgt tatcactcat ggttatggca gcactgcata   5760
attctcttac tgtcatgcca tccgtaagat gcttttctgt gactggtgag tactcaacca   5820
agtcattctg agaatagtgt atgcggcgac cgagttgctc ttgcccggcg tcaatacggg   5880
ataataccgc gccacatagc agaactttaa aagtgctcat cattggaaaa cgttcttcgg   5940
ggcgaaaact ctcaaggatc ttaccgctgt tgagatccag ttcgatgtaa cccactcgtg   6000
cacccaactg atcttcagca tcttttactt tcaccagcgt ttctgggtga gcaaaaacag   6060
gaaggcaaaa tgccgcaaaa aagggaataa gggcgacacg gaaatgttga atactcatac   6120
tcttcctttt tcaatattat tgaagcattt atcagggtta ttgtctcatg agcggataca   6180
tatttgaatg tatttagaaa aataaacaaa taggggttcc gcgcacattt ccccgaaaag   6240
tgccacctga cgtc                                                      6254
```

<210> SEQ ID NO 16
<211> LENGTH: 6254
<212> TYPE: DNA
<213> ORGANISM: Artificial Sequence
<220> FEATURE:
<223> OTHER INFORMATION: Plasmid

<400> SEQUENCE: 16

```
gacggatcgg gagatctgag ggcctatttc ccatgattcc ttcatatttg catatacgat     60
acaaggctgt tagagagata attggaatta atttgactgt aaacacaaag atattagtac    120
aaaatacgtg acgtagaaag taataatttc ttgggtagtt tgcagtttta aaattatgtt    180
ttaaaatgga ctatcatatg cttaccgtaa cttgaaagta tttcgatttc ttggctttat    240
atatcttgtg gaaaggacga aacaccggag cttcatccag tcgatcacga atgatcgact    300
ggatgaagct cctttttttac ccgatcccct atggtgcact ctcagtacaa tctgctctga    360
tgccgcatag ttaagccagt atctgctccc tgcttgtgtg ttggaggtcg ctgagtagtg    420
cgcgagcaaa atttaagcta caacaaggca aggcttgacc gacaattgca tgaagaatct    480
gcttagggtt aggcgttttg cgctgcttcg cgatgtacgg gccagatata cgcgttgaca    540
ttgattattg actagttatt aatagtaatc aattacgggg tcattagttc atagcccata    600
tatggagttc cgcgttacat aacttacggt aaatggcccg cctggctgac cgcccaacga    660
cccccgccca ttgacgtcaa taatgacgta tgttcccata gtaacgccaa tagggacttt    720
ccattgacgt caatgggtgg agtatttacg gtaaactgcc cacttggcag tacatcaagt    780
gtatcatatg ccaagtacgc cccctattga cgtcaatgac ggtaaatggc ccgcctggca    840
ttatgcccag tacatgacct tatgggactt tcctacttgg cagtacatct acgtattagt    900
catcgctatt accatggtga tgcggttttg gcagtacatc aatgggcgtg gatagcggtt    960
```

```
tgactcacgg ggatttccaa gtctccaccc cattgacgtc aatgggagtt tgttttggca   1020
ccaaaatcaa cgggactttc caaaatgtcg taacaactcc gccccattga cgcaaatggg   1080
cggtaggcgt gtacggtggg aggtctatat aagcagagct ctctggctaa ctagagaacc   1140
cactgcttac tggcttatcg ttaattaacc ggtgccacca tgatgtcccg ccttgataaa   1200
tcaaaagtaa taaacagtgc tcttgagctt ctcaatgaag ttggtataga agggttgacg   1260
actcggaaat tggcgcaaaa actcggtgtt gagcagccaa ccttgtattg gcatgttaaa   1320
aacaaacgag cactcctcga cgctttggcg atagagatgc tggacaggca ccacacgcat   1380
ttctgtcccc tcgaaggaga gtcatggcag gatttcctta gaaataacgc aaagtccttc   1440
agatgtgcgc tgcttagtca ccgcgacggc gcaaaagttc atctcggcac taggccaacc   1500
gagaaacagt acgagactct ggagaaccaa ctggcgtttt tgtgtcaaca gggttttagt   1560
ctcgaaaatg cgctctatgc tctctctgcg gttggccatt tcaccctcgg atgcgtactg   1620
gaagatcagg agcaccaagt ggccaaagaa gaacgggaaa cgccgactac ggacagcatg   1680
cctccgttgc tccggcaagc tatagagctc ttcgatcacc aaggcgctga gccagctttc   1740
ttgttcggat tggaacttat tatatgcggg ctcgaaaagc agcttaaatg cgagtcaggt   1800
taagcggccg ctcgagtcta gagggcccgt ttaaacccgc tgatcagcct cgactgtgcc   1860
ttctagttgc cagccatctg ttgtttgccc ctcccccgtg ccttccttga ccctggaagg   1920
tgccactccc actgtccttt cctaataaaa tgaggaaatt gcatcgcatt gtctgagtag   1980
gtgtcattct attctggggg gtggggtggg gcaggacagc aagggggagg attgggaaga   2040
caatagcagg catgctgggg atgcggtggg ctctatggct tctgaggcgg aaagaaccag   2100
ctggggctct agggggtatc cccacgcgcc ctgtagcggc gcattaagcg cggcgggtgt   2160
ggtggttacg cgcagcgtga ccgctacact tgccagcgcc ctagcgcccg ctcctttcgc   2220
tttcttccct tcctttctcg ccacgttcgc cggctttccc cgtcaagctc taaatcgggg   2280
gctcccttta gggttccgat ttagtgcttt acggcacctc gaccccaaaa aacttgatta   2340
gggtgatggt tcacgtagtg ggccatcgcc ctgatagacg gtttttcgcc ctttgacgtt   2400
ggagtccacg ttctttaata gtggactctt gttccaaact ggaacaacac tcaaccctat   2460
ctcggtctat tcttttgatt tataagggat tttgccgatt tcggcctatt ggttaaaaaa   2520
tgagctgatt taacaaaaat ttaacgcgaa ttaattctgt ggaatgtgtg tcagttaggg   2580
tgtggaaagt ccccaggctc cccagcaggc agaagtatgc aaagcatgca tctcaattag   2640
tcagcaacca ggtgtggaaa gtccccaggc tccccagcag gcagaagtat gcaaagcatg   2700
catctcaatt agtcagcaac catagtcccg cccctaactc cgcccatccc gcccctaact   2760
ccgcccagtt ccgcccattc tccgccccat ggctgactaa ttttttttat ttatgcagag   2820
gccgaggccg cctctgcctc tgagctattc cagaagtagt gaggaggctt ttttggaggc   2880
ctaggctttt gcaaaaagct cccgggagct tgtatatcca ttttcggatc tgatcaagag   2940
acaggatgag gatcgtttcg catgattgaa caagatggat tgcacgcagg ttctccggcc   3000
gcttgggtgg agaggctatt cggctatgac tgggcacaac agacaatcgg ctgctctgat   3060
gccgccgtgt tccggctgtc agcgcagggg cgcccggttc tttttgtcaa gaccgacctg   3120
tccggtgccc tgaatgaact gcaggacgag gcagcgcggc tatcgtggct ggccacgacg   3180
ggcgttcctt gcgcagctgt gctcgacgtt gtcactgaag cgggaaggga ctggctgcta   3240
ttgggcgaag tgccggggca ggatctcctg tcatctcacc ttgctcctgc cgagaaagta   3300
```

-continued

```
tccatcatgg ctgatgcaat gcggcggctg catacgcttg atccggctac ctgcccattc   3360
gaccaccaag cgaaacatcg catcgagcga gcacgtactc ggatggaagc cggtcttgtc   3420
gatcaggatg atctggacga agagcatcag gggctcgcgc cagccgaact gttcgccagg   3480
ctcaaggcgc gcatgcccga cggcgaggat ctcgtcgtga cccatggcga tgcctgcttg   3540
ccgaatatca tggtggaaaa tggccgcttt tctggattca tcgactgtgg ccggctgggt   3600
gtggcggacc gctatcagga catagcgttg gctacccgtg atattgctga agagcttggc   3660
ggcgaatggg ctgaccgctt cctcgtgctt tacggtatcg ccgctcccga ttcgcagcgc   3720
atcgccttct atcgccttct tgacgagttc ttctgagcgg gactctgggg ttcgaaatga   3780
ccgaccaagc gacgcccaac ctgccatcac gagatttcga ttccaccgcc gccttctatg   3840
aaaggttggg cttcggaatc gttttccggg acgccggctg gatgatcctc cagcgcgggg   3900
atctcatgct ggagttcttc gcccacccca acttgtttat tgcagcttat aatggttaca   3960
aataaagcaa tagcatcaca aatttcacaa ataaagcatt tttttcactg cattctagtt   4020
gtggtttgtc caaactcatc aatgtatctt atcatgtctg tataccgtcg acctctagct   4080
agagcttggc gtaatcatgg tcatagctgt ttcctgtgtg aaattgttat ccgctcacaa   4140
ttccacacaa catacgagcc ggaagcataa agtgtaaagc ctggggtgcc taatgagtga   4200
gctaactcac attaattgcg ttgcgctcac tgcccgcttt ccagtcggga aacctgtcgt   4260
gccagctgca ttaatgaatc ggccaacgcg cggggagagg cggtttgcgt attgggcgct   4320
cttccgcttc ctcgctcact gactcgctgc gctcggtcgt tcggctgcgg cgagcggtat   4380
cagctcactc aaaggcggta atacggttat ccacagaatc aggggataac gcaggaaaga   4440
acatgtgagc aaaaggccag caaaaggcca ggaaccgtaa aaaggccgcg ttgctggcgt   4500
ttttccatag gctccgcccc cctgacgagc atcacaaaaa tcgacgctca agtcagaggt   4560
ggcgaaaccc gacaggacta taaagatacc aggcgtttcc ccctggaagc tccctcgtgc   4620
gctctcctgt tccgaccctg ccgcttaccg gatacctgtc cgcctttctc ccttcgggaa   4680
gcgtggcgct ttctcatagc tcacgctgta ggtatctcag ttcggtgtag gtcgttcgct   4740
ccaagctggg ctgtgtgcac gaaccccccg ttcagcccga ccgctgcgcc ttatccggta   4800
actatcgtct tgagtccaac ccggtaagac acgacttatc gccactggca gcagccactg   4860
gtaacaggat tagcagagcg aggtatgtag gcggtgctac agagttcttg aagtggtggc   4920
ctaactacgg ctacactaga agaacagtat ttggtatctg cgctctgctg aagccagtta   4980
ccttcggaaa aagagttggt agctcttgat ccggcaaaca aaccaccgct ggtagcggtt   5040
tttttgtttg caagcagcag attacgcgca gaaaaaaagg atctcaagaa gatcctttga   5100
tcttttctac ggggtctgac gctcagtgga acgaaaactc acgttaaggg attttggtca   5160
tgagattatc aaaaaggatc ttcacctaga tccttttaaa ttaaaaatga agttttaaat   5220
caatctaaag tatatatgag taaacttggt ctgacagtta ccaatgctta atcagtgagg   5280
cacctatctc agcgatctgt ctatttcgtt catccatagt tgcctgactc cccgtcgtgt   5340
agataactac gatacgggag ggcttaccat ctggccccag tgctgcaatg ataccgcgag   5400
acccacgctc accggctcca gatttatcag caataaacca gccagccgga agggccgagc   5460
gcagaagtgg tcctgcaact ttatccgcct ccatccagtc tattaattgt tgccgggaag   5520
ctagagtaag tagttcgcca gttaatagtt tgcgcaacgt tgttgccatt gctacaggca   5580
tcgtggtgtc acgctcgtcg tttggtatgg cttcattcag ctccggttcc caacgatcaa   5640
ggcgagttac atgatccccc atgttgtgca aaaaagcggt tagctccttc ggtcctccga   5700
```

tcgttgtcag aagtaagttg gccgcagtgt tatcactcat ggttatggca gcactgcata 5760
attctcttac tgtcatgcca tccgtaagat gcttttctgt gactggtgag tactcaacca 5820
agtcattctg agaatagtgt atgcggcgac cgagttgctc ttgcccggcg tcaatacggg 5880
ataataccgc gccacatagc agaactttaa aagtgctcat cattggaaaa cgttcttcgg 5940
ggcgaaaact ctcaaggatc ttaccgctgt tgagatccag ttcgatgtaa cccactcgtg 6000
cacccaactg atcttcagca tcttttactt tcaccagcgt ttctgggtga gcaaaaacag 6060
gaaggcaaaa tgccgcaaaa aagggaataa gggcgacacg gaaatgttga atactcatac 6120
tcttcctttt tcaatattat tgaagcattt atcagggtta ttgtctcatg agcggataca 6180
tatttgaatg tatttagaaa aataaacaaa taggggttcc gcgcacattt ccccgaaaag 6240
tgccacctga cgtc 6254

<210> SEQ ID NO 17
<211> LENGTH: 6904
<212> TYPE: DNA
<213> ORGANISM: Artificial Sequence
<220> FEATURE:
<223> OTHER INFORMATION: Plasmid

<400> SEQUENCE: 17
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgctccg gtgcccgtca gtgggcagag cgcacatcgc 180
ccacagtccc cgagaagttg gggggagggg tcggcaattg aaccggtgcc tagagaaggt 240
ggcgcggggt aaactgggaa agtgatgtcg tgtactggct ccgccttttt cccgagggtg 300
ggggagaacc gtatataagt gcagtagtcg ccgtgaacgt tctttttcgc aacgctagct 360
aactaccggt gccaccatgg ccccaaagaa gaagcggaag gtcggtagta ctgtgggtac 420
tcgaagtggc tgcgtaccac acccgtcgca tggatccaag cggaactata tcctgggact 480
ggacatcgga attacctccg tgggatacgg catcatcgat tacgagacta gggacgtgat 540
tgacgccggc gtgagactct ttaaggaggc caacgtggaa aacaacgaag gtcgcagatc 600
caagcggggt gcaagacgcc tgaagcgccg gaggagacat cggatacagc gcgtgaagaa 660
gctccttttc gactacaacc tcctcactga ccactcggaa ttgtccggta tcaaccccta 720
cgaagcccgc gtgaaaggcc tgagccagaa gctgtccgaa gaggagttta gcgcagccct 780
gctgcacctg gctaagcgaa ggggggtgca caacgtgaac gaggtggagg aggacactgg 840
caacgaactg tccaccaagg agcagatttc acggaactcg aaggcgctgg aagagaaata 900
tgtggccgag ctgcagctgg agaggctcaa gaaggatggc gaagtccggg ggagcatcaa 960
tcgcttcaag acctcggact acgtgaagga agccaaacag ctgttgaagg tgcagaaggc 1020
ctaccaccaa ctggaccaat cattcattga cacttacatc gatctgcttg aaaccaggcg 1080
cacctactac gagggtcctg gagaaggcag ccctttcgga tggaaggaca tcaaggagtg 1140
gtatgagatg ctgatgggtc attgcaccta ctttccggaa gaactgcgct cagtgaagta 1200
cgcgtacaac gctgacctct acaacgctct caacgatctg aacaacctcg tgatcacccg 1260
ggacgagaac gaaaagctgg agtactacga aaagttccag attatcgaaa acgtgttcaa 1320
gcagaagaag aagcccaccc tgaagcagat tgcaaaggag atccttgtga acgaggagga 1380
tattaagggc taccgggtca cctccaccgg gaaaccagag ttcactaatc tcaaggtgta 1440

-continued

```
ccatgacatt aaggacatta ctgcccgcaa ggagatcatt gaaaacgcgg aactgctgga   1500
ccaaatcgcg aagatcctga ccatctatca gagctccgag gatatccagg aggaacttac   1560
taacctcaat tccgagctga cgcaggaaga aatcgagcaa attagcaacc tgaagggtta   1620
cactggaacc cacaacctca gcttgaaagc gattaacctt attttggatg aactttggca   1680
cactaatgac aatcagatcg ccattttcaa ccggctgaaa ctggtgccga agaaggtgga   1740
cctgagccaa cagaaggaaa tcccgaccac ccttgtggac gatttcatcc tgtcacctgt   1800
ggtgaagagg agcttcatcc agtcgatcaa ggtcatcaac gccatcataa agaagtacgg   1860
ccttcccaac gacatcatca tcgaactggc ccgcgagaag aactccaaag atgcccagaa   1920
gatgatcaac gagatgcaga agcgaaaccg gcagacgaac gaacggatcg aggagatcat   1980
ccggaccacc gggaaggaaa acgcgaagta cctgatcgag aaaatcaagc tgcatgatat   2040
gcaggaaggg aagtgtctct actccctgga ggccattccg ctggaggatt tgctgaacaa   2100
ccctttcaac tacgaagtcg atcatatcat tcctcgctcc gtgtccttcg ataactcctt   2160
caacaataag gtcctcgtga agcaggagga gaagtaagta tcaaggttac aagacaggtt   2220
taaggagacc aatagaaact gggctcgaga atgcgacggg tgtggtacgc agccacttcg   2280
agtacccaca gtactacctg cttgtcgaga cagagaagac tcttgcgttt ctgataggca   2340
cctattggtc ttactgacat ccactttgcc tttctctcca cagctcgaag aagggcaaca   2400
gaaccccgtt ccagtacctc tcgtcgtccg actccaagat cagctacgaa actttcaaga   2460
agcacattct gaacctggcc aagggcaaag ggagaattag caagaccaag aaggaatacc   2520
tcctggaaga gagagacatc aaccgcttct cggtgcaaaa ggatttcatc aaccgcaacc   2580
tggtcgatac cagatacgcc accaggggac tgatgaacct cctgcggtcc tacttccggg   2640
tcaacaatct ggacgtgaag gtcaaatcca tcaacggggg ctttacttct ttcctgcgcc   2700
ggaagtggaa gttcaagaag gaacggaaca agggatacaa gcaccacgct gaagatgccc   2760
tgattattgc caacgccgac ttcatcttta aggaatggaa aaagctggac aaggctaaga   2820
aggtcatgga gaaccagatg ttcgaagaaa agcaggccga gtccatgccc gaaatcgaaa   2880
ccgagcagga atacaaggag atcttcatca caccgcacca aatcaagcac atcaaggact   2940
tcaaggatta caagtacagc caccgggtgg acaagaagcc taacagagag cttatcaacg   3000
acaccctgta ctccacgcgc aaggacgaca agggaaacac attgatcgtg aacaacctga   3060
acggactgta tgacaaggac aatgacaaac tgaagaagct gatcaacaaa tcgccggaaa   3120
agctcctgat gtaccatcac gaccctcaaa cctaccagaa actgaagctc atcatggagc   3180
agtacggcga cgaaaagaat cccctgtaca aatactacga ggagactgga aattacctga   3240
ctaagtactc caagaaggat aacggccccg tgatcaagaa gattaagtac tacggaaaca   3300
aactgaacgc acatctcgac atcaccgatg attatccaaa ctcccgcaac aaagtcgtga   3360
agctctccct caaaccgtac cgcttcgacg tgtacctgga taatggggtg tacaagttcg   3420
tgaccgtgaa gaacctggac gtcattaaga aggaaaacta ctacgaagtg aactcaaagt   3480
gctacgagga agccaagaag ctcaagaaga tcagcaacca ggccgagttc atcgcatcgt   3540
tttacaacaa tgacctcatt aagattaatg gagaactgta cagagtgatc ggcgtgaaca   3600
acgacctcct gaaccggatt gaagtgaaca tgatcgatat tacctaccgg gagtatctgg   3660
agaacatgaa cgacaagcgc ccaccgagaa tcatcaaaac tattgcctcc aagacccaat   3720
ccattaagaa atactccacc gacatcctgg gcaacctgta cgaggtcaag tcgaagaagc   3780
acccccagat tatcaagaag ggaaaaaggc cggcggccac gaaaaaggcc ggccaggcaa   3840
```

-continued

```
aaaagaaaaa ggcttaagaa ttcctagagc tcgctgatca gcctcgaaac ttgtttattg   3900
cagcttataa tggttacaaa taaagcaata gcatcacaaa tttcacaaat aaagcatttt   3960
tttcactgca ttctagttgt ggtttgtcca aactcatcaa tgtatcttat catgtctgta   4020
taccagcagg ctttcctagg ttcgaacgct gacgtcatca acccgctcca aggaatcgcg   4080
ggcccagtgt cactaggcgg gaacacccag cgcgcgtgcg ccctggcagg aagatggctg   4140
tgagggacag gggagtggcg ccctgcaata tttgcatgtc gctatgtgtt ctgggaaatc   4200
accataaacg tgaaatccct atcagtgata gagacttata agttccctat cagtgataga   4260
gacaccgacg ggtgtggtac gcagccactg tttaagtact ctgtgctgga aacagcacag   4320
aatctactta aacaaggcaa aatgccgtgt ttatctcgtc aacttgttgg cgagattttt   4380
tcacgtgcgg accgaggctg cagcgtcgtc ctccctagga acccctagtg atggagttgg   4440
ccactccctc tctgcgcgct cgctcgctca ctgaggccgg gcgaccaaag gtcgcccgac   4500
gcccgggctt tgcccgggcg gcctcagtga gcgagcgagc gcgcagctgc ctgcaggggc   4560
gcctgatgcg gtattttctc cttacgcatc tgtgcggtat ttcacaccgc atacgtcaaa   4620
gcaaccatag tacgcgccct gtagcggcgc attaagcgcg gcgggtgtgg tggttacgcg   4680
cagcgtgacc gctacacttg ccagcgccct agcgcccgct cctttcgctt tcttcccttc   4740
ctttctcgcc acgttcgccg gctttccccg tcaagctcta aatcgggggc tccctttagg   4800
gttccgattt agtgctttac ggcacctcga ccccaaaaaa cttgatttgg gtgatggttc   4860
acgtagtggg ccatcgccct gatagacggt ttttcgccct ttgacgttgg agtccacgtt   4920
ctttaatagt ggactcttgt tccaaactgg aacaacactc aaccctatct cgggctattc   4980
ttttgattta taagggattt tgccgatttc ggcctattgg ttaaaaaatg agctgattta   5040
acaaaaattt aacgcgaatt ttaacaaaat attaacgttt acaattttat ggtgcactct   5100
cagtacaatc tgctctgatg ccgcatagtt aagccagccc cgacacccgc caacacccgc   5160
tgacgcgccc tgacgggctt gtctgctccc ggcatccgct tacagacaag ctgtgaccgt   5220
ctccgggagc tgcatgtgtc agaggttttc accgtcatca ccgaaacgcg cgagacgaaa   5280
gggcctcgtg atacgcctat ttttataggt taatgtcatg aacaataaaa ctgtctgctt   5340
acataaacag taatacaagg ggtgttatga gccatattca acgggaaacg tcgaggccgc   5400
gattaaattc caacatggat gctgatttat atgggtataa atgggctcgc gataatgtcg   5460
ggcaatcagg tgcgacaatc tatcgcttgt atgggaagcc cgatgcgcca gagttgtttc   5520
tgaaacatgg caaaggtagc gttgccaatg atgttacaga tgagatggtc agactaaact   5580
ggctgacgga atttatgcct cttccgacca tcaagcattt tatccgtact cctgatgatg   5640
catggttact caccactgcg atccccggaa aaacagcatt ccaggtatta gaagaatatc   5700
ctgattcagg tgaaaatatt gttgatgcgc tggcagtgtt cctgcgccgg ttgcattcga   5760
ttcctgtttg taattgtcct tttaacagcg atcgcgtatt tcgtctcgct caggcgcaat   5820
cacgaatgaa taacggtttg gttgatgcga gtgattttga tgacgagcgt aatggctggc   5880
ctgttgaaca agtctggaaa gaaatgcata aacttttgcc attctcaccg gattcagtcg   5940
tcactcatgg tgatttctca cttgataacc ttatttttga cgaggggaaa ttaataggtt   6000
gtattgatgt tggacgagtc ggaatcgcag accgatacca ggatcttgcc atcctatgga   6060
actgcctcgg tgagttttct ccttcattac agaaacggct tttcaaaaa tatggtattg    6120
ataatcctga tatgaataaa ttgcagtttc atttgatgct cgatgagttt ttctaatctc   6180
```

atgaccaaaa tcccttaacg tgagttttcg ttccactgag cgtcagaccc cgtagaaaag 6240
atcaaaggat cttcttgaga tcctttttt ctgcgcgtaa tctgctgctt gcaaacaaaa 6300
aaaccaccgc taccagcggt ggtttgtttg ccggatcaag agctaccaac tctttttccg 6360
aaggtaactg gcttcagcag agcgcagata ccaaatactg tccttctagt gtagccgtag 6420
ttaggccacc acttcaagaa ctctgtagca ccgcctacat acctcgctct gctaatcctg 6480
ttaccagtgg ctgctgccag tggcgataag tcgtgtctta ccgggttgga ctcaagacga 6540
tagttaccgg ataaggcgca gcggtcgggc tgaacggggg gttcgtgcac acagcccagc 6600
ttggagcgaa cgacctacac cgaactgaga tacctacagc gtgagctatg agaaagcgcc 6660
acgcttcccg aagggagaaa ggcggacagg tatccggtaa gcggcagggt cggaacagga 6720
gagcgcacga gggagcttcc agggggaaac gcctggtatc tttatagtcc tgtcgggttt 6780
cgccacctct gacttgagcg tcgatttttg tgatgctcgt caggggggcg gagcctatgg 6840
aaaaacgcca gcaacgcggc ctttttacgg ttcctggcct tttgctggcc ttttgctcac 6900
atgt 6904

<210> SEQ ID NO 18
<211> LENGTH: 8452
<212> TYPE: DNA
<213> ORGANISM: Artificial Sequence
<220> FEATURE:
<223> OTHER INFORMATION: Plasmid

<400> SEQUENCE: 18
ctagctaact accggtgcca ccatggcccc aaagaagaag cggaaggtcg gtagtactgt 60
gggtactcga agtggctgcg taccacaccc gtcgcatgga tccaagcgga actatatcct 120
gggactggac atcggaatta cctccgtggg atacggcatc atcgattacg agactaggga 180
cgtgattgac gccggcgtga gactctttaa ggaggccaac gtggaaaaca acgaaggtcg 240
cagatccaag cggggtgcaa gacgcctgaa gcgccggagg agacatcgga tacagcgcgt 300
gaagaagctc cttttcgact acaacctcct cactgaccac tcggaattgt ccggtatcaa 360
cccctacgaa gcccgcgtga aaggcctgag ccagaagctg tccgaagagg agtttagcgc 420
agccctgctg cacctggcta agcgaagggg ggtgcacaac gtgaacgagg tggaggagga 480
cactggcaac gaactgtcca ccaaggagca gatttcacgg aactcgaagg cgctggaaga 540
gaaatatgtg gccgagctgc agctggagag gctcaagaag gatggcgaag tccgggggag 600
catcaatcgc ttcaagacct cggactacgt gaaggaagcc aaacagctgt tgaaggtgca 660
gaaggcctac caccaactgg accaatcatt cattgacact tacatcgatc tgcttgaaac 720
caggcgcacc tactacgagg gtcctggaga aggcagccct ttcggatgga aggacatcaa 780
ggagtggtat gagatgctga tgggtcattg cacctacttt ccggaagaac tgcgctcagt 840
gaagtacgcg tacaacgctg acctctacaa cgctctcaac gatctgaaca acctcgtgat 900
cacccgggac gagaacgaaa agctggagta ctacgaaaag ttccagatta tcgaaaacgt 960
gttcaagcag aagaagaagc ccaccctgaa gcagattgca aaggagatcc ttgtgaacga 1020
ggaggatatt aagggctacc gggtcacctc caccgggaaa ccagagttca ctaatctcaa 1080
ggtgtaccat gacattaagg acattactgc ccgcaaggag atcattgaaa acgcggaact 1140
gctggaccaa atcgcgaaga tcctgaccat ctatcagagc tccgaggata tccaggagga 1200
acttactaac ctcaattccg agctgacgca ggaagaaatc gagcaaatta gcaacctgaa 1260
gggttacact ggaacccaca acctcagctt gaaagcgatt aaccttattt tggatgaact 1320

-continued

```
ttggcacact aatgacaatc agatcgccat tttcaaccgg ctgaaactgg tgccgaagaa   1380
ggtggacctg agccaacaga aggaaatccc gaccaccctt gtggacgatt tcatcctgtc   1440
acctgtggtg aagaggagct tcatccagtc gatcaaggtc atcaacgcca tcataaagaa   1500
gtacggcctt cccaacgaca tcatcatcga actggcccgc gagaagaact ccaaagatgc   1560
ccagaagatg atcaacgaga tgcagaagcg aaaccggcag acgaacgaac ggatcgagga   1620
gatcatccgg accaccggga aggaaaacgc gaagtacctg atcgagaaaa tcaagctgca   1680
tgatatgcag gaagggaagt gtctctactc cctggaggcc attccgctgg aggatttgct   1740
gaacaaccct ttcaactacg aagtcgatca tatcattcct cgctccgtgt ccttcgataa   1800
ctccttcaac aataaggtcc tcgtgaagca ggaggagaag taagtatcaa ggttacaaga   1860
caggtttaag gagaccaata gaaactgggc tcgagaatgc gacgggtgtg gtacgcagcc   1920
acttcgagta cccacagtac tacctgcttg tcgagacaga gaagactctt gcgtttctga   1980
taggcaccta ttggtcttac tgacatccac tttgcctttc tctccacagc tcgaagaagg   2040
gcaacagaac cccgttccag tacctctcgt cgtccgactc caagatcagc tacgaaactt   2100
tcaagaagca cattctgaac ctggccaagg gcaaagggag aattagcaag accaagaagg   2160
aatacctcct ggaagagaga gacatcaacc gcttctcggt gcaaaaggat ttcatcaacc   2220
gcaacctggt cgataccaga tacgccacca ggggactgat gaacctcctg cggtcctact   2280
tccgggtcaa caatctggac gtgaaggtca aatccatcaa cgggggcttt acttctttcc   2340
tgcgccggaa gtggaagttc aagaaggaac ggaacaaggg atacaagcac cacgctgaag   2400
atgccctgat tattgccaac gccgacttca tctttaagga atggaaaaag ctggacaagg   2460
ctaagaaggt catggagaac cagatgttcg aagaaaagca ggccgagtcc atgcccgaaa   2520
tcgaaaccga gcaggaatac aaggagatct tcatcacacc gcaccaaatc aagcacatca   2580
aggacttcaa ggattacaag tacagccacc gggtggacaa gaagcctaac agagagctta   2640
tcaacgacac cctgtactcc acgcgcaagg acgacaaggg aaacacattg atcgtgaaca   2700
acctgaacgg actgtatgac aaggacaatg acaaactgaa gaagctgatc aacaaatcgc   2760
cggaaaagct cctgatgtac catcacgacc ctcaaaccta ccagaaactg aagctcatca   2820
tggagcagta cggcgacgaa aagaatcccc tgtacaaata ctacgaggag actggaaatt   2880
acctgactaa gtactccaag aaggataacg gccccgtgat caagaagatt aagtactacg   2940
gaaacaaact gaacgcacat ctcgacatca ccgatgatta tccaaactcc cgcaacaaag   3000
tcgtgaagct ctccctcaaa ccgtaccgct tcgacgtgta cctggataat ggggtgtaca   3060
agttcgtgac cgtgaagaac ctggacgtca ttaagaagga aaactactac gaagtgaact   3120
caaagtgcta cgaggaagcc aagaagctca agaagatcag caaccaggcc gagttcatcg   3180
catcgtttta caacaatgac ctcattaaga ttaatggaga actgtacaga gtgatcggcg   3240
tgaacaacga cctcctgaac cggattgaag tgaacatgat cgatattacc taccgggagt   3300
atctggagaa catgaacgac aagcgcccac cgagaatcat caaaactatt gcctccaaga   3360
cccaatccat taagaaatac tccaccgaca tcctgggcaa cctgtacgag gtcaagtcga   3420
agaagcaccc ccagattatc aagaagggaa aaaggccggc ggccacgaaa aaggccggcc   3480
aggcaaaaaa gaaaaaggct taagaattcc tagagctcgc tgatcagcct cgaaacttgt   3540
ttattgcagc ttataatggt tacaaataaa gcaatagcat cacaaatttc acaaataaag   3600
catttttttc actgcattct agttgtggtt tgtccaaact catcaatgta tcttatcatg   3660
```

-continued

```
tctgtatacc agcaggcttt cctaggttcg aacgctgacg tcatcaaccc gctccaagga   3720
atcgcgggcc cagtgtcact aggcgggaac acccagcgcg cgtgcgccct ggcaggaaga   3780
tggctgtgag ggacagggga gtggcgccct gcaatatttg catgtcgcta tgtgttctgg   3840
gaaatcacca taaacgtgaa atccctatca gtgatagaga cttataagtt ccctatcagt   3900
gatagagaca ccgacgggtg tggtacgcag ccactgttta agtactctgt gctggaaaca   3960
gcacagaatc tacttaaaca aggcaaaatg ccgtgtttat ctcgtcaact tgttggcgag   4020
atttttcac gtgcggaccg aggctgcagc gtcgtcctcc ctaggaaccc ctagtgatgg   4080
agttggccac tccctctctg cgcgctcgct cgctcactga ggccgggcga ccaaaggtcg   4140
cccgacgccc gggctttgcc cgggcggcct cagtgagcga gcgagcgcgc agctgcctgc   4200
aggggcgcct gatgcggtat tttctcctta cgcatctgtg cggtatttca caccgcatac   4260
gtcaaagcaa ccatagtacg cgccctgtag cggcgcatta agcgcggcgg gtgtggtggt   4320
tacgcgcagc gtgaccgcta cacttgccag cgccctagcg cccgctcctt tcgctttctt   4380
cccttccttt ctcgccacgt tcgccggctt tccccgtcaa gctctaaatc gggggctccc   4440
tttagggttc cgatttagtg ctttacggca cctcgacccc aaaaaacttg atttgggtga   4500
tggttcacgt agtgggccat cgccctgata gacggttttt cgccctttga cgttggagtc   4560
cacgttcttt aatagtggac tcttgttcca aactggaaca acactcaacc ctatctcggg   4620
ctattctttt gatttataag ggattttgcc gatttcggcc tattggttaa aaaatgagct   4680
gatttaacaa aaatttaacg cgaattttaa caaaatatta acgttgacat tgattattga   4740
ctagttatta atagtaatca attacggggt cattagttca tagcccatat atggagttcc   4800
gcgttacata acttacggta aatggcccgc ctggctgacc gcccaacgac ccccgcccat   4860
tgacgtcaat aatgacgtat gttcccatag taacgccaat agggactttc cattgacgtc   4920
aatgggtgga gtatttacgg taaactgccc acttggcagt acatcaagtg tatcatatgc   4980
caagtacgcc ccctattgac gtcaatgacg gtaaatggcc cgcctggcat tatgcccagt   5040
acatgacctt atgggacttt cctacttggc agtacatcta cgtattagtc atcgctatta   5100
ccatggtgat gcggttttgg cagtacatca atgggcgtgg atagcggttt gactcacggg   5160
gatttccaag tctccacccc attgacgtca atgggagttt gttttggcac caaaatcaac   5220
gggactttcc aaaatgtcgt aacaactccg ccccattgac gcaaatgggc ggtaggcgtg   5280
tacggtggga ggtctatata agcagagctc tctggctaac tagagaaccc actgcttact   5340
ggcttatcgt taattaaccg gtgccaccat gatgtcccgc cttgataaat caaaagtaat   5400
aaacagtgct cttgagcttc tcaatgaagt tggtatagaa gggttgacga ctcggaaatt   5460
ggcgcaaaaa ctcggtgttg agcagccaac cttgtattgg catgttaaaa acaaacgagc   5520
actcctcgac gctttggcga tagagatgct ggacaggcac cacacgcatt tctgtcccct   5580
cgaaggagag tcatggcagg atttccttag aaataacgca aagtccttca gatgtgcgct   5640
gcttagtcac cgcgacggcg caaaagttca tctcggcact aggccaaccg agaaacagta   5700
cgagactctg gagaaccaac tggcgttttt gtgtcaacag ggttttagtc tcgaaaatgc   5760
gctctatgct ctctctgcgg ttggccattt caccctcgga tgcgtactgg aagatcagga   5820
gcaccaagtg gccaaagaag aacgggaaac gccgactacg gacagcatgc ctccgttgct   5880
ccggcaagct atagagctct tcgatcacca aggcgctgag ccagctttct tgttcggatt   5940
ggaacttatt atatgcgggc tcgaaaagca gcttaaatgc gagtcaggtt aagcggccgc   6000
tcgagtctag agggcccgtt taaacccgct gatcagcctc gactgtgcct tctagttgcc   6060
```

agccatctgt tgtttgcccc tcccccgtgc cttccttgac cctggaaggt gccactccca 6120
ctgtcctttc ctaataaaat gaggaaattg catcgcattg tctgagtagg tgtcattcta 6180
ttctgggggg tggggtgggg caggacagca agggggagga ttgggaagac aatagcaggc 6240
atgctgggga tgcggtgggc tctatggaac gtttacaatt ttatggtgca ctctcagtac 6300
aatctgctct gatgccgcat agttaagcca gccccgacac ccgccaacac ccgctgacgc 6360
gccctgacgg gcttgtctgc tcccggcatc cgcttacaga caagctgtga ccgtctccgg 6420
gagctgcatg tgtcagaggt tttcaccgtc atcaccgaaa cgcgcgagac gaaagggcct 6480
cgtgatacgc ctatttttat aggttaatgt catgaacaat aaaactgtct gcttacataa 6540
acagtaatac aaggggtgtt atgagccata ttcaacggga aacgtcgagg ccgcgattaa 6600
attccaacat ggatgctgat ttatatgggt ataaatgggc tcgcgataat gtcgggcaat 6660
caggtgcgac aatctatcgc ttgtatggga agcccgatgc gccagagttg tttctgaaac 6720
atggcaaagg tagcgttgcc aatgatgtta cagatgagat ggtcagacta aactggctga 6780
cggaatttat gcctcttccg accatcaagc attttatccg tactcctgat gatgcatggt 6840
tactcaccac tgcgatcccc ggaaaaacag cattccaggt attagaagaa tatcctgatt 6900
caggtgaaaa tattgttgat gcgctggcag tgttcctgcg ccggttgcat tcgattcctg 6960
tttgtaattg tccttttaac agcgatcgcg tatttcgtct cgctcaggcg caatcacgaa 7020
tgaataacgg tttggttgat gcgagtgatt ttgatgacga gcgtaatggc tggcctgttg 7080
aacaagtctg gaaagaaatg cataaacttt tgccattctc accggattca gtcgtcactc 7140
atggtgattt ctcacttgat aaccttattt ttgacgaggg gaaattaata ggttgtattg 7200
atgttggacg agtcggaatc gcagaccgat accaggatct tgccatccta tggaactgcc 7260
tcggtgagtt ttctccttca ttacagaaac ggctttttca aaaatatggt attgataatc 7320
ctgatatgaa taaattgcag tttcatttga tgctcgatga gtttttctaa tctcatgacc 7380
aaaatccctt aacgtgagtt ttcgttccac tgagcgtcag accccgtaga aaagatcaaa 7440
ggatcttctt gagatccttt ttttctgcgc gtaatctgct gcttgcaaac aaaaaaacca 7500
ccgctaccag cggtggtttg tttgccggat caagagctac caactctttt tccgaaggta 7560
actggcttca gcagagcgca gataccaaat actgtccttc tagtgtagcc gtagttaggc 7620
caccacttca agaactctgt agcaccgcct acatacctcg ctctgctaat cctgttacca 7680
gtggctgctg ccagtggcga taagtcgtgt cttaccgggt tggactcaag acgatagtta 7740
ccggataagg cgcagcggtc gggctgaacg gggggttcgt gcacacagcc cagcttggag 7800
cgaacgacct acaccgaact gagataccta cagcgtgagc tatgagaaag cgccacgctt 7860
cccgaaggga gaaaggcgga caggtatccg gtaagcggca gggtcggaac aggagagcgc 7920
acgagggagc ttccaggggg aaacgcctgg tatctttata gtcctgtcgg gtttcgccac 7980
ctctgacttg agcgtcgatt tttgtgatgc tcgtcagggg ggcggagcct atggaaaaac 8040
gccagcaacg cggccttttt acggttcctg gccttttgct ggccttttgc tcacatgtcc 8100
tgcaggcagc tgcgcgctcg ctcgctcact gaggccgccc gggcgtcggg cgacctttgg 8160
tcgcccggcc tcagtgagcg agcgagcgcg cagagaggga gtggccaact ccatcactag 8220
gggttcctgc ggccgcacgc gtgctccggt gcccgtcagt gggcagagcg cacatcgccc 8280
acagtccccg agaagttggg gggaggggtc ggcaattgaa ccggtgccta gagaaggtgg 8340
cgcggggtaa actgggaaag tgatgtcgtg tactggctcc gccttttttcc cgagggtggg 8400 ggagaaccgt atataagtgc agtagtcgcc gtgaacgttc tttttcgcaa cg 8452

<210> SEQ ID NO 19
<211> LENGTH: 6987
<212> TYPE: DNA
<213> ORGANISM: Artificial Sequence
<220> FEATURE:
<223> OTHER INFORMATION: Plasmid

<400> SEQUENCE: 19
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgggccc cagaagcctg gtggttgttt gtccttctca 180
ggggaaaagt gaggcggccc cttggaggaa ggggccgggc agaatgatct aatcggattc 240
caagcagctc aggggattgt ctttttctag caccttcttg ccactcctaa gcgtcctccg 300
tgaccccggc tgggatttag cctggtgctg tgtcagcccc ggtctcccag ggcttcccca 360
gtggtcccca ggaaccctcg acagggcccg gtctctctcg tccagcaagg gcagggacgg 420
gccacaggcc aagggcgcta gctaactacc ggtgccacca tggccccaaa gaagaagcgg 480
aaggtcggta gtactgtggg tactcgaagt ggctgcgtac cacacccgtc gcatggatcc 540
aagcggaact atatcctggg actggacatc ggaattacct ccgtgggata cggcatcatc 600
gattacgaga ctagggacgt gattgacgcc ggcgtgagac tctttaagga ggccaacgtg 660
gaaaacaacg aaggtcgcag atccaagcgg ggtgcaagac gcctgaagcg ccggaggaga 720
catcggatac agcgcgtgaa gaagctcctt ttcgactaca acctcctcac tgaccactcg 780
gaattgtccg gtatcaaccc ctacgaagcc cgcgtgaaag gcctgagcca gaagctgtcc 840
gaagaggagt ttagcgcagc cctgctgcac ctggctaagc gaagggggggt gcacaacgtg 900 aacgaggtgg aggaggacac tggcaacgaa ctgtccacca aggagcagat ttcacggaac 960
tcgaaggcgc tggaagagaa atatgtggcc gagctgcagc tggagaggct caagaaggat 1020
ggcgaagtcc gggggagcat caatcgcttc aagacctcgg actacgtgaa ggaagccaaa 1080
cagctgttga aggtgcagaa ggcctaccac caactggacc aatcattcat tgacacttac 1140
atcgatctgc ttgaaaccag gcgcacctac tacgagggtc ctggagaagg cagccctttc 1200
ggatggaagg acatcaagga gtggtatgag atgctgatgg gtcattgcac ctactttccg 1260
gaagaactgc gctcagtgaa gtacgcgtac aacgctgacc tctacaacgc tctcaacgat 1320
ctgaacaacc tcgtgatcac ccgggacgag aacgaaaagc tggagtacta cgaaaagttc 1380
cagattatcg aaaacgtgtt caagcagaag aagaagccca ccctgaagca gattgcaaag 1440
gagatccttg tgaacgagga ggatattaag ggctaccggg tcacctccac cgggaaacca 1500
gagttcacta atctcaaggt gtaccatgac attaaggaca ttactgcccg caaggagatc 1560
attgaaaacg cggaactgct ggaccaaatc gcgaagatcc tgaccatcta tcagagctcc 1620
gaggatatcc aggaggaact tactaacctc aattccgagc tgacgcagga agaaatcgag 1680
caaattagca acctgaaggg ttacactgga acccacaacc tcagcttgaa agcgattaac 1740
cttattttgg atgaactttg gcacactaat gacaatcaga tcgccatttt caaccggctg 1800
aaactggtgc cgaagaaggt ggacctgagc caacagaagg aaatcccgac cacccttgtg 1860
gacgatttca tcctgtcacc tgtggtgaag aggagcttca tccagtcgat caaggtcatc 1920

-continued

```
aacgccatca taaagaagta cggccttccc aacgacatca tcatcgaact ggcccgcgag   1980
aagaactcca aagatgccca gaagatgatc aacgagatgc agaagcgaaa ccggcagacg   2040
aacgaacgga tcgaggagat catccggacc accgggaagg aaaacgcgaa gtacctgatc   2100
gagaaaatca agctgcatga tatgcaggaa gggaagtgtc tctactccct ggaggccatt   2160
ccgctggagg atttgctgaa caacccttc aactacgaag tcgatcatat cattcctcgc   2220
tccgtgtcct tcgataactc cttcaacaat aaggtcctcg tgaagcagga ggagaagtaa   2280
gtatcaaggt tacaagacag gtttaaggag accaatagaa actgggctcg agaatgcgac   2340
gggtgtggta cgcagccact tcgagtaccc acagtactac ctgcttgtcg agacagagaa   2400
gactcttgcg tttctgatag gcacctattg gtcttactga catccacttt gcctttctct   2460
ccacagctcg aagaagggca acagaacccc gttccagtac ctctcgtcgt ccgactccaa   2520
gatcagctac gaaactttca agaagcacat tctgaacctg gccaagggca aagggagaat   2580
tagcaagacc aagaaggaat acctcctgga agagagagac atcaaccgct tctcggtgca   2640
aaaggatttc atcaaccgca acctggtcga taccagatac gccaccaggg gactgatgaa   2700
cctcctgcgg tcctacttcc gggtcaacaa tctggacgtg aaggtcaaat ccatcaacgg   2760
gggctttact tctttcctgc gccggaagtg gaagttcaag aaggaacgga acaagggata   2820
caagcaccac gctgaagatg ccctgattat tgccaacgcc gacttcatct ttaaggaatg   2880
gaaaaagctg gacaaggcta agaaggtcat ggagaaccag atgttcgaag aaaagcaggc   2940
cgagtccatg cccgaaatcg aaaccgagca ggaatacaag gagatcttca tcacaccgca   3000
ccaaatcaag cacatcaagg acttcaagga ttacaagtac agccaccggg tggacaagaa   3060
gcctaacaga gagcttatca acgacaccct gtactccacg cgcaaggacg acaagggaaa   3120
cacattgatc gtgaacaacc tgaacggact gtatgacaag gacaatgaca aactgaagaa   3180
gctgatcaac aaatcgccgg aaaagctcct gatgtaccat cacgaccctc aaacctacca   3240
gaaactgaag ctcatcatgg agcagtacgg cgacgaaaag aatcccctgt acaaatacta   3300
cgaggagact ggaaattacc tgactaagta ctccaagaag gataacggcc ccgtgatcaa   3360
gaagattaag tactacggaa acaaactgaa cgcacatctc gacatcaccg atgattatcc   3420
aaactcccgc aacaaagtcg tgaagctctc cctcaaaccg taccgcttcg acgtgtacct   3480
ggataatggg gtgtacaagt tcgtgaccgt gaagaacctg gacgtcatta agaaggaaaa   3540
ctactacgaa gtgaactcaa agtgctacga ggaagccaag aagctcaaga agatcagcaa   3600
ccaggccgag ttcatcgcat cgttttacaa caatgacctc attaagatta atggagaact   3660
gtacagagtg atcggcgtga acaacgacct cctgaaccgg attgaagtga acatgatcga   3720
tattacctac cgggagtatc tggagaacat gaacgacaag cgcccaccga gaatcatcaa   3780
aactattgcc tccaagaccc aatccattaa gaaatactcc accgacatcc tgggcaacct   3840
gtacgaggtc aagtcgaaga agcaccccca gattatcaag aagggaaaaa ggccggcggc   3900
cacgaaaaag gccggccagg caaaaaagaa aaaggcttaa gaattcctag agctcgctga   3960
tcagcctcga aacttgttta ttgcagctta taatggttac aaataaagca atagcatcac   4020
aaatttcaca aataaagcat ttttttcact gcattctagt tgtggtttgt ccaaactcat   4080
caatgtatct tatcatgtct gtataccagc aggctttcct aggttcgaac gctgacgtca   4140
tcaacccgct ccaaggaatc gcgggcccag tgtcactagg cgggaacacc cagcgcgcgt   4200
gcgccctggc aggaagatgg ctgtgaggga caggggagtg gcgccctgca atatttgcat   4260
gtcgctatgt gttctgggaa atcaccataa acgtgaaatc cctatcagtg atagagactt   4320
```

```
ataagttccc tatcagtgat agagacaccg acgggtgtgg tacgcagcca ctgtttaagt   4380
actctgtgct ggaaacagca cagaatctac ttaaacaagg caaaatgccg tgtttatctc   4440
gtcaacttgt tggcgagatt ttttcacgtg cggaccgagg ctgcagcgtc gtcctcccta   4500
ggaaccccta gtgatggagt tggccactcc ctctctgcgc gctcgctcgc tcactgaggc   4560
cgggcgacca aaggtcgccc gacgcccggg ctttgcccgg gcggcctcag tgagcgagcg   4620
agcgcgcagc tgcctgcagg ggcgcctgat gcggtatttt ctccttacgc atctgtgcgg   4680
tatttcacac cgcatacgtc aaagcaacca tagtacgcgc cctgtagcgg cgcattaagc   4740
gcggcgggtg tggtggttac gcgcagcgtg accgctacac ttgccagcgc cctagcgccc   4800
gctcctttcg ctttcttccc ttcctttctc gccacgttcg ccggctttcc ccgtcaagct   4860
ctaaatcggg ggctcccttt agggttccga tttagtgctt tacggcacct cgaccccaaa   4920
aaacttgatt tgggtgatgg ttcacgtagt gggccatcgc cctgatagac ggtttttcgc   4980
cctttgacgt tggagtccac gttctttaat agtggactct tgttccaaac tggaacaaca   5040
ctcaacccta tctcgggcta ttcttttgat ttataaggga ttttgccgat ttcggcctat   5100
tggttaaaaa atgagctgat ttaacaaaaa tttaacgcga attttaacaa aatattaacg   5160
tttacaattt tatggtgcac tctcagtaca atctgctctg atgccgcata gttaagccag   5220
ccccgacacc cgccaacacc cgctgacgcg ccctgacggg cttgtctgct cccggcatcc   5280
gcttacagac aagctgtgac cgtctccggg agctgcatgt gtcagaggtt ttcaccgtca   5340
tcaccgaaac gcgcgagacg aaagggcctc gtgatacgcc tatttttata ggttaatgtc   5400
atgaacaata aaactgtctg cttacataaa cagtaataca aggggtgtta tgagccatat   5460
tcaacgggaa acgtcgaggc cgcgattaaa ttccaacatg gatgctgatt tatatgggta   5520
taaatgggct cgcgataatg tcgggcaatc aggtgcgaca atctatcgct tgtatgggaa   5580
gcccgatgcg ccagagttgt ttctgaaaca tggcaaaggt agcgttgcca atgatgttac   5640
agatgagatg gtcagactaa actggctgac ggaatttatg cctcttccga ccatcaagca   5700
ttttatccgt actcctgatg atgcatggtt actcaccact gcgatccccg gaaaaacagc   5760
attccaggta ttagaagaat atcctgattc aggtgaaaat attgttgatg cgctggcagt   5820
gttcctgcgc cggttgcatt cgattcctgt ttgtaattgt ccttttaaca gcgatcgcgt   5880
atttcgtctc gctcaggcgc aatcacgaat gaataacggt ttggttgatg cgagtgattt   5940
tgatgacgag cgtaatggct ggcctgttga acaagtctgg aaagaaatgc ataaactttt   6000
gccattctca ccggattcag tcgtcactca tggtgatttc tcacttgata accttatttt   6060
tgacgagggg aaattaatag gttgtattga tgttggacga gtcggaatcg cagaccgata   6120
ccaggatctt gccatcctat ggaactgcct cggtgagttt tctccttcat tacagaaacg   6180
gctttttcaa aaatatggta ttgataatcc tgatatgaat aaattgcagt ttcatttgat   6240
gctcgatgag tttttctaat ctcatgacca aaatccctta acgtgagttt tcgttccact   6300
gagcgtcaga ccccgtagaa aagatcaaag gatcttcttg agatcctttt tttctgcgcg   6360
taatctgctg cttgcaaaca aaaaaaccac cgctaccagc ggtggtttgt ttgccggatc   6420
aagagctacc aactcttttt ccgaaggtaa ctggcttcag cagagcgcag ataccaaata   6480
ctgtccttct agtgtagccg tagttaggcc accacttcaa gaactctgta gcaccgccta   6540
catacctcgc tctgctaatc ctgttaccag tggctgctgc cagtggcgat aagtcgtgtc   6600
ttaccgggtt ggactcaaga cgatagttac cggataaggc gcagcggtcg ggctgaacgg   6660
```

-continued ggggttcgtg cacacagccc agcttggagc gaacgaccta caccgaactg agatacctac 6720
agcgtgagct atgagaaagc gccacgcttc ccgaagggag aaaggcggac aggtatccgg 6780
taagcggcag ggtcggaaca ggagagcgca cgagggagct tccaggggga aacgcctggt 6840
atctttatag tcctgtcggg tttcgccacc tctgacttga gcgtcgattt ttgtgatgct 6900
cgtcaggggg gcggagccta tggaaaaacg ccagcaacgc ggccttttta cggttcctgg 6960
ccttttgctg gccttttgct cacatgt 6987

<210> SEQ ID NO 20
<211> LENGTH: 8535
<212> TYPE: DNA
<213> ORGANISM: Artificial Sequence
<220> FEATURE:
<223> OTHER INFORMATION: Plasmid

<400> SEQUENCE: 20
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgggccc cagaagcctg gtggttgttt gtccttctca 180
ggggaaaagt gaggcggccc cttggaggaa ggggccgggc agaatgatct aatcggattc 240
caagcagctc aggggattgt ctttttctag caccttcttg ccactcctaa gcgtcctccg 300
tgaccccggc tgggatttag cctggtgctg tgtcagcccc ggtctcccag ggggcttccca 360 gtggtcccca ggaaccctcg acagggcccg gtctctctcg tccagcaagg gcagggacgg 420
gccacaggcc aagggcgcta gctaactacc ggtgccacca tggccccaaa gaagaagcgg 480
aaggtcggta gtactgtggg tactcgaagt ggctgcgtac cacacccgtc gcatggatcc 540
aagcggaact atatcctggg actggacatc ggaattacct ccgtgggata cggcatcatc 600
gattacgaga ctagggacgt gattgacgcc ggcgtgagac tctttaagga ggccaacgtg 660
gaaaacaacg aaggtcgcag atccaagcgg ggtgcaagac gcctgaagcg ccggaggaga 720
catcggatac agcgcgtgaa gaagctcctt ttcgactaca acctcctcac tgaccactcg 780
gaattgtccg gtatcaaccc ctacgaagcc cgcgtgaaag gcctgagcca gaagctgtcc 840
gaagaggagt ttagcgcagc cctgctgcac ctggctaagc gaagggggt gcacaacgtg 900 aacgaggtgg aggaggacac tggcaacgaa ctgtccacca aggagcagat ttcacggaac 960
tcgaaggcgc tggaagagaa atatgtggcc gagctgcagc tggagaggct caagaaggat 1020
ggcgaagtcc gggggagcat caatcgcttc aagacctcgg actacgtgaa ggaagccaaa 1080
cagctgttga aggtgcagaa ggcctaccac caactggacc aatcattcat tgacacttac 1140
atcgatctgc ttgaaaccag gcgcacctac tacgagggtc ctggagaagg cagccctttc 1200
ggatggaagg acatcaagga gtggtatgag atgctgatgg gtcattgcac ctactttccg 1260
gaagaactgc gctcagtgaa gtacgcgtac aacgctgacc tctacaacgc tctcaacgat 1320
ctgaacaacc tcgtgatcac ccgggacgag aacgaaaagc tggagtacta cgaaaagttc 1380
cagattatcg aaaacgtgtt caagcagaag aagaagccca ccctgaagca gattgcaaag 1440
gagatccttg tgaacgagga ggatattaag ggctaccggg tcacctccac cgggaaacca 1500
gagttcacta atctcaaggt gtaccatgac attaaggaca ttactgcccg caaggagatc 1560
attgaaaacg cggaactgct ggaccaaatc gcgaagatcc tgaccatcta tcagagctcc 1620
gaggatatcc aggaggaact tactaacctc aattccgagc tgacgcagga agaaatcgag 1680
caaattagca acctgaaggg ttacactgga acccacaacc tcagcttgaa agcgattaac 1740

```
cttattttgg atgaactttg gcacactaat gacaatcaga tcgccatttt caaccggctg   1800
aaactggtgc cgaagaaggt ggacctgagc caacagaagg aaatcccgac cacccttgtg   1860
gacgatttca tcctgtcacc tgtggtgaag aggagcttca tccagtcgat caaggtcatc   1920
aacgccatca taaagaagta cggccttccc aacgacatca tcatcgaact ggcccgcgag   1980
aagaactcca aagatgccca gaagatgatc aacgagatgc agaagcgaaa ccggcagacg   2040
aacgaacgga tcgaggagat catccggacc accgggaagg aaaacgcgaa gtacctgatc   2100
gagaaaatca agctgcatga tatgcaggaa gggaagtgtc tctactccct ggaggccatt   2160
ccgctggagg atttgctgaa caaccctttc aactacgaag tcgatcatat cattcctcgc   2220
tccgtgtcct tcgataactc cttcaacaat aaggtcctcg tgaagcagga ggagaagtaa   2280
gtatcaaggt tacaagacag gtttaaggag accaatagaa actgggctcg agaatgcgac   2340
gggtgtggta cgcagccact tcgagtaccc acagtactac ctgcttgtcg agacagagaa   2400
gactcttgcg tttctgatag gcacctattg gtcttactga catccacttt gcctttctct   2460
ccacagctcg aagaagggca acagaacccc gttccagtac ctctcgtcgt ccgactccaa   2520
gatcagctac gaaactttca agaagcacat tctgaacctg gccaagggca aagggagaat   2580
tagcaagacc aagaaggaat acctcctgga agagagagac atcaaccgct tctcggtgca   2640
aaaggatttc atcaaccgca acctggtcga taccagatac gccaccaggg gactgatgaa   2700
cctcctgcgg tcctacttcc gggtcaacaa tctggacgtg aaggtcaaat ccatcaacgg   2760
gggctttact tctttcctgc gccggaagtg gaagttcaag aaggaacgga acaagggata   2820
caagcaccac gctgaagatg ccctgattat tgccaacgcc gacttcatct ttaaggaatg   2880
gaaaaagctg gacaaggcta agaaggtcat ggagaaccag atgttcgaag aaaagcaggc   2940
cgagtccatg cccgaaatcg aaaccgagca ggaatacaag gagatcttca tcacaccgca   3000
ccaaatcaag cacatcaagg acttcaagga ttacaagtac agccaccggg tggacaagaa   3060
gcctaacaga gagcttatca acgacaccct gtactccacg cgcaaggacg acaagggaaa   3120
cacattgatc gtgaacaacc tgaacggact gtatgacaag gacaatgaca aactgaagaa   3180
gctgatcaac aaatcgccgg aaaagctcct gatgtaccat cacgaccctc aaacctacca   3240
gaaactgaag ctcatcatgg agcagtacgg cgacgaaaag aatcccctgt acaaatacta   3300
cgaggagact ggaaattacc tgactaagta ctccaagaag gataacggcc ccgtgatcaa   3360
gaagattaag tactacggaa acaaactgaa cgcacatctc gacatcaccg atgattatcc   3420
aaactcccgc aacaaagtcg tgaagctctc cctcaaaccg taccgcttcg acgtgtacct   3480
ggataatggg gtgtacaagt tcgtgaccgt gaagaacctg gacgtcatta agaaggaaaa   3540
ctactacgaa gtgaactcaa agtgctacga ggaagccaag aagctcaaga agatcagcaa   3600
ccaggccgag ttcatcgcat cgttttacaa caatgacctc attaagatta atggagaact   3660
gtacagagtg atcggcgtga acaacgacct cctgaaccgg attgaagtga acatgatcga   3720
tattacctac cgggagtatc tggagaacat gaacgacaag cgcccaccga gaatcatcaa   3780
aactattgcc tccaagaccc aatccattaa gaaatactcc accgacatcc tgggcaacct   3840
gtacgaggtc aagtcgaaga agcacccccca gattatcaag aagggaaaaa ggccggcggc   3900
cacgaaaaag gccggccagg caaaaaagaa aaaggcttaa gaattcctag agctcgctga   3960
tcagcctcga aacttgttta ttgcagctta taatggttac aaataaagca atagcatcac   4020
aaatttcaca aataaagcat ttttttcact gcattctagt tgtggtttgt ccaaactcat   4080
```

-continued

```
caatgtatct tatcatgtct gtataccagc aggctttcct aggttcgaac gctgacgtca   4140
tcaacccgct ccaaggaatc gcgggcccag tgtcactagg cgggaacacc cagcgcgcgt   4200
gcgccctggc aggaagatgg ctgtgaggga caggggagtg gcgccctgca atatttgcat   4260
gtcgctatgt gttctgggaa atcaccataa acgtgaaatc cctatcagtg atagagactt   4320
ataagttccc tatcagtgat agagacaccg acgggtgtgg tacgcagcca ctgtttaagt   4380
actctgtgct ggaaacagca cagaatctac ttaaacaagg caaaatgccg tgtttatctc   4440
gtcaacttgt tggcgagatt ttttcacgtg cggaccgagg ctgcagcgtc gtcctcccta   4500
ggaaccccta gtgatggagt tggccactcc ctctctgcgc gctcgctcgc tcactgaggc   4560
cgggcgacca aaggtcgccc gacgcccggg ctttgcccgg gcggcctcag tgagcgagcg   4620
agcgcgcagc tgcctgcagg ggcgcctgat gcggtatttt ctccttacgc atctgtgcgg   4680
tatttcacac cgcatacgtc aaagcaacca tagtacgcgc cctgtagcgg cgcattaagc   4740
gcggcgggtg tggtggttac gcgcagcgtg accgctacac ttgccagcgc cctagcgccc   4800
gctcctttcg ctttcttccc ttcctttctc gccacgttcg ccggctttcc ccgtcaagct   4860
ctaaatcggg ggctcccttt agggttccga tttagtgctt tacggcacct cgaccccaaa   4920
aaacttgatt tgggtgatgg ttcacgtagt gggccatcgc cctgatagac ggtttttcgc   4980
cctttgacgt tggagtccac gttctttaat agtggactct tgttccaaac tggaacaaca   5040
ctcaacccta tctcgggcta ttcttttgat ttataaggga ttttgccgat ttcggcctat   5100
tggttaaaaa atgagctgat ttaacaaaaa tttaacgcga attttaacaa aatattaacg   5160
ttgacattga ttattgacta gttattaata gtaatcaatt acggggtcat tagttcatag   5220
cccatatatg gagttccgcg ttacataact tacggtaaat ggcccgcctg gctgaccgcc   5280
caacgacccc cgcccattga cgtcaataat gacgtatgtt cccatagtaa cgccaatagg   5340
gactttccat tgacgtcaat gggtggagta tttacggtaa actgcccact tggcagtaca   5400
tcaagtgtat catatgccaa gtacgccccc tattgacgtc aatgacggta aatggcccgc   5460
ctggcattat gcccagtaca tgaccttatg ggactttcct acttggcagt acatctacgt   5520
attagtcatc gctattacca tggtgatgcg gttttggcag tacatcaatg ggcgtggata   5580
gcggtttgac tcacggggat ttccaagtct ccaccccatt gacgtcaatg ggagtttgtt   5640
ttggcaccaa aatcaacggg actttccaaa atgtcgtaac aactccgccc cattgacgca   5700
aatgggcggt aggcgtgtac ggtgggaggt ctatataagc agagctctct ggctaactag   5760
agaacccact gcttactggc ttatcgttaa ttaaccggtg ccaccatgat gtcccgcctt   5820
gataaatcaa aagtaataaa cagtgctctt gagcttctca atgaagttgg tatagaaggg   5880
ttgacgactc ggaaattggc gcaaaaactc ggtgttgagc agccaacctt gtattggcat   5940
gttaaaaaca aacgagcact cctcgacgct ttggcgatag agatgctgga caggcaccac   6000
acgcatttct gtcccctcga aggagagtca tggcaggatt tccttagaaa taacgcaaag   6060
tccttcagat gtgcgctgct tagtcaccgc gacggcgcaa aagttcatct cggcactagg   6120
ccaaccgaga aacagtacga gactctggag aaccaactgg cgtttttgtg tcaacagggt   6180
tttagtctcg aaaatgcgct ctatgctctc tctgcggttg gccatttcac cctcggatgc   6240
gtactggaag atcaggagca ccaagtggcc aaagaagaac gggaaacgcc gactacggac   6300
agcatgcctc cgttgctccg gcaagctata gagctcttcg atcaccaagg cgctgagcca   6360
gctttcttgt tcggattgga acttattata tgcgggctcg aaaagcagct taaatgcgag   6420
tcaggttaag cggccgctcg agtctagagg gcccgtttaa acccgctgat cagcctcgac   6480
```

-continued

```
tgtgccttct agttgccagc catctgttgt ttgcccctcc cccgtgcctt ccttgaccct   6540

ggaaggtgcc actcccactg tcctttccta ataaaatgag gaaattgcat cgcattgtct   6600

gagtaggtgt cattctattc tggggggtgg ggtggggcag gacagcaagg gggaggattg   6660

ggaagacaat agcaggcatg ctggggatgc ggtgggctct atggaacgtt tacaatttta   6720

tggtgcactc tcagtacaat ctgctctgat gccgcatagt taagccagcc ccgacacccg   6780

ccaacacccg ctgacgcgcc ctgacgggct tgtctgctcc cggcatccgc ttacagacaa   6840

gctgtgaccg tctccgggag ctgcatgtgt cagaggtttt caccgtcatc accgaaacgc   6900

gcgagacgaa agggcctcgt gatacgccta tttttatagg ttaatgtcat gaacaataaa   6960

actgtctgct tacataaaca gtaatacaag ggtgttatg agccatattc aacgggaaac    7020

gtcgaggccg cgattaaatt ccaacatgga tgctgattta tatgggtata aatgggctcg   7080

cgataatgtc gggcaatcag gtgcgacaat ctatcgcttg tatgggaagc ccgatgcgcc   7140

agagttgttt ctgaaacatg gcaaaggtag cgttgccaat gatgttacag atgagatggt   7200

cagactaaac tggctgacgg aatttatgcc tcttccgacc atcaagcatt ttatccgtac   7260

tcctgatgat gcatggttac tcaccactgc gatccccgga aaaacagcat tccaggtatt   7320

agaagaatat cctgattcag gtgaaaatat tgttgatgcg ctggcagtgt tcctgcgccg   7380

gttgcattcg attcctgttt gtaattgtcc ttttaacagc gatcgcgtat ttcgtctcgc   7440

tcaggcgcaa tcacgaatga ataacggttt ggttgatgcg agtgattttg atgacgagcg   7500

taatggctgg cctgttgaac aagtctggaa agaaatgcat aaacttttgc cattctcacc   7560

ggattcagtc gtcactcatg gtgatttctc acttgataac cttatttttg acgaggggaa   7620

attaataggt tgtattgatg ttggacgagt cggaatcgca gaccgatacc aggatcttgc   7680

catcctatgg aactgcctcg gtgagttttc tccttcatta cagaaacggc tttttcaaaa   7740

atatggtatt gataatcctg atatgaataa attgcagttt catttgatgc tcgatgagtt   7800

tttctaatct catgaccaaa atcccttaac gtgagttttc gttccactga gcgtcagacc   7860

ccgtagaaaa gatcaaagga tcttcttgag atcctttttt tctgcgcgta atctgctgct   7920

tgcaaacaaa aaaaccaccg ctaccagcgg tggtttgttt gccggatcaa gagctaccaa   7980

ctctttttcc gaaggtaact ggcttcagca gagcgcagat accaaatact gtccttctag   8040

tgtagccgta gttaggccac cacttcaaga actctgtagc accgcctaca tacctcgctc   8100

tgctaatcct gttaccagtg gctgctgcca gtggcgataa gtcgtgtctt accgggttgg   8160

actcaagacg atagttaccg gataaggcgc agcggtcggg ctgaacgggg ggttcgtgca   8220

cacagcccag cttggagcga acgacctaca ccgaactgag atacctacag cgtgagctat   8280

gagaaagcgc cacgcttccc gaagggagaa aggcggacag gtatccggta agcggcaggg   8340

tcggaacagg agagcgcacg agggagcttc caggggggaaa cgcctggtat ctttatagtc  8400

ctgtcgggtt tcgccacctc tgacttgagc gtcgattttt gtgatgctcg tcaggggggc   8460

ggagcctatg gaaaaacgcc agcaacgcgg cctttttacg gttcctggcc ttttgctggc   8520

cttttgctca catgt                                                    8535
```

<210> SEQ ID NO 21
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 21
ctagctaact accggtgcca cca 23

<210> SEQ ID NO 22
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 22
gaggtattcc ttcttggtct tgc 23

<210> SEQ ID NO 23
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 23
cccacagtcc ccgagaagtt g 21

<210> SEQ ID NO 24
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 24
accttcttgc cactcctaag c 21

<210> SEQ ID NO 25
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 25
cttctggctc aggcctttca c 21

<210> SEQ ID NO 26
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 26
cctgatcgag aaaatcaagc tgc 23

<210> SEQ ID NO 27
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 27
gcaagaccaa gaaggaatac ctc 23

<210> SEQ ID NO 28
<211> LENGTH: 1654

<212> TYPE: DNA
<213> ORGANISM: Artificial Sequence
<220> FEATURE:
<223> OTHER INFORMATION: Inserted sequence

<400> SEQUENCE: 28
ggtagtggtg aagggcgagg ctccttgctg acctgtggag atgttgaaga gaatcccggc 60
ccaggtacca tgcgacgggt gtggtacgca gccacttcga gtacccacag tactgctagc 120
gtgtctaagg gcgaagagct gattaaggag aacatgcaca tgaagctgta catggagggc 180
accgtggaca accatcactt caagtgcaca tccgagggcg aaggcaagcc ctacgagggc 240
acccagacca tgagaatcaa ggtggtcgag ggcggccctc tcccctcgc cttcgacatc 300 ctggctacta gcttcctcta cggcagcaag accttcatca accacaccca gggcatcccc 360
gacttcttca agcagtcctt ccctgagggc ttcacatggg agagagtcac cacatacgaa 420
gacgggggcg tgctgaccgc tacccaggac accagcctcc aggacggctg cctcatctac 480
aacgtcaaga tcagaggggt gaacttcaca tccaacggcc ctgtgatgca gaagaaaaca 540
ctcggctggg aggccttcac cgagacgctg taccccgctg acggcggcct ggaaggcaga 600
aacgacatgg ccctgaagct cgtgggcggg agccatctga tcgcaaacgc caagaccaca 660
tatagatcca agaaacccgc taagaacctc aagatgcctg gcgtctacta tgtggactac 720
agactggaaa gaatcaagga ggccaacaac gagacctacg tcgagcagca cgaggtggca 780
gtggccagat actgcgacct ccctagcaaa ctggggcaca aacttaataa gcttagccat 840
ggcttcccgc cggaggtgga ggagcaggat gatggcacgc tgcccatgtc ttgtgcccag 900
gagagcggga tggaccgtca ccctgcagcc tgtgcttctg ctaggatcaa tgtgcacccg 960
ggaagcgggg ctaccaactt cagtctcctc aaacaagctg gcgatgtgga ggaaaatcca 1020
ggtccggttc ctttgtctca agaagaatcc accctcattg aaagagcaac ggctacaatc 1080
aacagcatcc ccatctctga agactacagc gtcgccagcg cagctctctc tagcgacggc 1140
cgcatcttca ctggtgtcaa tgtatatcat tttactgggg gaccttgtgc agaactcgtg 1200
gtgctgggca ctgctgctgc tgcggcagct ggcaacctga cttgtatcgt cgcgatcgga 1260
aatgagaaca ggggcatctt gagcccctgc ggacggtgcc gacaggtgct tctcgatctg 1320
catcctggga tcaaagccat agtgaaggac agtgatggac agccgacggc agttgggatt 1380
cgtgaattgc tgccctctgg ttatgtgtgg gagggctaga gatctcgagc tgtgccttct 1440
agttgccagc catctgttgt ttgcccctcc cccgtgcctt ccttgaccct ggaaggtgcc 1500
actcccactg tcctttccta ataaaatgag gaaattgcat cgcattgtct gagtaggtgt 1560
cattctattc tggggggtgg ggtggggcag gacagcaagg gggaggattg ggaagacaat 1620
agcaggcatg ctggggatgc ggtgggctct atgg 1654

<210> SEQ ID NO 29
<211> LENGTH: 1542
<212> TYPE: DNA
<213> ORGANISM: Artificial Sequence
<220> FEATURE:
<223> OTHER INFORMATION: TetR construct sequence

<400> SEQUENCE: 29
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180

```
ctttccattg acgtcaatgg gtggagtatt tacggtaaac tgcccacttg gcagtacatc    240

aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg gtgatgcggt tttggcagta catcaatggg cgtggatagc    420

ggtttgactc acggggattt ccaagtctcc accccattga cgtcaatggg agtttgtttt    480

ggcaccaaaa tcaacgggac tttccaaaat gtcgtaacaa ctccgcccca ttgacgcaaa    540

tgggcggtag gcgtgtacgg tgggaggtct atataagcag agctctctgg ctaactagag    600

aacccactgc ttactggctt atcgttaatt aaccggtgcc accatgatgt cccgccttga    660

taaatcaaaa gtaataaaca gtgctcttga gcttctcaat gaagttggta tagaagggtt    720

gacgactcgg aaattggcgc aaaaactcgg tgttgagcag ccaaccttgt attggcatgt    780

taaaaacaaa cgagcactcc tcgacgcttt ggcgatagag atgctggaca ggcaccacac    840

gcatttctgt cccctcgaag gagagtcatg gcaggatttc cttagaaata acgcaaagtc    900

cttcagatgt gcgctgctta gtcaccgcga cggcgcaaaa gttcatctcg gcactaggcc    960

aaccgagaaa cagtacgaga ctctggagaa ccaactggcg tttttgtgtc aacagggttt   1020

tagtctcgaa aatgcgctct atgctctctc tgcggttggc catttcaccc tcggatgcgt   1080

actggaagat caggagcacc aagtggccaa agaagaacgg gaaacgccga ctacggacag   1140

catgcctccg ttgctccggc aagctataga gctcttcgat caccaaggcg ctgagccagc   1200

tttcttgttc ggattggaac ttattatatg cgggctcgaa aagcagctta aatgcgagtc   1260

aggttaagcg gccgctcgag tctagagggc ccgtttaaac ccgctgatca gcctcgactg   1320

tgccttctag ttgccagcca tctgttgttt gcccctcccc cgtgccttcc ttgaccctgg   1380

aaggtgccac tcccactgtc ctttcctaat aaaatgagga aattgcatcg cattgtctga   1440

gtaggtgtca ttctattctg gggggtgggg tggggcagga cagcaagggg gaggattggg   1500

aagacaatag caggcatgct ggggatgcgg tgggctctat gg                      1542


<210> SEQ ID NO 30
<211> LENGTH: 23
<212> TYPE: RNA
<213> ORGANISM: Artificial Sequence
<220> FEATURE:
<223> OTHER INFORMATION: Spacer sequence

<400> SEQUENCE: 30

gacgggugug guacgcagcc acu                                             23


<210> SEQ ID NO 31
<211> LENGTH: 23
<212> TYPE: DNA
<213> ORGANISM: Artificial Sequence
<220> FEATURE:
<223> OTHER INFORMATION: Target DNA sequence

<400> SEQUENCE: 31

gacgggtgtg gtacgcagcc act                                             23


<210> SEQ ID NO 32
<211> LENGTH: 23
<212> TYPE: DNA
<213> ORGANISM: Artificial Sequence
<220> FEATURE:
<223> OTHER INFORMATION: Sequence of strand opposite target DNA
```

<400> SEQUENCE: 32
agtggctgcg taccacaccc gtc 23

<210> SEQ ID NO 33
<211> LENGTH: 20
<212> TYPE: RNA
<213> ORGANISM: Artificial Sequence
<220> FEATURE:
<223> OTHER INFORMATION: Spacer sequence

<400> SEQUENCE: 33 gggugugua cgcagccacu 20

<210> SEQ ID NO 34
<211> LENGTH: 20
<212> TYPE: DNA
<213> ORGANISM: Artificial Sequence
<220> FEATURE:
<223> OTHER INFORMATION: Target DNA sequence

<400> SEQUENCE: 34
gggtgtggta cgcagccact 20

<210> SEQ ID NO 35
<211> LENGTH: 20
<212> TYPE: DNA
<213> ORGANISM: Artificial Sequence
<220> FEATURE:
<223> OTHER INFORMATION: Sequence of strand opposite target DNA

<400> SEQUENCE: 35
agtggctgcg taccacaccc 20

<210> SEQ ID NO 36
<211> LENGTH: 8457
<212> TYPE: DNA
<213> ORGANISM: Artificial Sequence
<220> FEATURE:
<223> OTHER INFORMATION: Plasmid

<400> SEQUENCE: 36
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgggccc cagaagcctg gtggttgttt gtccttctca 180
ggggaaaagt gaggcggccc cttggaggaa ggggccgggc agaatgatct aatcggattc 240
caagcagctc aggggattgt ctttttctag caccttcttg ccactcctaa gcgtcctccg 300
tgaccccggc tgggatttag cctggtgctg tgtcagcccc ggctagctaa ctaccggtgc 360
caccatggcc ccaaagaaga agcggaaggt cggtagtact gtgggtactc gaagtggctg 420
cgtaccacac ccgtcgcatg gatccaagcg gaactatatc ctgggactgg acatcggaat 480
tacctccgtg ggatacggca tcatcgatta cgagactagg gacgtgattg acgccggcgt 540
gagactcttt aaggaggcca acgtggaaaa caacgaaggt cgcagatcca agcggggtgc 600
aagacgcctg aagcgccgga ggagacatcg gatacagcgc gtgaagaagc tcctttttcga 660 ctacaacctc ctcactgacc actcggaatt gtccggtatc aacccctacg aagcccgcgt 720
gaaaggcctg agccagaagc tgtccgaaga ggagtttagc gcagccctgc tgcacctggc 780
taagcgaagg ggggtgcaca acgtgaacga ggtggaggag gacactggca acgaactgtc 840

-continued

```
caccaaggag cagatttcac ggaactcgaa ggcgctggaa gagaaatatg tggccgagct    900
gcagctggag aggctcaaga aggatggcga agtccggggg agcatcaatc gcttcaagac    960
ctcggactac gtgaaggaag ccaaacagct gttgaaggtg cagaaggcct accaccaact   1020
ggaccaatca ttcattgaca cttacatcga tctgcttgaa accaggcgca cctactacga   1080
gggtcctgga gaaggcagcc ctttcggatg gaaggacatc aaggagtggt atgagatgct   1140
gatgggtcat tgcacctact ttccggaaga actgcgctca gtgaagtacg cgtacaacgc   1200
tgacctctac aacgctctca acgatctgaa caacctcgtg atcacccggg acgagaacga   1260
aaagctggag tactacgaaa agttccagat tatcgaaaac gtgttcaagc agaagaagaa   1320
gcccaccctg aagcagattg caaaggagat ccttgtgaac gaggaggata ttaagggcta   1380
ccgggtcacc tccaccggga aaccagagtt cactaatctc aaggtgtacc atgacattaa   1440
ggacattact gcccgcaagg agatcattga aaacgcggaa ctgctggacc aaatcgcgaa   1500
gatcctgacc atctatcaga gctccgagga tatccaggag gaacttacta acctcaattc   1560
cgagctgacg caggaagaaa tcgagcaaat tagcaacctg aagggttaca ctggaaccca   1620
caacctcagc ttgaaagcga ttaaccttat tttggatgaa ctttggcaca ctaatgacaa   1680
tcagatcgcc attttcaacc ggctgaaact ggtgccgaag aaggtggacc tgagccaaca   1740
gaaggaaatc ccgaccaccc ttgtggacga tttcatcctg tcacctgtgg tgaagaggag   1800
cttcatccag tcgatcaagg tcatcaacgc catcataaag aagtacggcc ttcccaacga   1860
catcatcatc gaactggccc gcgagaagaa ctccaaagat gcccagaaga tgatcaacga   1920
gatgcagaag cgaaaccggc agacgaacga acggatcgag gagatcatcc ggaccaccgg   1980
gaaggaaaac gcgaagtacc tgatcgagaa aatcaagctg catgatatgc aggaagggaa   2040
gtgtctctac tccctggagg ccattccgct ggaggatttg ctgaacaacc ctttcaacta   2100
cgaagtcgat catatcattc ctcgctccgt gtccttcgat aactccttca acaataaggt   2160
cctcgtgaag caggaggaga agtaagtatc aaggttacaa gacaggttta aggagaccaa   2220
tagaaactgg gctcgagaat gcgacgggtg tggtacgcag ccacttcgag tacccacagt   2280
actacctgct tgtcgagaca gagaagactc ttgcgtttct gataggcacc tattggtctt   2340
actgacatcc actttgcctt tctctccaca gctcgaagaa gggcaacaga accccgttcc   2400
agtacctctc gtcgtccgac tccaagatca gctacgaaac tttcaagaag cacattctga   2460
acctggccaa gggcaaaggg agaattagca agaccaagaa ggaatacctc ctggaagaga   2520
gagacatcaa ccgcttctcg gtgcaaaagg atttcatcaa ccgcaacctg gtcgatacca   2580
gatacgccac caggggactg atgaacctcc tgcggtccta cttccgggtc aacaatctgg   2640
acgtgaaggt caaatccatc aacgggggct ttacttcttt cctgcgccgg aagtggaagt   2700
tcaagaagga acggaacaag ggatacaagc accacgctga agatgccctg attattgcca   2760
acgccgactt catctttaag gaatggaaaa agctggacaa ggctaagaag gtcatggaga   2820
accagatgtt cgaagaaaag caggccgagt ccatgcccga aatcgaaacc gagcaggaat   2880
acaaggagat cttcatcaca ccgcaccaaa tcaagcacat caaggacttc aaggattaca   2940
agtacagcca ccgggtggac aagaagccta acagagagct tatcaacgac accctgtact   3000
ccacgcgcaa ggacgacaag ggaaacacat tgatcgtgaa caacctgaac ggactgtatg   3060
acaaggacaa tgacaaactg aagaagctga tcaacaaatc gccggaaaag ctcctgatgt   3120
accatcacga ccctcaaacc taccagaaac tgaagctcat catggagcag tacggcgacg   3180
aaaagaatcc cctgtacaaa tactacgagg agactggaaa ttacctgact aagtactcca   3240
```

agaaggataa cggccccgtg atcaagaaga ttaagtacta cggaaacaaa ctgaacgcac 3300
atctcgacat caccgatgat tatccaaact cccgcaacaa agtcgtgaag ctctccctca 3360
aaccgtaccg cttcgacgtg tacctggata atggggtgta caagttcgtg accgtgaaga 3420
acctggacgt cattaagaag gaaaactact acgaagtgaa ctcaaagtgc tacgaggaag 3480
ccaagaagct caagaagatc agcaaccagg ccgagttcat cgcatcgttt tacaacaatg 3540
acctcattaa gattaatgga gaactgtaca gagtgatcgg cgtgaacaac gacctcctga 3600
accggattga agtgaacatg atcgatatta cctaccggga gtatctggag aacatgaacg 3660
acaagcgccc accgagaatc atcaaaacta ttgcctccaa gacccaatcc attaagaaat 3720
actccaccga catcctgggc aacctgtacg aggtcaagtc gaagaagcac ccccagatta 3780
tcaagaaggg aaaaaggccg gcggccacga aaaaggccgg ccaggcaaaa aagaaaaagg 3840
cttaagaatt cctagagctc gctgatcagc ctcgaaactt gtttattgca gcttataatg 3900
gttacaaata aagcaatagc atcacaaatt tcacaaataa agcatttttt tcactgcatt 3960
ctagttgtgg tttgtccaaa ctcatcaatg tatcttatca tgtctgtata ccagcaggct 4020
ttcctaggtt cgaacgctga cgtcatcaac ccgctccaag gaatcgcggg cccagtgtca 4080
ctaggcggga acacccagcg cgcgtgcgcc ctggcaggaa gatggctgtg agggacaggg 4140
gagtggcgcc ctgcaatatt tgcatgtcgc tatgtgttct gggaaatcac cataaacgtg 4200
aaatccctat cagtgataga gacttataag ttccctatca gtgatagaga caccgggtgt 4260
ggtacgcagc cactgtttaa gtactctgtg ctggaaacag cacagaatct acttaaacaa 4320
ggcaaaatgc cgtgtttatc tcgtcaactt gttggcgaga tttttcacg tgcggaccga 4380
ggctgcagcg tcgtcctccc taggaacccc tagtgatgga gttggccact ccctctctgc 4440
gcgctcgctc gctcactgag gccgggcgac caaaggtcgc ccgacgcccg ggctttgccc 4500
gggcggcctc agtgagcgag cgagcgcgca gctgcctgca ggggcgcctg atgcggtatt 4560
ttctccttac gcatctgtgc ggtatttcac accgcatacg tcaaagcaac catagtacgc 4620
gccctgtagc ggcgcattaa gcgcggcggg tgtggtggtt acgcgcagcg tgaccgctac 4680
acttgccagc gccttagcgc ccgctccttt cgctttcttc ccttcctttc tcgccacgtt 4740
cgccggcttt ccccgtcaag ctctaaatcg ggggctccct ttagggttcc gatttagtgc 4800
tttacggcac ctcgacccca aaaaacttga tttgggtgat ggttcacgta gtgggccatc 4860
gccctgatag acggtttttc gccctttgac gttggagtcc acgttcttta atagtggact 4920
cttgttccaa actggaacaa cactcaactc tatctcgggc tattcttttg atttataagg 4980
gattttgccg atttcggtct attggttaaa aaatgagctg atttaacaaa aatttaacgc 5040
gaattttaac aaaatattaa cgttagcgct gacattgatt attgactagt tattaatagt 5100
aatcaattac ggggtcatta gttcatagcc catatatgga gttccgcgtt acataactta 5160
cggtaaatgg cccgcctggc tgaccgccca acgacccccg cccattgacg tcaataatga 5220
cgtatgttcc catagtaacg ccaataggga ctttccattg acgtcaatgg gtggagtatt 5280
tacggtaaac tgcccacttg gcagtacatc aagtgtatca tatgccaagt acgcccccta 5340
ttgacgtcaa tgacggtaaa tggcccgcct ggcattatgc ccagtacatg accttatggg 5400
actttcctac ttggcagtac atctacgtat tagtcatcgc tattaccatg gtgatgcggt 5460
tttggcagta catcaatggg cgtggatagc ggtttgactc acggggattt ccaagtctcc 5520
accccattga cgtcaatggg agtttgtttt ggcaccaaaa tcaacgggac tttccaaaat 5580

-continued

```
gtcgtaacaa ctccgcccca ttgacgcaaa tgggcggtag gcgtgtacgg tgggaggtct   5640
atataagcag agctctctgg ctaactagag aacccactgc ttactggctt atcgttaatt   5700
aaccggtgcc accatgatgt cccgccttga taaatcaaaa gtaataaaca gtgctcttga   5760
gcttctcaat gaagttggta tagaagggtt gacgactcgg aaattggcgc aaaaactcgg   5820
tgttgagcag ccaaccttgt attggcatgt taaaaacaaa cgagcactcc tcgacgcttt   5880
ggcgatagag atgctggaca ggcaccacac gcatttctgt cccctcgaag gagagtcatg   5940
gcaggatttc cttagaaata acgcaaagtc cttcagatgt gcgctgctta gtcaccgcga   6000
cggcgcaaaa gttcatctcg gcactaggcc aaccgagaaa cagtacgaga ctctggagaa   6060
ccaactggcg tttttgtgtc aacagggttt tagtctcgaa aatgcgctct atgctctctc   6120
tgcggttggc catttcaccc tcggatgcgt actggaagat caggagcacc aagtggccaa   6180
agaagaacgg gaaacgccga ctacggacag catgcctccg ttgctccggc aagctataga   6240
gctcttcgat caccaaggcg ctgagccagc tttcttgttc ggattggaac ttattatatg   6300
cgggctcgaa aagcagctta aatgcgagtc aggttaagtt taaacccgct gatcagcctc   6360
gactgtgcct tctagttgcc agccatctgt tgtttgcccc tcccccgtgc cttccttgac   6420
cctggaaggt gccactccca ctgtcctttc ctaataaaat gaggaaattg catcgcattg   6480
tctgagtagg tgtcattcta ttctgggggg tggggtgggg caggacagca agggggagga   6540
ttgggaagac aatagcaggc atgctgggga tgcggtgggc tctatggctt ctgagttagt   6600
ccattgtcga cttccgagga ccgcggaacg tttacaattt tatggtgcac tctcagtaca   6660
atctgctctg atgccgcata gttaagccag ccccgacacc cgccaacacc cgctgacgcg   6720
ccctgacggg cttgtctgct cccggcatcc gcttacagac aagctgtgac cgtctccggg   6780
agctgcatgt gtcagaggtt ttcaccgtca tcaccgaaac gcgcgagacg aaagggcctc   6840
gtgatacgcc tatttttata ggttaatgtc atgaacaata aaactgtctg cttacataaa   6900
cagtaataca aggggtgtta tgagccatat tcaacgggaa acgtcgaggc cgcgattaaa   6960
ttccaacatg gatgctgatt tatatgggta taaatgggct cgcgataatg tcgggcaatc   7020
aggtgcgaca atctatcgct tgtatgggaa gcccgatgcg ccagagttgt ttctgaaaca   7080
tggcaaaggt agcgttgcca atgatgttac agatgagatg gtcagactaa actggctgac   7140
ggaatttatg cctcttccga ccatcaagca ttttatccgt actcctgatg atgcatggtt   7200
actcaccact gcgatccccg gaaaaacagc attccaggta ttagaagaat atcctgattc   7260
aggtgaaaat attgttgatg cgctggcagt gttcctgcgc cggttgcatt cgattcctgt   7320
ttgtaattgt ccttttaaca gcgatcgcgt atttcgtctc gctcaggcgc aatcacgaat   7380
gaataacggt ttggttgatg cgagtgattt tgatgacgag cgtaatggct ggcctgttga   7440
acaagtctgg aaagaaatgc ataaactttt gccattctca ccggattcag tcgtcactca   7500
tggtgatttc tcacttgata accttatttt tgacgagggg aaattaatag gttgtattga   7560
tgttggacga gtcggaatcg cagaccgata ccaggatctt gccatcctat ggaactgcct   7620
cggtgagttt tctccttcat tacagaaacg gctttttcaa aaatatggta ttgataatcc   7680
tgatatgaat aaattgcagt ttcatttgat gctcgatgag tttttctaat ctcatgacca   7740
aaatccctta acgtgagttt tcgttccact gagcgtcaga ccccgtagaa aagatcaaag   7800
gatcttcttg agatcctttt tttctgcgcg taatctgctg cttgcaaaca aaaaaaccac   7860
cgctaccagc ggtggtttgt ttgccggatc aagagctacc aactcttttt ccgaaggtaa   7920
ctggcttcag cagagcgcag ataccaaata ctgtccttct agtgtagccg tagttaggcc   7980
```

```
accacttcaa gaactctgta gcaccgccta catacctcgc tctgctaatc ctgttaccag   8040
tggctgctgc cagtggcgat aagtcgtgtc ttaccgggtt ggactcaaga cgatagttac   8100
cggataaggc gcagcggtcg ggctgaacgg ggggttcgtg cacacagccc agcttggagc   8160
gaacgaccta caccgaactg agatacctac agcgtgagct atgagaaagc gccacgcttc   8220
ccgaagggag aaaggcggac aggtatccgg taagcggcag ggtcggaaca ggagagcgca   8280
cgagggagct tccaggggga aacgcctggt atctttatag tcctgtcggg tttcgccacc   8340
tctgacttga gcgtcgattt ttgtgatgct cgtcaggggg gcggagccta tggaaaaacg   8400
ccagcaacgc ggccttttta cggttcctgg ccttttgctg gccttttgct cacatgt      8457
```

<210> SEQ ID NO 37
<211> LENGTH: 7230
<212> TYPE: DNA
<213> ORGANISM: Artificial Sequence
<220> FEATURE:
<223> OTHER INFORMATION: Plasmid

<400> SEQUENCE: 37

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcac gcgtgggccc cagaagcctg gtggttgttt gtccttctca    180
ggggaaaagt gaggcggccc cttggaggaa ggggccgggc agaatgatct aatcggattc    240
caagcagctc aggggattgt ctttttctag caccttcttg ccactcctaa gcgtcctccg    300
tgaccccggc tgggatttag cctggtgctg tgtcagcccc ggctagctaa ctaccggtgc    360
caccatggcc ccaaagaaga agcggaaggt cggtagtact gtgggtactc gaagtggctg    420
cgtaccacac ccgtcgcatg gatccaagcg gaactatatc ctgggactgg acatcggaat    480
tacctccgtg ggatacggca tcatcgatta cgagactagg gacgtgattg acgccggcgt    540
gagactcttt aaggaggcca acgtggaaaa caacgaaggt cgcagatcca agcggggtgc    600
aagacgcctg aagcgccgga ggagacatcg gatacagcgc gtgaagaagc tcctttttcga   660
ctacaacctc ctcactgacc actcggaatt gtccggtatc aacccctacg aagcccgcgt    720
gaaaggcctg agccagaagc tgtccgaaga ggagtttagc gcagccctgc tgcacctggc    780
taagcgaagg ggggtgcaca acgtgaacga ggtggaggag gacactggca acgaactgtc    840
caccaaggag cagatttcac ggaactcgaa ggcgctggaa gagaaatatg tggccgagct    900
gcagctggag aggctcaaga aggatggcga agtccggggg agcatcaatc gcttcaagac    960
ctcggactac gtgaaggaag ccaaacagct gttgaaggtg cagaaggcct accaccaact   1020
ggaccaatca ttcattgaca cttacatcga tctgcttgaa accaggcgca cctactacga   1080
gggtcctgga gaaggcagcc ctttcggatg gaaggacatc aaggagtggt atgagatgct   1140
gatgggtcat tgcacctact ttccggaaga actgcgctca gtgaagtacg cgtacaacgc   1200
tgacctctac aacgctctca acgatctgaa caacctcgtg atcacccggg acgagaacga   1260
aaagctggag tactacgaaa agttccagat tatcgaaaac gtgttcaagc agaagaagaa   1320
gcccaccctg aagcagattg caaaggagat ccttgtgaac gaggaggata ttaagggcta   1380
ccgggtcacc tccaccggga aaccagagtt cactaatctc aaggtgtacc atgacattaa   1440
ggacattact gcccgcaagg agatcattga aaacgcggaa ctgctggacc aaatcgcgaa   1500
gatcctgacc atctatcaga gctccgagga tatccaggag gaacttacta acctcaattc   1560
```

-continued

```
cgagctgacg caggaagaaa tcgagcaaat tagcaacctg aagggttaca ctggaaccca   1620
caacctcagc ttgaaagcga ttaaccttat tttggatgaa ctttggcaca ctaatgacaa   1680
tcagatcgcc attttcaacc ggctgaaact ggtgccgaag aaggtggacc tgagccaaca   1740
gaaggaaatc ccgaccaccc ttgtggacga tttcatcctg tcacctgtgg tgaagaggag   1800
cttcatccag tcgatcaagg tcatcaacgc catcataaag aagtacggcc ttcccaacga   1860
catcatcatc gaactggccc gcgagaagaa ctccaaagat gcccagaaga tgatcaacga   1920
gatgcagaag cgaaaccggc agacgaacga acggatcgag gagatcatcc ggaccaccgg   1980
gaaggaaaac gcgaagtacc tgatcgagaa aatcaagctg catgatatgc aggaagggaa   2040
gtgtctctac tccctggagg ccattccgct ggaggatttg ctgaacaacc ctttcaacta   2100
cgaagtcgat catatcattc ctcgctccgt gtccttcgat aactccttca acaataaggt   2160
cctcgtgaag caggaggaga agtaagtatc aaggttacaa gacaggttta aggagaccaa   2220
tagaaactgg gctcgagaat gcgacgggtg tggtacgcag ccacttcgag tacccacagt   2280
actacctgct tgtcgagaca gagaagactc ttgcgtttct gataggcacc tattggtctt   2340
actgacatcc actttgcctt tctctccaca gctcgaagaa gggcaacaga accccgttcc   2400
agtacctctc gtcgtccgac tccaagatca gctacgaaac tttcaagaag cacattctga   2460
acctggccaa gggcaaaggg agaattagca agaccaagaa ggaatacctc ctggaagaga   2520
gagacatcaa ccgcttctcg gtgcaaaagg atttcatcaa ccgcaacctg gtcgatacca   2580
gatacgccac caggggactg atgaacctcc tgcggtccta cttccgggtc aacaatctgg   2640
acgtgaaggt caaatccatc aacgggggct ttacttcttt cctgcgccgg aagtggaagt   2700
tcaagaagga acggaacaag ggatacaagc accacgctga agatgccctg attattgcca   2760
acgccgactt catctttaag gaatggaaaa agctggacaa ggctaagaag gtcatggaga   2820
accagatgtt cgaagaaaag caggccgagt ccatgcccga aatcgaaacc gagcaggaat   2880
acaaggagat cttcatcaca ccgcaccaaa tcaagcacat caaggacttc aaggattaca   2940
agtacagcca ccgggtggac aagaagccta acagagagct tatcaacgac accctgtact   3000
ccacgcgcaa ggacgacaag ggaaacacat tgatcgtgaa caacctgaac ggactgtatg   3060
acaaggacaa tgacaaactg aagaagctga tcaacaaatc gccggaaaag ctcctgatgt   3120
accatcacga ccctcaaacc taccagaaac tgaagctcat catggagcag tacggcgacg   3180
aaaagaatcc cctgtacaaa tactacgagg agactggaaa ttacctgact aagtactcca   3240
agaaggataa cggccccgtg atcaagaaga ttaagtacta cggaaacaaa ctgaacgcac   3300
atctcgacat caccgatgat tatccaaact cccgcaacaa agtcgtgaag ctctccctca   3360
aaccgtaccg cttcgacgtg tacctggata atggggtgta caagttcgtg accgtgaaga   3420
acctggacgt cattaagaag gaaaactact acgaagtgaa ctcaaagtgc tacgaggaag   3480
ccaagaagct caagaagatc agcaaccagg ccgagttcat cgcatcgttt tacaacaatg   3540
acctcattaa gattaatgga gaactgtaca gagtgatcgg cgtgaacaac gacctcctga   3600
accggattga agtgaacatg atcgatatta cctaccggga gtatctggag aacatgaacg   3660
acaagcgccc accgagaatc atcaaaacta ttgcctccaa gacccaatcc attaagaaat   3720
actccaccga catcctgggc aacctgtacg aggtcaagtc gaagaagcac ccccagatta   3780
tcaagaaggg aaaaaggccg gcggccacga aaaaggccgg ccaggcaaaa aagaaaaagg   3840
cttaagaatt cctagagctc gctgatcagc ctcgaaactt gtttattgca gcttataatg   3900
gttacaaata aagcaatagc atcacaaatt tcacaaataa agcatttttt tcactgcatt   3960
```

```
ctagttgtgg tttgtccaaa ctcatcaatg tatcttatca tgtctgtata ccagcaggct   4020
ttcctaggtt cgaacgctga cgtcatcaac ccgctccaag gaatcgcggg cccagtgtca   4080
ctaggcggga acacccagcg cgcgtgcgcc ctggcaggaa gatggctgtg agggacaggg   4140
gagtggcgcc ctgcaatatt tgcatgtcgc tatgtgttct gggaaatcac cataaacgtg   4200
aaatccctat cagtgataga gacttataag ttccctatca gtgatagaga caccgggtgt   4260
ggtacgcagc cactgtttaa gtactctgtg ctggaaacag cacagaatct acttaaacaa   4320
ggcaaaatgc cgtgtttatc tcgtcaactt gttggcgaga ttttttcacg tgcggaccga   4380
ggctgcagcg tcgtcctccc taggaacccc tagtgatgga gttggccact ccctctctgc   4440
gcgctcgctc gctcactgag gccgggcgac caaaggtcgc ccgacgcccg ggctttgccc   4500
gggcggcctc agtgagcgag cgagcgcgca gctgcctgca ggggcgcctg atgcggtatt   4560
ttctccttac gcatctgtgc ggtatttcac accgcatacg tcaaagcaac catagtacgc   4620
gccctgtagc ggcgcattaa gcgcggcggg tgtggtggtt acgcgcagcg tgaccgctac   4680
acttgccagc gccttagcgc ccgctccttt cgctttcttc ccttcctttc tcgccacgtt   4740
cgccggcttt ccccgtcaag ctctaaatcg ggggctccct ttagggttcc gatttagtgc   4800
tttacggcac ctcgacccca aaaaacttga tttgggtgat ggttcacgta gtgggccatc   4860
gccctgatag acggtttttc gccctttgac gttggagtcc acgttcttta atagtggact   4920
cttgttccaa actggaacaa cactcaactc tatctcgggc tattcttttg atttataagg   4980
gattttgccg atttcggtct attggttaaa aaatgagctg atttaacaaa aatttaacgc   5040
gaattttaac aaaatattaa cgttagcgct tccattgtcg acttccgagg acgagggcct   5100
atttcccatg attccttcat atttgcatat acgatacaag gctgttagag agataattgg   5160
aattaatttg actgtaaaca caaagatatt agtacaaaat acgtgacgta gaaagtaata   5220
atttcttggg tagtttgcag ttttaaaatt atgttttaaa atggactatc atatgcttac   5280
cgtaacttga aagtatttcg atttcttggc tttatatatc ttgtggaaag gacgaaacac   5340
cggagcttca tccagtcgat cacgaatgat cgactggatg aagctccttt tttccgcgga   5400
acgtttacaa ttttatggtg cactctcagt acaatctgct ctgatgccgc atagttaagc   5460
cagccccgac acccgccaac acccgctgac gcgccctgac gggcttgtct gctcccggca   5520
tccgcttaca gacaagctgt gaccgtctcc gggagctgca tgtgtcagag gttttcaccg   5580
tcatcaccga aacgcgcgag acgaaagggc ctcgtgatac gcctattttt ataggttaat   5640
gtcatgaaca ataaaactgt ctgcttacat aaacagtaat acaaggggtg ttatgagcca   5700
tattcaacgg gaaacgtcga ggccgcgatt aaattccaac atggatgctg atttatatgg   5760
gtataaatgg gctcgcgata atgtcgggca atcaggtgcg acaatctatc gcttgtatgg   5820
gaagcccgat gcgccagagt tgtttctgaa acatggcaaa ggtagcgttg ccaatgatgt   5880
tacagatgag atggtcagac taaactggct gacggaattt atgcctcttc cgaccatcaa   5940
gcattttatc cgtactcctg atgatgcatg gttactcacc actgcgatcc ccggaaaaac   6000
agcattccag gtattagaag aatatcctga ttcaggtgaa aatattgttg atgcgctggc   6060
agtgttcctg cgccggttgc attcgattcc tgtttgtaat tgtcctttta acagcgatcg   6120
cgtatttcgt ctcgctcagg cgcaatcacg aatgaataac ggtttggttg atgcgagtga   6180
ttttgatgac gagcgtaatg gctggcctgt tgaacaagtc tggaaagaaa tgcataaact   6240
tttgccattc tcaccggatt cagtcgtcac tcatggtgat ttctcacttg ataaccttat   6300
```

-continued

```
ttttgacgag gggaaattaa taggttgtat tgatgttgga cgagtcggaa tcgcagaccg   6360
ataccaggat cttgccatcc tatggaactg cctcggtgag ttttctcctt cattacagaa   6420
acggcttttt caaaaatatg gtattgataa tcctgatatg aataaattgc agtttcattt   6480
gatgctcgat gagtttttct aatctcatga ccaaaatccc ttaacgtgag ttttcgttcc   6540
actgagcgtc agaccccgta gaaaagatca aaggatcttc ttgagatcct ttttttctgc   6600
gcgtaatctg ctgcttgcaa acaaaaaaac caccgctacc agcggtggtt tgtttgccgg   6660
atcaagagct accaactctt tttccgaagg taactggctt cagcagagcg cagataccaa   6720
atactgtcct tctagtgtag ccgtagttag gccaccactt caagaactct gtagcaccgc   6780
ctacatacct cgctctgcta atcctgttac cagtggctgc tgccagtggc gataagtcgt   6840
gtcttaccgg gttggactca agacgatagt taccggataa ggcgcagcgg tcgggctgaa   6900
cggggggttc gtgcacacag cccagcttgg agcgaacgac ctacaccgaa ctgagatacc   6960
tacagcgtga gctatgagaa agcgccacgc ttcccgaagg gagaaaggcg gacaggtatc   7020
cggtaagcgg cagggtcgga acaggagagc gcacgaggga gcttccaggg ggaaacgcct   7080
ggtatcttta tagtcctgtc gggtttcgcc acctctgact tgagcgtcga tttttgtgat   7140
gctcgtcagg ggggcggagc ctatggaaaa acgccagcaa cgcggccttt ttacggttcc   7200
tggccttttg ctggcctttt gctcacatgt                                   7230
```

<210> SEQ ID NO 38
<211> LENGTH: 8759
<212> TYPE: DNA
<213> ORGANISM: Artificial Sequence
<220> FEATURE:
<223> OTHER INFORMATION: Plasmid

<400> SEQUENCE: 38

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcac gcgtgggccc cagaagcctg gtggttgttt gtccttctca    180
ggggaaaagt gaggcggccc cttggaggaa ggggccgggc agaatgatct aatcggattc    240
caagcagctc aggggattgt ctttttctag caccttcttg ccactcctaa gcgtcctccg    300
tgaccccggc tgggatttag cctggtgctg tgtcagcccc ggctagctaa ctaccggtgc    360
caccatggcc ccaaagaaga agcggaaggt cggtagtact gtgggtactc gaagtggctg    420
cgtaccacac ccgtcgcatg gatccaagcg gaactatatc ctgggactgg acatcggaat    480
tacctccgtg ggatacggca tcatcgatta cgagactagg gacgtgattg acgccggcgt    540
gagactcttt aaggaggcca acgtggaaaa caacgaaggt cgcagatcca agcggggtgc    600
aagacgcctg aagcgccgga ggagacatcg gatacagcgc gtgaagaagc tcctttttcga    660
ctacaacctc ctcactgacc actcggaatt gtccggtatc aacccctacg aagcccgcgt    720
gaaaggcctg agccagaagc tgtccgaaga ggagtttagc gcagccctgc tgcacctggc    780
taagcgaagg ggggtgcaca acgtgaacga ggtggaggag gacactggca acgaactgtc    840
caccaaggag cagatttcac ggaactcgaa ggcgctggaa gagaaatatg tggccgagct    900
gcagctggag aggctcaaga aggatggcga agtccggggg agcatcaatc gcttcaagac    960
ctcggactac gtgaaggaag ccaaacagct gttgaaggtg cagaaggcct accaccaact   1020
ggaccaatca ttcattgaca cttacatcga tctgcttgaa accaggcgca cctactacga   1080
gggtcctgga gaaggcagcc ctttcggatg gaaggacatc aaggagtggt atgagatgct   1140
```

gatgggtcat tgcacctact ttccggaaga actgcgctca gtgaagtacg cgtacaacgc 1200
tgacctctac aacgctctca acgatctgaa caacctcgtg atcacccggg acgagaacga 1260
aaagctggag tactacgaaa agttccagat tatcgaaaac gtgttcaagc agaagaagaa 1320
gcccaccctg aagcagattg caaaggagat ccttgtgaac gaggaggata ttaagggcta 1380
ccgggtcacc tccaccggga aaccagagtt cactaatctc aaggtgtacc atgacattaa 1440
ggacattact gcccgcaagg agatcattga aaacgcggaa ctgctggacc aaatcgcgaa 1500
gatcctgacc atctatcaga gctccgagga tatccaggag gaacttacta acctcaattc 1560
cgagctgacg caggaagaaa tcgagcaaat tagcaacctg aagggttaca ctggaaccca 1620
caacctcagc ttgaaagcga ttaaccttat tttggatgaa ctttggcaca ctaatgacaa 1680
tcagatcgcc attttcaacc ggctgaaact ggtgccgaag aaggtggacc tgagccaaca 1740
gaaggaaatc ccgaccaccc ttgtggacga tttcatcctg tcacctgtgg tgaagaggag 1800
cttcatccag tcgatcaagg tcatcaacgc catcataaag aagtacggcc ttcccaacga 1860
catcatcatc gaactggccc gcgagaagaa ctccaaagat gcccagaaga tgatcaacga 1920
gatgcagaag cgaaaccggc agacgaacga acggatcgag gagatcatcc ggaccaccgg 1980
gaaggaaaac gcgaagtacc tgatcgagaa aatcaagctg catgatatgc aggaagggaa 2040
gtgtctctac tccctggagg ccattccgct ggaggatttg ctgaacaacc ctttcaacta 2100
cgaagtcgat catatcattc ctcgctccgt gtccttcgat aactccttca acaataaggt 2160
cctcgtgaag caggaggaga agtaagtatc aaggttacaa gacaggttta aggagaccaa 2220
tagaaactgg gctcgagaat gcgacgggtg tggtacgcag ccacttcgag tacccacagt 2280
actacctgct tgtcgagaca gagaagactc ttgcgtttct gataggcacc tattggtctt 2340
actgacatcc actttgcctt tctctccaca gctcgaagaa gggcaacaga accccgttcc 2400
agtacctctc gtcgtccgac tccaagatca gctacgaaac tttcaagaag cacattctga 2460
acctggccaa gggcaaaggg agaattagca agaccaagaa ggaatacctc ctggaagaga 2520
gagacatcaa ccgcttctcg gtgcaaaagg atttcatcaa ccgcaacctg gtcgatacca 2580
gatacgccac caggggactg atgaacctcc tgcggtccta cttccgggtc aacaatctgg 2640
acgtgaaggt caaatccatc aacgggggct ttacttcttt cctgcgccgg aagtggaagt 2700
tcaagaagga acggaacaag ggatacaagc accacgctga agatgccctg attattgcca 2760
acgccgactt catctttaag gaatggaaaa agctggacaa ggctaagaag gtcatggaga 2820
accagatgtt cgaagaaaag caggccgagt ccatgcccga aatcgaaacc gagcaggaat 2880
acaaggagat cttcatcaca ccgcaccaaa tcaagcacat caaggacttc aaggattaca 2940
agtacagcca ccgggtggac aagaagccta acagagagct tatcaacgac accctgtact 3000
ccacgcgcaa ggacgacaag ggaaacacat tgatcgtgaa caacctgaac ggactgtatg 3060
acaaggacaa tgacaaactg aagaagctga tcaacaaatc gccggaaaag ctcctgatgt 3120
accatcacga ccctcaaacc taccagaaac tgaagctcat catggagcag tacggcgacg 3180
aaaagaatcc cctgtacaaa tactacgagg agactggaaa ttacctgact aagtactcca 3240
agaaggataa cggccccgtg atcaagaaga ttaagtacta cggaaacaaa ctgaacgcac 3300
atctcgacat caccgatgat tatccaaact cccgcaacaa agtcgtgaag ctctccctca 3360
aaccgtaccg cttcgacgtg tacctggata atggggtgta caagttcgtg accgtgaaga 3420
acctggacgt cattaagaag gaaaactact acgaagtgaa ctcaaagtgc tacgaggaag 3480

-continued

```
ccaagaagct caagaagatc agcaaccagg ccgagttcat cgcatcgttt tacaacaatg   3540
acctcattaa gattaatgga gaactgtaca gagtgatcgg cgtgaacaac gacctcctga   3600
accggattga agtgaacatg atcgatatta cctaccggga gtatctggag aacatgaacg   3660
acaagcgccc accgagaatc atcaaaacta ttgcctccaa gacccaatcc attaagaaat   3720
actccaccga catcctgggc aacctgtacg aggtcaagtc gaagaagcac ccccagatta   3780
tcaagaaggg aaaaaggccg gcggccacga aaaaggccgg ccaggcaaaa aagaaaaagg   3840
cttaagaatt cctagagctc gctgatcagc ctcgaaactt gtttattgca gcttataatg   3900
gttacaaata aagcaatagc atcacaaatt tcacaaataa agcatttttt tcactgcatt   3960
ctagttgtgg tttgtccaaa ctcatcaatg tatcttatca tgtctgtata ccagcaggct   4020
ttcctaggtt cgaacgctga cgtcatcaac ccgctccaag gaatcgcggg cccagtgtca   4080
ctaggcggga acacccagcg cgcgtgcgcc ctggcaggaa gatggctgtg agggacaggg   4140
gagtggcgcc ctgcaatatt tgcatgtcgc tatgtgttct gggaaatcac cataaacgtg   4200
aaatccctat cagtgataga gacttataag ttccctatca gtgatagaga caccgggtgt   4260
ggtacgcagc cactgtttaa gtactctgtg ctggaaacag cacagaatct acttaaacaa   4320
ggcaaaatgc cgtgtttatc tcgtcaactt gttggcgaga tttttcacg tgcggaccga   4380
ggctgcagcg tcgtcctccc taggaacccc tagtgatgga gttggccact ccctctctgc   4440
gcgctcgctc gctcactgag gccgggcgac caaaggtcgc ccgacgcccg ggctttgccc   4500
gggcggcctc agtgagcgag cgagcgcgca gctgcctgca ggggcgcctg atgcggtatt   4560
ttctccttac gcatctgtgc ggtatttcac accgcatacg tcaaagcaac catagtacgc   4620
gccctgtagc ggcgcattaa gcgcggcggg tgtggtggtt acgcgcagcg tgaccgctac   4680
acttgccagc gccttagcgc ccgctccttt cgctttcttc ccttcctttc tcgccacgtt   4740
cgccggcttt ccccgtcaag ctctaaatcg ggggctccct ttagggttcc gatttagtgc   4800
tttacggcac ctcgacccca aaaaacttga tttgggtgat ggttcacgta gtgggccatc   4860
gccctgatag acggtttttc gccctttgac gttggagtcc acgttcttta atagtggact   4920
cttgttccaa actggaacaa cactcaactc tatctcgggc tattcttttg atttataagg   4980
gattttgccg atttcggtct attggttaaa aaatgagctg atttaacaaa aatttaacgc   5040
gaattttaac aaaatattaa cgttagcgct gacattgatt attgactagt tattaatagt   5100
aatcaattac ggggtcatta gttcatagcc catatatgga gttccgcgtt acataactta   5160
cggtaaatgg cccgcctggc tgaccgccca acgacccccg cccattgacg tcaataatga   5220
cgtatgttcc catagtaacg ccaataggga ctttccattg acgtcaatgg gtggagtatt   5280
tacggtaaac tgcccacttg gcagtacatc aagtgtatca tatgccaagt acgcccccta   5340
ttgacgtcaa tgacggtaaa tggcccgcct ggcattatgc ccagtacatg accttatggg   5400
actttcctac ttggcagtac atctacgtat tagtcatcgc tattaccatg gtgatgcggt   5460
tttggcagta catcaatggg cgtggatagc ggtttgactc acggggattt ccaagtctcc   5520
accccattga cgtcaatggg agtttgtttt ggcaccaaaa tcaacgggac tttccaaaat   5580
gtcgtaacaa ctccgcccca ttgacgcaaa tgggcggtag gcgtgtacgg tgggaggtct   5640
atataagcag agctctctgg ctaactagag aacccactgc ttactggctt atcgttaatt   5700
aaccggtgcc accatgatgt cccgccttga taaatcaaaa gtaataaaca gtgctcttga   5760
gcttctcaat gaagttggta tagaagggtt gacgactcgg aaattggcgc aaaaactcgg   5820
tgttgagcag ccaaccttgt attggcatgt taaaaacaaa cgagcactcc tcgacgcttt   5880
```

```
ggcgatagag atgctggaca ggcaccacac gcatttctgt cccctcgaag gagagtcatg   5940
gcaggatttc cttagaaata acgcaaagtc cttcagatgt gcgctgctta gtcaccgcga   6000
cggcgcaaaa gttcatctcg gcactaggcc aaccgagaaa cagtacgaga ctctggagaa   6060
ccaactggcg tttttgtgtc aacagggttt tagtctcgaa aatgcgctct atgctctctc   6120
tgcggttggc catttcaccc tcggatgcgt actggaagat caggagcacc aagtggccaa   6180
agaagaacgg gaaacgccga ctacggacag catgcctccg ttgctccggc aagctataga   6240
gctcttcgat caccaaggcg ctgagccagc tttcttgttc ggattggaac ttattatatg   6300
cgggctcgaa aagcagctta aatgcgagtc aggttaagtt taaacccgct gatcagcctc   6360
gactgtgcct tctagttgcc agccatctgt tgtttgcccc tcccccgtgc cttccttgac   6420
cctggaaggt gccactccca ctgtcctttc ctaataaaat gaggaaattg catcgcattg   6480
tctgagtagg tgtcattcta ttctgggggg tggggtgggg caggacagca agggggagga   6540
ttgggaagac aatagcaggc atgctgggga tgcggtgggc tctatggctt ctgagttagt   6600
ccattgtcga cttccgagga cgagggccta tttcccatga ttccttcata tttgcatata   6660
cgatacaagg ctgttagaga gataattgga attaatttga ctgtaaacac aaagatatta   6720
gtacaaaata cgtgacgtag aaagtaataa tttcttgggt agtttgcagt tttaaaatta   6780
tgttttaaaa tggactatca tatgcttacc gtaacttgaa agtatttcga tttcttggct   6840
ttatatatct tgtggaaagg acgaaacacc ggagcttcat ccagtcgatc acgaatgatc   6900
gactggatga agctcctttt ttccgcggaa cgtttacaat tttatggtgc actctcagta   6960
caatctgctc tgatgccgca tagttaagcc agccccgaca cccgccaaca cccgctgacg   7020
cgccctgacg ggcttgtctg ctcccggcat ccgcttacag acaagctgtg accgtctccg   7080
ggagctgcat gtgtcagagg ttttcaccgt catcaccgaa acgcgcgaga cgaaagggcc   7140
tcgtgatacg cctattttta taggttaatg tcatgaacaa taaaactgtc tgcttacata   7200
aacagtaata caaggggtgt tatgagccat attcaacggg aaacgtcgag gccgcgatta   7260
aattccaaca tggatgctga tttatatggg tataaatggg ctcgcgataa tgtcgggcaa   7320
tcaggtgcga caatctatcg cttgtatggg aagcccgatg cgccagagtt gtttctgaaa   7380
catggcaaag gtagcgttgc caatgatgtt acagatgaga tggtcagact aaactggctg   7440
acggaattta tgcctcttcc gaccatcaag cattttatcc gtactcctga tgatgcatgg   7500
ttactcacca ctgcgatccc cggaaaaaca gcattccagg tattagaaga atatcctgat   7560
tcaggtgaaa atattgttga tgcgctggca gtgttcctgc gccggttgca ttcgattcct   7620
gtttgtaatt gtccttttaa cagcgatcgc gtatttcgtc tcgctcaggc gcaatcacga   7680
atgaataacg gtttggttga tgcgagtgat tttgatgacg agcgtaatgg ctggcctgtt   7740
gaacaagtct ggaaagaaat gcataaactt ttgccattct caccggattc agtcgtcact   7800
catggtgatt tctcacttga taaccttatt tttgacgagg ggaaattaat aggttgtatt   7860
gatgttggac gagtcggaat cgcagaccga taccaggatc ttgccatcct atggaactgc   7920
ctcggtgagt tttctccttc attacagaaa cggctttttc aaaaatatgg tattgataat   7980
cctgatatga ataaattgca gtttcatttg atgctcgatg agtttttcta atctcatgac   8040
caaaatccct taacgtgagt tttcgttcca ctgagcgtca gaccccgtag aaaagatcaa   8100
aggatcttct tgagatcctt tttttctgcg cgtaatctgc tgcttgcaaa caaaaaaacc   8160
accgctacca gcggtggttt gtttgccgga tcaagagcta ccaactcttt ttccgaaggt   8220
```

```
aactggcttc agcagagcgc agataccaaa tactgtcctt ctagtgtagc cgtagttagg   8280

ccaccacttc aagaactctg tagcaccgcc tacatacctc gctctgctaa tcctgttacc   8340

agtggctgct gccagtggcg ataagtcgtg tcttaccggg ttggactcaa gacgatagtt   8400

accggataag gcgcagcggt cgggctgaac ggggggttcg tgcacacagc ccagcttgga   8460

gcgaacgacc tacaccgaac tgagatacct acagcgtgag ctatgagaaa gcgccacgct   8520

tcccgaaggg agaaaggcgg acaggtatcc ggtaagcggc agggtcggaa caggagagcg   8580

cacgagggag cttccagggg gaaacgcctg gtatctttat agtcctgtcg ggtttcgcca   8640

cctctgactt gagcgtcgat ttttgtgatg ctcgtcaggg gggcggagcc tatggaaaaa   8700

cgccagcaac gcggcctttt tacggttcct ggccttttgc tggccttttg ctcacatgt    8759
```

```
<210> SEQ ID NO 39
<211> LENGTH: 6889
<212> TYPE: DNA
<213> ORGANISM: Artificial Sequence
<220> FEATURE:
<223> OTHER INFORMATION: Plasmid

<400> SEQUENCE: 39
```

```
cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccgcac gcgtgggccc cagaagcctg gtggttgttt gtccttctca    180

ggggaaaagt gaggcggccc cttggaggaa ggggccgggc agaatgatct aatcggattc    240

caagcagctc aggggattgt ctttttctag caccttcttg ccactcctaa gcgtcctccg    300

tgaccccggc tgggatttag cctggtgctg tgtcagcccc ggctagctaa ctaccggtgc    360

caccatggcc ccaaagaaga agcggaaggt cggtagtact gtgggtactc gaagtggctg    420

cgtaccacac ccgtcgcatg gatccaagcg gaactatatc ctgggactgg acatcggaat    480

tacctccgtg ggatacggca tcatcgatta cgagactagg gacgtgattg acgccggcgt    540

gagactcttt aaggaggcca acgtggaaaa caacgaaggt cgcagatcca agcggggtgc    600

aagacgcctg aagcgccgga ggagacatcg gatacagcgc gtgaagaagc tccttttcga    660

ctacaacctc ctcactgacc actcggaatt gtccggtatc aacccctacg aagcccgcgt    720

gaaaggcctg agccagaagc tgtccgaaga ggagtttagc gcagccctgc tgcacctggc    780

taagcgaagg ggggtgcaca acgtgaacga ggtggaggag gacactggca acgaactgtc    840

caccaaggag cagatttcac ggaactcgaa ggcgctggaa gagaaatatg tggccgagct    900

gcagctggag aggctcaaga aggatggcga agtccggggg agcatcaatc gcttcaagac    960

ctcggactac gtgaaggaag ccaaacagct gttgaaggtg cagaaggcct accaccaact   1020

ggaccaatca ttcattgaca cttacatcga tctgcttgaa accaggcgca cctactacga   1080

gggtcctgga gaaggcagcc ctttcggatg gaaggacatc aaggagtggt atgagatgct   1140

gatgggtcat tgcacctact ttccggaaga actgcgctca gtgaagtacg cgtacaacgc   1200

tgacctctac aacgctctca acgatctgaa caacctcgtg atcacccggg acgagaacga   1260

aaagctggag tactacgaaa agttccagat tatcgaaaac gtgttcaagc agaagaagaa   1320

gcccaccctg aagcagattg caaaggagat ccttgtgaac gaggaggata ttaagggcta   1380

ccgggtcacc tccaccggga aaccagagtt cactaatctc aaggtgtacc atgacattaa   1440

ggacattact gcccgcaagg agatcattga aaacgcggaa ctgctggacc aaatcgcgaa   1500

gatcctgacc atctatcaga gctccgagga tatccaggag gaacttacta acctcaattc   1560
```

-continued

```
cgagctgacg caggaagaaa tcgagcaaat tagcaacctg aagggttaca ctggaaccca   1620
caacctcagc ttgaaagcga ttaaccttat tttggatgaa ctttggcaca ctaatgacaa   1680
tcagatcgcc attttcaacc ggctgaaact ggtgccgaag aaggtggacc tgagccaaca   1740
gaaggaaatc ccgaccaccc ttgtggacga tttcatcctg tcacctgtgg tgaagaggag   1800
cttcatccag tcgatcaagg tcatcaacgc catcataaag aagtacggcc ttcccaacga   1860
catcatcatc gaactggccc gcgagaagaa ctccaaagat gcccagaaga tgatcaacga   1920
gatgcagaag cgaaaccggc agacgaacga acggatcgag gagatcatcc ggaccaccgg   1980
gaaggaaaac gcgaagtacc tgatcgagaa aatcaagctg catgatatgc aggaagggaa   2040
gtgtctctac tccctggagg ccattccgct ggaggatttg ctgaacaacc ctttcaacta   2100
cgaagtcgat catatcattc ctcgctccgt gtccttcgat aactccttca acaataaggt   2160
cctcgtgaag caggaggaga agtaagtatc aaggttacaa gacaggttta aggagaccaa   2220
tagaaactgg gctcgagaat gcgacgggtg tggtacgcag ccacttcgag tacccacagt   2280
actacctgct tgtcgagaca gagaagactc ttgcgtttct gataggcacc tattggtctt   2340
actgacatcc actttgcctt tctctccaca gctcgaagaa gggcaacaga accccgttcc   2400
agtacctctc gtcgtccgac tccaagatca gctacgaaac tttcaagaag cacattctga   2460
acctggccaa gggcaaaggg agaattagca agaccaagaa ggaatacctc ctggaagaga   2520
gagacatcaa ccgcttctcg gtgcaaaagg atttcatcaa ccgcaacctg gtcgatacca   2580
gatacgccac caggggactg atgaacctcc tgcggtccta cttccgggtc aacaatctgg   2640
acgtgaaggt caaatccatc aacgggggct ttacttcttt cctgcgccgg aagtggaagt   2700
tcaagaagga acggaacaag ggatacaagc accacgctga agatgccctg attattgcca   2760
acgccgactt catctttaag gaatggaaaa agctggacaa ggctaagaag gtcatggaga   2820
accagatgtt cgaagaaaag caggccgagt ccatgcccga aatcgaaacc gagcaggaat   2880
acaaggagat cttcatcaca ccgcaccaaa tcaagcacat caaggacttc aaggattaca   2940
agtacagcca ccgggtggac aagaagccta acagagagct tatcaacgac accctgtact   3000
ccacgcgcaa ggacgacaag ggaaacacat tgatcgtgaa caacctgaac ggactgtatg   3060
acaaggacaa tgacaaactg aagaagctga tcaacaaatc gccggaaaag ctcctgatgt   3120
accatcacga ccctcaaacc taccagaaac tgaagctcat catggagcag tacggcgacg   3180
aaaagaatcc cctgtacaaa tactacgagg agactggaaa ttacctgact aagtactcca   3240
agaaggataa cggccccgtg atcaagaaga ttaagtacta cggaaacaaa ctgaacgcac   3300
atctcgacat caccgatgat tatccaaact cccgcaacaa agtcgtgaag ctctccctca   3360
aaccgtaccg cttcgacgtg tacctggata atggggtgta caagttcgtg accgtgaaga   3420
acctggacgt cattaagaag gaaaactact acgaagtgaa ctcaaagtgc tacgaggaag   3480
ccaagaagct caagaagatc agcaaccagg ccgagttcat cgcatcgttt tacaacaatg   3540
acctcattaa gattaatgga gaactgtaca gagtgatcgg cgtgaacaac gacctcctga   3600
accggattga agtgaacatg atcgatatta cctaccggga gtatctggag aacatgaacg   3660
acaagcgccc accgagaatc atcaaaacta ttgcctccaa gacccaatcc attaagaaat   3720
actccaccga catcctgggc aacctgtacg aggtcaagtc gaagaagcac ccccagatta   3780
tcaagaaggg aaaaaggccg gcggccacga aaaaggccgg ccaggcaaaa aagaaaaagg   3840
cttaagaatt cctagagctc gctgatcagc ctcgaaactt gtttattgca gcttataatg   3900
```

-continued

```
gttacaaata aagcaatagc atcacaaatt tcacaaataa agcatttttt tcactgcatt   3960
ctagttgtgg tttgtccaaa ctcatcaatg tatcttatca tgtctgtata ccagcaggct   4020
ttcctaggtt cgaacgctga cgtcatcaac ccgctccaag gaatcgcggg cccagtgtca   4080
ctaggcggga acacccagcg cgcgtgcgcc ctggcaggaa gatggctgtg agggacaggg   4140
gagtggcgcc ctgcaatatt tgcatgtcgc tatgtgttct gggaaatcac cataaacgtg   4200
aaatccctat cagtgataga gacttataag ttccctatca gtgatagaga caccgggtgt   4260
ggtacgcagc cactgtttaa gtactctgtg ctggaaacag cacagaatct acttaaacaa   4320
ggcaaaatgc cgtgtttatc tcgtcaactt gttggcgaga tttttcacg tgcggaccga   4380
ggctgcagcg tcgtcctccc taggaacccc tagtgatgga gttggccact ccctctctgc   4440
gcgctcgctc gctcactgag gccgggcgac caaaggtcgc ccgacgcccg ggctttgccc   4500
gggcggcctc agtgagcgag cgagcgcgca gctgcctgca ggggcgcctg atgcggtatt   4560
ttctccttac gcatctgtgc ggtatttcac accgcatacg tcaaagcaac catagtacgc   4620
gccctgtagc ggcgcattaa gcgcggcggg tgtggtggtt acgcgcagcg tgaccgctac   4680
acttgccagc gccctagcgc ccgctccttt cgctttcttc ccttcctttc tcgccacgtt   4740
cgccggcttt ccccgtcaag ctctaaatcg ggggctccct ttagggttcc gatttagtgc   4800
tttacggcac ctcgacccca aaaaacttga tttgggtgat ggttcacgta gtgggccatc   4860
gccctgatag acggtttttc gccctttgac gttggagtcc acgttcttta atagtggact   4920
cttgttccaa actggaacaa cactcaaccc tatctcgggc tattcttttg atttataagg   4980
gattttgccg atttcggcct attggttaaa aaatgagctg atttaacaaa aatttaacgc   5040
gaattttaac aaaatattaa cgtttacaat tttatggtgc actctcagta caatctgctc   5100
tgatgccgca tagttaagcc agccccgaca cccgccaaca cccgctgacg cgccctgacg   5160
ggcttgtctg ctcccggcat ccgcttacag acaagctgtg accgtctccg ggagctgcat   5220
gtgtcagagg ttttcaccgt catcaccgaa acgcgcgaga cgaaagggcc tcgtgatacg   5280
cctattttta taggttaatg tcatgaacaa taaaactgtc tgcttacata aacagtaata   5340
caaggggtgt tatgagccat attcaacggg aaacgtcgag gccgcgatta aattccaaca   5400
tggatgctga tttatatggg tataaatggg ctcgcgataa tgtcgggcaa tcaggtgcga   5460
caatctatcg cttgtatggg aagcccgatg cgccagagtt gtttctgaaa catggcaaag   5520
gtagcgttgc caatgatgtt acagatgaga tggtcagact aaactggctg acggaattta   5580
tgcctcttcc gaccatcaag cattttatcc gtactcctga tgatgcatgg ttactcacca   5640
ctgcgatccc cggaaaaaca gcattccagg tattagaaga atatcctgat tcaggtgaaa   5700
atattgttga tgcgctggca gtgttcctgc gccggttgca ttcgattcct gtttgtaatt   5760
gtccttttaa cagcgatcgc gtatttcgtc tcgctcaggc gcaatcacga atgaataacg   5820
gtttggttga tgcgagtgat tttgatgacg agcgtaatgg ctggcctgtt gaacaagtct   5880
ggaaagaaat gcataaactt ttgccattct caccggattc agtcgtcact catggtgatt   5940
tctcacttga taaccttatt tttgacgagg ggaaattaat aggttgtatt gatgttggac   6000
gagtcggaat cgcagaccga taccaggatc ttgccatcct atggaactgc ctcggtgagt   6060
tttctccttc attacagaaa cggctttttc aaaaatatgg tattgataat cctgatatga   6120
ataaattgca gtttcatttg atgctcgatg agtttttcta atctcatgac caaaatccct   6180
taacgtgagt tttcgttcca ctgagcgtca gaccccgtag aaaagatcaa aggatcttct   6240
tgagatcctt tttttctgcg cgtaatctgc tgcttgcaaa caaaaaaacc accgctacca   6300
```

gcggtggttt gtttgccgga tcaagagcta ccaactcttt ttccgaaggt aactggcttc 6360
agcagagcgc agataccaaa tactgtcctt ctagtgtagc cgtagttagg ccaccacttc 6420
aagaactctg tagcaccgcc tacatacctc gctctgctaa tcctgttacc agtggctgct 6480
gccagtggcg ataagtcgtg tcttaccggg ttggactcaa gacgatagtt accggataag 6540
gcgcagcggt cgggctgaac ggggggttcg tgcacacagc ccagcttgga gcgaacgacc 6600
tacaccgaac tgagatacct acagcgtgag ctatgagaaa gcgccacgct tcccgaaggg 6660
agaaaggcgg acaggtatcc ggtaagcggc agggtcggaa caggagagcg cacgagggag 6720
cttccagggg gaaacgcctg gtatctttat agtcctgtcg ggtttcgcca cctctgactt 6780
gagcgtcgat ttttgtgatg ctcgtcaggg gggcggagcc tatggaaaaa cgccagcaac 6840
gcggcctttt tacggttcct ggccttttgc tggccttttg ctcacatgt 6889

<210> SEQ ID NO 40
<211> LENGTH: 6901
<212> TYPE: DNA
<213> ORGANISM: Artificial Sequence
<220> FEATURE:
<223> OTHER INFORMATION: Plasmid

<400> SEQUENCE: 40
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgctccg gtgcccgtca gtgggcagag cgcacatcgc 180
ccacagtccc cgagaagttg gggggagggg tcggcaattg aaccggtgcc tagagaaggt 240
ggcgcggggt aaactgggaa agtgatgtcg tgtactggct ccgccttttt cccgagggtg 300
ggggagaacc gtatataagt gcagtagtcg ccgtgaacgt tctttttcgc aacgctagct 360
aactaccggt gccaccatgg ccccaaagaa gaagcggaag gtcggtagta ctgtgggtac 420
tcgaagtggc tgcgtaccac acccgtcgca tggatccaag cggaactata tcctgggact 480
ggacatcgga attacctccg tgggatacgg catcatcgat tacgagacta gggacgtgat 540
tgacgccggc gtgagactct ttaaggaggc caacgtggaa aacaacgaag gtcgcagatc 600
caagcggggt gcaagacgcc tgaagcgccg gaggagacat cggatacagc gcgtgaagaa 660
gctccttttc gactacaacc tcctcactga ccactcggaa ttgtccggta tcaaccccta 720
cgaagcccgc gtgaaaggcc tgagccagaa gctgtccgaa gaggagttta gcgcagccct 780
gctgcacctg gctaagcgaa ggggggtgca caacgtgaac gaggtggagg aggacactgg 840
caacgaactg tccaccaagg agcagatttc acggaactcg aaggcgctgg aagagaaata 900
tgtggccgag ctgcagctgg agaggctcaa gaaggatggc gaagtccggg ggagcatcaa 960
tcgcttcaag acctcggact acgtgaagga agccaaacag ctgttgaagg tgcagaaggc 1020
ctaccaccaa ctggaccaat cattcattga cacttacatc gatctgcttg aaaccaggcg 1080
cacctactac gagggtcctg gagaaggcag cccctttcgga tggaaggaca tcaaggagtg 1140
gtatgagatg ctgatgggtc attgcaccta ctttccggaa gaactgcgct cagtgaagta 1200
cgcgtacaac gctgacctct acaacgctct caacgatctg aacaacctcg tgatcacccg 1260
ggacgagaac gaaaagctgg agtactacga aaagttccag attatcgaaa acgtgttcaa 1320
gcagaagaag aagcccaccc tgaagcagat tgcaaaggag atccttgtga acgaggagga 1380
tattaagggc taccgggtca cctccaccgg gaaaccagag ttcactaatc tcaaggtgta 1440

-continued

```
ccatgacatt aaggacatta ctgcccgcaa ggagatcatt gaaaacgcgg aactgctgga   1500
ccaaatcgcg aagatcctga ccatctatca gagctccgag gatatccagg aggaacttac   1560
taacctcaat tccgagctga cgcaggaaga aatcgagcaa attagcaacc tgaagggtta   1620
cactggaacc cacaacctca gcttgaaagc gattaacctt attttggatg aactttggca   1680
cactaatgac aatcagatcg ccattttcaa ccggctgaaa ctggtgccga agaaggtgga   1740
cctgagccaa cagaaggaaa tcccgaccac ccttgtggac gatttcatcc tgtcacctgt   1800
ggtgaagagg agcttcatcc agtcgatcaa ggtcatcaac gccatcataa agaagtacgg   1860
ccttcccaac gacatcatca tcgaactggc ccgcgagaag aactccaaag atgcccagaa   1920
gatgatcaac gagatgcaga agcgaaaccg gcagacgaac gaacggatcg aggagatcat   1980
ccggaccacc gggaaggaaa acgcgaagta cctgatcgag aaaatcaagc tgcatgatat   2040
gcaggaaggg aagtgtctct actccctgga ggccattccg ctggaggatt tgctgaacaa   2100
ccctttcaac tacgaagtcg atcatatcat tcctcgctcc gtgtccttcg ataactcctt   2160
caacaataag gtcctcgtga agcaggagga gaagtaagta tcaaggttac aagacaggtt   2220
taaggagacc aatagaaact gggctcgaga atgcgacggg tgtggtacgc agccacttcg   2280
agtacccaca gtactacctg cttgtcgaga cagagaagac tcttgcgttt ctgataggca   2340
cctattggtc ttactgacat ccactttgcc tttctctcca cagctcgaag aagggcaaca   2400
gaaccccgtt ccagtacctc tcgtcgtccg actccaagat cagctacgaa actttcaaga   2460
agcacattct gaacctggcc aagggcaaag ggagaattag caagaccaag aaggaatacc   2520
tcctggaaga gagagacatc aaccgcttct cggtgcaaaa ggatttcatc aaccgcaacc   2580
tggtcgatac cagatacgcc accaggggac tgatgaacct cctgcggtcc tacttccggg   2640
tcaacaatct ggacgtgaag gtcaaatcca tcaacggggg ctttacttct ttcctgcgcc   2700
ggaagtggaa gttcaagaag gaacggaaca agggatacaa gcaccacgct gaagatgccc   2760
tgattattgc caacgccgac ttcatcttta aggaatggaa aaagctggac aaggctaaga   2820
aggtcatgga gaaccagatg ttcgaagaaa agcaggccga gtccatgccc gaaatcgaaa   2880
ccgagcagga atacaaggag atcttcatca caccgcacca aatcaagcac atcaaggact   2940
tcaaggatta caagtacagc caccgggtgg acaagaagcc taacagagag cttatcaacg   3000
acaccctgta ctccacgcgc aaggacgaca agggaaacac attgatcgtg aacaacctga   3060
acggactgta tgacaaggac aatgacaaac tgaagaagct gatcaacaaa tcgccggaaa   3120
agctcctgat gtaccatcac gaccctcaaa cctaccagaa actgaagctc atcatggagc   3180
agtacggcga cgaaaagaat cccctgtaca aatactacga ggagactgga aattacctga   3240
ctaagtactc caagaaggat aacggccccg tgatcaagaa gattaagtac tacggaaaca   3300
aactgaacgc acatctcgac atcaccgatg attatccaaa ctcccgcaac aaagtcgtga   3360
agctctccct caaaccgtac cgcttcgacg tgtacctgga taatggggtg tacaagttcg   3420
tgaccgtgaa gaacctggac gtcattaaga aggaaaacta ctacgaagtg aactcaaagt   3480
gctacgagga agccaagaag ctcaagaaga tcagcaacca ggccgagttc atcgcatcgt   3540
tttacaacaa tgacctcatt aagattaatg gagaactgta cagagtgatc ggcgtgaaca   3600
acgacctcct gaaccggatt gaagtgaaca tgatcgatat tacctaccgg gagtatctgg   3660
agaacatgaa cgacaagcgc ccaccgagaa tcatcaaaac tattgcctcc aagacccaat   3720
ccattaagaa atactccacc gacatcctgg gcaacctgta cgaggtcaag tcgaagaagc   3780
acccccagat tatcaagaag ggaaaaaggc cggcggccac gaaaaaggcc ggccaggcaa   3840
```

```
aaaagaaaaa ggcttaagaa ttcctagagc tcgctgatca gcctcgaaac ttgtttattg   3900
cagcttataa tggttacaaa taaagcaata gcatcacaaa tttcacaaat aaagcatttt   3960
tttcactgca ttctagttgt ggtttgtcca aactcatcaa tgtatcttat catgtctgta   4020
taccagcagg ctttcctagg ttcgaacgct gacgtcatca acccgctcca aggaatcgcg   4080
ggcccagtgt cactaggcgg gaacacccag cgcgcgtgcg ccctggcagg aagatggctg   4140
tgagggacag gggagtggcg ccctgcaata tttgcatgtc gctatgtgtt ctgggaaatc   4200
accataaacg tgaaatccct atcagtgata gagacttata agttccctat cagtgataga   4260
gacaccgggt gtggtacgca gccactgttt aagtactctg tgctggaaac agcacagaat   4320
ctacttaaac aaggcaaaat gccgtgttta tctcgtcaac ttgttggcga gatttttca   4380
cgtgcggacc gaggctgcag cgtcgtcctc cctaggaacc cctagtgatg gagttggcca   4440
ctccctctct gcgcgctcgc tcgctcactg aggccgggcg accaaaggtc gcccgacgcc   4500
cgggctttgc ccgggcggcc tcagtgagcg agcgagcgcg cagctgcctg caggggcgcc   4560
tgatgcggta ttttctcctt acgcatctgt gcggtatttc acaccgcata cgtcaaagca   4620
accatagtac gcgccctgta gcggcgcatt aagcgcggcg ggtgtggtgg ttacgcgcag   4680
cgtgaccgct acacttgcca gcgccctagc gcccgctcct ttcgctttct tcccttcctt   4740
tctcgccacg ttcgccggct ttccccgtca agctctaaat cgggggctcc ctttagggtt   4800
ccgatttagt gctttacggc acctcgaccc caaaaaactt gatttgggtg atggttcacg   4860
tagtgggcca tcgccctgat agacggtttt tcgccctttg acgttggagt ccacgttctt   4920
taatagtgga ctcttgttcc aaactggaac aacactcaac cctatctcgg gctattcttt   4980
tgatttataa gggattttgc cgatttcggc ctattggtta aaaaatgagc tgatttaaca   5040
aaaatttaac gcgaatttta acaaaatatt aacgtttaca attttatggt gcactctcag   5100
tacaatctgc tctgatgccg catagttaag ccagccccga cacccgccaa cacccgctga   5160
cgcgccctga cgggcttgtc tgctcccggc atccgcttac agacaagctg tgaccgtctc   5220
cgggagctgc atgtgtcaga ggttttcacc gtcatcaccg aaacgcgcga gacgaaaggg   5280
cctcgtgata cgcctatttt tataggttaa tgtcatgaac aataaaactg tctgcttaca   5340
taaacagtaa tacaaggggt gttatgagcc atattcaacg ggaaacgtcg aggccgcgat   5400
taaattccaa catggatgct gatttatatg ggtataaatg ggctcgcgat aatgtcgggc   5460
aatcaggtgc gacaatctat cgcttgtatg ggaagcccga tgcgccagag ttgtttctga   5520
aacatggcaa aggtagcgtt gccaatgatg ttacagatga gatggtcaga ctaaactggc   5580
tgacggaatt tatgcctctt ccgaccatca agcattttat ccgtactcct gatgatgcat   5640
ggttactcac cactgcgatc cccggaaaaa cagcattcca ggtattagaa gaatatcctg   5700
attcaggtga aaatattgtt gatgcgctgg cagtgttcct gcgccggttg cattcgattc   5760
ctgtttgtaa ttgtcctttt aacagcgatc gcgtatttcg tctcgctcag gcgcaatcac   5820
gaatgaataa cggtttggtt gatgcgagtg attttgatga cgagcgtaat ggctggcctg   5880
ttgaacaagt ctggaaagaa atgcataaac ttttgccatt ctcaccggat tcagtcgtca   5940
ctcatggtga tttctcactt gataacctta tttttgacga ggggaaatta ataggttgta   6000
ttgatgttgg acgagtcgga atcgcagacc gataccagga tcttgccatc ctatggaact   6060
gcctcggtga gttttctcct tcattacaga aacggctttt tcaaaaatat ggtattgata   6120
atcctgatat gaataaattg cagtttcatt tgatgctcga tgagtttttc taatctcatg   6180
```

-continued

```
accaaaatcc cttaacgtga gttttcgttc cactgagcgt cagaccccgt agaaaagatc   6240

aaaggatctt cttgagatcc tttttttctg cgcgtaatct gctgcttgca aacaaaaaaa   6300

ccaccgctac cagcggtggt ttgtttgccg gatcaagagc taccaactct ttttccgaag   6360

gtaactggct tcagcagagc gcagatacca aatactgtcc ttctagtgta gccgtagtta   6420

ggccaccact tcaagaactc tgtagcaccg cctacatacc tcgctctgct aatcctgtta   6480

ccagtggctg ctgccagtgg cgataagtcg tgtcttaccg ggttggactc aagacgatag   6540

ttaccggata aggcgcagcg gtcgggctga acggggggtt cgtgcacaca gcccagcttg   6600

gagcgaacga cctacaccga actgagatac ctacagcgtg agctatgaga aagcgccacg   6660

cttcccgaag ggagaaaggc ggacaggtat ccggtaagcg gcagggtcgg aacaggagag   6720

cgcacgaggg agcttccagg gggaaacgcc tggtatcttt atagtcctgt cgggtttcgc   6780

cacctctgac ttgagcgtcg atttttgtga tgctcgtcag gggggcggag cctatggaaa   6840

aacgccagca acgcggcctt tttacggttc ctggcctttt gctggccttt tgctcacatg   6900

t                                                                   6901
```

```
<210> SEQ ID NO 41
<211> LENGTH: 8469
<212> TYPE: DNA
<213> ORGANISM: Artificial Sequence
<220> FEATURE:
<223> OTHER INFORMATION: Plasmid

<400> SEQUENCE: 41
```

```
cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccgcac gcgtgctccg gtgcccgtca gtgggcagag cgcacatcgc    180

ccacagtccc cgagaagttg gggggagggg tcggcaattg aaccggtgcc tagagaaggt    240

ggcgcggggt aaactgggaa agtgatgtcg tgtactggct ccgccttttt cccgagggtg    300

ggggagaacc gtatataagt gcagtagtcg ccgtgaacgt tctttttcgc aacgctagct    360

aactaccggt gccaccatgg ccccaaagaa gaagcggaag gtcggtagta ctgtgggtac    420

tcgaagtggc tgcgtaccac acccgtcgca tggatccaag cggaactata tcctgggact    480

ggacatcgga attacctccg tgggatacgg catcatcgat tacgagacta gggacgtgat    540

tgacgccggc gtgagactct ttaaggaggc caacgtggaa aacaacgaag gtcgcagatc    600

caagcggggt gcaagacgcc tgaagcgccg gaggagacat cggatacagc gcgtgaagaa    660

gctccttttc gactacaacc tcctcactga ccactcggaa ttgtccggta tcaaccccta    720

cgaagcccgc gtgaaaggcc tgagccagaa gctgtccgaa gaggagttta gcgcagccct    780

gctgcacctg gctaagcgaa gggggggtgca caacgtgaac gaggtggagg aggacactgg    840

caacgaactg tccaccaagg agcagatttc acggaactcg aaggcgctgg aagagaaata    900

tgtggccgag ctgcagctgg agaggctcaa gaaggatggc gaagtccggg ggagcatcaa    960

tcgcttcaag acctcggact acgtgaagga agccaaacag ctgttgaagg tgcagaaggc   1020

ctaccaccaa ctggaccaat cattcattga cacttacatc gatctgcttg aaaccaggcg   1080

cacctactac gagggtcctg gagaaggcag ccctttcgga tggaaggaca tcaaggagtg   1140

gtatgagatg ctgatgggtc attgcaccta ctttccggaa gaactgcgct cagtgaagta   1200

cgcgtacaac gctgacctct acaacgctct caacgatctg aacaacctcg tgatcacccg   1260

ggacgagaac gaaaagctgg agtactacga aaagttccag attatcgaaa acgtgttcaa   1320
```

```
gcagaagaag aagcccaccc tgaagcagat tgcaaaggag atccttgtga acgaggagga   1380
tattaagggc taccgggtca cctccaccgg gaaaccagag ttcactaatc tcaaggtgta   1440
ccatgacatt aaggacatta ctgcccgcaa ggagatcatt gaaaacgcgg aactgctgga   1500
ccaaatcgcg aagatcctga ccatctatca gagctccgag gatatccagg aggaacttac   1560
taacctcaat tccgagctga cgcaggaaga aatcgagcaa attagcaacc tgaagggtta   1620
cactggaacc cacaacctca gcttgaaagc gattaacctt attttggatg aactttggca   1680
cactaatgac aatcagatcg ccattttcaa ccggctgaaa ctggtgccga agaaggtgga   1740
cctgagccaa cagaaggaaa tcccgaccac ccttgtggac gatttcatcc tgtcacctgt   1800
ggtgaagagg agcttcatcc agtcgatcaa ggtcatcaac gccatcataa agaagtacgg   1860
ccttcccaac gacatcatca tcgaactggc ccgcgagaag aactccaaag atgcccagaa   1920
gatgatcaac gagatgcaga agcgaaaccg gcagacgaac gaacggatcg aggagatcat   1980
ccggaccacc gggaaggaaa acgcgaagta cctgatcgag aaaatcaagc tgcatgatat   2040
gcaggaaggg aagtgtctct actccctgga ggccattccg ctggaggatt tgctgaacaa   2100
ccctttcaac tacgaagtcg atcatatcat tcctcgctcc gtgtccttcg ataactcctt   2160
caacaataag gtcctcgtga agcaggagga gaagtaagta tcaaggttac aagacaggtt   2220
taaggagacc aatagaaact gggctcgaga atgcgacggg tgtggtacgc agccacttcg   2280
agtacccaca gtactacctg cttgtcgaga cagagaagac tcttgcgttt ctgataggca   2340
cctattggtc ttactgacat ccactttgcc tttctctcca cagctcgaag aagggcaaca   2400
gaaccccgtt ccagtacctc tcgtcgtccg actccaagat cagctacgaa actttcaaga   2460
agcacattct gaacctggcc aagggcaaag ggagaattag caagaccaag aaggaatacc   2520
tcctggaaga gagagacatc aaccgcttct cggtgcaaaa ggatttcatc aaccgcaacc   2580
tggtcgatac cagatacgcc accaggggac tgatgaacct cctgcggtcc tacttccggg   2640
tcaacaatct ggacgtgaag gtcaaatcca tcaacggggg ctttacttct ttcctgcgcc   2700
ggaagtggaa gttcaagaag gaacggaaca agggatacaa gcaccacgct gaagatgccc   2760
tgattattgc caacgccgac ttcatcttta aggaatggaa aaagctggac aaggctaaga   2820
aggtcatgga gaaccagatg ttcgaagaaa agcaggccga gtccatgccc gaaatcgaaa   2880
ccgagcagga atacaaggag atcttcatca caccgcacca aatcaagcac atcaaggact   2940
tcaaggatta caagtacagc caccgggtgg acaagaagcc taacagagag cttatcaacg   3000
acaccctgta ctccacgcgc aaggacgaca agggaaacac attgatcgtg aacaacctga   3060
acggactgta tgacaaggac aatgacaaac tgaagaagct gatcaacaaa tcgccggaaa   3120
agctcctgat gtaccatcac gaccctcaaa cctaccagaa actgaagctc atcatggagc   3180
agtacggcga cgaaaagaat cccctgtaca aatactacga ggagactgga aattacctga   3240
ctaagtactc caagaaggat aacggccccg tgatcaagaa gattaagtac tacggaaaca   3300
aactgaacgc acatctcgac atcaccgatg attatccaaa ctcccgcaac aaagtcgtga   3360
agctctccct caaaccgtac cgcttcgacg tgtacctgga taatggggtg tacaagttcg   3420
tgaccgtgaa gaacctggac gtcattaaga aggaaaacta ctacgaagtg aactcaaagt   3480
gctacgagga agccaagaag ctcaagaaga tcagcaacca ggccgagttc atcgcatcgt   3540
tttacaacaa tgacctcatt aagattaatg gagaactgta cagagtgatc ggcgtgaaca   3600
acgacctcct gaaccggatt gaagtgaaca tgatcgatat tacctaccgg gagtatctgg   3660
```

-continued

```
agaacatgaa cgacaagcgc ccaccgagaa tcatcaaaac tattgcctcc aagacccaat   3720
ccattaagaa atactccacc gacatcctgg gcaacctgta cgaggtcaag tcgaagaagc   3780
acccccagat tatcaagaag ggaaaaaggc cggcggccac gaaaaaggcc ggccaggcaa   3840
aaaagaaaaa ggcttaagaa ttcctagagc tcgctgatca gcctcgaaac ttgtttattg   3900
cagcttataa tggttacaaa taaagcaata gcatcacaaa tttcacaaat aaagcatttt   3960
tttcactgca ttctagttgt ggtttgtcca aactcatcaa tgtatcttat catgtctgta   4020
taccagcagg ctttcctagg ttcgaacgct gacgtcatca acccgctcca aggaatcgcg   4080
ggcccagtgt cactaggcgg gaacacccag cgcgcgtgcg ccctggcagg aagatggctg   4140
tgagggacag gggagtggcg ccctgcaata tttgcatgtc gctatgtgtt ctgggaaatc   4200
accataaacg tgaaatccct atcagtgata gagacttata agttccctat cagtgataga   4260
gacaccgggt gtggtacgca gccactgttt aagtactctg tgctggaaac agcacagaat   4320
ctacttaaac aaggcaaaat gccgtgttta tctcgtcaac ttgttggcga gatttttca    4380
cgtgcggacc gaggctgcag cgtcgtcctc cctaggaacc cctagtgatg gagttggcca   4440
ctccctctct gcgcgctcgc tcgctcactg aggccgggcg accaaaggtc gcccgacgcc   4500
cgggctttgc ccgggcggcc tcagtgagcg agcgagcgcg cagctgcctg caggggcgcc   4560
tgatgcggta ttttctcctt acgcatctgt gcggtatttc acaccgcata cgtcaaagca   4620
accatagtac gcgccctgta gcggcgcatt aagcgcggcg ggtgtggtgg ttacgcgcag   4680
cgtgaccgct acacttgcca gcgccttagc gcccgctcct ttcgctttct tcccttcctt   4740
tctcgccacg ttcgccggct ttccccgtca agctctaaat cgggggctcc ctttagggtt   4800
ccgatttagt gctttacggc acctcgaccc caaaaaactt gatttgggtg atggttcacg   4860
tagtgggcca tcgccctgat agacggtttt tcgccctttg acgttggagt ccacgttctt   4920
taatagtgga ctcttgttcc aaactggaac aacactcaac tctatctcgg gctattcttt   4980
tgatttataa gggattttgc cgatttcggt ctattggtta aaaaatgagc tgatttaaca   5040
aaaatttaac gcgaatttta acaaaatatt aacgttagcg ctgacattga ttattgacta   5100
gttattaata gtaatcaatt acggggtcat tagttcatag cccatatatg gagttccgcg   5160
ttacataact tacggtaaat ggcccgcctg gctgaccgcc caacgacccc cgcccattga   5220
cgtcaataat gacgtatgtt cccatagtaa cgccaatagg gactttccat tgacgtcaat   5280
gggtggagta tttacggtaa actgcccact tggcagtaca tcaagtgtat catatgccaa   5340
gtacgccccc tattgacgtc aatgacggta aatggcccgc ctggcattat gcccagtaca   5400
tgaccttatg ggactttcct acttggcagt acatctacgt attagtcatc gctattacca   5460
tggtgatgcg gttttggcag tacatcaatg ggcgtggata gcggtttgac tcacggggat   5520
ttccaagtct ccaccccatt gacgtcaatg ggagtttgtt ttggcaccaa aatcaacggg   5580
actttccaaa atgtcgtaac aactccgccc cattgacgca aatgggcggt aggcgtgtac   5640
ggtgggaggt ctatataagc agagctctct ggctaactag agaacccact gcttactggc   5700
ttatcgttaa ttaaccggtg ccaccatgat gtcccgcctt gataaatcaa aagtaataaa   5760
cagtgctctt gagcttctca atgaagttgg tatagaaggg ttgacgactc ggaaattggc   5820
gcaaaaactc ggtgttgagc agccaacctt gtattggcat gttaaaaaca aacgagcact   5880
cctcgacgct ttggcgatag agatgctgga caggcaccac acgcatttct gtcccctcga   5940
aggagagtca tggcaggatt tccttagaaa taacgcaaag tccttcagat gtgcgctgct   6000
tagtcaccgc gacggcgcaa aagttcatct cggcactagg ccaaccgaga aacagtacga   6060
```

```
gactctggag aaccaactgg cgtttttgtg tcaacagggt tttagtctcg aaaatgcgct   6120
ctatgctctc tctgcggttg gccatttcac cctcggatgc gtactggaag atcaggagca   6180
ccaagtggcc aaagaagaac gggaaacgcc gactacggac agcatgcctc cgttgctccg   6240
gcaagctata gagctcttcg atcaccaagg cgctgagcca gctttcttgt tcggattgga   6300
acttattata tgcgggctcg aaaagcagct taaatgcgag tcaggttaag tttaaacccg   6360
ctgatcagcc tcgactgtgc cttctagttg ccagccatct gttgtttgcc cctcccccgt   6420
gccttccttg accctggaag gtgccactcc cactgtcctt tcctaataaa atgaggaaat   6480
tgcatcgcat tgtctgagta ggtgtcattc tattctgggg ggtggggtgg ggcaggacag   6540
caagggggag gattgggaag acaatagcag gcatgctggg gatgcggtgg gctctatggc   6600
ttctgagtta gtccattgtc gacttccgag gaccgcggaa cgtttacaat tttatggtgc   6660
actctcagta caatctgctc tgatgccgca tagttaagcc agccccgaca cccgccaaca   6720
cccgctgacg cgccctgacg ggcttgtctg ctcccggcat ccgcttacag acaagctgtg   6780
accgtctccg ggagctgcat gtgtcagagg ttttcaccgt catcaccgaa acgcgcgaga   6840
cgaaagggcc tcgtgatacg cctattttta taggttaatg tcatgaacaa taaaactgtc   6900
tgcttacata aacagtaata caaggggtgt tatgagccat attcaacggg aaacgtcgag   6960
gccgcgatta aattccaaca tggatgctga tttatatggg tataaatggg ctcgcgataa   7020
tgtcgggcaa tcaggtgcga caatctatcg cttgtatggg aagcccgatg cgccagagtt   7080
gtttctgaaa catggcaaag gtagcgttgc caatgatgtt acagatgaga tggtcagact   7140
aaactggctg acggaattta tgcctcttcc gaccatcaag cattttatcc gtactcctga   7200
tgatgcatgg ttactcacca ctgcgatccc cggaaaaaca gcattccagg tattagaaga   7260
atatcctgat tcaggtgaaa atattgttga tgcgctggca gtgttcctgc gccggttgca   7320
ttcgattcct gtttgtaatt gtccttttaa cagcgatcgc gtatttcgtc tcgctcaggc   7380
gcaatcacga atgaataacg gtttggttga tgcgagtgat tttgatgacg agcgtaatgg   7440
ctggcctgtt gaacaagtct ggaaagaaat gcataaactt ttgccattct caccggattc   7500
agtcgtcact catggtgatt tctcacttga taaccttatt tttgacgagg ggaaattaat   7560
aggttgtatt gatgttggac gagtcggaat cgcagaccga taccaggatc ttgccatcct   7620
atggaactgc ctcggtgagt tttctccttc attacagaaa cggctttttc aaaaatatgg   7680
tattgataat cctgatatga ataaattgca gtttcatttg atgctcgatg agtttttcta   7740
atctcatgac caaaatccct taacgtgagt tttcgttcca ctgagcgtca gaccccgtag   7800
aaaagatcaa aggatcttct tgagatcctt tttttctgcg cgtaatctgc tgcttgcaaa   7860
caaaaaaacc accgctacca gcggtggttt gtttgccgga tcaagagcta ccaactcttt   7920
ttccgaaggt aactggcttc agcagagcgc agataccaaa tactgtcctt ctagtgtagc   7980
cgtagttagg ccaccacttc aagaactctg tagcaccgcc tacatacctc gctctgctaa   8040
tcctgttacc agtggctgct gccagtggcg ataagtcgtg tcttaccggg ttggactcaa   8100
gacgatagtt accggataag gcgcagcggt cgggctgaac ggggggttcg tgcacacagc   8160
ccagcttgga gcgaacgacc tacaccgaac tgagatacct acagcgtgag ctatgagaaa   8220
gcgccacgct tcccgaaggg agaaaggcgg acaggtatcc ggtaagcggc agggtcggaa   8280
caggagagcg cacgagggag cttccagggg gaaacgcctg gtatctttat agtcctgtcg   8340
ggtttcgcca cctctgactt gagcgtcgat ttttgtgatg ctcgtcaggg gggcggagcc   8400
```

tatggaaaaa cgccagcaac gcggcctttt tacggttcct ggccttttgc tggccttttg 8460
ctcacatgt 8469

<210> SEQ ID NO 42
<211> LENGTH: 7242
<212> TYPE: DNA
<213> ORGANISM: Artificial Sequence
<220> FEATURE:
<223> OTHER INFORMATION: Plasmid

<400> SEQUENCE: 42
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgctccg gtgcccgtca gtgggcagag cgcacatcgc 180
ccacagtccc cgagaagttg gggggagggg tcggcaattg aaccggtgcc tagagaaggt 240
ggcgcggggt aaactgggaa agtgatgtcg tgtactggct ccgccttttt cccgagggtg 300
ggggagaacc gtatataagt gcagtagtcg ccgtgaacgt tctttttcgc aacgctagct 360
aactaccggt gccaccatgg ccccaaagaa gaagcggaag gtcggtagta ctgtgggtac 420
tcgaagtggc tgcgtaccac acccgtcgca tggatccaag cggaactata tcctgggact 480
ggacatcgga attacctccg tgggatacgg catcatcgat tacgagacta gggacgtgat 540
tgacgccggc gtgagactct ttaaggaggc caacgtggaa aacaacgaag gtcgcagatc 600
caagcggggt gcaagacgcc tgaagcgccg gaggagacat cggatacagc gcgtgaagaa 660
gctccttttc gactacaacc tcctcactga ccactcggaa ttgtccggta tcaaccccta 720
cgaagcccgc gtgaaaggcc tgagccagaa gctgtccgaa gaggagttta gcgcagccct 780
gctgcacctg gctaagcgaa ggggggtgca caacgtgaac gaggtggagg aggacactgg 840
caacgaactg tccaccaagg agcagatttc acggaactcg aaggcgctgg aagagaaata 900
tgtggccgag ctgcagctgg agaggctcaa gaaggatggc gaagtccggg ggagcatcaa 960
tcgcttcaag acctcggact acgtgaagga agccaaacag ctgttgaagg tgcagaaggc 1020
ctaccaccaa ctggaccaat cattcattga cacttacatc gatctgcttg aaaccaggcg 1080
cacctactac gagggtcctg gagaaggcag cccctttcgga tggaaggaca tcaaggagtg 1140
gtatgagatg ctgatgggtc attgcaccta ctttccggaa gaactgcgct cagtgaagta 1200
cgcgtacaac gctgacctct acaacgctct caacgatctg aacaacctcg tgatcacccg 1260
ggacgagaac gaaaagctgg agtactacga aaagttccag attatcgaaa acgtgttcaa 1320
gcagaagaag aagcccaccc tgaagcagat tgcaaaggag atccttgtga acgaggagga 1380
tattaagggc taccgggtca cctccaccgg gaaaccagag ttcactaatc tcaaggtgta 1440
ccatgacatt aaggacatta ctgcccgcaa ggagatcatt gaaaacgcgg aactgctgga 1500
ccaaatcgcg aagatcctga ccatctatca gagctccgag gatatccagg aggaacttac 1560
taacctcaat tccgagctga cgcaggaaga aatcgagcaa attagcaacc tgaagggtta 1620
cactggaacc cacaacctca gcttgaaagc gattaacctt attttggatg aactttggca 1680
cactaatgac aatcagatcg ccattttcaa ccggctgaaa ctggtgccga agaaggtgga 1740
cctgagccaa cagaaggaaa tcccgaccac ccttgtggac gatttcatcc tgtcacctgt 1800
ggtgaagagg agcttcatcc agtcgatcaa ggtcatcaac gccatcataa agaagtacgg 1860
ccttcccaac gacatcatca tcgaactggc ccgcgagaag aactccaaag atgcccagaa 1920
gatgatcaac gagatgcaga agcgaaaccg gcagacgaac gaacggatcg aggagatcat 1980

-continued

```
ccggaccacc gggaaggaaa acgcgaagta cctgatcgag aaaatcaagc tgcatgatat   2040
gcaggaaggg aagtgtctct actccctgga ggccattccg ctggaggatt tgctgaacaa   2100
ccctttcaac tacgaagtcg atcatatcat tcctcgctcc gtgtccttcg ataactcctt   2160
caacaataag gtcctcgtga agcaggagga gaagtaagta tcaaggttac aagacaggtt   2220
taaggagacc aatagaaact gggctcgaga atgcgacggg tgtggtacgc agccacttcg   2280
agtacccaca gtactacctg cttgtcgaga cagagaagac tcttgcgttt ctgataggca   2340
cctattggtc ttactgacat ccactttgcc tttctctcca cagctcgaag aagggcaaca   2400
gaaccccgtt ccagtacctc tcgtcgtccg actccaagat cagctacgaa actttcaaga   2460
agcacattct gaacctggcc aagggcaaag ggagaattag caagaccaag aaggaatacc   2520
tcctggaaga gagagacatc aaccgcttct cggtgcaaaa ggatttcatc aaccgcaacc   2580
tggtcgatac cagatacgcc accaggggac tgatgaacct cctgcggtcc tacttccggg   2640
tcaacaatct ggacgtgaag gtcaaatcca tcaacggggg ctttacttct ttcctgcgcc   2700
ggaagtggaa gttcaagaag gaacggaaca agggatacaa gcaccacgct gaagatgccc   2760
tgattattgc caacgccgac ttcatcttta aggaatggaa aaagctggac aaggctaaga   2820
aggtcatgga gaaccagatg ttcgaagaaa agcaggccga gtccatgccc gaaatcgaaa   2880
ccgagcagga atacaaggag atcttcatca caccgcacca aatcaagcac atcaaggact   2940
tcaaggatta caagtacagc caccgggtgg acaagaagcc taacagagag cttatcaacg   3000
acaccctgta ctccacgcgc aaggacgaca agggaaacac attgatcgtg aacaacctga   3060
acggactgta tgacaaggac aatgacaaac tgaagaagct gatcaacaaa tcgccggaaa   3120
agctcctgat gtaccatcac gaccctcaaa cctaccagaa actgaagctc atcatggagc   3180
agtacggcga cgaaaagaat cccctgtaca aatactacga ggagactgga aattacctga   3240
ctaagtactc caagaaggat aacggccccg tgatcaagaa gattaagtac tacggaaaca   3300
aactgaacgc acatctcgac atcaccgatg attatccaaa ctcccgcaac aaagtcgtga   3360
agctctccct caaaccgtac cgcttcgacg tgtacctgga taatggggtg tacaagttcg   3420
tgaccgtgaa gaacctggac gtcattaaga aggaaaacta ctacgaagtg aactcaaagt   3480
gctacgagga agccaagaag ctcaagaaga tcagcaacca ggccgagttc atcgcatcgt   3540
tttacaacaa tgacctcatt aagattaatg gagaactgta cagagtgatc ggcgtgaaca   3600
acgacctcct gaaccggatt gaagtgaaca tgatcgatat tacctaccgg gagtatctgg   3660
agaacatgaa cgacaagcgc ccaccgagaa tcatcaaaac tattgcctcc aagacccaat   3720
ccattaagaa atactccacc gacatcctgg gcaacctgta cgaggtcaag tcgaagaagc   3780
acccccagat tatcaagaag ggaaaaaggc cggcggccac gaaaaaggcc ggccaggcaa   3840
aaaagaaaaa ggcttaagaa ttcctagagc tcgctgatca gcctcgaaac ttgtttattg   3900
cagcttataa tggttacaaa taaagcaata gcatcacaaa tttcacaaat aaagcatttt   3960
tttcactgca ttctagttgt ggtttgtcca aactcatcaa tgtatcttat catgtctgta   4020
taccagcagg ctttcctagg ttcgaacgct gacgtcatca acccgctcca aggaatcgcg   4080
ggcccagtgt cactaggcgg gaacacccag cgcgcgtgcg ccctggcagg aagatggctg   4140
tgagggacag gggagtggcg ccctgcaata tttgcatgtc gctatgtgtt ctgggaaatc   4200
accataaacg tgaaatccct atcagtgata gagacttata agttccctat cagtgataga   4260
gacaccgggt gtggtacgca gccactgttt aagtactctg tgctggaaac agcacagaat   4320
```

-continued ctacttaaac aaggcaaaat gccgtgttta tctcgtcaac ttgttggcga gatttttttca 4380 cgtgcggacc gaggctgcag cgtcgtcctc cctaggaacc cctagtgatg gagttggcca 4440
ctccctctct gcgcgctcgc tcgctcactg aggccgggcg accaaaggtc gcccgacgcc 4500
cgggctttgc ccgggcggcc tcagtgagcg agcgagcgcg cagctgcctg caggggcgcc 4560
tgatgcggta ttttctcctt acgcatctgt gcggtatttc acaccgcata cgtcaaagca 4620
accatagtac gcgccctgta gcggcgcatt aagcgcggcg ggtgtggtgg ttacgcgcag 4680
cgtgaccgct acacttgcca gcgccttagc gcccgctcct ttcgctttct tcccttcctt 4740
tctcgccacg ttcgccggct ttccccgtca agctctaaat cgggggctcc ctttagggtt 4800
ccgatttagt gctttacggc acctcgaccc caaaaaactt gatttgggtg atggttcacg 4860
tagtgggcca tcgccctgat agacggtttt tcgccctttg acgttggagt ccacgttctt 4920
taatagtgga ctcttgttcc aaactggaac aacactcaac tctatctcgg gctattcttt 4980
tgatttataa gggattttgc cgatttcggt ctattggtta aaaaatgagc tgatttaaca 5040
aaaatttaac gcgaatttta acaaaatatt aacgttagcg cttccattgt cgacttccga 5100
ggacgagggc ctatttccca tgattccttc atatttgcat atacgataca aggctgttag 5160
agagataatt ggaattaatt tgactgtaaa cacaaagata ttagtacaaa atacgtgacg 5220
tagaaagtaa taatttcttg ggtagtttgc agttttaaaa ttatgtttta aaatggacta 5280
tcatatgctt accgtaactt gaaagtattt cgatttcttg gctttatata tcttgtggaa 5340
aggacgaaac accggagctt catccagtcg atcacgaatg atcgactgga tgaagctcct 5400
tttttccgcg gaacgtttac aattttatgg tgcactctca gtacaatctg ctctgatgcc 5460
gcatagttaa gccagccccg acacccgcca acacccgctg acgcgccctg acgggcttgt 5520
ctgctcccgg catccgctta cagacaagct gtgaccgtct ccgggagctg catgtgtcag 5580
aggttttcac cgtcatcacc gaaacgcgcg agacgaaagg gcctcgtgat acgcctattt 5640
ttataggtta atgtcatgaa caataaaact gtctgcttac ataaacagta atacaagggg 5700
tgttatgagc catattcaac gggaaacgtc gaggccgcga ttaaattcca acatggatgc 5760
tgatttatat gggtataaat gggctcgcga taatgtcggg caatcaggtg cgacaatcta 5820
tcgcttgtat gggaagcccg atgcgccaga gttgtttctg aaacatggca aaggtagcgt 5880
tgccaatgat gttacagatg agatggtcag actaaactgg ctgacggaat ttatgcctct 5940
tccgaccatc aagcatttta tccgtactcc tgatgatgca tggttactca ccactgcgat 6000
ccccggaaaa acagcattcc aggtattaga agaatatcct gattcaggtg aaaatattgt 6060
tgatgcgctg gcagtgttcc tgcgccggtt gcattcgatt cctgtttgta attgtccttt 6120
taacagcgat cgcgtatttc gtctcgctca ggcgcaatca cgaatgaata acggtttggt 6180
tgatgcgagt gattttgatg acgagcgtaa tggctggcct gttgaacaag tctggaaaga 6240
aatgcataaa cttttgccat tctcaccgga ttcagtcgtc actcatggtg atttctcact 6300
tgataacctt atttttgacg aggggaaatt aataggttgt attgatgttg gacgagtcgg 6360
aatcgcagac cgataccagg atcttgccat cctatggaac tgcctcggtg agttttctcc 6420
ttcattacag aaacggcttt ttcaaaaata tggtattgat aatcctgata tgaataaatt 6480
gcagtttcat ttgatgctcg atgagttttt ctaatctcat gaccaaaatc ccttaacgtg 6540
agttttcgtt ccactgagcg tcagaccccg tagaaaagat caaaggatct tcttgagatc 6600 cttttttttct gcgcgtaatc tgctgcttgc aaacaaaaaa accaccgcta ccagcggtgg 6660
tttgtttgcc ggatcaagag ctaccaactc tttttccgaa ggtaactggc ttcagcagag 6720

```
cgcagatacc aaatactgtc cttctagtgt agccgtagtt aggccaccac ttcaagaact   6780
ctgtagcacc gcctacatac ctcgctctgc taatcctgtt accagtggct gctgccagtg   6840
gcgataagtc gtgtcttacc gggttggact caagacgata gttaccggat aaggcgcagc   6900
ggtcgggctg aacggggggt tcgtgcacac agcccagctt ggagcgaacg acctacaccg   6960
aactgagata cctacagcgt gagctatgag aaagcgccac gcttcccgaa gggagaaagg   7020
cggacaggta tccggtaagc ggcagggtcg gaacaggaga gcgcacgagg gagcttccag   7080
ggggaaacgc ctggtatctt tatagtcctg tcgggtttcg ccacctctga cttgagcgtc   7140
gatttttgtg atgctcgtca ggggggcgga gcctatggaa aaacgccagc aacgcggcct   7200
ttttacggtt cctggccttt tgctggcctt ttgctcacat gt                     7242
```

<210> SEQ ID NO 43
<211> LENGTH: 8771
<212> TYPE: DNA
<213> ORGANISM: Artificial Sequence
<220> FEATURE:
<223> OTHER INFORMATION: Plasmid

<400> SEQUENCE: 43

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcac gcgtgctccg gtgcccgtca gtgggcagag cgcacatcgc    180
ccacagtccc cgagaagttg gggggagggg tcggcaattg aaccggtgcc tagagaaggt    240
ggcgcggggt aaactgggaa agtgatgtcg tgtactggct ccgccttttt cccgagggtg    300
ggggagaacc gtatataagt gcagtagtcg ccgtgaacgt tctttttcgc aacgctagct    360
aactaccggt gccaccatgg ccccaaagaa gaagcggaag gtcggtagta ctgtgggtac    420
tcgaagtggc tgcgtaccac acccgtcgca tggatccaag cggaactata tcctgggact    480
ggacatcgga attacctccg tgggatacgg catcatcgat tacgagacta gggacgtgat    540
tgacgccggc gtgagactct ttaaggaggc caacgtggaa aacaacgaag gtcgcagatc    600
caagcggggt gcaagacgcc tgaagcgccg gaggagacat cggatacagc gcgtgaagaa    660
gctccttttc gactacaacc tcctcactga ccactcggaa ttgtccggta tcaaccccta    720
cgaagcccgc gtgaaaggcc tgagccagaa gctgtccgaa gaggagttta gcgcagccct    780
gctgcacctg gctaagcgaa gggggtgca caacgtgaac gaggtggagg aggacactgg    840
caacgaactg tccaccaagg agcagatttc acggaactcg aaggcgctgg aagagaaata    900
tgtggccgag ctgcagctgg agaggctcaa gaaggatggc gaagtccggg ggagcatcaa    960
tcgcttcaag acctcggact acgtgaagga agccaaacag ctgttgaagg tgcagaaggc   1020
ctaccaccaa ctggaccaat cattcattga cacttacatc gatctgcttg aaaccaggcg   1080
cacctactac gagggtcctg gagaaggcag ccctttcgga tggaaggaca tcaaggagtg   1140
gtatgagatg ctgatgggtc attgcaccta ctttccggaa gaactgcgct cagtgaagta   1200
cgcgtacaac gctgacctct acaacgctct caacgatctg aacaacctcg tgatcacccg   1260
ggacgagaac gaaaagctgg agtactacga aaagttccag attatcgaaa acgtgttcaa   1320
gcagaagaag aagcccaccc tgaagcagat tgcaaaggag atccttgtga acgaggagga   1380
tattaagggc taccgggtca cctccaccgg gaaaccagag ttcactaatc tcaaggtgta   1440
ccatgacatt aaggacatta ctgcccgcaa ggagatcatt gaaaacgcgg aactgctgga   1500
```

-continued

```
ccaaatcgcg aagatcctga ccatctatca gagctccgag gatatccagg aggaacttac   1560
taacctcaat tccgagctga cgcaggaaga aatcgagcaa attagcaacc tgaagggtta   1620
cactggaacc cacaacctca gcttgaaagc gattaacctt attttggatg aactttggca   1680
cactaatgac aatcagatcg ccattttcaa ccggctgaaa ctggtgccga agaaggtgga   1740
cctgagccaa cagaaggaaa tcccgaccac ccttgtggac gatttcatcc tgtcacctgt   1800
ggtgaagagg agcttcatcc agtcgatcaa ggtcatcaac gccatcataa agaagtacgg   1860
ccttcccaac gacatcatca tcgaactggc ccgcgagaag aactccaaag atgcccagaa   1920
gatgatcaac gagatgcaga agcgaaaccg gcagacgaac gaacggatcg aggagatcat   1980
ccggaccacc gggaaggaaa acgcgaagta cctgatcgag aaaatcaagc tgcatgatat   2040
gcaggaaggg aagtgtctct actccctgga ggccattccg ctggaggatt tgctgaacaa   2100
ccctttcaac tacgaagtcg atcatatcat tcctcgctcc gtgtccttcg ataactcctt   2160
caacaataag gtcctcgtga agcaggagga gaagtaagta tcaaggttac aagacaggtt   2220
taaggagacc aatagaaact gggctcgaga atgcgacggg tgtggtacgc agccacttcg   2280
agtacccaca gtactacctg cttgtcgaga cagagaagac tcttgcgttt ctgataggca   2340
cctattggtc ttactgacat ccactttgcc tttctctcca cagctcgaag aagggcaaca   2400
gaaccccgtt ccagtacctc tcgtcgtccg actccaagat cagctacgaa actttcaaga   2460
agcacattct gaacctggcc aagggcaaag ggagaattag caagaccaag aaggaatacc   2520
tcctggaaga gagagacatc aaccgcttct cggtgcaaaa ggatttcatc aaccgcaacc   2580
tggtcgatac cagatacgcc accaggggac tgatgaacct cctgcggtcc tacttccggg   2640
tcaacaatct ggacgtgaag gtcaaatcca tcaacggggg ctttacttct ttcctgcgcc   2700
ggaagtggaa gttcaagaag gaacggaaca agggatacaa gcaccacgct gaagatgccc   2760
tgattattgc caacgccgac ttcatcttta aggaatggaa aaagctggac aaggctaaga   2820
aggtcatgga gaaccagatg ttcgaagaaa agcaggccga gtccatgccc gaaatcgaaa   2880
ccgagcagga atacaaggag atcttcatca caccgcacca aatcaagcac atcaaggact   2940
tcaaggatta caagtacagc caccgggtgg acaagaagcc taacagagag cttatcaacg   3000
acaccctgta ctccacgcgc aaggacgaca agggaaacac attgatcgtg aacaacctga   3060
acggactgta tgacaaggac aatgacaaac tgaagaagct gatcaacaaa tcgccggaaa   3120
agctcctgat gtaccatcac gaccctcaaa cctaccagaa actgaagctc atcatggagc   3180
agtacggcga cgaaaagaat cccctgtaca aatactacga ggagactgga aattacctga   3240
ctaagtactc caagaaggat aacggccccg tgatcaagaa gattaagtac tacggaaaca   3300
aactgaacgc acatctcgac atcaccgatg attatccaaa ctcccgcaac aaagtcgtga   3360
agctctccct caaaccgtac cgcttcgacg tgtacctgga taatggggtg tacaagttcg   3420
tgaccgtgaa gaacctggac gtcattaaga aggaaaacta ctacgaagtg aactcaaagt   3480
gctacgagga agccaagaag ctcaagaaga tcagcaacca ggccgagttc atcgcatcgt   3540
tttacaacaa tgacctcatt aagattaatg gagaactgta cagagtgatc ggcgtgaaca   3600
acgacctcct gaaccggatt gaagtgaaca tgatcgatat tacctaccgg gagtatctgg   3660
agaacatgaa cgacaagcgc ccaccgagaa tcatcaaaac tattgcctcc aagacccaat   3720
ccattaagaa atactccacc gacatcctgg gcaacctgta cgaggtcaag tcgaagaagc   3780
acccccagat tatcaagaag ggaaaaaggc cggcggccac gaaaaaggcc ggccaggcaa   3840
aaaagaaaaa ggcttaagaa ttcctagagc tcgctgatca gcctcgaaac ttgtttattg   3900
```

-continued

```
cagcttataa tggttacaaa taaagcaata gcatcacaaa tttcacaaat aaagcatttt   3960
tttcactgca ttctagttgt ggtttgtcca aactcatcaa tgtatcttat catgtctgta   4020
taccagcagg ctttcctagg ttcgaacgct gacgtcatca acccgctcca aggaatcgcg   4080
ggcccagtgt cactaggcgg gaacacccag cgcgcgtgcg ccctggcagg aagatggctg   4140
tgagggacag gggagtggcg ccctgcaata tttgcatgtc gctatgtgtt ctgggaaatc   4200
accataaacg tgaaatccct atcagtgata gagacttata agttccctat cagtgataga   4260
gacaccgggt gtggtacgca gccactgttt aagtactctg tgctggaaac agcacagaat   4320
ctacttaaac aaggcaaaat gccgtgttta tctcgtcaac ttgttggcga gatttttca    4380
cgtgcggacc gaggctgcag cgtcgtcctc cctaggaacc cctagtgatg gagttggcca   4440
ctccctctct gcgcgctcgc tcgctcactg aggccgggcg accaaaggtc gcccgacgcc   4500
cgggctttgc ccgggcggcc tcagtgagcg agcgagcgcg cagctgcctg caggggcgcc   4560
tgatgcggta ttttctcctt acgcatctgt gcggtatttc acaccgcata cgtcaaagca   4620
accatagtac gcgccctgta gcggcgcatt aagcgcggcg ggtgtggtgg ttacgcgcag   4680
cgtgaccgct acacttgcca gcgccttagc gcccgctcct ttcgctttct tcccttcctt   4740
tctcgccacg ttcgccggct ttccccgtca agctctaaat cgggggctcc ctttagggtt   4800
ccgatttagt gctttacggc acctcgaccc caaaaaactt gatttgggtg atggttcacg   4860
tagtgggcca tcgccctgat agacggtttt tcgccctttg acgttggagt ccacgttctt   4920
taatagtgga ctcttgttcc aaactggaac aacactcaac tctatctcgg gctattcttt   4980
tgatttataa gggattttgc cgatttcggt ctattggtta aaaaatgagc tgatttaaca   5040
aaaatttaac gcgaatttta acaaaatatt aacgttagcg ctgacattga ttattgacta   5100
gttattaata gtaatcaatt acggggtcat tagttcatag cccatatatg gagttccgcg   5160
ttacataact tacggtaaat ggcccgcctg gctgaccgcc caacgacccc cgcccattga   5220
cgtcaataat gacgtatgtt cccatagtaa cgccaatagg gactttccat tgacgtcaat   5280
gggtggagta tttacggtaa actgcccact tggcagtaca tcaagtgtat catatgccaa   5340
gtacgccccc tattgacgtc aatgacggta aatggcccgc ctggcattat gcccagtaca   5400
tgaccttatg ggactttcct acttggcagt acatctacgt attagtcatc gctattacca   5460
tggtgatgcg gttttggcag tacatcaatg ggcgtggata gcggtttgac tcacggggat   5520
ttccaagtct ccaccccatt gacgtcaatg ggagtttgtt ttggcaccaa aatcaacggg   5580
actttccaaa atgtcgtaac aactccgccc cattgacgca aatgggcggt aggcgtgtac   5640
ggtgggaggt ctatataagc agagctctct ggctaactag agaacccact gcttactggc   5700
ttatcgttaa ttaaccggtg ccaccatgat gtcccgcctt gataaatcaa aagtaataaa   5760
cagtgctctt gagcttctca atgaagttgg tatagaaggg ttgacgactc ggaaattggc   5820
gcaaaaactc ggtgttgagc agccaacctt gtattggcat gttaaaaaca aacgagcact   5880
cctcgacgct ttggcgatag agatgctgga caggcaccac acgcatttct gtcccctcga   5940
aggagagtca tggcaggatt tccttagaaa taacgcaaag tccttcagat gtgcgctgct   6000
tagtcaccgc gacggcgcaa aagttcatct cggcactagg ccaaccgaga aacagtacga   6060
gactctggag aaccaactgg cgtttttgtg tcaacagggt tttagtctcg aaaatgcgct   6120
ctatgctctc tctgcggttg gccatttcac cctcggatgc gtactggaag atcaggagca   6180
ccaagtggcc aaagaagaac gggaaacgcc gactacggac agcatgcctc cgttgctccg   6240
```

```
gcaagctata gagctcttcg atcaccaagg cgctgagcca gctttcttgt tcggattgga   6300
acttattata tgcgggctcg aaaagcagct taaatgcgag tcaggttaag tttaaacccg   6360
ctgatcagcc tcgactgtgc cttctagttg ccagccatct gttgtttgcc cctcccccgt   6420
gccttccttg accctggaag gtgccactcc cactgtcctt tcctaataaa atgaggaaat   6480
tgcatcgcat tgtctgagta ggtgtcattc tattctgggg ggtggggtgg ggcaggacag   6540
caagggggag gattgggaag acaatagcag gcatgctggg gatgcggtgg gctctatggc   6600
ttctgagtta gtccattgtc gacttccgag gacgagggcc tatttcccat gattccttca   6660
tatttgcata tacgatacaa ggctgttaga gagataattg gaattaattt gactgtaaac   6720
acaaagatat tagtacaaaa tacgtgacgt agaaagtaat aatttcttgg gtagtttgca   6780
gttttaaaat tatgttttaa aatggactat catatgctta ccgtaacttg aaagtatttc   6840
gatttcttgg ctttatatat cttgtggaaa ggacgaaaca ccggagcttc atccagtcga   6900
tcacgaatga tcgactggat gaagctcctt ttttccgcgg aacgtttaca attttatggt   6960
gcactctcag tacaatctgc tctgatgccg catagttaag ccagccccga cacccgccaa   7020
cacccgctga cgcgccctga cgggcttgtc tgctcccggc atccgcttac agacaagctg   7080
tgaccgtctc cgggagctgc atgtgtcaga ggttttcacc gtcatcaccg aaacgcgcga   7140
gacgaaaggg cctcgtgata cgcctatttt tataggttaa tgtcatgaac aataaaactg   7200
tctgcttaca taaacagtaa tacaaggggt gttatgagcc atattcaacg ggaaacgtcg   7260
aggccgcgat taaattccaa catggatgct gatttatatg ggtataaatg ggctcgcgat   7320
aatgtcgggc aatcaggtgc gacaatctat cgcttgtatg ggaagcccga tgcgccagag   7380
ttgtttctga aacatggcaa aggtagcgtt gccaatgatg ttacagatga gatggtcaga   7440
ctaaactggc tgacggaatt tatgcctctt ccgaccatca agcattttat ccgtactcct   7500
gatgatgcat ggttactcac cactgcgatc cccggaaaaa cagcattcca ggtattagaa   7560
gaatatcctg attcaggtga aaatattgtt gatgcgctgg cagtgttcct gcgccggttg   7620
cattcgattc ctgtttgtaa ttgtcctttt aacagcgatc gcgtatttcg tctcgctcag   7680
gcgcaatcac gaatgaataa cggtttggtt gatgcgagtg attttgatga cgagcgtaat   7740
ggctggcctg ttgaacaagt ctggaaagaa atgcataaac ttttgccatt ctcaccggat   7800
tcagtcgtca ctcatggtga tttctcactt gataacctta tttttgacga ggggaaatta   7860
ataggttgta ttgatgttgg acgagtcgga atcgcagacc gataccagga tcttgccatc   7920
ctatggaact gcctcggtga gttttctcct tcattacaga aacggctttt tcaaaaatat   7980
ggtattgata atcctgatat gaataaattg cagtttcatt tgatgctcga tgagtttttc   8040
taatctcatg accaaaatcc cttaacgtga gttttcgttc cactgagcgt cagaccccgt   8100
agaaaagatc aaaggatctt cttgagatcc tttttttctg cgcgtaatct gctgcttgca   8160
aacaaaaaaa ccaccgctac cagcggtggt ttgtttgccg gatcaagagc taccaactct   8220
ttttccgaag gtaactggct tcagcagagc gcagatacca aatactgtcc ttctagtgta   8280
gccgtagtta ggccaccact tcaagaactc tgtagcaccg cctacatacc tcgctctgct   8340
aatcctgtta ccagtggctg ctgccagtgg cgataagtcg tgtcttaccg ggttggactc   8400
aagacgatag ttaccggata aggcgcagcg gtcgggctga acggggggtt cgtgcacaca   8460
gcccagcttg gagcgaacga cctacaccga actgagatac ctacagcgtg agctatgaga   8520
aagcgccacg cttcccgaag ggagaaaggc ggacaggtat ccggtaagcg gcagggtcgg   8580
aacaggagag cgcacgaggg agcttccagg gggaaacgcc tggtatcttt atagtcctgt   8640
```

cgggtttcgc cacctctgac ttgagcgtcg atttttgtga tgctcgtcag gggggcggag 8700
cctatggaaa aacgccagca acgcggcctt tttacggttc ctggcctttt gctggccttt 8760
tgctcacatg t 8771

<210> SEQ ID NO 44
<211> LENGTH: 5823
<212> TYPE: DNA
<213> ORGANISM: Artificial Sequence
<220> FEATURE:
<223> OTHER INFORMATION: Plasmid encoding BFP reporter construct

<400> SEQUENCE: 44
ggggttgggg ttgcgccttt tccaaggcag ccctgggttt gcgcagggac gcggctgctc 60
tgggcgtggt tccgggaaac gcagcggcgc cgaccctggg tctcgcacat tcttcacgtc 120
cgttcgcagc gtcacccgga tcttcgccgc tacccttgtg ggcccccegg cgacgcttcc 180 tgctccgccc ctaagtcggg aaggttcctt gcggttcgcg gcgtgccgga cgtgacaaac 240
ggaagccgca cgtctcacta gtaccctcgc agacggacag cgccagggag caatggcagc 300
gcgccgaccg cgatgggctg tggccaatag cggctgctca gcagggcgcg ccgagagcag 360
cggccgggaa ggggcggtgc gggaggcggg gtgtggggcg gtagtgtggg ccctgttcct 420
gcccgcgcgg tgttccgcat tctgcaagcc tccggagcgc acgtcggcag tcggctccct 480
cgttgaccga atcaccgacc tctctcccca ggctagccac catgggcctg aggctacagc 540
tctccctggg catcatccca gttgaggagg agaacccgga cttctggaac cgcgaggcag 600
ccgaggccct gggtgccgcc aagaagctgc agcctgcaca gacagccgcc aagaacctca 660
tcatcttcct gggcgatggg atgggggtgt ctacggtgac agctgccagg atcgatctgc 720
ttcctggccc tgctgggcct gctcatcctc tgggagccct ggcctgccca ggcttttgtc 780
aacagcacct ttgtggttct cacttggtgg aagctctcta cctggtgtgt ggggagcgtg 840
gattcttcta cacacccatg tcccgccgcg aagtggagga cccacaaggt aagctctgct 900
cctgaattaa ttctatccca agtgctaact accctgtttg tctttcaccc ttgagacctt 960
gtaaattgtg ccctaggtgt ggagggtctc aggctaacca gtgggggca catttctgtg 1020 ggcagctaga catatgtaaa catggtagct gccaggaagg agtgagaatc cttccttaag 1080
tctcctaggt ggtgacgggt ggctaggccc caggataggt accgggcccc ccctcgagca 1140
ttaaataatg ttacttatgt tatacagccc atttcctttt ttatcagagt caggctgaaa 1200
gttcattttt ctgcaaaact gcagtgccca ttcttaattt ttgttttgag aaataactgt 1260
tgtaccctct ttattatcac aagattaata atatttcttt attttattgc tcctcttaca 1320
tttggatctt ttattatgag ctgtcaaaaa ttcttttggg aagtagttgg ggtataaata 1380
ataaatcgat aaaagaattc atgattaaag acaagataga atccattatt ctgttaacat 1440
atcagtagtg aataacaaaa ggctacattg acaattagca tgcaatatat tgctttatat 1500
aattatacat ccatatattt gccactttga tttttaattc actggtaaat ttaggggata 1560
ctcatttatg gagttaatat taccaaaaag agtttttaaa ctgagcgagg ctttaattag 1620
aatggtaaaa tattgcttca gggcaacaat gagaatgtaa caagaaaact gactgatcag 1680
tcatgggtaa ctcgaatagc aaacaagtag agaagactca caaaaccact gaaagttata 1740
tacacactca agttgtgagt cattcaaact gggtattcat acacatgtat acaaatacaa 1800
acaagtgtgt gcgcacacac cctttccaat atacacacct gaatataaaa ctaaataagc 1860

-continued

```
agattcctct gttaacaatt ttattactct attttaggct ggggctgaac ttttgaagct   1920
gatgagcaaa atagtttccc ataaaagata atttcatttg ccaaaatgaa actactttcc   1980
gttattaatg ttgcaatgaa atggtttgaa atatgagtct gtgatctgga cagaaaggat   2040
gctcctgttc ccagctccaa gagggagttc tctaaacaat tacacccacg gagagcgctg   2100
taaggttgta ttttcatcac cggccagctg agctgtgtgc ctgtcatact cccagtctcc   2160
cctccagtga cagccgcatt gacaacatgt tatactccac attgatttta cagttaagga   2220
gctgattgtg atatatagag attttaagaa ttcagctgag aggctgactt ttgcctttta   2280
tcattccatt aaaattttat aaccatcttt ttcatgtcat ttcatccatg aattcttact   2340
ttagaaagtg atagctactg ctgtgagcat aacttttctc atgttcagag ctttttattg   2400
tattagcaaa ctaccccaat tatagttatt actcatgttt tacataattg tggtggccct   2460
ttcaaccatg cagttgcagg ccagttgatt tgtatataga attagatgat tcggcttatc   2520
attttaaagc actaaattga aagagtgcca ggagtcaggt tttaacactt ccctagccaa   2580
aggagctaat taagctgctt tcagcttcct ctccagaatc acacaagtta aaggaccctt   2640
ctgcaacaag agcagcgaat ctactcagcc agagcaggaa gctaataaaa tgtatgctgg   2700
cttttaaggg ggaaacaaat catgaaattg aaattgaaca cctctccttt cccaaggtaa   2760
gagatcatct ttaagaaaag gctgtgtatt gtgggggttt gaagtgcaag ttcatctcat   2820
tatcatggat gtttcaccca taatactatc atcatatgca ggagaaataa aagccttatc   2880
ccccaatcac agagaacaaa ctgcatcatt gttgtttctt ttccctgaag atgctcacag   2940
tttgatagtt cacatatgag gaataattat gcaagaccca gatgaaaacc ctaataaaaa   3000
atattctgat ttttaagtgt atattactct ctttggggaa gagagggtga gataaggtta   3060
gacattaaag acttgaatct ccaccattga ttttacgaaa cccaatctca ggggatttgg   3120
gggttttttt agatttcaaa acaacattga tatcttacaa gactcgtact tgcttttctc   3180
tgggaaatag ccaaatctag atgacaagca taaataagaa aggagctgta tccccatttt   3240
gatataataa ttgctactgc tactgtatac cagagagcaa aagtaagaaa tggcatagtg   3300
gttttaagaa agctttaaaa tgaaagctaa caagagactg aaacggaaag tgtgatttat   3360
accatgactg ctggttttag ggtttttttt agggatttct cttcaaatag gatacattac   3420
caaattgtca gaaatagctt gatttcagag ttagtgcact ataacatctt ttgcttcgaa   3480
aagtgattat gattctacca tcagtccagt tggtgacaaa tacgtggatc ctgttgtgtg   3540
aaagtgtact catataacca actattattg cagtcactgg ccctgcaaag cagtggttgc   3600
atttaaaatt tcaaccttct ttgtaacact gaatcgcata cacacactca caagatcaac   3660
gctgttttaa acaattacta aatccaagta tatctttttt aaagattttc aataaaatct   3720
aatgttcaca gaaaaatctc ataaatgtca aaattgctgt gggcagaaaa gggggggatac   3780
agtattttct tgatctgttt tagcaattta tagatttcag gccgtggttt ataagaatgc   3840
taaatgttct ggaattacag ctgttactga tcagtgattg agccagattt gtgttattgc   3900
accatgttct tgcttgtacc tagagagcag taaagcctca atataataaa aagcacctgc   3960
attttaaatg aaatttcaat tgaaaaactt aacagccctt caaattgcag aatttaacgc   4020
agcccagtaa agcttaaata acactttgcc cccgcaggct gaggggtttg cattcaaggt   4080
gacttgattg tgtcgcatgg tgaaattatt tacaattaag gaatttctct ggagggctgc   4140
agaatatttg ctgttccaca acacctatgc aggcatatgg tgggcctttt tcagtattca   4200
tggagcctcc tgaaccttta tgataattga atcagttaga gtgctgagtg gagcaagcat   4260
```

aaaacctgtt aacctaaagg tcagatctga gctcggtacc tatttgggga ccccatagag 4320
cactgcactg actgagggat ggtaacagga tgtgtaggtt ttggaggccc atatgtccat 4380
tcatgaccag tgacttgtct cacagccatg caacccttgc ctcctgtgct gacttagcag 4440
gggataaagt gagagaaagc ctgggctaat caggggggtcg ctcagctcct cctaactgga 4500
ttgtcctatg tgtctttgct tctgtgctgc tgatgctctg ccctgtgctg acatgacctc 4560
cctggcagtg gcacaactgg agctgggtgg aggcccggga agcggggcta ccaacttcag 4620
tctcctcaaa caagctggcg atgtggagga aaatccaggt ccggtgtcta agggcgaaga 4680
gctgattaag gagaacatgc acatgaagct gtacatggag ggcaccgtgg acaaccatca 4740
cttcaagtgc acatccgagg gcgaaggcaa gccctacgag ggcacccaga ccatgagaat 4800
caaggtggtc gagggcggcc ctctcccctt cgccttcgac atcctggcta ctagcttcct 4860
ctacggcagc aagaccttca tcaaccacac ccagggcatc cccgacttct tcaagcagtc 4920
cttccctgag ggcttcacat gggagagagt caccacatac gaagacgggg gcgtgctgac 4980
cgctacccag gacaccagcc tccaggacgg ctgcctcatc tacaacgtca agatcagagg 5040
ggtgaacttc acatccaacg gccctgtgat gcagaagaaa acactcggct gggaggcctt 5100
caccgagacg ctgtaccccg ctgacggcgg cctggaaggc agaaacgaca tggccctgaa 5160
gctcgtgggc gggagccatc tgatcgcaaa cgccaagacc acatatagat ccaagaaacc 5220
cgctaagaac ctcaagatgc ctggcgtcta ctatgtggac tacagactgg aaagaatcaa 5280
ggaggccaac aacgagacct acgtcgagca gcacgaggtg gcagtggcca gatactgcga 5340
cctccctagc aaactggggc acaaacttaa ttgaccttca gaccttggca ctggaggtgg 5400
cccggcagaa gcgcggcatc gtggatcagt gctgcaccag catctgctct ctctaccaac 5460
tggagaacta ctgcaactag gcccaccact accctgtcca cccctctgca atgaataaaa 5520
cctttgaaag agcactacaa gttgtgtgta catgcgtgca tgtgcatatg tggtgcgggg 5580
ggaacatgag tggggctggc tggagtggcg atgataagct gtcaaacatg agaattcttg 5640
aagacgaaag ggcctcgtga tacgcctatt tttataggtt aatgtcatga taataatggt 5700
ttcttagacg tttaaacggg ggaggctaac tgaaacacgg aaggagacaa taccggaagg 5760
aacccgcgct atgacggcaa taaaaagaca gaataaaacg cacgggtgtt gggtcgtttg 5820
ttc 5823

<210> SEQ ID NO 45
<211> LENGTH: 8229
<212> TYPE: DNA
<213> ORGANISM: Artificial Sequence
<220> FEATURE:
<223> OTHER INFORMATION: Plasmid

<400> SEQUENCE: 45
ctgggcggtt ctgataacga gtaatcgtta atccgcaaat aacgtaaaaa cccgcttcgg 60
cgggtttttt tatgggggga gtttagggaa agagcatttg tcagaatatt taagggcgcc 120
tgtcactttg cttgatatat gagaattatt taaccttata aatgagaaaa aagcaacgca 180
ctttaaataa gatacgttgc tttttcgatt gatgaacacc tataattaaa ctattcatct 240
attatttatg attttttgta tatacaatat ttctagtttg ttaaagagaa ttaagaaaat 300
aaatctcgaa aataataaag ggaaaatcag tttttgatat caaaattata catgtcaacg 360
ataatacaaa atataataca aactataaga tgttatcagt atttattatg catttagaat 420

```
aaattttgtg tcgcccttat tcgactcact atagaagttc ctattctcta gaaagtatag    480
gaacttcact tcattttgct agcggtgtga gggcctattt cccatgattc cttcatattt    540
gcatatacga tacaaggctg ttagagagat aattggaatt aatttgactg taaacacaaa    600
gatattagta caaaatacgt gacgtagaaa gtaataattt cttgggtagt ttgcagtttt    660
aaaattatgt tttaaaatgg actatcatat gcttaccgta acttgaaagt atttcgattt    720
cttggcttta tatatcttgt ggaaaggacg aaacaccgtt aaagatgatc tcttacctgt    780
ttcagtactc tggaaacaga atctactgaa acaagacaat atgtcgtgtt tatcccatca    840
atttattggt gggatttttt tcaacaccgg taccgcgtta cataacttac ggtaaatggc    900
ccgcctggct gaccgcccaa cgacccccgc ccattgacgt caatagtaac gccaataggg    960
actttccatt gacgtcaatg ggtggagtat ttacggtaaa ctgcccactt ggcagtacat   1020
caagtgtatc atatgccaag tacgccccct attgacgtca atgacggtaa atggcccgcc   1080
tggcattgtg cccagtacat gaccttatgg gactttccta cttggcagta catctacgta   1140
ttagtcatcg ctattaccat ggtcgaggtg agccccacgt tctgcttcac tctccccatc   1200
tcccccccct ccccaccccc aattttgtat ttatttattt tttaattatt ttgtgcagcg   1260
atgggggcgg gggggggggg ggcgcgcgcc aggtggggcg gggcggggcg aggggcgggg   1320
cggggcgagg cggagaggtg cggcggcagc caatcagagc ggcgcgctcc gaaagtttcc   1380
ttttatggcg aggcggcggc ggcggcggcc ctataaaaag cgaagcgcgc ggcgggcggg   1440
agtcgctgcg cgctgccttc gccccgtgcc ccgctccgcc gccgcctcgc gccgcccgcc   1500
ccggctctga ctgaccgcgt tactcccaca ggtgagcggg cgggacggcc cttctcctcc   1560
gggctgtaat tagctgagca agaggtaagg gtttaaggga tggttggttg gtggggtatt   1620
aatgtttaat tacctggagc acctgcctga aatcactttt tttcaggttg gcaaccgcgg   1680
acacccaagc ggccgccacc atggattaca aagaccacga cggagactac aaggatcacg   1740
acattgatta caaggatgat gatgataagg ccccaaagaa gaagcggaag gtcggtatcc   1800
acggagtccc agcagccgga tccgccatga accagaagtt cattctcggt ctggacattg   1860
gcattactag cgtgggatac ggcttgattg actacgagac taagaacatc atcgatgccg   1920
gcgtccgcct gttcccggaa gccaacgtgg agaacaatga gggccggagg tcgaagagag   1980
gctcccgccg cctgaagcgg cggcgaatcc accggctgga gagagtgaag ctgctgctca   2040
ccgaatacga cctgatcaac aaagaacaga tcccgacctc caacaacccg taccagatca   2100
gagtgaaggg tctgtcagaa atcctgtcca aggacgaact ggcaatcgcc ctgctgcacc   2160
tggccaagcg gcgcggaatc cacaacgtgg atgtggctgc cgacaaggaa gaaaccgctt   2220
ccgactccct gagcactaag gaccagatca acaagaacgc caagttcttg gagtcccgct   2280
acgtgtgcga gctgcagaag gaacggctgg aaaacgaagg tcacgtgcgc ggagtggaaa   2340
accggttcct gacaaaggac attgtgcgcg aagcgaagaa gatcattgat acccaaatgc   2400
agtactaccc tgaaatcgac gagactttca aggaaaagta catttccctg gtggaaaccc   2460
ggcgggaata cttcgaaggc cccggacagg gatcgccgtt cggatggaac ggggacctca   2520
agaagtggta cgagatgctg atggggcact gtacctactt tccgcaagaa ctgcgctccg   2580
tgaagtacgc gtactccgcg gatctcttca acgcgttgaa tgacctgaac aacctgatca   2640
ttcagagaga caattccgaa aagctcgagt accacgagaa gtatcacatc atcgagaatg   2700
tgttcaagca gaagaagaaa ccgaccctca agcaaatcgc caaggagatt ggcgtcaacc   2760
cagaggacat caagggatat cggattacca agagcggcac tcccgagttt acctctttca   2820
```

agctgtttca tgatctgaag aaagtcgtga aggaccatgc cattctcgac gacattgatc 2880
tcctgaatca gatcgcagag atcctgacta tctaccaaga caaggactcg attgtggcag 2940
agctgggtca gctcgaatac ctgatgtccg aggccgacaa gcagtccatc tccgaactga 3000
cagggtacac ggggactcat agcctgtcgc tgaagtgcat gaacatgatc attgatgaac 3060
tgtggcacag ctccatgaac caaatggaag tgtttaccta cctcaacatg cgccctaaga 3120
agtacgaact gaaaggctac cagcgcatcc ccaccgacat gatcgacgac gcgatcttgt 3180
cccctgtggt caagaggacc ttcattcaat ccatcaacgt gatcaacaag gtcatcgaaa 3240
agtacggaat accagaagat atcatcattg agctcgctcg ggagaacaac tcggatgacc 3300
ggaagaagtt catcaacaat cttcagaaga agaacgaagc gactcggaaa cggatcaacg 3360
agatcatcgg acagaccgga aaccagaacg ccaaacggat tgtcgaaaag attagactgc 3420
acgaccagca ggaagggaag tgcctgtact cactcgagtc aataccgctc gaggacctgt 3480
tgaacaaccc taaccactat gaagtggacc acatcatccc tcggtccgtg agcttcgaca 3540
actcgtacca caacaaagtg ctcgtgaagc agtccgaaaa ctccaagaaa tccaacctga 3600
ccccgtacca atacttcaat tcgggaaagt cgaagctgtc gtacaaccag ttcaaacaac 3660
acatactcaa ccttagcaaa agccaggatc gcatttccaa gaagaagaag gaatacctcc 3720
tcgaggaaag ggacatcaac aagttcgaag tgcagaaaga gttcatcaat cgcaacttgg 3780
tggataccag atatgccacc cgggaactca ccaactatct caaggcctac ttttccgcca 3840
acaacatgaa cgtgaaggtc aagaccatca acgggtcctt cactgactac ctgagaaagg 3900
tctggaagtt caagaaggaa cgcaaccacg gatacaagca ccacgctgag gacgctctga 3960
tcatcgccaa tgccgacttc ctgttcaagg aaaacaagaa gctgaaagct gtcaactcag 4020
tgctggaaaa gcctgaaatc gagactaagc agctggatat ccaagtggac tctgaggaca 4080
actacagcga gatgttcatc atccctaaac aagtgcagga tatcaaggac tttcgcaact 4140
tcaagtactc acaccgggtg gacaagaaac cgaatagaca gctgatcaac gacacgttgt 4200
attccacccg gaagaaggat aactcaacct acattgtgca gactatcaag gatatctacg 4260
ccaaagataa cactactctg aagaaacaat tcgacaagtc cccagagaag ttcctgatgt 4320
accagcacga cccccgaacc tttgagaagc ttgaagtgat catgaagcag tacgccaacg 4380
agaagaaccc gctggccaag taccatgaag aaaccggaga atacctgacc aagtacagca 4440
agaagaacaa cggtcccatt gtcaagagcc tgaagtacat cggcaacaag ctgggatccc 4500
acctcgacgt gacacatcag ttcaagtcgt cgactaagaa gcttgtgaag ctgtcaatca 4560
agaactatag attcgacgtg tacttgaccg aaaagggata caagttcgtg accatagcct 4620
atctgaacgt gttcaagaaa gataactact actacatccc caaggacaag taccaggagc 4680
tcaaagaaaa gaagaagatc aaagacaccg accagttcat tgcctccttc tacaagaacg 4740
acctgatcaa actgaacggc gacctctaca agatcattgg agtgaacagc gatgacagga 4800
acatcattga gctggactac tacgacatca agtacaagga ctactgcgag atcaacaaca 4860
tcaagggcga accccggatc aagaaaacta ttggaaagaa aaccgagtcc attgagaagt 4920
tcaccactga cgtgctggga aacctttacc tccactccac cgagaaggca ccacaactga 4980
tcttcaagcg cggcctgggt ggaaagctta aaaggccggc ggccacgaaa aaggccggcc 5040
aggcaaaaaa gaaaaagggt actagtgagg gcaggggaag tctgctaaca tgcggggacg 5100
tggaggaaaa tcccggcccc atgactgccc tgaccgaagg tgctaagctg tttgagaagg 5160
agattccgta catcaccgag ctggaagggg acgtcgaagg aatgaagttc atcatcaagg 5220
gagaaggaac cggggacgct acgactggaa ccattaaggc caagtatatc tgtaccactg 5280
gagatctgcc agtgccttgg gccaccccttg tgtcaaccct ctcgtatgga gtgcagtgtt 5340
ttgctaagta ccctagccac attaaggact tcttcaaatc cgccatgccg gaaggttata 5400
cccaagagcg caccatttct tttgagggag atggagtgta caagacccgc gcgatggtca 5460
cctatgagag ggatctatc tacaaccggg tgactctgac tggagaaaac tttaagaagg 5520
acgggcatat tcttcggaag aatgtcgcct tccagtgccc tcccagcatc ctttacattc 5580
tccccgacac tgtgaacaac ggaatccgcg tggagttcaa tcaagcctac gacatcgagg 5640
gggtgacgga gaagctggtg accaagtgta gccagatgaa tcggccactg gccggttcag 5700
cggctgtcca cattccgcgc taccatcata tcacttatca cactaagctc tccaaagacc 5760
gcgatgagag gagagatcac atgtgcctgg tggaagtggt caaggccgtc gatctcgata 5820
cctatcagta agtcgactga ataagtgaac tcgagatcag cctcgactgt gccttctagt 5880
tgccagccat ctgttgtttg cccctccccc gtgccttcct tgaccctgga aggtgccact 5940
cccactgtcc tttcctaata aaatgaggaa attgcatccc cacttcagaa gttcctatac 6000
tttctagaga ataggaactt cactatagag tcgaataagg gcgacacccc ctaattagcc 6060
cgggcgaaag gcccagtctt tcgactgagc ctttcgtttt atttgatgcc tggcagttcc 6120
ctactctcgc atggggagtc cccacactac catcggcgct acggcgtttc acttctgagt 6180
tcggcatggg gtcaggtggg accaccgcgc tactgccgcc aggcaaacaa ggggtgttat 6240
gagccatatt caggtataaa tgggctcgcg ataatgttca gaattggtta attggttgta 6300
acactgaccc ctatttgttt atttttctaa atacattcaa atatgtatcc gctcatgaga 6360
caataaccct gataaatgct tcaataatat tgaaaaagga agaatatgag ccatattcaa 6420
cgggaaacgt cgaggccgcg attaaattcc aacatggatg ctgatttata tgggtataaa 6480
tgggctcgcg ataatgtcgg gcaatcaggt gcgacaatct atcgcttgta tgggaagccc 6540
gatgcgccag agttgtttct gaaacatggc aaaggtagcg ttgccaatga tgttacagat 6600
gagatggtca gactaaactg gctgacggaa tttatgccac ttccgaccat caagcatttt 6660
atccgtactc ctgatgatgc atggttactc accactgcga tccccggaaa aacagcgttc 6720
caggtattag aagaatatcc tgattcaggt gaaaatattg ttgatgcgct ggcagtgttc 6780
ctgcgccggt tgcactcgat tcctgtttgt aattgtcctt ttaacagcga tcgcgtattt 6840
cgcctcgctc aggcgcaatc acgaatgaat aacggtttgg ttgatgcgag tgattttgat 6900
gacgagcgta atggctggcc tgttgaacaa gtctggaaag aaatgcataa acttttgcca 6960
ttctcaccgg attcagtcgt cactcatggt gatttctcac ttgataacct tatttttgac 7020
gaggggaaat taataggttg tattgatgtt ggacgagtcg gaatcgcaga ccgataccag 7080
gatcttgcca tcctatggaa ctgcctcggt gagttttctc cttcattaca gaaacggctt 7140
tttcaaaaat atggtattga taatcctgat atgaataaat tgcagtttca tttgatgctc 7200
gatgagtttt tctaaaagca gagcattacg ctgacttgac gggacggcgc aagctcatga 7260
ccaaaatccc ttaacgtgag ttacgcgcgc gtcgttccac tgagcgtcag accccgtaga 7320
aaagatcaaa ggatcttctt gagatccttt ttttctgcgc gtaatctgct gcttgcaaac 7380
aaaaaaacca ccgctaccag cggtggtttg tttgccggat caagagctac caactctttt 7440
tccgaaggta actggcttca gcagagcgca gataccaaat actgttcttc tagtgtagcc 7500
gtagttagcc caccacttca agaactctgt agcaccgcct acatacctcg ctctgctaat 7560
cctgttacca gtggctgctg ccagtggcga taagtcgtgt cttaccgggt tggactcaag 7620
acgatagtta ccggataagg cgcagcggtc gggctgaacg gggggttcgt gcacacagcc 7680
cagcttggag cgaacgacct acaccgaact gagataccta cagcgtgagc tatgagaaag 7740
cgccacgctt cccgaaggga gaaaggcgga caggtatccg gtaagcggca gggtcggaac 7800
aggagagcgc acgagggagc ttccaggggg aaacgcctgg tatctttata gtcctgtcgg 7860
gtttcgccac ctctgacttg agcgtcgatt tttgtgatgc tcgtcagggg ggcggagcct 7920
atggaaaaac gccagcaacg cggccttttt acggttcctg gccttttgct ggccttttgc 7980
tcacatgttc tttcctgcgt tatcccctga ttctgtggat aaccgtatta ccgcctttga 8040
gtgagctgat accgctcgcc gcagccgaac gaccgagcgc agcgagtcag tgagcgagga 8100
agcggaaggc gagagtaggg aactgccagg catcaaacta agcagaaggc ccctgacgga 8160
tggccttttt gcgtttctac aaactctttc tgtgttgtaa aacgacggcc agtcttaagc 8220
tcgggcccc 8229

<210> SEQ ID NO 46
<211> LENGTH: 104
<212> TYPE: RNA
<213> ORGANISM: Artificial Sequence
<220> FEATURE:
<223> OTHER INFORMATION: sgRNA sequence

<400> SEQUENCE: 46
guuaaagaug aucucuuacc uguuucagua cucuggaaac agaaucuacu gaaacaagac 60
aauaugucgu guuuauccca ucaauuuauu ggugggauuu uuuu 104

<210> SEQ ID NO 47
<211> LENGTH: 21
<212> TYPE: RNA
<213> ORGANISM: Artificial Sequence
<220> FEATURE:
<223> OTHER INFORMATION: Spacer sequence

<400> SEQUENCE: 47
guuaaagaug aucucuuacc u 21

<210> SEQ ID NO 48
<211> LENGTH: 21
<212> TYPE: DNA
<213> ORGANISM: Artificial Sequence
<220> FEATURE:
<223> OTHER INFORMATION: Target DNA sequence

<400> SEQUENCE: 48
gttaaagatg atctcttacc t 21

<210> SEQ ID NO 49
<211> LENGTH: 21
<212> TYPE: DNA
<213> ORGANISM: Artificial Sequence
<220> FEATURE:
<223> OTHER INFORMATION: Sequence of strand opposite target DNA

<400> SEQUENCE: 49
aggtaagaga tcatctttaa c 21

<210> SEQ ID NO 50
<211> LENGTH: 6254
<212> TYPE: DNA

<213> ORGANISM: Artificial Sequence
<220> FEATURE:
<223> OTHER INFORMATION: Plasmid

<400> SEQUENCE: 50
gacggatcgg gagatctgag ggcctatttc ccatgattcc ttcatatttg catatacgat 60
acaaggctgt tagagagata attggaatta atttgactgt aaacacaaag atattagtac 120
aaaatacgtg acgtagaaag taataatttc ttgggtagtt tgcagtttta aaattatgtt 180
ttaaaatgga ctatcatatg cttaccgtaa cttgaaagta tttcgatttc ttggctttat 240
atatcttgtg gaaaggacga aacaccgcga agaagatcat tgatacccga aggtatcaat 300
gatcttcttc gctttttttac ccgatcccct atggtgcact ctcagtacaa tctgctctga 360
tgccgcatag ttaagccagt atctgctccc tgcttgtgtg ttggaggtcg ctgagtagtg 420
cgcgagcaaa atttaagcta caacaaggca aggcttgacc gacaattgca tgaagaatct 480
gcttagggtt aggcgttttg cgctgcttcg cgatgtacgg gccagatata cgcgttgaca 540
ttgattattg actagttatt aatagtaatc aattacgggg tcattagttc atagcccata 600
tatggagttc cgcgttacat aacttacggt aaatggcccg cctggctgac cgcccaacga 660
cccccgccca ttgacgtcaa taatgacgta tgttcccata gtaacgccaa tagggacttt 720
ccattgacgt caatgggtgg agtatttacg gtaaactgcc cacttggcag tacatcaagt 780
gtatcatatg ccaagtacgc cccctattga cgtcaatgac ggtaaatggc ccgcctggca 840
ttatgcccag tacatgacct tatgggactt tcctacttgg cagtacatct acgtattagt 900
catcgctatt accatggtga tgcggttttg gcagtacatc aatgggcgtg gatagcggtt 960
tgactcacgg ggatttccaa gtctccaccc cattgacgtc aatgggagtt tgttttggca 1020
ccaaaatcaa cgggactttc caaaatgtcg taacaactcc gccccattga cgcaaatggg 1080
cggtaggcgt gtacggtggg aggtctatat aagcagagct ctctggctaa ctagagaacc 1140
cactgcttac tggcttatcg ttaattaacc ggtgccacca tgatgtcccg ccttgataaa 1200
tcaaaagtaa taaacagtgc tcttgagctt ctcaatgaag ttggtataga agggttgacg 1260
actcggaaat tggcgcaaaa actcggtgtt gagcagccaa ccttgtattg gcatgttaaa 1320
aacaaacgag cactcctcga cgctttggcg atagagatgc tggacaggca ccacacgcat 1380
ttctgtcccc tcgaaggaga gtcatggcag gatttcctta gaaataacgc aaagtccttc 1440
agatgtgcgc tgcttagtca ccgcgacggc gcaaaagttc atctcggcac taggccaacc 1500
gagaaacagt acgagactct ggagaaccaa ctggcgtttt tgtgtcaaca gggttttagt 1560
ctcgaaaatg cgctctatgc tctctctgcg gttggccatt tcaccctcgg atgcgtactg 1620
gaagatcagg agcaccaagt ggccaaagaa gaacgggaaa cgccgactac ggacagcatg 1680
cctccgttgc tccggcaagc tatagagctc ttcgatcacc aaggcgctga gccagctttc 1740
ttgttcggat tggaacttat tatatgcggg ctcgaaaagc agcttaaatg cgagtcaggt 1800
taagcggccg ctcgagtcta gagggcccgt ttaaacccgc tgatcagcct cgactgtgcc 1860
ttctagttgc cagccatctg ttgtttgccc ctcccccgtg ccttccttga ccctggaagg 1920
tgccactccc actgtccttt cctaataaaa tgaggaaatt gcatcgcatt gtctgagtag 1980
gtgtcattct attctggggg gtggggtggg gcaggacagc aagggggagg attgggaaga 2040
caatagcagg catgctgggg atgcggtggg ctctatggct tctgaggcgg aaagaaccag 2100
ctggggctct agggggtatc cccacgcgcc ctgtagcggc gcattaagcg cggcgggtgt 2160
ggtggttacg cgcagcgtga ccgctacact tgccagcgcc ctagcgcccg ctcctttcgc 2220

```
tttcttccct tcctttctcg ccacgttcgc cggctttccc cgtcaagctc taaatcgggg   2280
gctcccttta gggttccgat ttagtgcttt acggcacctc gaccccaaaa aacttgatta   2340
gggtgatggt tcacgtagtg ggccatcgcc ctgatagacg gtttttcgcc ctttgacgtt   2400
ggagtccacg ttctttaata gtggactctt gttccaaact ggaacaacac tcaaccctat   2460
ctcggtctat tcttttgatt tataagggat tttgccgatt tcggcctatt ggttaaaaaa   2520
tgagctgatt taacaaaaat ttaacgcgaa ttaattctgt ggaatgtgtg tcagttaggg   2580
tgtggaaagt ccccaggctc cccagcaggc agaagtatgc aaagcatgca tctcaattag   2640
tcagcaacca ggtgtggaaa gtccccaggc tccccagcag gcagaagtat gcaaagcatg   2700
catctcaatt agtcagcaac catagtcccg cccctaactc cgcccatccc gcccctaact   2760
ccgcccagtt ccgcccattc tccgccccat ggctgactaa ttttttttat ttatgcagag   2820
gccgaggccg cctctgcctc tgagctattc cagaagtagt gaggaggctt ttttggaggc   2880
ctaggctttt gcaaaaagct cccgggagct tgtatatcca ttttcggatc tgatcaagag   2940
acaggatgag gatcgtttcg catgattgaa caagatggat tgcacgcagg ttctccggcc   3000
gcttgggtgg agaggctatt cggctatgac tgggcacaac agacaatcgg ctgctctgat   3060
gccgccgtgt tccggctgtc agcgcagggg cgcccggttc tttttgtcaa gaccgacctg   3120
tccggtgccc tgaatgaact gcaggacgag gcagcgcggc tatcgtggct ggccacgacg   3180
ggcgttcctt gcgcagctgt gctcgacgtt gtcactgaag cgggaaggga ctggctgcta   3240
ttgggcgaag tgccggggca ggatctcctg tcatctcacc ttgctcctgc cgagaaagta   3300
tccatcatgg ctgatgcaat gcggcggctg catacgcttg atccggctac ctgcccattc   3360
gaccaccaag cgaaacatcg catcgagcga gcacgtactc ggatggaagc cggtcttgtc   3420
gatcaggatg atctggacga agagcatcag gggctcgcgc cagccgaact gttcgccagg   3480
ctcaaggcgc gcatgcccga cggcgaggat ctcgtcgtga cccatggcga tgcctgcttg   3540
ccgaatatca tggtggaaaa tggccgcttt tctggattca tcgactgtgg ccggctgggt   3600
gtggcggacc gctatcagga catagcgttg gctacccgtg atattgctga agagcttggc   3660
ggcgaatggg ctgaccgctt cctcgtgctt tacggtatcg ccgctcccga ttcgcagcgc   3720
atcgccttct atcgccttct tgacgagttc ttctgagcgg gactctgggg ttcgaaatga   3780
ccgaccaagc gacgcccaac ctgccatcac gagatttcga ttccaccgcc gccttctatg   3840
aaaggttggg cttcggaatc gttttccggg acgccggctg gatgatcctc cagcgcgggg   3900
atctcatgct ggagttcttc gcccacccca acttgtttat tgcagcttat aatggttaca   3960
aataaagcaa tagcatcaca aatttcacaa ataaagcatt tttttcactg cattctagtt   4020
gtggtttgtc caaactcatc aatgtatctt atcatgtctg tataccgtcg acctctagct   4080
agagcttggc gtaatcatgg tcatagctgt ttcctgtgtg aaattgttat ccgctcacaa   4140
ttccacacaa catacgagcc ggaagcataa agtgtaaagc ctggggtgcc taatgagtga   4200
gctaactcac attaattgcg ttgcgctcac tgcccgcttt ccagtcggga aacctgtcgt   4260
gccagctgca ttaatgaatc ggccaacgcg cggggagagg cggtttgcgt attgggcgct   4320
cttccgcttc ctcgctcact gactcgctgc gctcggtcgt tcggctgcgg cgagcggtat   4380
cagctcactc aaaggcggta atacggttat ccacagaatc aggggataac gcaggaaaga   4440
acatgtgagc aaaaggccag caaaaggcca ggaaccgtaa aaaggccgcg ttgctggcgt   4500
ttttccatag gctccgcccc cctgacgagc atcacaaaaa tcgacgctca agtcagaggt   4560
```

ggcgaaaccc gacaggacta taaagatacc aggcgtttcc ccctggaagc tccctcgtgc 4620
gctctcctgt tccgaccctg ccgcttaccg gatacctgtc cgcctttctc ccttcgggaa 4680
gcgtggcgct ttctcatagc tcacgctgta ggtatctcag ttcggtgtag gtcgttcgct 4740
ccaagctggg ctgtgtgcac gaaccccccg ttcagcccga ccgctgcgcc ttatccggta 4800
actatcgtct tgagtccaac ccggtaagac acgacttatc gccactggca gcagccactg 4860
gtaacaggat tagcagagcg aggtatgtag gcggtgctac agagttcttg aagtggtggc 4920
ctaactacgg ctacactaga agaacagtat ttggtatctg cgctctgctg aagccagtta 4980
ccttcggaaa aagagttggt agctcttgat ccggcaaaca aaccaccgct ggtagcggtt 5040
tttttgtttg caagcagcag attacgcgca gaaaaaaagg atctcaagaa gatcctttga 5100
tcttttctac ggggtctgac gctcagtgga acgaaaactc acgttaaggg attttggtca 5160
tgagattatc aaaaaggatc ttcacctaga tccttttaaa ttaaaaatga agttttaaat 5220
caatctaaag tatatatgag taaacttggt ctgacagtta ccaatgctta atcagtgagg 5280
cacctatctc agcgatctgt ctatttcgtt catccatagt tgcctgactc cccgtcgtgt 5340
agataactac gatacgggag ggcttaccat ctggccccag tgctgcaatg ataccgcgag 5400
acccacgctc accggctcca gatttatcag caataaacca gccagccgga agggccgagc 5460
gcagaagtgg tcctgcaact ttatccgcct ccatccagtc tattaattgt tgccgggaag 5520
ctagagtaag tagttcgcca gttaatagtt tgcgcaacgt tgttgccatt gctacaggca 5580
tcgtggtgtc acgctcgtcg tttggtatgg cttcattcag ctccggttcc caacgatcaa 5640
ggcgagttac atgatccccc atgttgtgca aaaaagcggt tagctccttc ggtcctccga 5700
tcgttgtcag aagtaagttg gccgcagtgt tatcactcat ggttatggca gcactgcata 5760
attctcttac tgtcatgcca tccgtaagat gcttttctgt gactggtgag tactcaacca 5820
agtcattctg agaatagtgt atgcggcgac cgagttgctc ttgcccggcg tcaatacggg 5880
ataataccgc gccacatagc agaactttaa aagtgctcat cattggaaaa cgttcttcgg 5940
ggcgaaaact ctcaaggatc ttaccgctgt tgagatccag ttcgatgtaa cccactcgtg 6000
cacccaactg atcttcagca tcttttactt tcaccagcgt ttctgggtga gcaaaaacag 6060
gaaggcaaaa tgccgcaaaa aagggaataa gggcgacacg gaaatgttga atactcatac 6120
tcttcctttt tcaatattat tgaagcattt atcagggtta ttgtctcatg agcggataca 6180
tatttgaatg tatttagaaa aataaacaaa taggggttcc gcgcacattt ccccgaaaag 6240
tgccacctga cgtc 6254

<210> SEQ ID NO 51
<211> LENGTH: 6254
<212> TYPE: DNA
<213> ORGANISM: Artificial Sequence
<220> FEATURE:
<223> OTHER INFORMATION: Plasmid

<400> SEQUENCE: 51
gacggatcgg gagatctgag ggcctatttc ccatgattcc ttcatatttg catatacgat 60
acaaggctgt tagagagata attggaatta atttgactgt aaacacaaag atattagtac 120
aaaatacgtg acgtagaaag taataatttc ttgggtagtt tgcagtttta aaattatgtt 180
ttaaaatgga ctatcatatg cttaccgtaa cttgaaagta tttcgatttc ttggctttat 240
atatcttgtg gaaaggacga aacaccgcaa atcgccaagg agattggcga accaatctcc 300
ttggcgattt gctttttttac ccgatcccct atggtgcact ctcagtacaa tctgctctga 360

```
tgccgcatag ttaagccagt atctgctccc tgcttgtgtg ttggaggtcg ctgagtagtg    420
cgcgagcaaa atttaagcta caacaaggca aggcttgacc gacaattgca tgaagaatct    480
gcttagggtt aggcgttttg cgctgcttcg cgatgtacgg gccagatata cgcgttgaca    540
ttgattattg actagttatt aatagtaatc aattacgggg tcattagttc atagcccata    600
tatggagttc cgcgttacat aacttacggt aaatggcccg cctggctgac cgcccaacga    660
cccccgccca ttgacgtcaa taatgacgta tgttcccata gtaacgccaa tagggacttt    720
ccattgacgt caatgggtgg agtatttacg gtaaactgcc cacttggcag tacatcaagt    780
gtatcatatg ccaagtacgc cccctattga cgtcaatgac ggtaaatggc ccgcctggca    840
ttatgcccag tacatgacct tatgggactt tcctacttgg cagtacatct acgtattagt    900
catcgctatt accatggtga tgcggttttg gcagtacatc aatgggcgtg gatagcggtt    960
tgactcacgg ggatttccaa gtctccaccc cattgacgtc aatgggagtt tgttttggca   1020
ccaaaatcaa cgggactttc caaaatgtcg taacaactcc gccccattga cgcaaatggg   1080
cggtaggcgt gtacggtggg aggtctatat aagcagagct ctctggctaa ctagagaacc   1140
cactgcttac tggcttatcg ttaattaacc ggtgccacca tgatgtcccg ccttgataaa   1200
tcaaaagtaa taaacagtgc tcttgagctt ctcaatgaag ttggtataga agggttgacg   1260
actcggaaat tggcgcaaaa actcggtgtt gagcagccaa ccttgtattg gcatgttaaa   1320
aacaaacgag cactcctcga cgctttggcg atagagatgc tggacaggca ccacacgcat   1380
ttctgtcccc tcgaaggaga gtcatggcag gatttcctta gaaataacgc aaagtccttc   1440
agatgtgcgc tgcttagtca ccgcgacggc gcaaaagttc atctcggcac taggccaacc   1500
gagaaacagt acgagactct ggagaaccaa ctggcgtttt tgtgtcaaca gggttttagt   1560
ctcgaaaatg cgctctatgc tctctctgcg gttggccatt tcaccctcgg atgcgtactg   1620
gaagatcagg agcaccaagt ggccaaagaa gaacgggaaa cgccgactac ggacagcatg   1680
cctccgttgc tccggcaagc tatagagctc ttcgatcacc aaggcgctga gccagctttc   1740
ttgttcggat tggaacttat tatatgcggg ctcgaaaagc agcttaaatg cgagtcaggt   1800
taagcggccg ctcgagtcta gagggcccgt ttaaacccgc tgatcagcct cgactgtgcc   1860
ttctagttgc cagccatctg ttgtttgccc ctcccccgtg ccttccttga ccctggaagg   1920
tgccactccc actgtccttt cctaataaaa tgaggaaatt gcatcgcatt gtctgagtag   1980
gtgtcattct attctggggg gtggggtggg gcaggacagc aagggggagg attgggaaga   2040
caatagcagg catgctgggg atgcggtggg ctctatggct tctgaggcgg aaagaaccag   2100
ctggggctct agggggtatc cccacgcgcc ctgtagcggc gcattaagcg cggcgggtgt   2160
ggtggttacg cgcagcgtga ccgctacact tgccagcgcc ctagcgcccg ctcctttcgc   2220
tttcttccct tcctttctcg ccacgttcgc cggctttccc cgtcaagctc taaatcgggg   2280
gctcccttta gggttccgat ttagtgcttt acggcacctc gaccccaaaa aacttgatta   2340
gggtgatggt tcacgtagtg ggccatcgcc ctgatagacg gtttttcgcc ctttgacgtt   2400
ggagtccacg ttctttaata gtggactctt gttccaaact ggaacaacac tcaaccctat   2460
ctcggtctat tcttttgatt tataagggat tttgccgatt tcggcctatt ggttaaaaaa   2520
tgagctgatt taacaaaaat ttaacgcgaa ttaattctgt ggaatgtgtg tcagttaggg   2580
tgtggaaagt ccccaggctc cccagcaggc agaagtatgc aaagcatgca tctcaattag   2640
tcagcaacca ggtgtggaaa gtccccaggc tccccagcag gcagaagtat gcaaagcatg   2700
```

-continued

```
catctcaatt agtcagcaac catagtcccg cccctaactc cgcccatccc gcccctaact   2760
ccgcccagtt ccgcccattc tccgccccat ggctgactaa ttttttttat ttatgcagag   2820
gccgaggccg cctctgcctc tgagctattc cagaagtagt gaggaggctt ttttggaggc   2880
ctaggctttt gcaaaaagct cccgggagct tgtatatcca ttttcggatc tgatcaagag   2940
acaggatgag gatcgtttcg catgattgaa caagatggat tgcacgcagg ttctccggcc   3000
gcttgggtgg agaggctatt cggctatgac tgggcacaac agacaatcgg ctgctctgat   3060
gccgccgtgt tccggctgtc agcgcagggg cgcccggttc tttttgtcaa gaccgacctg   3120
tccggtgccc tgaatgaact gcaggacgag gcagcgcggc tatcgtggct ggccacgacg   3180
ggcgttcctt gcgcagctgt gctcgacgtt gtcactgaag cgggaaggga ctggctgcta   3240
ttgggcgaag tgccggggca ggatctcctg tcatctcacc ttgctcctgc cgagaaagta   3300
tccatcatgg ctgatgcaat gcggcggctg catacgcttg atccggctac ctgcccattc   3360
gaccaccaag cgaaacatcg catcgagcga gcacgtactc ggatggaagc cggtcttgtc   3420
gatcaggatg atctggacga agagcatcag gggctcgcgc cagccgaact gttcgccagg   3480
ctcaaggcgc gcatgcccga cggcgaggat ctcgtcgtga cccatggcga tgcctgcttg   3540
ccgaatatca tggtggaaaa tggccgcttt tctggattca tcgactgtgg ccggctgggt   3600
gtggcggacc gctatcagga catagcgttg gctacccgtg atattgctga agagcttggc   3660
ggcgaatggg ctgaccgctt cctcgtgctt tacggtatcg ccgctcccga ttcgcagcgc   3720
atcgccttct atcgccttct tgacgagttc ttctgagcgg gactctgggg ttcgaaatga   3780
ccgaccaagc gacgcccaac ctgccatcac gagatttcga ttccaccgcc gccttctatg   3840
aaaggttggg cttcggaatc gttttccggg acgccggctg gatgatcctc cagcgcgggg   3900
atctcatgct ggagttcttc gcccacccca acttgtttat tgcagcttat aatggttaca   3960
aataaagcaa tagcatcaca aatttcacaa ataaagcatt tttttcactg cattctagtt   4020
gtggtttgtc caaactcatc aatgtatctt atcatgtctg tataccgtcg acctctagct   4080
agagcttggc gtaatcatgg tcatagctgt ttcctgtgtg aaattgttat ccgctcacaa   4140
ttccacacaa catacgagcc ggaagcataa agtgtaaagc ctggggtgcc taatgagtga   4200
gctaactcac attaattgcg ttgcgctcac tgcccgcttt ccagtcggga aacctgtcgt   4260
gccagctgca ttaatgaatc ggccaacgcg cggggagagg cggtttgcgt attgggcgct   4320
cttccgcttc ctcgctcact gactcgctgc gctcggtcgt tcggctgcgg cgagcggtat   4380
cagctcactc aaaggcggta atacggttat ccacagaatc aggggataac gcaggaaaga   4440
acatgtgagc aaaaggccag caaaaggcca ggaaccgtaa aaaggccgcg ttgctggcgt   4500
ttttccatag gctccgcccc cctgacgagc atcacaaaaa tcgacgctca agtcagaggt   4560
ggcgaaaccc gacaggacta taaagatacc aggcgtttcc ccctggaagc tccctcgtgc   4620
gctctcctgt tccgaccctg ccgcttaccg gatacctgtc cgcctttctc ccttcgggaa   4680
gcgtggcgct ttctcatagc tcacgctgta ggtatctcag ttcggtgtag gtcgttcgct   4740
ccaagctggg ctgtgtgcac gaaccccccg ttcagcccga ccgctgcgcc ttatccggta   4800
actatcgtct tgagtccaac ccggtaagac acgacttatc gccactggca gcagccactg   4860
gtaacaggat tagcagagcg aggtatgtag gcggtgctac agagttcttg aagtggtggc   4920
ctaactacgg ctacactaga agaacagtat ttggtatctg cgctctgctg aagccagtta   4980
ccttcggaaa aagagttggt agctcttgat ccggcaaaca aaccaccgct ggtagcggtt   5040
tttttgtttg caagcagcag attacgcgca gaaaaaaagg atctcaagaa gatcctttga   5100
```

tcttttctac ggggtctgac gctcagtgga acgaaaactc acgttaaggg attttggtca 5160
tgagattatc aaaaaggatc ttcacctaga tccttttaaa ttaaaaatga agttttaaat 5220
caatctaaag tatatatgag taaacttggt ctgacagtta ccaatgctta atcagtgagg 5280
cacctatctc agcgatctgt ctatttcgtt catccatagt tgcctgactc cccgtcgtgt 5340
agataactac gatacgggag ggcttaccat ctggccccag tgctgcaatg ataccgcgag 5400
acccacgctc accggctcca gatttatcag caataaacca gccagccgga agggccgagc 5460
gcagaagtgg tcctgcaact ttatccgcct ccatccagtc tattaattgt tgccgggaag 5520
ctagagtaag tagttcgcca gttaatagtt tgcgcaacgt tgttgccatt gctacaggca 5580
tcgtggtgtc acgctcgtcg tttggtatgg cttcattcag ctccggttcc caacgatcaa 5640
ggcgagttac atgatccccc atgttgtgca aaaaagcggt tagctccttc ggtcctccga 5700
tcgttgtcag aagtaagttg gccgcagtgt tatcactcat ggttatggca gcactgcata 5760
attctcttac tgtcatgcca tccgtaagat gcttttctgt gactggtgag tactcaacca 5820
agtcattctg agaatagtgt atgcggcgac cgagttgctc ttgcccggcg tcaatacggg 5880
ataataccgc gccacatagc agaactttaa aagtgctcat cattggaaaa cgttcttcgg 5940
ggcgaaaact ctcaaggatc ttaccgctgt tgagatccag ttcgatgtaa cccactcgtg 6000
cacccaactg atcttcagca tcttttactt tcaccagcgt ttctgggtga gcaaaaacag 6060
gaaggcaaaa tgccgcaaaa aagggaataa gggcgacacg gaaatgttga atactcatac 6120
tcttcctttt tcaatattat tgaagcattt atcagggtta ttgtctcatg agcggataca 6180
tatttgaatg tatttagaaa aataaacaaa taggggttcc gcgcacattt ccccgaaaag 6240
tgccacctga cgtc 6254

<210> SEQ ID NO 52
<211> LENGTH: 6254
<212> TYPE: DNA
<213> ORGANISM: Artificial Sequence
<220> FEATURE:
<223> OTHER INFORMATION: Plasmid

<400> SEQUENCE: 52
gacggatcgg gagatctgag ggcctatttc ccatgattcc ttcatatttg catatacgat 60
acaaggctgt tagagagata attggaatta atttgactgt aaacacaaag atattagtac 120
aaaatacgtg acgtagaaag taataatttc ttgggtagtt tgcagtttta aaattatgtt 180
ttaaaatgga ctatcatatg cttaccgtaa cttgaaagta tttcgatttc ttggctttat 240
atatcttgtg gaaaggacga aacaccgcac agctccatga accaaatcga aatttggttc 300
atggagctgt gctttttttac ccgatcccct atggtgcact ctcagtacaa tctgctctga 360
tgccgcatag ttaagccagt atctgctccc tgcttgtgtg ttggaggtcg ctgagtagtg 420
cgcgagcaaa atttaagcta caacaaggca aggcttgacc gacaattgca tgaagaatct 480
gcttagggtt aggcgttttg cgctgcttcg cgatgtacgg gccagatata cgcgttgaca 540
ttgattattg actagttatt aatagtaatc aattacgggg tcattagttc atagcccata 600
tatggagttc cgcgttacat aacttacggt aaatggcccg cctggctgac cgcccaacga 660
cccccgccca ttgacgtcaa taatgacgta tgttcccata gtaacgccaa tagggacttt 720
ccattgacgt caatgggtgg agtatttacg gtaaactgcc cacttggcag tacatcaagt 780
gtatcatatg ccaagtacgc cccctattga cgtcaatgac ggtaaatggc ccgcctggca 840
ttatgcccag tacatgacct tatgggactt tcctacttgg cagtacatct acgtattagt 900
catcgctatt accatggtga tgcggttttg gcagtacatc aatgggcgtg gatagcggtt 960
tgactcacgg ggatttccaa gtctccaccc cattgacgtc aatgggagtt tgttttggca 1020
ccaaaatcaa cgggactttc caaaatgtcg taacaactcc gccccattga cgcaaatggg 1080
cggtaggcgt gtacggtggg aggtctatat aagcagagct ctctggctaa ctagagaacc 1140
cactgcttac tggcttatcg ttaattaacc ggtgccacca tgatgtcccg ccttgataaa 1200
tcaaaagtaa taaacagtgc tcttgagctt ctcaatgaag ttggtataga agggttgacg 1260
actcggaaat tggcgcaaaa actcggtgtt gagcagccaa ccttgtattg gcatgttaaa 1320
aacaaacgag cactcctcga cgctttggcg atagagatgc tggacaggca ccacacgcat 1380
ttctgtcccc tcgaaggaga gtcatggcag gatttcctta gaaataacgc aaagtccttc 1440
agatgtgcgc tgcttagtca ccgcgacggc gcaaaagttc atctcggcac taggccaacc 1500
gagaaacagt acgagactct ggagaaccaa ctggcgtttt tgtgtcaaca gggttttagt 1560
ctcgaaaatg cgctctatgc tctctctgcg gttggccatt tcaccctcgg atgcgtactg 1620
gaagatcagg agcaccaagt ggccaaagaa gaacgggaaa cgccgactac ggacagcatg 1680
cctccgttgc tccggcaagc tatagagctc ttcgatcacc aaggcgctga gccagctttc 1740
ttgttcggat tggaacttat tatatgcggg ctcgaaaagc agcttaaatg cgagtcaggt 1800
taagcggccg ctcgagtcta gagggcccgt ttaaacccgc tgatcagcct cgactgtgcc 1860
ttctagttgc cagccatctg ttgtttgccc ctcccccgtg ccttccttga ccctggaagg 1920
tgccactccc actgtccttt cctaataaaa tgaggaaatt gcatcgcatt gtctgagtag 1980
gtgtcattct attctggggg gtggggtggg gcaggacagc aagggggagg attgggaaga 2040
caatagcagg catgctgggg atgcggtggg ctctatggct tctgaggcgg aaagaaccag 2100
ctggggctct agggggtatc cccacgcgcc ctgtagcggc gcattaagcg cggcgggtgt 2160
ggtggttacg cgcagcgtga ccgctacact tgccagcgcc ctagcgcccg ctcctttcgc 2220
tttcttccct tcctttctcg ccacgttcgc cggctttccc cgtcaagctc taaatcgggg 2280
gctcccttta gggttccgat ttagtgcttt acggcacctc gaccccaaaa aacttgatta 2340
gggtgatggt tcacgtagtg ggccatcgcc ctgatagacg gtttttcgcc ctttgacgtt 2400
ggagtccacg ttctttaata gtggactctt gttccaaact ggaacaacac tcaaccctat 2460
ctcggtctat tcttttgatt tataagggat tttgccgatt tcggcctatt ggttaaaaaa 2520
tgagctgatt taacaaaaat ttaacgcgaa ttaattctgt ggaatgtgtg tcagttaggg 2580
tgtggaaagt ccccaggctc cccagcaggc agaagtatgc aaagcatgca tctcaattag 2640
tcagcaacca ggtgtggaaa gtccccaggc tccccagcag gcagaagtat gcaaagcatg 2700
catctcaatt agtcagcaac catagtcccg cccctaactc cgcccatccc gcccctaact 2760
ccgcccagtt ccgcccattc tccgccccat ggctgactaa ttttttttat ttatgcagag 2820
gccgaggccg cctctgcctc tgagctattc cagaagtagt gaggaggctt ttttggaggc 2880
ctaggctttt gcaaaaagct cccgggagct tgtatatcca ttttcggatc tgatcaagag 2940
acaggatgag gatcgtttcg catgattgaa caagatggat tgcacgcagg ttctccggcc 3000
gcttgggtgg agaggctatt cggctatgac tgggcacaac agacaatcgg ctgctctgat 3060
gccgccgtgt tccggctgtc agcgcagggg cgcccggttc tttttgtcaa gaccgacctg 3120
tccggtgccc tgaatgaact gcaggacgag gcagcgcggc tatcgtggct ggccacgacg 3180
ggcgttcctt gcgcagctgt gctcgacgtt gtcactgaag cgggaaggga ctggctgcta 3240

```
ttgggcgaag tgccggggca ggatctcctg tcatctcacc ttgctcctgc cgagaaagta   3300
tccatcatgg ctgatgcaat gcggcggctg catacgcttg atccggctac ctgcccattc   3360
gaccaccaag cgaaacatcg catcgagcga gcacgtactc ggatggaagc cggtcttgtc   3420
gatcaggatg atctggacga agagcatcag gggctcgcgc cagccgaact gttcgccagg   3480
ctcaaggcgc gcatgcccga cggcgaggat ctcgtcgtga cccatggcga tgcctgcttg   3540
ccgaatatca tggtggaaaa tggccgcttt tctggattca tcgactgtgg ccggctgggt   3600
gtggcggacc gctatcagga catagcgttg gctacccgtg atattgctga agagcttggc   3660
ggcgaatggg ctgaccgctt cctcgtgctt tacggtatcg ccgctcccga ttcgcagcgc   3720
atcgccttct atcgccttct tgacgagttc ttctgagcgg gactctgggg ttcgaaatga   3780
ccgaccaagc gacgcccaac ctgccatcac gagatttcga ttccaccgcc gccttctatg   3840
aaaggttggg cttcggaatc gttttccggg acgccggctg gatgatcctc cagcgcgggg   3900
atctcatgct ggagttcttc gcccacccca acttgtttat tgcagcttat aatggttaca   3960
aataaagcaa tagcatcaca aatttcacaa ataaagcatt tttttcactg cattctagtt   4020
gtggtttgtc caaactcatc aatgtatctt atcatgtctg tataccgtcg acctctagct   4080
agagcttggc gtaatcatgg tcatagctgt ttcctgtgtg aaattgttat ccgctcacaa   4140
ttccacacaa catacgagcc ggaagcataa agtgtaaagc ctggggtgcc taatgagtga   4200
gctaactcac attaattgcg ttgcgctcac tgcccgcttt ccagtcggga aacctgtcgt   4260
gccagctgca ttaatgaatc ggccaacgcg cggggagagg cggtttgcgt attgggcgct   4320
cttccgcttc ctcgctcact gactcgctgc gctcggtcgt tcggctgcgg cgagcggtat   4380
cagctcactc aaaggcggta atacggttat ccacagaatc aggggataac gcaggaaaga   4440
acatgtgagc aaaaggccag caaaaggcca ggaaccgtaa aaaggccgcg ttgctggcgt   4500
ttttccatag gctccgcccc cctgacgagc atcacaaaaa tcgacgctca agtcagaggt   4560
ggcgaaaccc gacaggacta taaagatacc aggcgtttcc ccctggaagc tccctcgtgc   4620
gctctcctgt tccgaccctg ccgcttaccg gatacctgtc cgcctttctc ccttcgggaa   4680
gcgtggcgct ttctcatagc tcacgctgta ggtatctcag ttcggtgtag gtcgttcgct   4740
ccaagctggg ctgtgtgcac gaaccccccg ttcagcccga ccgctgcgcc ttatccggta   4800
actatcgtct tgagtccaac ccggtaagac acgacttatc gccactggca gcagccactg   4860
gtaacaggat tagcagagcg aggtatgtag gcggtgctac agagttcttg aagtggtggc   4920
ctaactacgg ctacactaga agaacagtat ttggtatctg cgctctgctg aagccagtta   4980
ccttcggaaa aagagttggt agctcttgat ccggcaaaca aaccaccgct ggtagcggtt   5040
tttttgtttg caagcagcag attacgcgca gaaaaaaagg atctcaagaa gatcctttga   5100
tcttttctac ggggtctgac gctcagtgga acgaaaactc acgttaaggg attttggtca   5160
tgagattatc aaaaaggatc ttcacctaga tccttttaaa ttaaaaatga agttttaaat   5220
caatctaaag tatatatgag taaacttggt ctgacagtta ccaatgctta atcagtgagg   5280
cacctatctc agcgatctgt ctatttcgtt catccatagt tgcctgactc cccgtcgtgt   5340
agataactac gatacgggag ggcttaccat ctggccccag tgctgcaatg ataccgcgag   5400
acccacgctc accggctcca gatttatcag caataaacca gccagccgga agggccgagc   5460
gcagaagtgg tcctgcaact ttatccgcct ccatccagtc tattaattgt tgccgggaag   5520
ctagagtaag tagttcgcca gttaatagtt tgcgcaacgt tgttgccatt gctacaggca   5580
```

-continued

```
tcgtggtgtc acgctcgtcg tttggtatgg cttcattcag ctccggttcc caacgatcaa   5640

ggcgagttac atgatccccc atgttgtgca aaaaagcggt tagctccttc ggtcctccga   5700

tcgttgtcag aagtaagttg gccgcagtgt tatcactcat ggttatggca gcactgcata   5760

attctcttac tgtcatgcca tccgtaagat gcttttctgt gactggtgag tactcaacca   5820

agtcattctg agaatagtgt atgcggcgac cgagttgctc ttgcccggcg tcaatacggg   5880

ataataccgc gccacatagc agaactttaa aagtgctcat cattggaaaa cgttcttcgg   5940

ggcgaaaact ctcaaggatc ttaccgctgt tgagatccag ttcgatgtaa cccactcgtg   6000

cacccaactg atcttcagca tcttttactt tcaccagcgt ttctgggtga gcaaaaacag   6060

gaaggcaaaa tgccgcaaaa aagggaataa gggcgacacg gaaatgttga atactcatac   6120

tcttcctttt tcaatattat tgaagcattt atcagggtta ttgtctcatg agcggataca   6180

tatttgaatg tatttagaaa aataaacaaa taggggttcc gcgcacattt ccccgaaaag   6240

tgccacctga cgtc                                                     6254
```

```
<210> SEQ ID NO 53
<211> LENGTH: 6254
<212> TYPE: DNA
<213> ORGANISM: Artificial Sequence
<220> FEATURE:
<223> OTHER INFORMATION: Plasmid

<400> SEQUENCE: 53
```

```
gacggatcgg gagatctgag ggcctatttc ccatgattcc ttcatatttg catatacgat     60

acaaggctgt tagagagata attggaatta atttgactgt aaacacaaag atattagtac    120

aaaatacgtg acgtagaaag taataatttc ttgggtagtt tgcagtttta aaattatgtt    180

ttaaaatgga ctatcatatg cttaccgtaa cttgaaagta tttcgatttc ttggctttat    240

atatcttgtg gaaaggacga aacaccggac cttcattcaa tccatcacga atgatggatt    300

gaatgaaggt cctttttttac ccgatcccct atggtgcact ctcagtacaa tctgctctga    360

tgccgcatag ttaagccagt atctgctccc tgcttgtgtg ttggaggtcg ctgagtagtg    420

cgcgagcaaa atttaagcta caacaaggca aggcttgacc gacaattgca tgaagaatct    480

gcttagggtt aggcgttttg cgctgcttcg cgatgtacgg gccagatata cgcgttgaca    540

ttgattattg actagttatt aatagtaatc aattacgggg tcattagttc atagcccata    600

tatggagttc cgcgttacat aacttacggt aaatggcccg cctggctgac cgcccaacga    660

cccccgccca ttgacgtcaa taatgacgta tgttcccata gtaacgccaa tagggacttt    720

ccattgacgt caatgggtgg agtatttacg gtaaactgcc cacttggcag tacatcaagt    780

gtatcatatg ccaagtacgc cccctattga cgtcaatgac ggtaaatggc ccgcctggca    840

ttatgcccag tacatgacct tatgggactt tcctacttgg cagtacatct acgtattagt    900

catcgctatt accatggtga tgcggttttg gcagtacatc aatgggcgtg gatagcggtt    960

tgactcacgg ggatttccaa gtctccaccc cattgacgtc aatgggagtt tgttttggca   1020

ccaaaatcaa cgggactttc caaaatgtcg taacaactcc gccccattga cgcaaatggg   1080

cggtaggcgt gtacggtggg aggtctatat aagcagagct ctctggctaa ctagagaacc   1140

cactgcttac tggcttatcg ttaattaacc ggtgccacca tgatgtcccg ccttgataaa   1200

tcaaaagtaa taaacagtgc tcttgagctt ctcaatgaag ttggtataga agggttgacg   1260

actcggaaat tggcgcaaaa actcggtgtt gagcagccaa ccttgtattg gcatgttaaa   1320

aacaaacgag cactcctcga cgctttggcg atagagatgc tggacaggca ccacacgcat   1380
```

-continued

```
ttctgtcccc tcgaaggaga gtcatggcag gatttcctta gaaataacgc aaagtccttc   1440
agatgtgcgc tgcttagtca ccgcgacggc gcaaaagttc atctcggcac taggccaacc   1500
gagaaacagt acgagactct ggagaaccaa ctggcgtttt tgtgtcaaca gggttttagt   1560
ctcgaaaatg cgctctatgc tctctctgcg gttggccatt tcaccctcgg atgcgtactg   1620
gaagatcagg agcaccaagt ggccaaagaa gaacgggaaa cgccgactac ggacagcatg   1680
cctccgttgc tccggcaagc tatagagctc ttcgatcacc aaggcgctga gccagctttc   1740
ttgttcggat tggaacttat tatatgcggg ctcgaaaagc agcttaaatg cgagtcaggt   1800
taagcggccg ctcgagtcta gagggcccgt ttaaacccgc tgatcagcct cgactgtgcc   1860
ttctagttgc cagccatctg ttgtttgccc ctcccccgtg ccttccttga ccctggaagg   1920
tgccactccc actgtccttt cctaataaaa tgaggaaatt gcatcgcatt gtctgagtag   1980
gtgtcattct attctggggg gtggggtggg gcaggacagc aagggggagg attgggaaga   2040
caatagcagg catgctgggg atgcggtggg ctctatggct tctgaggcgg aaagaaccag   2100
ctggggctct agggggtatc cccacgcgcc ctgtagcggc gcattaagcg cggcgggtgt   2160
ggtggttacg cgcagcgtga ccgctacact tgccagcgcc ctagcgcccg ctcctttcgc   2220
tttcttccct tcctttctcg ccacgttcgc cggctttccc cgtcaagctc taaatcgggg   2280
gctcccttta gggttccgat ttagtgcttt acggcacctc gaccccaaaa aacttgatta   2340
gggtgatggt tcacgtagtg ggccatcgcc ctgatagacg gtttttcgcc ctttgacgtt   2400
ggagtccacg ttctttaata gtggactctt gttccaaact ggaacaacac tcaaccctat   2460
ctcggtctat tcttttgatt tataagggat tttgccgatt tcggcctatt ggttaaaaaa   2520
tgagctgatt taacaaaaat ttaacgcgaa ttaattctgt ggaatgtgtg tcagttaggg   2580
tgtggaaagt ccccaggctc cccagcaggc agaagtatgc aaagcatgca tctcaattag   2640
tcagcaacca ggtgtggaaa gtccccaggc tccccagcag gcagaagtat gcaaagcatg   2700
catctcaatt agtcagcaac catagtcccg cccctaactc cgcccatccc gcccctaact   2760
ccgcccagtt ccgcccattc tccgccccat ggctgactaa ttttttttat ttatgcagag   2820
gccgaggccg cctctgcctc tgagctattc cagaagtagt gaggaggctt ttttggaggc   2880
ctaggctttt gcaaaaagct cccgggagct tgtatatcca ttttcggatc tgatcaagag   2940
acaggatgag gatcgtttcg catgattgaa caagatggat tgcacgcagg ttctccggcc   3000
gcttgggtgg agaggctatt cggctatgac tgggcacaac agacaatcgg ctgctctgat   3060
gccgccgtgt tccggctgtc agcgcagggg cgcccggttc tttttgtcaa gaccgacctg   3120
tccggtgccc tgaatgaact gcaggacgag gcagcgcggc tatcgtggct ggccacgacg   3180
ggcgttcctt gcgcagctgt gctcgacgtt gtcactgaag cgggaaggga ctggctgcta   3240
ttgggcgaag tgccggggca ggatctcctg tcatctcacc ttgctcctgc cgagaaagta   3300
tccatcatgg ctgatgcaat gcggcggctg catacgcttg atccggctac ctgcccattc   3360
gaccaccaag cgaaacatcg catcgagcga gcacgtactc ggatggaagc cggtcttgtc   3420
gatcaggatg atctggacga agagcatcag gggctcgcgc cagccgaact gttcgccagg   3480
ctcaaggcgc gcatgcccga cggcgaggat ctcgtcgtga cccatggcga tgcctgcttg   3540
ccgaatatca tggtggaaaa tggccgcttt tctggattca tcgactgtgg ccggctgggt   3600
gtggcggacc gctatcagga catagcgttg gctacccgtg atattgctga agagcttggc   3660
ggcgaatggg ctgaccgctt cctcgtgctt tacggtatcg ccgctcccga ttcgcagcgc   3720
```

```
atcgccttct atcgccttct tgacgagttc ttctgagcgg gactctgggg ttcgaaatga   3780
ccgaccaagc gacgcccaac ctgccatcac gagatttcga ttccaccgcc gccttctatg   3840
aaaggttggg cttcggaatc gttttccggg acgccggctg gatgatcctc cagcgcgggg   3900
atctcatgct ggagttcttc gcccacccca acttgtttat tgcagcttat aatggttaca   3960
aataaagcaa tagcatcaca aatttcacaa ataaagcatt tttttcactg cattctagtt   4020
gtggtttgtc caaactcatc aatgtatctt atcatgtctg tataccgtcg acctctagct   4080
agagcttggc gtaatcatgg tcatagctgt ttcctgtgtg aaattgttat ccgctcacaa   4140
ttccacacaa catacgagcc ggaagcataa agtgtaaagc ctggggtgcc taatgagtga   4200
gctaactcac attaattgcg ttgcgctcac tgcccgcttt ccagtcggga aacctgtcgt   4260
gccagctgca ttaatgaatc ggccaacgcg cggggagagg cggtttgcgt attgggcgct   4320
cttccgcttc ctcgctcact gactcgctgc gctcggtcgt tcggctgcgg cgagcggtat   4380
cagctcactc aaaggcggta atacggttat ccacagaatc aggggataac gcaggaaaga   4440
acatgtgagc aaaaggccag caaaaggcca ggaaccgtaa aaaggccgcg ttgctggcgt   4500
ttttccatag gctccgcccc cctgacgagc atcacaaaaa tcgacgctca agtcagaggt   4560
ggcgaaaccc gacaggacta taaagatacc aggcgtttcc ccctggaagc tccctcgtgc   4620
gctctcctgt tccgaccctg ccgcttaccg gatacctgtc cgcctttctc ccttcgggaa   4680
gcgtggcgct ttctcatagc tcacgctgta ggtatctcag ttcggtgtag gtcgttcgct   4740
ccaagctggg ctgtgtgcac gaaccccccg ttcagcccga ccgctgcgcc ttatccggta   4800
actatcgtct tgagtccaac ccggtaagac acgacttatc gccactggca gcagccactg   4860
gtaacaggat tagcagagcg aggtatgtag gcggtgctac agagttcttg aagtggtggc   4920
ctaactacgg ctacactaga agaacagtat ttggtatctg cgctctgctg aagccagtta   4980
ccttcggaaa aagagttggt agctcttgat ccggcaaaca aaccaccgct ggtagcggtt   5040
tttttgtttg caagcagcag attacgcgca gaaaaaaagg atctcaagaa gatcctttga   5100
tcttttctac ggggtctgac gctcagtgga acgaaaactc acgttaaggg attttggtca   5160
tgagattatc aaaaaggatc ttcacctaga tccttttaaa ttaaaaatga agttttaaat   5220
caatctaaag tatatatgag taaacttggt ctgacagtta ccaatgctta atcagtgagg   5280
cacctatctc agcgatctgt ctatttcgtt catccatagt tgcctgactc cccgtcgtgt   5340
agataactac gatacgggag ggcttaccat ctggccccag tgctgcaatg ataccgcgag   5400
acccacgctc accggctcca gatttatcag caataaacca gccagccgga agggccgagc   5460
gcagaagtgg tcctgcaact ttatccgcct ccatccagtc tattaattgt tgccgggaag   5520
ctagagtaag tagttcgcca gttaatagtt tgcgcaacgt tgttgccatt gctacaggca   5580
tcgtggtgtc acgctcgtcg tttggtatgg cttcattcag ctccggttcc caacgatcaa   5640
ggcgagttac atgatccccc atgttgtgca aaaaagcggt tagctccttc ggtcctccga   5700
tcgttgtcag aagtaagttg gccgcagtgt tatcactcat ggttatggca gcactgcata   5760
attctcttac tgtcatgcca tccgtaagat gcttttctgt gactggtgag tactcaacca   5820
agtcattctg agaatagtgt atgcggcgac cgagttgctc ttgcccggcg tcaatacggg   5880
ataataccgc gccacatagc agaactttaa aagtgctcat cattggaaaa cgttcttcgg   5940
ggcgaaaact ctcaaggatc ttaccgctgt tgagatccag ttcgatgtaa cccactcgtg   6000
cacccaactg atcttcagca tcttttactt tcaccagcgt ttctgggtga gcaaaaacag   6060
gaaggcaaaa tgccgcaaaa aagggaataa gggcgacacg gaaatgttga atactcatac   6120
```

tcttcctttt tcaatattat tgaagcattt atcagggtta ttgtctcatg agcggataca 6180
tatttgaatg tatttagaaa aataaacaaa taggggttcc gcgcacattt ccccgaaaag 6240
tgccacctga cgtc 6254

<210> SEQ ID NO 54
<211> LENGTH: 6254
<212> TYPE: DNA
<213> ORGANISM: Artificial Sequence
<220> FEATURE:
<223> OTHER INFORMATION: Plasmid

<400> SEQUENCE: 54
gacggatcgg gagatctgag ggcctatttc ccatgattcc ttcatatttg catatacgat 60
acaaggctgt tagagagata attggaatta atttgactgt aaacacaaag atattagtac 120
aaaatacgtg acgtagaaag taataatttc ttgggtagtt tgcagtttta aaattatgtt 180
ttaaaatgga ctatcatatg cttaccgtaa cttgaaagta tttcgatttc ttggctttat 240
atatcttgtg gaaaggacga aacaccggaa gaagttcatc aacaatccga agattgttga 300
tgaacttctt cctttttac ccgatcccct atggtgcact ctcagtacaa tctgctctga 360
tgccgcatag ttaagccagt atctgctccc tgcttgtgtg ttggaggtcg ctgagtagtg 420
cgcgagcaaa atttaagcta caacaaggca aggcttgacc gacaattgca tgaagaatct 480
gcttagggtt aggcgttttg cgctgcttcg cgatgtacgg gccagatata cgcgttgaca 540
ttgattattg actagttatt aatagtaatc aattacgggg tcattagttc atagcccata 600
tatggagttc cgcgttacat aacttacggt aaatggcccg cctggctgac cgcccaacga 660
cccccgccca ttgacgtcaa taatgacgta tgttcccata gtaacgccaa tagggacttt 720
ccattgacgt caatgggtgg agtatttacg gtaaactgcc cacttggcag tacatcaagt 780
gtatcatatg ccaagtacgc cccctattga cgtcaatgac ggtaaatggc ccgcctggca 840
ttatgcccag tacatgacct tatgggactt tcctacttgg cagtacatct acgtattagt 900
catcgctatt accatggtga tgcggttttg gcagtacatc aatgggcgtg gatagcggtt 960
tgactcacgg ggatttccaa gtctccaccc cattgacgtc aatgggagtt tgttttggca 1020
ccaaaatcaa cgggactttc caaaatgtcg taacaactcc gccccattga cgcaaatggg 1080
cggtaggcgt gtacggtggg aggtctatat aagcagagct ctctggctaa ctagagaacc 1140
cactgcttac tggcttatcg ttaattaacc ggtgccacca tgatgtcccg ccttgataaa 1200
tcaaaagtaa taaacagtgc tcttgagctt ctcaatgaag ttggtataga agggttgacg 1260
actcggaaat tggcgcaaaa actcggtgtt gagcagccaa ccttgtattg gcatgttaaa 1320
aacaaacgag cactcctcga cgctttggcg atagagatgc tggacaggca ccacacgcat 1380
ttctgtcccc tcgaaggaga gtcatggcag gatttcctta gaaataacgc aaagtccttc 1440
agatgtgcgc tgcttagtca ccgcgacggc gcaaaagttc atctcggcac taggccaacc 1500
gagaaacagt acgagactct ggagaaccaa ctggcgtttt tgtgtcaaca gggttttagt 1560
ctcgaaaatg cgctctatgc tctctctgcg gttggccatt tcaccctcgg atgcgtactg 1620
gaagatcagg agcaccaagt ggccaaagaa gaacgggaaa cgccgactac ggacagcatg 1680
cctccgttgc tccggcaagc tatagagctc ttcgatcacc aaggcgctga gccagctttc 1740
ttgttcggat tggaacttat tatatgcggg ctcgaaaagc agcttaaatg cgagtcaggt 1800
taagcggccg ctcgagtcta gagggcccgt ttaaacccgc tgatcagcct cgactgtgcc 1860

-continued

```
ttctagttgc cagccatctg ttgtttgccc ctcccccgtg ccttccttga ccctggaagg   1920
tgccactccc actgtccttt cctaataaaa tgaggaaatt gcatcgcatt gtctgagtag   1980
gtgtcattct attctggggg gtggggtggg gcaggacagc aagggggagg attgggaaga   2040
caatagcagg catgctgggg atgcggtggg ctctatggct tctgaggcgg aaagaaccag   2100
ctggggctct agggggtatc cccacgcgcc ctgtagcggc gcattaagcg cggcgggtgt   2160
ggtggttacg cgcagcgtga ccgctacact tgccagcgcc ctagcgcccg ctcctttcgc   2220
tttcttccct tcctttctcg ccacgttcgc cggctttccc cgtcaagctc taaatcgggg   2280
gctcccttta gggttccgat ttagtgcttt acggcacctc gaccccaaaa aacttgatta   2340
gggtgatggt tcacgtagtg ggccatcgcc ctgatagacg gtttttcgcc ctttgacgtt   2400
ggagtccacg ttctttaata gtggactctt gttccaaact ggaacaacac tcaaccctat   2460
ctcggtctat tcttttgatt tataagggat tttgccgatt tcggcctatt ggttaaaaaa   2520
tgagctgatt taacaaaaat ttaacgcgaa ttaattctgt ggaatgtgtg tcagttaggg   2580
tgtggaaagt ccccaggctc cccagcaggc agaagtatgc aaagcatgca tctcaattag   2640
tcagcaacca ggtgtggaaa gtccccaggc tccccagcag gcagaagtat gcaaagcatg   2700
catctcaatt agtcagcaac catagtcccg cccctaactc cgcccatccc gcccctaact   2760
ccgcccagtt ccgcccattc tccgccccat ggctgactaa ttttttttat ttatgcagag   2820
gccgaggccg cctctgcctc tgagctattc cagaagtagt gaggaggctt ttttggaggc   2880
ctaggctttt gcaaaaagct cccgggagct tgtatatcca ttttcggatc tgatcaagag   2940
acaggatgag gatcgtttcg catgattgaa caagatggat tgcacgcagg ttctccggcc   3000
gcttgggtgg agaggctatt cggctatgac tgggcacaac agacaatcgg ctgctctgat   3060
gccgccgtgt tccggctgtc agcgcagggg cgcccggttc tttttgtcaa gaccgacctg   3120
tccggtgccc tgaatgaact gcaggacgag gcagcgcggc tatcgtggct ggccacgacg   3180
ggcgttcctt gcgcagctgt gctcgacgtt gtcactgaag cgggaaggga ctggctgcta   3240
ttgggcgaag tgccggggca ggatctcctg tcatctcacc ttgctcctgc cgagaaagta   3300
tccatcatgg ctgatgcaat gcggcggctg catacgcttg atccggctac ctgcccattc   3360
gaccaccaag cgaaacatcg catcgagcga gcacgtactc ggatggaagc cggtcttgtc   3420
gatcaggatg atctggacga agagcatcag gggctcgcgc cagccgaact gttcgccagg   3480
ctcaaggcgc gcatgcccga cggcgaggat ctcgtcgtga cccatggcga tgcctgcttg   3540
ccgaatatca tggtggaaaa tggccgcttt tctggattca tcgactgtgg ccggctgggt   3600
gtggcggacc gctatcagga catagcgttg gctacccgtg atattgctga agagcttggc   3660
ggcgaatggg ctgaccgctt cctcgtgctt tacggtatcg ccgctcccga ttcgcagcgc   3720
atcgccttct atcgccttct tgacgagttc ttctgagcgg gactctgggg ttcgaaatga   3780
ccgaccaagc gacgcccaac ctgccatcac gagatttcga ttccaccgcc gccttctatg   3840
aaaggttggg cttcggaatc gttttccggg acgccggctg gatgatcctc cagcgcgggg   3900
atctcatgct ggagttcttc gcccacccca acttgtttat tgcagcttat aatggttaca   3960
aataaagcaa tagcatcaca aatttcacaa ataaagcatt tttttcactg cattctagtt   4020
gtggtttgtc caaactcatc aatgtatctt atcatgtctg tataccgtcg acctctagct   4080
agagcttggc gtaatcatgg tcatagctgt ttcctgtgtg aaattgttat ccgctcacaa   4140
ttccacacaa catacgagcc ggaagcataa agtgtaaagc ctggggtgcc taatgagtga   4200
gctaactcac attaattgcg ttgcgctcac tgcccgcttt ccagtcggga aacctgtcgt   4260
```

-continued

```
gccagctgca ttaatgaatc ggccaacgcg cggggagagg cggtttgcgt attgggcgct   4320

cttccgcttc ctcgctcact gactcgctgc gctcggtcgt tcggctgcgg cgagcggtat   4380

cagctcactc aaaggcggta atacggttat ccacagaatc aggggataac gcaggaaaga   4440

acatgtgagc aaaaggccag caaaaggcca ggaaccgtaa aaaggccgcg ttgctggcgt   4500

ttttccatag gctccgcccc cctgacgagc atcacaaaaa tcgacgctca agtcagaggt   4560

ggcgaaaccc gacaggacta taaagatacc aggcgtttcc ccctggaagc tccctcgtgc   4620

gctctcctgt tccgaccctg ccgcttaccg gatacctgtc cgcctttctc ccttcgggaa   4680

gcgtggcgct ttctcatagc tcacgctgta ggtatctcag ttcggtgtag gtcgttcgct   4740

ccaagctggg ctgtgtgcac gaacccccg ttcagcccga ccgctgcgcc ttatccggta   4800

actatcgtct tgagtccaac ccggtaagac acgacttatc gccactggca gcagccactg   4860

gtaacaggat tagcagagcg aggtatgtag gcggtgctac agagttcttg aagtggtggc   4920

ctaactacgg ctacactaga agaacagtat ttggtatctg cgctctgctg aagccagtta   4980

ccttcggaaa aagagttggt agctcttgat ccggcaaaca aaccaccgct ggtagcggtt   5040

tttttgtttg caagcagcag attacgcgca gaaaaaaagg atctcaagaa gatcctttga   5100

tcttttctac ggggtctgac gctcagtgga acgaaaactc acgttaaggg attttggtca   5160

tgagattatc aaaaaggatc ttcacctaga tccttttaaa ttaaaaatga agttttaaat   5220

caatctaaag tatatatgag taaacttggt ctgacagtta ccaatgctta atcagtgagg   5280

cacctatctc agcgatctgt ctatttcgtt catccatagt tgcctgactc cccgtcgtgt   5340

agataactac gatacgggag ggcttaccat ctggccccag tgctgcaatg ataccgcgag   5400

acccacgctc accggctcca gatttatcag caataaacca gccagccgga agggccgagc   5460

gcagaagtgg tcctgcaact ttatccgcct ccatccagtc tattaattgt tgccgggaag   5520

ctagagtaag tagttcgcca gttaatagtt tgcgcaacgt tgttgccatt gctacaggca   5580

tcgtggtgtc acgctcgtcg tttggtatgg cttcattcag ctccggttcc caacgatcaa   5640

ggcgagttac atgatccccc atgttgtgca aaaaagcggt tagctccttc ggtcctccga   5700

tcgttgtcag aagtaagttg gccgcagtgt tatcactcat ggttatggca gcactgcata   5760

attctcttac tgtcatgcca tccgtaagat gcttttctgt gactggtgag tactcaacca   5820

agtcattctg agaatagtgt atgcggcgac cgagttgctc ttgcccggcg tcaatacggg   5880

ataataccgc gccacatagc agaactttaa aagtgctcat cattggaaaa cgttcttcgg   5940

ggcgaaaact ctcaaggatc ttaccgctgt tgagatccag ttcgatgtaa cccactcgtg   6000

cacccaactg atcttcagca tcttttactt tcaccagcgt ttctgggtga gcaaaaacag   6060

gaaggcaaaa tgccgcaaaa aagggaataa gggcgacacg gaaatgttga atactcatac   6120

tcttcctttt tcaatattat tgaagcattt atcagggtta ttgtctcatg agcggataca   6180

tatttgaatg tatttagaaa aataaacaaa taggggttcc gcgcacattt ccccgaaaag   6240

tgccacctga cgtc                                                     6254
```

<210> SEQ ID NO 55
<211> LENGTH: 52
<212> TYPE: RNA
<213> ORGANISM: Artificial Sequence
<220> FEATURE:
<223> OTHER INFORMATION: Short hairpin RNA (shRNA)

<400> SEQUENCE: 55
gcgaagaaga ucauugauac ccgaagguau caaugaucuu cuucgcuuuu uu 52

<210> SEQ ID NO 56
<211> LENGTH: 52
<212> TYPE: RNA
<213> ORGANISM: Artificial Sequence
<220> FEATURE:
<223> OTHER INFORMATION: Short hairpin RNA (shRNA)

<400> SEQUENCE: 56
gcaaaucgcc aaggagauug gcgaaccaau cuccuuggcg auuugcuuuu uu 52

<210> SEQ ID NO 57
<211> LENGTH: 52
<212> TYPE: RNA
<213> ORGANISM: Artificial Sequence
<220> FEATURE:
<223> OTHER INFORMATION: Short hairpin RNA (shRNA)

<400> SEQUENCE: 57
gcacagcucc augaaccaaa ucgaaauuug guucauggag cugugcuuuu uu 52

<210> SEQ ID NO 58
<211> LENGTH: 52
<212> TYPE: RNA
<213> ORGANISM: Artificial Sequence
<220> FEATURE:
<223> OTHER INFORMATION: Short hairpin RNA (shRNA)

<400> SEQUENCE: 58
ggaccuucau ucaauccauc acgaaugaug gauugaauga agguccuuuu uu 52

<210> SEQ ID NO 59
<211> LENGTH: 52
<212> TYPE: RNA
<213> ORGANISM: Artificial Sequence
<220> FEATURE:
<223> OTHER INFORMATION: Short hairpin RNA (shRNA)

<400> SEQUENCE: 59
ggaagaaguu caucaacaau ccgaagauug uugaugaacu ucuuccuuuu uu 52

<210> SEQ ID NO 60
<211> LENGTH: 1057
<212> TYPE: PRT
<213> ORGANISM: Artificial Sequence
<220> FEATURE:
<223> OTHER INFORMATION: sRGN protein sequence

<400> SEQUENCE: 60

```
Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Arg Ile His Arg Leu
    50                  55                  60

Glu Arg Val Lys Leu Leu Leu Thr Glu Tyr Asp Leu Ile Asn Lys Glu
65                  70                  75                  80
```

```
Gln Ile Pro Thr Ser Asn Asn Pro Tyr Gln Ile Arg Val Lys Gly Leu
                85                  90                  95

Ser Glu Ile Leu Ser Lys Asp Glu Leu Ala Ile Ala Leu Leu His Leu
            100                 105                 110

Ala Lys Arg Arg Gly Ile His Asn Val Asp Val Ala Ala Asp Lys Glu
        115                 120                 125

Glu Thr Ala Ser Asp Ser Leu Ser Thr Lys Asp Gln Ile Asn Lys Asn
    130                 135                 140

Ala Lys Phe Leu Glu Ser Arg Tyr Val Cys Glu Leu Gln Lys Glu Arg
145                 150                 155                 160

Leu Glu Asn Glu Gly His Val Arg Gly Val Glu Asn Arg Phe Leu Thr
                165                 170                 175

Lys Asp Ile Val Arg Glu Ala Lys Lys Ile Ile Asp Thr Gln Met Gln
            180                 185                 190

Tyr Tyr Pro Glu Ile Asp Glu Thr Phe Lys Glu Lys Tyr Ile Ser Leu
        195                 200                 205

Val Glu Thr Arg Arg Glu Tyr Phe Glu Gly Pro Gly Gln Gly Ser Pro
    210                 215                 220

Phe Gly Trp Asn Gly Asp Leu Lys Lys Trp Tyr Glu Met Leu Met Gly
225                 230                 235                 240

His Cys Thr Tyr Phe Pro Gln Glu Leu Arg Ser Val Lys Tyr Ala Tyr
                245                 250                 255

Ser Ala Asp Leu Phe Asn Ala Leu Asn Asp Leu Asn Asn Leu Ile Ile
            260                 265                 270

Gln Arg Asp Asn Ser Glu Lys Leu Glu Tyr His Glu Lys Tyr His Ile
        275                 280                 285

Ile Glu Asn Val Phe Lys Gln Lys Lys Lys Pro Thr Leu Lys Gln Ile
    290                 295                 300

Ala Lys Glu Ile Gly Val Asn Pro Glu Asp Ile Lys Gly Tyr Arg Ile
305                 310                 315                 320

Thr Lys Ser Gly Thr Pro Glu Phe Thr Ser Phe Lys Leu Phe His Asp
                325                 330                 335

Leu Lys Lys Val Val Lys Asp His Ala Ile Leu Asp Asp Ile Asp Leu
            340                 345                 350

Leu Asn Gln Ile Ala Glu Ile Leu Thr Ile Tyr Gln Asp Lys Asp Ser
        355                 360                 365

Ile Val Ala Glu Leu Gly Gln Leu Glu Tyr Leu Met Ser Glu Ala Asp
    370                 375                 380

Lys Gln Ser Ile Ser Glu Leu Thr Gly Tyr Thr Gly Thr His Ser Leu
385                 390                 395                 400

Ser Leu Lys Cys Met Asn Met Ile Ile Asp Glu Leu Trp His Ser Ser
                405                 410                 415

Met Asn Gln Met Glu Val Phe Thr Tyr Leu Asn Met Arg Pro Lys Lys
            420                 425                 430

Tyr Glu Leu Lys Gly Tyr Gln Arg Ile Pro Thr Asp Met Ile Asp Asp
        435                 440                 445

Ala Ile Leu Ser Pro Val Val Lys Arg Thr Phe Ile Gln Ser Ile Asn
    450                 455                 460

Val Ile Asn Lys Val Ile Glu Lys Tyr Gly Ile Pro Glu Asp Ile Ile
465                 470                 475                 480

Ile Glu Leu Ala Arg Glu Asn Asn Ser Asp Asp Arg Lys Lys Phe Ile
                485                 490                 495
```

-continued

```
Asn Asn Leu Gln Lys Lys Asn Glu Ala Thr Arg Lys Arg Ile Asn Glu
            500                 505                 510

Ile Ile Gly Gln Thr Gly Asn Gln Asn Ala Lys Arg Ile Val Glu Lys
        515                 520                 525

Ile Arg Leu His Asp Gln Gln Glu Gly Lys Cys Leu Tyr Ser Leu Glu
    530                 535                 540

Ser Ile Pro Leu Glu Asp Leu Leu Asn Asn Pro Asn His Tyr Glu Val
545                 550                 555                 560

Asp His Ile Ile Pro Arg Ser Val Ser Phe Asp Asn Ser Tyr His Asn
                565                 570                 575

Lys Val Leu Val Lys Gln Ser Glu Asn Ser Lys Lys Ser Asn Leu Thr
            580                 585                 590

Pro Tyr Gln Tyr Phe Asn Ser Gly Lys Ser Lys Leu Ser Tyr Asn Gln
        595                 600                 605

Phe Lys Gln His Ile Leu Asn Leu Ser Lys Ser Gln Asp Arg Ile Ser
    610                 615                 620

Lys Lys Lys Lys Glu Tyr Leu Leu Glu Glu Arg Asp Ile Asn Lys Phe
625                 630                 635                 640

Glu Val Gln Lys Glu Phe Ile Asn Arg Asn Leu Val Asp Thr Arg Tyr
                645                 650                 655

Ala Thr Arg Glu Leu Thr Asn Tyr Leu Lys Ala Tyr Phe Ser Ala Asn
            660                 665                 670

Asn Met Asn Val Lys Val Lys Thr Ile Asn Gly Ser Phe Thr Asp Tyr
        675                 680                 685

Leu Arg Lys Val Trp Lys Phe Lys Lys Glu Arg Asn His Gly Tyr Lys
    690                 695                 700

His His Ala Glu Asp Ala Leu Ile Ile Ala Asn Ala Asp Phe Leu Phe
705                 710                 715                 720

Lys Glu Asn Lys Lys Leu Lys Ala Val Asn Ser Val Leu Glu Lys Pro
                725                 730                 735

Glu Ile Glu Thr Lys Gln Leu Asp Ile Gln Val Asp Ser Glu Asp Asn
            740                 745                 750

Tyr Ser Glu Met Phe Ile Ile Pro Lys Gln Val Gln Asp Ile Lys Asp
        755                 760                 765

Phe Arg Asn Phe Lys Tyr Ser His Arg Val Asp Lys Lys Pro Asn Arg
    770                 775                 780

Gln Leu Ile Asn Asp Thr Leu Tyr Ser Thr Arg Lys Lys Asp Asn Ser
785                 790                 795                 800

Thr Tyr Ile Val Gln Thr Ile Lys Asp Ile Tyr Ala Lys Asp Asn Thr
                805                 810                 815

Thr Leu Lys Lys Gln Phe Asp Lys Ser Pro Glu Lys Phe Leu Met Tyr
            820                 825                 830

Gln His Asp Pro Arg Thr Phe Glu Lys Leu Glu Val Ile Met Lys Gln
        835                 840                 845

Tyr Ala Asn Glu Lys Asn Pro Leu Ala Lys Tyr His Glu Glu Thr Gly
    850                 855                 860

Glu Tyr Leu Thr Lys Tyr Ser Lys Lys Asn Asn Gly Pro Ile Val Lys
865                 870                 875                 880

Ser Leu Lys Tyr Ile Gly Asn Lys Leu Gly Ser His Leu Asp Val Thr
                885                 890                 895

His Gln Phe Lys Ser Ser Thr Lys Lys Leu Val Lys Leu Ser Ile Lys
            900                 905                 910
```

```
Asn Tyr Arg Phe Asp Val Tyr Leu Thr Glu Lys Gly Tyr Lys Phe Val
        915                 920                 925

Thr Ile Ala Tyr Leu Asn Val Phe Lys Lys Asp Asn Tyr Tyr Tyr Ile
    930                 935                 940

Pro Lys Asp Lys Tyr Gln Glu Leu Lys Glu Lys Lys Lys Ile Lys Asp
945                 950                 955                 960

Thr Asp Gln Phe Ile Ala Ser Phe Tyr Lys Asn Asp Leu Ile Lys Leu
                965                 970                 975

Asn Gly Asp Leu Tyr Lys Ile Ile Gly Val Asn Ser Asp Asp Arg Asn
            980                 985                 990

Ile Ile Glu Leu Asp Tyr Tyr Asp  Ile Lys Tyr Lys Asp  Tyr Cys Glu
        995                 1000                 1005

Ile Asn  Asn Ile Lys Gly Glu  Pro Arg Ile Lys Lys  Thr Ile Gly
    1010                 1015                 1020

Lys Lys  Thr Glu Ser Ile Glu  Lys Phe Thr Thr Asp  Val Leu Gly
    1025                 1030                 1035

Asn Leu  Tyr Leu His Ser Thr  Glu Lys Ala Pro Gln  Leu Ile Phe
    1040                 1045                 1050

Lys Arg  Gly Leu
    1055
```

<210> SEQ ID NO 61
<211> LENGTH: 3171
<212> TYPE: DNA
<213> ORGANISM: Artificial Sequence
<220> FEATURE:
<223> OTHER INFORMATION: sRGN sequence

<400> SEQUENCE: 61

```
atgaaccaga agttcattct cggtctggac attggcatta ctagcgtggg atacggcttg     60

attgactacg agactaagaa catcatcgat gccggcgtcc gcctgttccc ggaagccaac    120

gtggagaaca atgagggccg gaggtcgaag agaggctccc gccgcctgaa gcggcggcga    180

atccaccggc tggagagagt gaagctgctg ctcaccgaat acgacctgat caacaaagaa    240

cagatcccga cctccaacaa cccgtaccag atcagagtga agggtctgtc agaaatcctg    300

tccaaggacg aactggcaat cgccctgctg cacctggcca agcggcgcgg aatccacaac    360

gtggatgtgg ctgccgacaa ggaagaaacc gcttccgact ccctgagcac taaggaccag    420

atcaacaaga acgccaagtt cttggagtcc cgctacgtgt gcgagctgca gaaggaacgg    480

ctggaaaacg aaggtcacgt gcgcggagtg gaaaaccggt tcctgacaaa ggacattgtg    540

cgcgaagcga agaagatcat tgatacccaa atgcagtact accctgaaat cgacgagact    600

ttcaaggaaa agtacatttc cctggtggaa acccggcggg aatacttcga aggccccgga    660

cagggatcgc cgttcggatg gaacggggac ctcaagaagt ggtacgagat gctgatgggg    720

cactgtacct actttccgca agaactgcgc tccgtgaagt acgcgtactc cgcggatctc    780

ttcaacgcgt tgaatgacct gaacaacctg atcattcaga gagacaattc cgaaaagctc    840

gagtaccacg agaagtatca catcatcgag aatgtgttca agcagaagaa gaaaccgacc    900

ctcaagcaaa tcgccaagga gattggcgtc aacccagagg acatcaaggg atatcggatt    960

accaagagcg gcactcccga gtttacctct ttcaagctgt ttcatgatct gaagaaagtc   1020

gtgaaggacc atgccattct cgacgacatt gatctcctga atcagatcgc agagatcctg   1080

actatctacc aagacaagga ctcgattgtg gcagagctgg gtcagctcga atacctgatg   1140
```

```
tccgaggccg acaagcagtc catctccgaa ctgacagggt acacggggac tcatagcctg   1200
tcgctgaagt gcatgaacat gatcattgat gaactgtggc acagctccat gaaccaaatg   1260
gaagtgttta cctacctcaa catgcgccct aagaagtacg aactgaaagg ctaccagcgc   1320
atccccaccg acatgatcga cgacgcgatc ttgtcccctg tggtcaagag gaccttcatt   1380
caatccatca acgtgatcaa caaggtcatc gaaaagtacg gaataccaga agatatcatc   1440
attgagctcg ctcgggagaa caactcggat gaccggaaga agttcatcaa caatcttcag   1500
aagaagaacg aagcgactcg gaaacggatc aacgagatca tcggacagac cggaaaccag   1560
aacgccaaac ggattgtcga aaagattaga ctgcacgacc agcaggaagg gaagtgcctg   1620
tactcactcg agtcaatacc gctcgaggac ctgttgaaca accctaacca ctatgaagtg   1680
gaccacatca tccctcggtc cgtgagcttc gacaactcgt accacaacaa agtgctcgtg   1740
aagcagtccg aaaactccaa gaaatccaac ctgaccccgt accaatactt caattcggga   1800
aagtcgaagc tgtcgtacaa ccagttcaaa caacacatac tcaaccttag caaaagccag   1860
gatcgcattt ccaagaagaa gaaggaatac ctcctcgagg aaagggacat caacaagttc   1920
gaagtgcaga aagagttcat caatcgcaac ttggtggata ccagatatgc cacccgggaa   1980
ctcaccaact atctcaaggc ctacttttcc gccaacaaca tgaacgtgaa ggtcaagacc   2040
atcaacgggt ccttcactga ctacctgaga aaggtctgga agttcaagaa ggaacgcaac   2100
cacggataca agcaccacgc tgaggacgct ctgatcatcg ccaatgccga cttcctgttc   2160
aaggaaaaca agaagctgaa agctgtcaac tcagtgctgg aaaagcctga aatcgagact   2220
aagcagctgg atatccaagt ggactctgag gacaactaca gcgagatgtt catcatccct   2280
aaacaagtgc aggatatcaa ggactttcgc aacttcaagt actcacaccg ggtggacaag   2340
aaaccgaata gacagctgat caacgacacg ttgtattcca cccggaagaa ggataactca   2400
acctacattg tgcagactat caaggatatc tacgccaaag ataacactac tctgaagaaa   2460
caattcgaca agtccccaga gaagttcctg atgtaccagc acgacccccg aacctttgag   2520
aagcttgaag tgatcatgaa gcagtacgcc aacgagaaga acccgctggc caagtaccat   2580
gaagaaaccg gagaatacct gaccaagtac agcaagaaga acaacggtcc cattgtcaag   2640
agcctgaagt acatcggcaa caagctggga tcccacctcg acgtgacaca tcagttcaag   2700
tcgtcgacta agaagcttgt gaagctgtca atcaagaact atagattcga cgtgtacttg   2760
accgaaaagg gatacaagtt cgtgaccata gcctatctga acgtgttcaa gaaagataac   2820
tactactaca tccccaagga caagtaccag gagctcaaag aaaagaagaa gatcaaagac   2880
accgaccagt tcattgcctc cttctacaag aacgacctga tcaaactgaa cggcgacctc   2940
tacaagatca ttggagtgaa cagcgatgac aggaacatca ttgagctgga ctactacgac   3000
atcaagtaca aggactactg cgagatcaac aacatcaagg gcgaaccccg gatcaagaaa   3060
actattggaa agaaaaccga gtccattgag aagttcacca ctgacgtgct gggaaacctt   3120
tacctccact ccaccgagaa ggcaccacaa ctgatcttca agcgcggcct g            3171
```

<210> SEQ ID NO 62
<211> LENGTH: 624
<212> TYPE: DNA
<213> ORGANISM: Artificial Sequence
<220> FEATURE:
<223> OTHER INFORMATION: TetR coding sequence

<400> SEQUENCE: 62

```
atgatgtccc gccttgataa atcaaaagta ataaacagtg ctcttgagct tctcaatgaa     60

gttggtatag aagggttgac gactcggaaa ttggcgcaaa aactcggtgt tgagcagcca    120

accttgtatt ggcatgttaa aaacaaacga gcactcctcg acgctttggc gatagagatg    180

ctggacaggc accacacgca tttctgtccc ctcgaaggag agtcatggca ggatttcctt    240

agaaataacg caaagtcctt cagatgtgcg ctgcttagtc accgcgacgg cgcaaaagtt    300

catctcggca ctaggccaac cgagaaacag tacgagactc tggagaacca actggcgttt    360

ttgtgtcaac agggttttag tctcgaaaat gcgctctatg ctctctctgc ggttggccat    420

ttcaccctcg gatgcgtact ggaagatcag gagcaccaag tggccaaaga agaacgggaa    480

acgccgacta cggacagcat gcctccgttg ctccggcaag ctatagagct cttcgatcac    540

caaggcgctg agccagcttt cttgttcgga ttggaactta ttatatgcgg gctcgaaaag    600

cagcttaaat gcgagtcagg ttaa                                           624
```

<210> SEQ ID NO 63
<211> LENGTH: 207
<212> TYPE: PRT
<213> ORGANISM: Artificial Sequence
<220> FEATURE:
<223> OTHER INFORMATION: TetR protein sequence

<400> SEQUENCE: 63

```
Met Met Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly
        195                 200                 205
```

<210> SEQ ID NO 64
<211> LENGTH: 3156
<212> TYPE: DNA
<213> ORGANISM: Artificial Sequence
<220> FEATURE:
<223> OTHER INFORMATION: SaCas9 DNA sequence

<400> SEQUENCE: 64
aagcggaact atatcctggg actggacatc ggaattacct ccgtgggata cggcatcatc 60
gattacgaga ctagggacgt gattgacgcc ggcgtgagac tctttaagga ggccaacgtg 120
gaaaacaacg aaggtcgcag atccaagcgg ggtgcaagac gcctgaagcg ccggaggaga 180
catcggatac agcgcgtgaa gaagctcctt ttcgactaca acctcctcac tgaccactcg 240
gaattgtccg gtatcaaccc ctacgaagcc cgcgtgaaag gcctgagcca gaagctgtcc 300
gaagaggagt ttagcgcagc cctgctgcac ctggctaagc gaagggggt gcacaacgtg 360 aacgaggtgg aggaggacac tggcaacgaa ctgtccacca aggagcagat ttcacggaac 420
tcgaaggcgc tggaagagaa atatgtggcc gagctgcagc tggagaggct caagaaggat 480
ggcgaagtcc gggggagcat caatcgcttc aagacctcgg actacgtgaa ggaagccaaa 540
cagctgttga aggtgcagaa ggcctaccac caactggacc aatcattcat tgacacttac 600
atcgatctgc ttgaaaccag gcgcacctac tacgagggtc ctggagaagg cagccctttc 660
ggatggaagg acatcaagga gtggtatgag atgctgatgg gtcattgcac ctactttccg 720
gaagaactgc gctcagtgaa gtacgcgtac aacgctgacc tctacaacgc tctcaacgat 780
ctgaacaacc tcgtgatcac ccgggacgag aacgaaaagc tggagtacta cgaaaagttc 840
cagattatcg aaaacgtgtt caagcagaag aagaagccca ccctgaagca gattgcaaag 900
gagatccttg tgaacgagga ggatattaag ggctaccggg tcacctccac cgggaaacca 960
gagttcacta atctcaaggt gtaccatgac attaaggaca ttactgcccg caaggagatc 1020
attgaaaacg cggaactgct ggaccaaatc gcgaagatcc tgaccatcta tcagagctcc 1080
gaggatatcc aggaggaact tactaacctc aattccgagc tgacgcagga agaaatcgag 1140
caaattagca acctgaaggg ttacactgga acccacaacc tcagcttgaa agcgattaac 1200
cttattttgg atgaactttg gcacactaat gacaatcaga tcgccatttt caaccggctg 1260
aaactggtgc cgaagaaggt ggacctgagc caacagaagg aaatcccgac caccccttgtg 1320 gacgatttca tcctgtcacc tgtggtgaag aggagcttca tccagtcgat caaggtcatc 1380
aacgccatca taaagaagta cggccttccc aacgacatca tcatcgaact ggcccgcgag 1440
aagaactcca aagatgccca gaagatgatc aacgagatgc agaagcgaaa ccggcagacg 1500
aacgaacgga tcgaggagat catccggacc accgggaagg aaaacgcgaa gtacctgatc 1560
gagaaaatca agctgcatga tatgcaggaa gggaagtgtc tctactccct ggaggccatt 1620
ccgctggagg atttgctgaa caaccctttc aactacgaag tcgatcatat cattcctcgc 1680
tccgtgtcct tcgataactc cttcaacaat aaggtcctcg tgaagcagga ggagaactcg 1740
aagaagggca acagaacccc gttccagtac ctctcgtcgt ccgactccaa gatcagctac 1800
gaaactttca agaagcacat tctgaacctg gccaagggca aagggagaat tagcaagacc 1860
aagaaggaat acctcctgga agagagagac atcaaccgct tctcggtgca aaaggatttc 1920
atcaaccgca acctggtcga taccagatac gccaccaggg gactgatgaa cctcctgcgg 1980
tcctacttcc gggtcaacaa tctggacgtg aaggtcaaat ccatcaacgg gggctttact 2040
tctttcctgc gccggaagtg gaagttcaag aaggaacgga acaagggata caagcaccac 2100
gctgaagatg ccctgattat tgccaacgcc gacttcatct ttaaggaatg gaaaaagctg 2160
gacaaggcta agaaggtcat ggagaaccag atgttcgaag aaaagcaggc cgagtccatg 2220

-continued

```
cccgaaatcg aaaccgagca ggaatacaag gagatcttca tcacaccgca ccaaatcaag   2280

cacatcaagg acttcaagga ttacaagtac agccaccggg tggacaagaa gcctaacaga   2340

gagcttatca acgacaccct gtactccacg cgcaaggacg acaagggaaa cacattgatc   2400

gtgaacaacc tgaacggact gtatgacaag gacaatgaca aactgaagaa gctgatcaac   2460

aaatcgccgg aaaagctcct gatgtaccat cacgaccctc aaacctacca gaaactgaag   2520

ctcatcatgg agcagtacgg cgacgaaaag aatcccctgt acaaatacta cgaggagact   2580

ggaaattacc tgactaagta ctccaagaag gataacggcc ccgtgatcaa gaagattaag   2640

tactacggaa acaaactgaa cgcacatctc gacatcaccg atgattatcc aaactcccgc   2700

aacaaagtcg tgaagctctc cctcaaaccg taccgcttcg acgtgtacct ggataatggg   2760

gtgtacaagt tcgtgaccgt gaagaacctg gacgtcatta agaaggaaaa ctactacgaa   2820

gtgaactcaa agtgctacga ggaagccaag aagctcaaga agatcagcaa ccaggccgag   2880

ttcatcgcat cgttttacaa caatgacctc attaagatta atggagaact gtacagagtg   2940

atcggcgtga acaacgacct cctgaaccgg attgaagtga acatgatcga tattacctac   3000

cgggagtatc tggagaacat gaacgacaag cgcccaccga gaatcatcaa aactattgcc   3060

tccaagaccc aatccattaa gaaatactcc accgacatcc tgggcaacct gtacgaggtc   3120

aagtcgaaga agcaccccca gattatcaag aaggga                             3156
```

<210> SEQ ID NO 65
<211> LENGTH: 1052
<212> TYPE: PRT
<213> ORGANISM: Artificial Sequence
<220> FEATURE:
<223> OTHER INFORMATION: SaCas9 protein sequence

<400> SEQUENCE: 65

```
Lys Arg Asn Tyr Ile Leu Gly Leu Asp Ile Gly Ile Thr Ser Val Gly
1               5                   10                  15

Tyr Gly Ile Ile Asp Tyr Glu Thr Arg Asp Val Ile Asp Ala Gly Val
            20                  25                  30

Arg Leu Phe Lys Glu Ala Asn Val Glu Asn Asn Glu Gly Arg Arg Ser
        35                  40                  45

Lys Arg Gly Ala Arg Arg Leu Lys Arg Arg Arg Arg His Arg Ile Gln
    50                  55                  60

Arg Val Lys Lys Leu Leu Phe Asp Tyr Asn Leu Leu Thr Asp His Ser
65                  70                  75                  80

Glu Leu Ser Gly Ile Asn Pro Tyr Glu Ala Arg Val Lys Gly Leu Ser
                85                  90                  95

Gln Lys Leu Ser Glu Glu Glu Phe Ser Ala Ala Leu Leu His Leu Ala
            100                 105                 110

Lys Arg Arg Gly Val His Asn Val Asn Glu Val Glu Glu Asp Thr Gly
        115                 120                 125

Asn Glu Leu Ser Thr Lys Glu Gln Ile Ser Arg Asn Ser Lys Ala Leu
    130                 135                 140

Glu Glu Lys Tyr Val Ala Glu Leu Gln Leu Glu Arg Leu Lys Lys Asp
145                 150                 155                 160

Gly Glu Val Arg Gly Ser Ile Asn Arg Phe Lys Thr Ser Asp Tyr Val
                165                 170                 175

Lys Glu Ala Lys Gln Leu Leu Lys Val Gln Lys Ala Tyr His Gln Leu
            180                 185                 190
```

-continued

```
Asp Gln Ser Phe Ile Asp Thr Tyr Ile Asp Leu Leu Glu Thr Arg Arg
        195                 200                 205

Thr Tyr Tyr Glu Gly Pro Gly Glu Gly Ser Pro Phe Gly Trp Lys Asp
    210                 215                 220

Ile Lys Glu Trp Tyr Glu Met Leu Met Gly His Cys Thr Tyr Phe Pro
225                 230                 235                 240

Glu Glu Leu Arg Ser Val Lys Tyr Ala Tyr Asn Ala Asp Leu Tyr Asn
                245                 250                 255

Ala Leu Asn Asp Leu Asn Asn Leu Val Ile Thr Arg Asp Glu Asn Glu
            260                 265                 270

Lys Leu Glu Tyr Tyr Glu Lys Phe Gln Ile Ile Glu Asn Val Phe Lys
        275                 280                 285

Gln Lys Lys Lys Pro Thr Leu Lys Gln Ile Ala Lys Glu Ile Leu Val
    290                 295                 300

Asn Glu Glu Asp Ile Lys Gly Tyr Arg Val Thr Ser Thr Gly Lys Pro
305                 310                 315                 320

Glu Phe Thr Asn Leu Lys Val Tyr His Asp Ile Lys Asp Ile Thr Ala
                325                 330                 335

Arg Lys Glu Ile Ile Glu Asn Ala Glu Leu Leu Asp Gln Ile Ala Lys
            340                 345                 350

Ile Leu Thr Ile Tyr Gln Ser Ser Glu Asp Ile Gln Glu Glu Leu Thr
        355                 360                 365

Asn Leu Asn Ser Glu Leu Thr Gln Glu Glu Ile Glu Gln Ile Ser Asn
    370                 375                 380

Leu Lys Gly Tyr Thr Gly Thr His Asn Leu Ser Leu Lys Ala Ile Asn
385                 390                 395                 400

Leu Ile Leu Asp Glu Leu Trp His Thr Asn Asp Asn Gln Ile Ala Ile
                405                 410                 415

Phe Asn Arg Leu Lys Leu Val Pro Lys Lys Val Asp Leu Ser Gln Gln
            420                 425                 430

Lys Glu Ile Pro Thr Thr Leu Val Asp Asp Phe Ile Leu Ser Pro Val
        435                 440                 445

Val Lys Arg Ser Phe Ile Gln Ser Ile Lys Val Ile Asn Ala Ile Ile
    450                 455                 460

Lys Lys Tyr Gly Leu Pro Asn Asp Ile Ile Ile Glu Leu Ala Arg Glu
465                 470                 475                 480

Lys Asn Ser Lys Asp Ala Gln Lys Met Ile Asn Glu Met Gln Lys Arg
                485                 490                 495

Asn Arg Gln Thr Asn Glu Arg Ile Glu Glu Ile Ile Arg Thr Thr Gly
            500                 505                 510

Lys Glu Asn Ala Lys Tyr Leu Ile Glu Lys Ile Lys Leu His Asp Met
        515                 520                 525

Gln Glu Gly Lys Cys Leu Tyr Ser Leu Glu Ala Ile Pro Leu Glu Asp
    530                 535                 540

Leu Leu Asn Asn Pro Phe Asn Tyr Glu Val Asp His Ile Ile Pro Arg
545                 550                 555                 560

Ser Val Ser Phe Asp Asn Ser Phe Asn Asn Lys Val Leu Val Lys Gln
                565                 570                 575

Glu Glu Asn Ser Lys Lys Gly Asn Arg Thr Pro Phe Gln Tyr Leu Ser
            580                 585                 590

Ser Ser Asp Ser Lys Ile Ser Tyr Glu Thr Phe Lys Lys His Ile Leu
        595                 600                 605
```

-continued

```
Asn Leu Ala Lys Gly Lys Gly Arg Ile Ser Lys Thr Lys Lys Glu Tyr
    610                 615                 620

Leu Leu Glu Glu Arg Asp Ile Asn Arg Phe Ser Val Gln Lys Asp Phe
625                 630                 635                 640

Ile Asn Arg Asn Leu Val Asp Thr Arg Tyr Ala Thr Arg Gly Leu Met
                645                 650                 655

Asn Leu Leu Arg Ser Tyr Phe Arg Val Asn Asn Leu Asp Val Lys Val
            660                 665                 670

Lys Ser Ile Asn Gly Gly Phe Thr Ser Phe Leu Arg Arg Lys Trp Lys
        675                 680                 685

Phe Lys Lys Glu Arg Asn Lys Gly Tyr Lys His His Ala Glu Asp Ala
    690                 695                 700

Leu Ile Ile Ala Asn Ala Asp Phe Ile Phe Lys Glu Trp Lys Lys Leu
705                 710                 715                 720

Asp Lys Ala Lys Lys Val Met Glu Asn Gln Met Phe Glu Glu Lys Gln
                725                 730                 735

Ala Glu Ser Met Pro Glu Ile Glu Thr Glu Gln Glu Tyr Lys Glu Ile
            740                 745                 750

Phe Ile Thr Pro His Gln Ile Lys His Ile Lys Asp Phe Lys Asp Tyr
        755                 760                 765

Lys Tyr Ser His Arg Val Asp Lys Lys Pro Asn Arg Glu Leu Ile Asn
    770                 775                 780

Asp Thr Leu Tyr Ser Thr Arg Lys Asp Asp Lys Gly Asn Thr Leu Ile
785                 790                 795                 800

Val Asn Asn Leu Asn Gly Leu Tyr Asp Lys Asp Asn Asp Lys Leu Lys
                805                 810                 815

Lys Leu Ile Asn Lys Ser Pro Glu Lys Leu Leu Met Tyr His His Asp
            820                 825                 830

Pro Gln Thr Tyr Gln Lys Leu Lys Leu Ile Met Glu Gln Tyr Gly Asp
        835                 840                 845

Glu Lys Asn Pro Leu Tyr Lys Tyr Tyr Glu Glu Thr Gly Asn Tyr Leu
    850                 855                 860

Thr Lys Tyr Ser Lys Lys Asp Asn Gly Pro Val Ile Lys Lys Ile Lys
865                 870                 875                 880

Tyr Tyr Gly Asn Lys Leu Asn Ala His Leu Asp Ile Thr Asp Asp Tyr
                885                 890                 895

Pro Asn Ser Arg Asn Lys Val Val Lys Leu Ser Leu Lys Pro Tyr Arg
            900                 905                 910

Phe Asp Val Tyr Leu Asp Asn Gly Val Tyr Lys Phe Val Thr Val Lys
        915                 920                 925

Asn Leu Asp Val Ile Lys Lys Glu Asn Tyr Tyr Glu Val Asn Ser Lys
    930                 935                 940

Cys Tyr Glu Glu Ala Lys Lys Leu Lys Lys Ile Ser Asn Gln Ala Glu
945                 950                 955                 960

Phe Ile Ala Ser Phe Tyr Asn Asn Asp Leu Ile Lys Ile Asn Gly Glu
                965                 970                 975

Leu Tyr Arg Val Ile Gly Val Asn Asn Asp Leu Leu Asn Arg Ile Glu
            980                 985                 990

Val Asn Met Ile Asp Ile Thr Tyr  Arg Glu Tyr Leu Glu  Asn Met Asn
        995                 1000                1005

Asp Lys  Arg Pro Pro Arg Ile  Ile Lys Thr Ile Ala  Ser Lys Thr
    1010                1015                1020
```

```
Gln Ser  Ile Lys Lys Tyr Ser  Thr Asp Ile Leu Gly  Asn Leu Tyr
    1025                1030                1035

Glu Val  Lys Ser Lys Lys His  Pro Gln Ile Ile Lys  Lys Gly
    1040                1045                1050


<210> SEQ ID NO 66
<211> LENGTH: 4557
<212> TYPE: DNA
<213> ORGANISM: Artificial Sequence
<220> FEATURE:
<223> OTHER INFORMATION: Sequence packaged from pSIA111 and pSIA121

<400> SEQUENCE: 66

cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccgcac gcgtgctccg gtgcccgtca gtgggcagag cgcacatcgc    180

ccacagtccc cgagaagttg gggggagggg tcggcaattg aaccggtgcc tagagaaggt    240

ggcgcggggt aaactgggaa agtgatgtcg tgtactggct ccgccttttt cccgagggtg    300

ggggagaacc gtatataagt gcagtagtcg ccgtgaacgt tctttttcgc aacgctagct    360

aactaccggt gccaccatgg ccccaaagaa gaagcggaag gtcggtagta ctgtgggtac    420

tcgaagtggc tgcgtaccac acccgtcgca tggatccaag cggaactata tcctgggact    480

ggacatcgga attacctccg tgggatacgg catcatcgat tacgagacta gggacgtgat    540

tgacgccggc gtgagactct ttaaggaggc caacgtggaa aacaacgaag gtcgcagatc    600

caagcggggt gcaagacgcc tgaagcgccg gaggagacat cggatacagc gcgtgaagaa    660

gctccttttc gactacaacc tcctcactga ccactcggaa ttgtccggta tcaaccccta    720

cgaagcccgc gtgaaaggcc tgagccagaa gctgtccgaa gaggagttta gcgcagccct    780

gctgcacctg gctaagcgaa ggggggtgca caacgtgaac gaggtggagg aggacactgg    840

caacgaactg tccaccaagg agcagatttc acggaactcg aaggcgctgg aagagaaata    900

tgtggccgag ctgcagctgg agaggctcaa gaaggatggc gaagtccggg ggagcatcaa    960

tcgcttcaag acctcggact acgtgaagga agccaaacag ctgttgaagg tgcagaaggc   1020

ctaccaccaa ctggaccaat cattcattga cacttacatc gatctgcttg aaaccaggcg   1080

cacctactac gagggtcctg gagaaggcag cccctttcgga tggaaggaca tcaaggagtg   1140

gtatgagatg ctgatgggtc attgcaccta ctttccggaa gaactgcgct cagtgaagta   1200

cgcgtacaac gctgacctct acaacgctct caacgatctg aacaacctcg tgatcacccg   1260

ggacgagaac gaaaagctgg agtactacga aaagttccag attatcgaaa acgtgttcaa   1320

gcagaagaag aagcccaccc tgaagcagat tgcaaaggag atccttgtga acgaggagga   1380

tattaagggc taccgggtca cctccaccgg gaaaccagag ttcactaatc tcaaggtgta   1440

ccatgacatt aaggacatta ctgcccgcaa ggagatcatt gaaaacgcgg aactgctgga   1500

ccaaatcgcg aagatcctga ccatctatca gagctccgag gatatccagg aggaacttac   1560

taacctcaat tccgagctga cgcaggaaga aatcgagcaa attagcaacc tgaagggtta   1620

cactggaacc cacaacctca gcttgaaagc gattaacctt attttggatg aactttggca   1680

cactaatgac aatcagatcg ccattttcaa ccggctgaaa ctggtgccga agaaggtgga   1740

cctgagccaa cagaaggaaa tcccgaccac ccttgtggac gatttcatcc tgtcacctgt   1800

ggtgaagagg agcttcatcc agtcgatcaa ggtcatcaac gccatcataa agaagtacgg   1860
```

```
ccttcccaac gacatcatca tcgaactggc ccgcgagaag aactccaaag atgcccagaa   1920
gatgatcaac gagatgcaga agcgaaaccg gcagacgaac gaacggatcg aggagatcat   1980
ccggaccacc gggaaggaaa acgcgaagta cctgatcgag aaaatcaagc tgcatgatat   2040
gcaggaaggg aagtgtctct actccctgga ggccattccg ctggaggatt tgctgaacaa   2100
ccctttcaac tacgaagtcg atcatatcat tcctcgctcc gtgtccttcg ataactcctt   2160
caacaataag gtcctcgtga agcaggagga gaagtaagta tcaaggttac aagacaggtt   2220
taaggagacc aatagaaact gggctcgaga atgcgacggg tgtggtacgc agccacttcg   2280
agtacccaca gtactacctg cttgtcgaga cagagaagac tcttgcgttt ctgataggca   2340
cctattggtc ttactgacat ccactttgcc tttctctcca cagctcgaag aagggcaaca   2400
gaaccccgtt ccagtacctc tcgtcgtccg actccaagat cagctacgaa actttcaaga   2460
agcacattct gaacctggcc aagggcaaag ggagaattag caagaccaag aaggaatacc   2520
tcctggaaga gagagacatc aaccgcttct cggtgcaaaa ggatttcatc aaccgcaacc   2580
tggtcgatac cagatacgcc accaggggac tgatgaacct cctgcggtcc tacttccggg   2640
tcaacaatct ggacgtgaag gtcaaatcca tcaacggggg ctttacttct ttcctgcgcc   2700
ggaagtggaa gttcaagaag gaacggaaca agggatacaa gcaccacgct gaagatgccc   2760
tgattattgc caacgccgac ttcatcttta aggaatggaa aaagctggac aaggctaaga   2820
aggtcatgga gaaccagatg ttcgaagaaa agcaggccga gtccatgccc gaaatcgaaa   2880
ccgagcagga atacaaggag atcttcatca caccgcacca aatcaagcac atcaaggact   2940
tcaaggatta caagtacagc caccgggtgg acaagaagcc taacagagag cttatcaacg   3000
acaccctgta ctccacgcgc aaggacgaca agggaaacac attgatcgtg aacaacctga   3060
acggactgta tgacaaggac aatgacaaac tgaagaagct gatcaacaaa tcgccggaaa   3120
agctcctgat gtaccatcac gaccctcaaa cctaccagaa actgaagctc atcatggagc   3180
agtacggcga cgaaaagaat cccctgtaca aatactacga ggagactgga aattacctga   3240
ctaagtactc caagaaggat aacggccccg tgatcaagaa gattaagtac tacggaaaca   3300
aactgaacgc acatctcgac atcaccgatg attatccaaa ctcccgcaac aaagtcgtga   3360
agctctccct caaaccgtac cgcttcgacg tgtacctgga taatggggtg tacaagttcg   3420
tgaccgtgaa gaacctggac gtcattaaga aggaaaacta ctacgaagtg aactcaaagt   3480
gctacgagga agccaagaag ctcaagaaga tcagcaacca ggccgagttc atcgcatcgt   3540
tttacaacaa tgacctcatt aagattaatg gagaactgta cagagtgatc ggcgtgaaca   3600
acgacctcct gaaccggatt gaagtgaaca tgatcgatat tacctaccgg gagtatctgg   3660
agaacatgaa cgacaagcgc ccaccgagaa tcatcaaaac tattgcctcc aagacccaat   3720
ccattaagaa atactccacc gacatcctgg gcaacctgta cgaggtcaag tcgaagaagc   3780
acccccagat tatcaagaag ggaaaaaggc cggcggccac gaaaaaggcc ggccaggcaa   3840
aaaagaaaaa ggcttaagaa ttcctagagc tcgctgatca gcctcgaaac ttgtttattg   3900
cagcttataa tggttacaaa taaagcaata gcatcacaaa tttcacaaat aaagcatttt   3960
tttcactgca ttctagttgt ggtttgtcca aactcatcaa tgtatcttat catgtctgta   4020
taccagcagg ctttcctagg ttcgaacgct gacgtcatca acccgctcca aggaatcgcg   4080
ggcccagtgt cactaggcgg gaacacccag cgcgcgtgcg ccctggcagg aagatggctg   4140
tgagggacag gggagtggcg ccctgcaata tttgcatgtc gctatgtgtt ctgggaaatc   4200
accataaacg tgaaatccct atcagtgata gagacttata agttccctat cagtgataga   4260
```

gacaccgacg ggtgtggtac gcagccactg tttaagtact ctgtgctgga aacagcacag 4320
aatctactta aacaaggcaa aatgccgtgt ttatctcgtc aacttgttgg cgagattttt 4380
tcacgtgcgg accgaggctg cagcgtcgtc ctccctagga acccctagtg atggagttgg 4440
ccactccctc tctgcgcgct cgctcgctca ctgaggccgg gcgaccaaag gtcgcccgac 4500
gcccgggctt tgcccgggcg gcctcagtga gcgagcgagc gcgcagctgc ctgcagg 4557

<210> SEQ ID NO 67
<211> LENGTH: 4640
<212> TYPE: DNA
<213> ORGANISM: Artificial Sequence
<220> FEATURE:
<223> OTHER INFORMATION: Sequence packaged from pSIA142 and pSIA119

<400> SEQUENCE: 67
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgggccc cagaagcctg gtggttgttt gtccttctca 180
ggggaaaagt gaggcggccc cttggaggaa ggggccgggc agaatgatct aatcggattc 240
caagcagctc aggggattgt ctttttctag caccttcttg ccactcctaa gcgtcctccg 300
tgaccccggc tgggatttag cctggtgctg tgtcagcccc ggtctcccag ggcttcccca 360
gtggtcccca ggaaccctcg acagggcccg gtctctctcg tccagcaagg gcagggacgg 420
gccacaggcc aagggcgcta gctaactacc ggtgccacca tggccccaaa gaagaagcgg 480
aaggtcggta gtactgtggg tactcgaagt ggctgcgtac cacacccgtc gcatggatcc 540
aagcggaact atatcctggg actggacatc ggaattacct ccgtgggata cggcatcatc 600
gattacgaga ctagggacgt gattgacgcc ggcgtgagac tctttaagga ggccaacgtg 660
gaaaacaacg aaggtcgcag atccaagcgg ggtgcaagac gcctgaagcg ccggaggaga 720
catcggatac agcgcgtgaa gaagctcctt ttcgactaca acctcctcac tgaccactcg 780
gaattgtccg gtatcaaccc ctacgaagcc cgcgtgaaag gcctgagcca gaagctgtcc 840
gaagaggagt ttagcgcagc cctgctgcac ctggctaagc gaagggggt gcacaacgtg 900 aacgaggtgg aggaggacac tggcaacgaa ctgtccacca aggagcagat ttcacggaac 960
tcgaaggcgc tggaagagaa atatgtggcc gagctgcagc tggagaggct caagaaggat 1020
ggcgaagtcc gggggagcat caatcgcttc aagacctcgg actacgtgaa ggaagccaaa 1080
cagctgttga aggtgcagaa ggcctaccac caactggacc aatcattcat tgacacttac 1140
atcgatctgc ttgaaaccag gcgcacctac tacgagggtc ctggagaagg cagccctttc 1200
ggatggaagg acatcaagga gtggtatgag atgctgatgg gtcattgcac ctactttccg 1260
gaagaactgc gctcagtgaa gtacgcgtac aacgctgacc tctacaacgc tctcaacgat 1320
ctgaacaacc tcgtgatcac ccgggacgag aacgaaaagc tggagtacta cgaaaagttc 1380
cagattatcg aaaacgtgtt caagcagaag aagaagccca ccctgaagca gattgcaaag 1440
gagatccttg tgaacgagga ggatattaag ggctaccggg tcacctccac cgggaaacca 1500
gagttcacta atctcaaggt gtaccatgac attaaggaca ttactgcccg caaggagatc 1560
attgaaaacg cggaactgct ggaccaaatc gcgaagatcc tgaccatcta tcagagctcc 1620
gaggatatcc aggaggaact tactaacctc aattccgagc tgacgcagga agaaatcgag 1680
caaattagca acctgaaggg ttacactgga acccacaacc tcagcttgaa agcgattaac 1740

-continued

```
cttattttgg atgaactttg gcacactaat gacaatcaga tcgccatttt caaccggctg   1800
aaactggtgc cgaagaaggt ggacctgagc caacagaagg aaatcccgac cacccttgtg   1860
gacgatttca tcctgtcacc tgtggtgaag aggagcttca tccagtcgat caaggtcatc   1920
aacgccatca taaagaagta cggccttccc aacgacatca tcatcgaact ggcccgcgag   1980
aagaactcca aagatgccca gaagatgatc aacgagatgc agaagcgaaa ccggcagacg   2040
aacgaacgga tcgaggagat catccggacc accgggaagg aaaacgcgaa gtacctgatc   2100
gagaaaatca agctgcatga tatgcaggaa gggaagtgtc tctactccct ggaggccatt   2160
ccgctggagg atttgctgaa caaccctttc aactacgaag tcgatcatat cattcctcgc   2220
tccgtgtcct tcgataactc cttcaacaat aaggtcctcg tgaagcagga ggagaagtaa   2280
gtatcaaggt tacaagacag gtttaaggag accaatagaa actgggctcg agaatgcgac   2340
gggtgtggta cgcagccact tcgagtaccc acagtactac ctgcttgtcg agacagagaa   2400
gactcttgcg tttctgatag gcacctattg gtcttactga catccacttt gcctttctct   2460
ccacagctcg aagaagggca acagaacccc gttccagtac ctctcgtcgt ccgactccaa   2520
gatcagctac gaaactttca agaagcacat tctgaacctg gccaagggca aagggagaat   2580
tagcaagacc aagaaggaat acctcctgga agagagagac atcaaccgct tctcggtgca   2640
aaaggatttc atcaaccgca acctggtcga taccagatac gccaccaggg gactgatgaa   2700
cctcctgcgg tcctacttcc gggtcaacaa tctggacgtg aaggtcaaat ccatcaacgg   2760
gggctttact tctttcctgc gccggaagtg gaagttcaag aaggaacgga acaagggata   2820
caagcaccac gctgaagatg ccctgattat tgccaacgcc gacttcatct ttaaggaatg   2880
gaaaaagctg gacaaggcta agaaggtcat ggagaaccag atgttcgaag aaaagcaggc   2940
cgagtccatg cccgaaatcg aaaccgagca ggaatacaag gagatcttca tcacaccgca   3000
ccaaatcaag cacatcaagg acttcaagga ttacaagtac agccaccggg tggacaagaa   3060
gcctaacaga gagcttatca acgacaccct gtactccacg cgcaaggacg acaagggaaa   3120
cacattgatc gtgaacaacc tgaacggact gtatgacaag gacaatgaca aactgaagaa   3180
gctgatcaac aaatcgccgg aaaagctcct gatgtaccat cacgaccctc aaacctacca   3240
gaaactgaag ctcatcatgg agcagtacgg cgacgaaaag aatcccctgt acaaatacta   3300
cgaggagact ggaaattacc tgactaagta ctccaagaag gataacggcc ccgtgatcaa   3360
gaagattaag tactacggaa acaaactgaa cgcacatctc gacatcaccg atgattatcc   3420
aaactcccgc aacaaagtcg tgaagctctc cctcaaaccg taccgcttcg acgtgtacct   3480
ggataatggg gtgtacaagt tcgtgaccgt gaagaacctg gacgtcatta agaaggaaaa   3540
ctactacgaa gtgaactcaa agtgctacga ggaagccaag aagctcaaga agatcagcaa   3600
ccaggccgag ttcatcgcat cgttttacaa caatgacctc attaagatta atggagaact   3660
gtacagagtg atcggcgtga acaacgacct cctgaaccgg attgaagtga acatgatcga   3720
tattacctac cgggagtatc tggagaacat gaacgacaag cgcccaccga gaatcatcaa   3780
aactattgcc tccaagaccc aatccattaa gaaatactcc accgacatcc tgggcaacct   3840
gtacgaggtc aagtcgaaga agcaccccca gattatcaag aagggaaaaa ggccggcggc   3900
cacgaaaaag gccggccagg caaaaaagaa aaaggcttaa gaattcctag agctcgctga   3960
tcagcctcga aacttgttta ttgcagctta taatggttac aaataaagca atagcatcac   4020
aaatttcaca aataaagcat ttttttcact gcattctagt tgtggtttgt ccaaactcat   4080
caatgtatct tatcatgtct gtataccagc aggctttcct aggttcgaac gctgacgtca   4140
```

```
tcaacccgct ccaaggaatc gcgggcccag tgtcactagg cgggaacacc cagcgcgcgt   4200

gcgccctggc aggaagatgg ctgtgaggga caggggagtg gcgccctgca atatttgcat   4260

gtcgctatgt gttctgggaa atcaccataa acgtgaaatc cctatcagtg atagagactt   4320

ataagttccc tatcagtgat agagacaccg acgggtgtgg tacgcagcca ctgtttaagt   4380

actctgtgct ggaaacagca cagaatctac ttaaacaagg caaaatgccg tgtttatctc   4440

gtcaacttgt tggcgagatt ttttcacgtg cggaccgagg ctgcagcgtc gtcctcccta   4500

ggaaccccta gtgatggagt tggccactcc ctctctgcgc gctcgctcgc tcactgaggc   4560

cgggcgacca aaggtcgccc gacgcccggg ctttgcccgg gcggcctcag tgagcgagcg   4620

agcgcgcagc tgcctgcagg                                               4640
```

<210> SEQ ID NO 68
<211> LENGTH: 4542
<212> TYPE: DNA
<213> ORGANISM: Artificial Sequence
<220> FEATURE:
<223> OTHER INFORMATION: sequence packaged from pSIA185-pSIA187 and pSIA036

<400> SEQUENCE: 68

```
cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccgcac gcgtgggccc cagaagcctg gtggttgttt gtccttctca    180

ggggaaaagt gaggcggccc cttggaggaa ggggccgggc agaatgatct aatcggattc    240

caagcagctc aggggattgt ctttttctag caccttcttg ccactcctaa gcgtcctccg    300

tgaccccggc tgggatttag cctggtgctg tgtcagcccc ggctagctaa ctaccggtgc    360

caccatggcc ccaaagaaga agcggaaggt cggtagtact gtgggtactc gaagtggctg    420

cgtaccacac ccgtcgcatg gatccaagcg gaactatatc ctgggactgg acatcggaat    480

tacctccgtg ggatacggca tcatcgatta cgagactagg gacgtgattg acgccggcgt    540

gagactcttt aaggaggcca acgtggaaaa caacgaaggt cgcagatcca agcggggtgc    600

aagacgcctg aagcgccgga ggagacatcg gatacagcgc gtgaagaagc tcctttttcga    660

ctacaacctc ctcactgacc actcggaatt gtccggtatc aacccctacg aagcccgcgt    720

gaaaggcctg agccagaagc tgtccgaaga ggagtttagc gcagccctgc tgcacctggc    780

taagcgaagg ggggtgcaca acgtgaacga ggtggaggag gacactggca acgaactgtc    840

caccaaggag cagatttcac ggaactcgaa ggcgctggaa gagaaatatg tggccgagct    900

gcagctggag aggctcaaga aggatggcga agtccggggg agcatcaatc gcttcaagac    960

ctcggactac gtgaaggaag ccaaacagct gttgaaggtg cagaaggcct accaccaact   1020

ggaccaatca ttcattgaca cttacatcga tctgcttgaa accaggcgca cctactacga   1080

gggtcctgga gaaggcagcc ctttcggatg gaaggacatc aaggagtggt atgagatgct   1140

gatgggtcat tgcacctact ttccggaaga actgcgctca gtgaagtacg cgtacaacgc   1200

tgacctctac aacgctctca acgatctgaa caacctcgtg atcacccggg acgagaacga   1260

aaagctggag tactacgaaa agttccagat tatcgaaaac gtgttcaagc agaagaagaa   1320

gcccaccctg aagcagattg caaaggagat ccttgtgaac gaggaggata ttaagggcta   1380

ccgggtcacc tccaccggga aaccagagtt cactaatctc aaggtgtacc atgacattaa   1440

ggacattact gcccgcaagg agatcattga aaacgcggaa ctgctggacc aaatcgcgaa   1500
```

```
gatcctgacc atctatcaga gctccgagga tatccaggag gaacttacta acctcaattc   1560
cgagctgacg caggaagaaa tcgagcaaat tagcaacctg aagggttaca ctggaaccca   1620
caacctcagc ttgaaagcga ttaaccttat tttggatgaa ctttggcaca ctaatgacaa   1680
tcagatcgcc attttcaacc ggctgaaact ggtgccgaag aaggtggacc tgagccaaca   1740
gaaggaaatc ccgaccaccc ttgtggacga tttcatcctg tcacctgtgg tgaagaggag   1800
cttcatccag tcgatcaagg tcatcaacgc catcataaag aagtacggcc ttcccaacga   1860
catcatcatc gaactggccc gcgagaagaa ctccaaagat gcccagaaga tgatcaacga   1920
gatgcagaag cgaaaccggc agacgaacga acggatcgag gagatcatcc ggaccaccgg   1980
gaaggaaaac gcgaagtacc tgatcgagaa aatcaagctg catgatatgc aggaagggaa   2040
gtgtctctac tccctggagg ccattccgct ggaggatttg ctgaacaacc ctttcaacta   2100
cgaagtcgat catatcattc ctcgctccgt gtccttcgat aactccttca acaataaggt   2160
cctcgtgaag caggaggaga agtaagtatc aaggttacaa gacaggttta aggagaccaa   2220
tagaaactgg gctcgagaat gcgacgggtg tggtacgcag ccacttcgag tacccacagt   2280
actacctgct tgtcgagaca gagaagactc ttgcgtttct gataggcacc tattggtctt   2340
actgacatcc actttgcctt tctctccaca gctcgaagaa gggcaacaga accccgttcc   2400
agtacctctc gtcgtccgac tccaagatca gctacgaaac tttcaagaag cacattctga   2460
acctggccaa gggcaaaggg agaattagca agaccaagaa ggaatacctc ctggaagaga   2520
gagacatcaa ccgcttctcg gtgcaaaagg atttcatcaa ccgcaacctg gtcgatacca   2580
gatacgccac caggggactg atgaacctcc tgcggtccta cttccgggtc aacaatctgg   2640
acgtgaaggt caaatccatc aacgggggct ttacttcttt cctgcgccgg aagtggaagt   2700
tcaagaagga acggaacaag ggatacaagc accacgctga agatgccctg attattgcca   2760
acgccgactt catctttaag gaatggaaaa agctggacaa ggctaagaag gtcatggaga   2820
accagatgtt cgaagaaaag caggccgagt ccatgcccga aatcgaaacc gagcaggaat   2880
acaaggagat cttcatcaca ccgcaccaaa tcaagcacat caaggacttc aaggattaca   2940
agtacagcca ccgggtggac aagaagccta acagagagct tatcaacgac accctgtact   3000
ccacgcgcaa ggacgacaag ggaaacacat tgatcgtgaa caacctgaac ggactgtatg   3060
acaaggacaa tgacaaactg aagaagctga tcaacaaatc gccggaaaag ctcctgatgt   3120
accatcacga ccctcaaacc taccagaaac tgaagctcat catggagcag tacggcgacg   3180
aaaagaatcc cctgtacaaa tactacgagg agactggaaa ttacctgact aagtactcca   3240
agaaggataa cggccccgtg atcaagaaga ttaagtacta cggaaacaaa ctgaacgcac   3300
atctcgacat caccgatgat tatccaaact cccgcaacaa agtcgtgaag ctctccctca   3360
aaccgtaccg cttcgacgtg tacctggata atggggtgta caagttcgtg accgtgaaga   3420
acctggacgt cattaagaag gaaaactact acgaagtgaa ctcaaagtgc tacgaggaag   3480
ccaagaagct caagaagatc agcaaccagg ccgagttcat cgcatcgttt tacaacaatg   3540
acctcattaa gattaatgga gaactgtaca gagtgatcgg cgtgaacaac gacctcctga   3600
accggattga agtgaacatg atcgatatta cctaccggga gtatctggag aacatgaacg   3660
acaagcgccc accgagaatc atcaaaacta ttgcctccaa gacccaatcc attaagaaat   3720
actccaccga catcctgggc aacctgtacg aggtcaagtc gaagaagcac ccccagatta   3780
tcaagaaggg aaaaaggccg gcggccacga aaaaggccgg ccaggcaaaa aagaaaaagg   3840
```

```
cttaagaatt cctagagctc gctgatcagc ctcgaaactt gtttattgca gcttataatg   3900

gttacaaata aagcaatagc atcacaaatt tcacaaataa agcatttttt tcactgcatt   3960

ctagttgtgg tttgtccaaa ctcatcaatg tatcttatca tgtctgtata ccagcaggct   4020

ttcctaggtt cgaacgctga cgtcatcaac ccgctccaag gaatcgcggg cccagtgtca   4080

ctaggcggga acacccagcg cgcgtgcgcc ctggcaggaa gatggctgtg agggacaggg   4140

gagtggcgcc ctgcaatatt tgcatgtcgc tatgtgttct gggaaatcac cataaacgtg   4200

aaatccctat cagtgataga gacttataag ttccctatca gtgatagaga caccgggtgt   4260

ggtacgcagc cactgtttaa gtactctgtg ctggaaacag cacagaatct acttaaacaa   4320

ggcaaaatgc cgtgtttatc tcgtcaactt gttggcgaga tttttcacg tgcggaccga   4380

ggctgcagcg tcgtcctccc taggaacccc tagtgatgga gttggccact ccctctctgc   4440

gcgctcgctc gctcactgag gccgggcgac caaaggtcgc ccgacgcccg ggctttgccc   4500

gggcggcctc agtgagcgag cgagcgcgca gctgcctgca gg                      4542
```

<210> SEQ ID NO 69
<211> LENGTH: 4554
<212> TYPE: DNA
<213> ORGANISM: Artificial Sequence
<220> FEATURE:
<223> OTHER INFORMATION: sequence packaged from pSIA069, pSIA188-pSIA190

<400> SEQUENCE: 69

```
cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccgcac gcgtgctccg gtgcccgtca gtgggcagag cgcacatcgc    180

ccacagtccc cgagaagttg gggggagggg tcggcaattg aaccggtgcc tagagaaggt    240

ggcgcggggt aaactgggaa agtgatgtcg tgtactggct ccgccttttt cccgagggtg    300

ggggagaacc gtatataagt gcagtagtcg ccgtgaacgt tctttttcgc aacgctagct    360

aactaccggt gccaccatgg ccccaaagaa gaagcggaag gtcggtagta ctgtgggtac    420

tcgaagtggc tgcgtaccac acccgtcgca tggatccaag cggaactata tcctgggact    480

ggacatcgga attacctccg tgggatacgg catcatcgat tacgagacta gggacgtgat    540

tgacgccggc gtgagactct ttaaggaggc caacgtggaa aacaacgaag gtcgcagatc    600

caagcggggt gcaagacgcc tgaagcgccg gaggagacat cggatacagc gcgtgaagaa    660

gctccttttc gactacaacc tcctcactga ccactcggaa ttgtccggta tcaaccccta    720

cgaagcccgc gtgaaaggcc tgagccagaa gctgtccgaa gaggagttta gcgcagccct    780

gctgcacctg gctaagcgaa ggggggtgca caacgtgaac gaggtggagg aggacactgg    840

caacgaactg tccaccaagg agcagatttc acggaactcg aaggcgctgg aagagaaata    900

tgtggccgag ctgcagctgg agaggctcaa gaaggatggc gaagtccggg ggagcatcaa    960

tcgcttcaag acctcggact acgtgaagga agccaaacag ctgttgaagg tgcagaaggc   1020

ctaccaccaa ctggaccaat cattcattga cacttacatc gatctgcttg aaaccaggcg   1080

cacctactac gagggtcctg gagaaggcag cccctttcgga tggaaggaca tcaaggagtg   1140

gtatgagatg ctgatgggtc attgcaccta ctttccggaa gaactgcgct cagtgaagta   1200

cgcgtacaac gctgacctct acaacgctct caacgatctg aacaacctcg tgatcacccg   1260

ggacgagaac gaaaagctgg agtactacga aaagttccag attatcgaaa acgtgttcaa   1320

gcagaagaag aagcccaccc tgaagcagat tgcaaaggag atccttgtga acgaggagga   1380
```

```
tattaagggc taccgggtca cctccaccgg gaaaccagag ttcactaatc tcaaggtgta   1440
ccatgacatt aaggacatta ctgcccgcaa ggagatcatt gaaaacgcgg aactgctgga   1500
ccaaatcgcg aagatcctga ccatctatca gagctccgag gatatccagg aggaacttac   1560
taacctcaat tccgagctga cgcaggaaga aatcgagcaa attagcaacc tgaagggtta   1620
cactggaacc cacaacctca gcttgaaagc gattaacctt attttggatg aactttggca   1680
cactaatgac aatcagatcg ccattttcaa ccggctgaaa ctggtgccga agaaggtgga   1740
cctgagccaa cagaaggaaa tcccgaccac ccttgtggac gatttcatcc tgtcacctgt   1800
ggtgaagagg agcttcatcc agtcgatcaa ggtcatcaac gccatcataa agaagtacgg   1860
ccttcccaac gacatcatca tcgaactggc ccgcgagaag aactccaaag atgcccagaa   1920
gatgatcaac gagatgcaga agcgaaaccg gcagacgaac gaacggatcg aggagatcat   1980
ccggaccacc gggaaggaaa acgcgaagta cctgatcgag aaaatcaagc tgcatgatat   2040
gcaggaaggg aagtgtctct actccctgga ggccattccg ctggaggatt tgctgaacaa   2100
ccctttcaac tacgaagtcg atcatatcat tcctcgctcc gtgtccttcg ataactcctt   2160
caacaataag gtcctcgtga agcaggagga gaagtaagta tcaaggttac aagacaggtt   2220
taaggagacc aatagaaact gggctcgaga atgcgacggg tgtggtacgc agccacttcg   2280
agtacccaca gtactacctg cttgtcgaga cagagaagac tcttgcgttt ctgataggca   2340
cctattggtc ttactgacat ccactttgcc tttctctcca cagctcgaag aagggcaaca   2400
gaaccccgtt ccagtacctc tcgtcgtccg actccaagat cagctacgaa actttcaaga   2460
agcacattct gaacctggcc aagggcaaag ggagaattag caagaccaag aaggaatacc   2520
tcctggaaga gagagacatc aaccgcttct cggtgcaaaa ggatttcatc aaccgcaacc   2580
tggtcgatac cagatacgcc accaggggac tgatgaacct cctgcggtcc tacttccggg   2640
tcaacaatct ggacgtgaag gtcaaatcca tcaacggggg ctttacttct ttcctgcgcc   2700
ggaagtggaa gttcaagaag gaacggaaca agggatacaa gcaccacgct gaagatgccc   2760
tgattattgc caacgccgac ttcatcttta aggaatggaa aaagctggac aaggctaaga   2820
aggtcatgga gaaccagatg ttcgaagaaa agcaggccga gtccatgccc gaaatcgaaa   2880
ccgagcagga atacaaggag atcttcatca caccgcacca aatcaagcac atcaaggact   2940
tcaaggatta caagtacagc caccgggtgg acaagaagcc taacagagag cttatcaacg   3000
acaccctgta ctccacgcgc aaggacgaca agggaaacac attgatcgtg aacaacctga   3060
acggactgta tgacaaggac aatgacaaac tgaagaagct gatcaacaaa tcgccggaaa   3120
agctcctgat gtaccatcac gaccctcaaa cctaccagaa actgaagctc atcatggagc   3180
agtacggcga cgaaaagaat cccctgtaca aatactacga ggagactgga aattacctga   3240
ctaagtactc caagaaggat aacggccccg tgatcaagaa gattaagtac tacggaaaca   3300
aactgaacgc acatctcgac atcaccgatg attatccaaa ctcccgcaac aaagtcgtga   3360
agctctccct caaaccgtac cgcttcgacg tgtacctgga taatggggtg tacaagttcg   3420
tgaccgtgaa gaacctggac gtcattaaga aggaaaacta ctacgaagtg aactcaaagt   3480
gctacgagga agccaagaag ctcaagaaga tcagcaacca ggccgagttc atcgcatcgt   3540
tttacaacaa tgacctcatt aagattaatg gagaactgta cagagtgatc ggcgtgaaca   3600
acgacctcct gaaccggatt gaagtgaaca tgatcgatat tacctaccgg gagtatctgg   3660
agaacatgaa cgacaagcgc ccaccgagaa tcatcaaaac tattgcctcc aagacccaat   3720
```

-continued

```
ccattaagaa atactccacc gacatcctgg gcaacctgta cgaggtcaag tcgaagaagc   3780

acccccagat tatcaagaag ggaaaaaggc cggcggccac gaaaaaggcc ggccaggcaa   3840

aaaagaaaaa ggcttaagaa ttcctagagc tcgctgatca gcctcgaaac ttgtttattg   3900

cagcttataa tggttacaaa taaagcaata gcatcacaaa tttcacaaat aaagcatttt   3960

tttcactgca ttctagttgt ggtttgtcca aactcatcaa tgtatcttat catgtctgta   4020

taccagcagg ctttcctagg ttcgaacgct gacgtcatca acccgctcca aggaatcgcg   4080

ggcccagtgt cactaggcgg gaacacccag cgcgcgtgcg ccctggcagg aagatggctg   4140

tgagggacag gggagtggcg ccctgcaata tttgcatgtc gctatgtgtt ctgggaaatc   4200

accataaacg tgaaatccct atcagtgata gagacttata agttccctat cagtgataga   4260

gacaccgggt gtggtacgca gccactgttt aagtactctg tgctggaaac agcacagaat   4320

ctacttaaac aaggcaaaat gccgtgttta tctcgtcaac ttgttggcga gatttttca    4380

cgtgcggacc gaggctgcag cgtcgtcctc cctaggaacc cctagtgatg gagttggcca   4440

ctccctctct gcgcgctcgc tcgctcactg aggccgggcg accaaaggtc gcccgacgcc   4500

cgggctttgc ccgggcggcc tcagtgagcg agcgagcgcg cagctgcctg cagg         4554
```

MATERIALS AND METHODS FOR CONTROLLING GENE EDITING

RELATED APPLICATION

This application claims the benefit of U.S. Provisional Application Ser. No. 62/868,209, filed on Jun. 28, 2019, which is hereby incorporated by reference in its entirety.

FIELD

The present disclosure generally relates to the field of molecular biology, including materials and methods for controlling gene editing by a Cas nuclease.

INCORPORATION BY REFERENCE OF SEQUENCE LISTING

This application contains a Sequence Listing in computer readable form (filename: Sequence_Listing_CBTN_005: 328,549 bytes—ASCII text file; Jun. 26, 2020), which is incorporated by reference in its entirety and forms part of the disclosure.

BACKGROUND

The use of proteins, polynucleotides, and other technology related to clustered regularly interspaced short palindromic repeats (CRISPR) systems is a possible avenue of treatment for various diseases caused by genetic defects and/or ameliorated by genetic treatments. For example, a vector carrying CRISPR-related genes can be introduced into diseased cells in vitro or in vivo, and the resulting cells can then ameliorate or eliminate the disease, based on genetic modification of the cells by the CRISPR-related genes or gene products. A CRISPR system can perform at least some of the system's intended genetic modification functions, leading to amelioration of a disease. However, the CRISPR-related genes may continue to be expressed after the expression is no longer desired.

Currently, there is a lack of efficient and effective materials and methods for controlling expression of CRISPR-related genes that are delivered to cells.

SUMMARY

This section provides a general summary of the disclosure, and is not comprehensive of its full scope or all of its features.

Provided herein is a CRISPR/Cas system. The CRISPR/Cas system comprises: a nuclease segment comprising a codon optimized nucleotide sequence that encodes a Cas nuclease or variant thereof; a guide RNA (gRNA) segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a pharmaceutical composition. The pharmaceutical composition comprises a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a packaging cell. The packaging cell comprises a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a method of controlling transcription of gRNAs during AAV packaging. The method comprises contacting a packaging cell with a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a method of reducing mutagenesis at one or more SIN site in a recombinant AAV vector. The method comprises contacting a packaging cell with a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Provided herein is a recombinant Adeno-associated virus (AAV) vector. The recombinant AAV vector comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a pharmaceutical composition. The pharmaceutical composition comprises a recombinant AAV vector. The recombinant AAV vector comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a genetically modified cell. The genetically modified cell comprises a recombinant AAV vector. The recombinant AAV vector comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a method of controlling transcription of gRNAs during AAV packaging. The method comprises: contacting a packaging cell with a nucleic acid encoding a recombinant AAV vector; and contacting the packaging cell with at least one vector comprising nucleic acid sequence encoding a tetracycline repressor. The recombinant AAV vector comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a method of reducing mutagenesis at one or more SIN site in a recombinant AAV vector. The method comprises: contacting a packaging cell with nucleic acid encoding a recombinant AAV vector; and contacting the packaging cell with at least one vector comprising nucleic acid sequence encoding a tetracycline repressor. The recombinant AAV vector comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a method of producing a recombinant AAV vector. The method comprises: introducing into a packaging cell: (i) a first vector comprising a repressor segment, wherein the repressor segment comprises a nucleotide sequence that encodes a tetracycline repressor protein; (ii) a nucleic acid comprising sequence encoding a recombinant AAV vector; and (iii) one or more viral components for producing the recombinant AAV vector; culturing the packaging cell; and isolating the recombinant AAV vector comprising the nucleic acid from the packaging cell. The recombinant AAV vector comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a method of producing a recombinant AAV vector. The method comprises: introducing into a packaging cell a nucleic acid comprising a sequence encoding a recombinant AAV vector; introducing into the packaging cell one or more viral components for producing the AAV; culturing the packaging cell; and isolating the recombinant AAV vector comprising the nucleic acid from the packaging cell. The packaging cell expresses a tetracycline repressor protein. The recombinant AAV vector comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Provided herein is a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; and a short-hairpin RNA (shRNA) segment comprising a nucleotide sequence that encodes a shRNA that comprises sequence that is complementary to a transcript from the nuclease segment.

Also provided herein is a pharmaceutical composition comprising a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; and a shRNA segment comprising a nucleotide sequence that encodes a shRNA that comprises sequence that is complementary to a transcript from the nuclease segment.

Also provided herein is a packaging cell comprising a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; and a shRNA segment comprising a nucleotide sequence that encodes a shRNA that comprises sequence that is complementary to a transcript from the nuclease segment.

Also provided herein is a method of controlling post-transcriptional expression of Cas nuclease during AAV packaging. The method comprises: contacting a packaging cell with a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; and a shRNA segment comprising a nucleotide sequence that encodes a shRNA that comprises sequence that is complementary to a transcript from the nuclease segment.

Also provided herein is a method of reducing mutagenesis at one or more SIN site in a recombinant AAV vector. The method comprises: contacting a cell with a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; and a shRNA segment comprising a nucleotide sequence that encodes a shRNA that comprises sequence that is complementary to a transcript from the nuclease segment.

Also provided herein is a method of controlling post-transcriptional expression of Cas nuclease during AAV packaging. The method comprises: contacting a packaging cell with a nucleic acid comprising a sequence encoding a recombinant AAV vector; and contacting the packaging cell with at least one vector comprising nucleic acid sequence encoding a shRNA segment. The recombinant AAV vector comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a method of producing a recombinant AAV vector. The method comprises: introducing into a packaging cell: (i) a first vector comprising a shRNA segment comprising a nucleotide sequence that encodes a shRNA that comprises sequence that is complementary to a transcript from the nuclease segment; (ii) a nucleic acid comprising sequence encoding a recombinant AAV vector;

and (iii) one or more viral components for producing the recombinant AAV vector; culturing the packaging cell; and isolating the recombinant AAV vector comprising the nucleic acid from the packaging cell. The recombinant AAV vector comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a method of producing a recombinant AAV vector. The method comprises: introducing into a packaging cell a nucleic acid comprising sequence encoding a recombinant AAV vector; introducing into the packaging cell one or more viral components for producing the AAV; culturing the packaging cell; and isolating the recombinant AAV vector comprising the nucleic acid from the packaging cell. The packaging cell expresses a shRNA. The recombinant AAV vector comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Provided herein is a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; a promoter segment comprising a nucleotide sequence that encodes a first promoter comprising one or more tetracycline operator sequences, wherein the gRNA segment is operably linked to the promoter segment; and a shRNA segment comprising a nucleotide sequence that encodes a shRNA that comprises sequence that is complementary to a transcript from the nuclease segment.

Also provided herein is a pharmaceutical composition comprising a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; a promoter segment comprising a nucleotide sequence that encodes a first promoter comprising one or more tetracycline operator sequences, wherein the gRNA segment is operably linked to the promoter segment; and a shRNA segment comprising a nucleotide sequence that encodes a shRNA that comprises sequence that is complementary to a transcript from the nuclease segment.

Also provided herein is a packaging cell comprising a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; a promoter segment comprising a nucleotide sequence that encodes a first promoter comprising one or more tetracycline operator sequences, wherein the gRNA segment is operably linked to the promoter segment; and a shRNA segment comprising a nucleotide sequence that encodes a shRNA that comprises sequence that is complementary to a transcript from the nuclease segment.

Also provided herein is a method of controlling transcription of gRNAs and post-transcriptional expression of Cas nuclease during AAV packaging. The method comprises: contacting a packaging cell with a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; a promoter segment comprising a nucleotide sequence that encodes a first promoter comprising one or more tetracycline operator sequences, wherein the gRNA segment is operably linked to the promoter segment; and a shRNA segment comprising a nucleotide sequence that encodes a shRNA that comprises sequence that is complementary to a transcript from the nuclease segment.

Also provided herein is a method of reducing mutagenesis at one or more SIN site in a recombinant AAV vector. The method comprises: contacting a cell with a CRISPR/Cas system. The CRISPR/Cas system comprises: a nuclease segment comprising a codon optimized nucleotide sequence that encodes a Cas nuclease or variant thereof; a gRNA segment comprising a nucleotide sequence that encodes a gRNA or sgRNA; a promoter segment comprising a nucleotide sequence that encodes a first promoter comprising one or more tetracycline operator sequences, wherein the gRNA segment is operably linked to the promoter segment; and a shRNA segment comprising a nucleotide sequence that encodes a shRNA that comprises sequence that is complementary to a transcript from the nuclease segment.

Also provided herein is a method of controlling transcription of gRNAs and post-transcriptional expression of Cas nuclease during AAV packaging. The method comprises: contacting a packaging cell with a nucleic acid comprising sequence encoding a recombinant AAV vector; and contacting the packaging cell with a nucleic acid sequence encoding a tetracycline repressor segment and a shRNA segment. The recombinant AAV vector comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a method of producing a recombinant AAV vector. The method comprises: introducing into a packaging cell: (i) a first vector comprising a repressor segment, wherein the repressor segment comprises a nucleotide sequence that encodes a tetracycline repressor protein; (ii) a second vector comprising a shRNA segment comprising a nucleotide sequence that encodes a shRNA that comprises sequence that is complementary to a transcript from the nuclease segment; (iii) a nucleic acid comprising sequence encoding a recombinant AAV vector; and (iv) one or more viral components for producing the recombinant AAV vector; culturing the packaging cell; and isolating the recombinant AAV vector comprising the nucleic acid of (iii) from the packaging cell. The recombinant AAV vector comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

Also provided herein is a method of producing a recombinant AAV vector. The method comprises: introducing into packaging cell a nucleic acid comprising sequence encoding a recombinant AAV vector; introducing into the packaging cell one or more viral components for producing the AAV; culturing the packaging cell; and isolating the recombinant AAV vector comprising the nucleic acid from the packaging cell. The packaging cell expresses a tetracycline repressor protein and a shRNA. The recombinant AAV vector comprises: a nuclease segment comprising a codon optimized nucleotide sequence that encodes a Cas nuclease or variant thereof; a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

The foregoing summary is illustrative only and is not intended to be in any way limiting. In addition to the illustrative examples and features described herein, further aspects, examples, objects and features of the disclosure will become fully apparent from the drawings and the detailed description and the claims.

BRIEF DESCRIPTION OF THE DRAWINGS

Various aspects of materials and methods disclosed and described in this specification can be better understood by reference to the accompanying figures, in which:

FIG. 1A is a depiction of a reporter sequence comprising a P23H target site integrated in an endogenous β-tubulin gene locus of HEK 293FT cells, generating HEK 293FT reporter cells.

FIG. 1B is a depiction of pSIA113.

FIG. 1C is a depiction of pSIA122.

FIG. 1D shows flow cytometry data for the HEK 293FT reporter cells transfected with pSIA113 and NC026.

FIG. 1E shows flow cytometry data for HEK 293FT reporter cells transfected with pSIA122 and NC026.

FIG. 1F is a western blot showing SaCas9 and β-actin expression in HEK 293FT reporter cells transfected with NC026 and either pSIA113 or pSIA122.

FIG. 2A is a depiction of pSIA071.

FIG. 2B is a depiction of pSIA087.

FIG. 2C is a bar graph showing the percentage of BFP negative ("BFP−") cells and RFP positive (RFP+) cells within the HEK 293FT reporter cells transfected with NC026 and either pSIA071 or pSIA087.

FIG. 2D is a western blot showing SaCas9 and β-actin expression in HEK 293FT reporter cells transfected with NC026 and either pSIA071 or SIA087.

FIG. 3A is a depiction of pSIA132.

FIG. 3B is a depiction of pDL122.

FIG. 3C is a generalized depiction of pDL151, pDL152, and pDL153.

FIG. 3D is a western blot showing SaCas9 and β-actin expression in HEK 293FT reporter cells co-transfected with pSIA132, NC026, and either (1) pDL122, (2) pDL151, (3) pDL152, or (4) pDL153.

FIG. 3E is a bar graph showing the percentage of BFP− cells and RFP+ cells in HEK 293FT reporter cells co-transfected with pSIA132, NC026, and either (1) pDL122, (2) pDL151, (3) pDL152, or pDL153.

FIG. 4A is a depiction of pSIA111.

FIG. 4B is a depiction of pSIA121.

FIG. 4C is a depiction of pSIA142.

FIG. 4D is a depiction of pSIA119.

FIG. 5 also compares AAV5 vectors packaged with either pSIA142 or pSIA119.

FIG. 8A is a depiction of pSIA187.

FIG. 8B shows PCR results comparing AAV5 vectors packaged with either (1) pSIA185, (2) pSIA186, (3) pSIA187, or (4) pSIA036 as the template for recombinant AAV vector production.

FIG. 9A is a depiction of pSIA190.

FIG. 9B is an alkaline electrophoresis gel comparing AAV6 vectors packaged with either (1) pSIA069, (2) pSIA071, (3) pSIA188, (4) pSIA189, or (5) pSIA190 as the template for recombinant AAV vector production.

FIG. 9C is a bar graph showing the percentage of BFP− HEK 293FT reporter cells transduced with a recombinant AAV vector prepared with pSIA190 as the template for recombinant AAV vector production.

FIG. 10A is a depiction of a BFP splicing reporter sequence integrated in Jump-In™ Grip Tite™ HEK 293 cells, generating BFP splicing reporter cells.

FIG. 10B is a depiction of pD105.

FIG. 10C is a representative depiction of pDL258, pDL259, pDL260, pDL261, and pDL262.

FIG. 10D is a depiction of a transfection control, NC026.

FIG. 1E shows flow cytometry results (ratio of GFP to RFP) for BFP splicing reporter cells co-transfected with pD105, NC025, and one of either (1) pDL122, (2) pDL258, (3) pDL259, (4) pDL260, (5) pDL261, or (6) pDL262.

FIG. 10F shows flow cytometry results (% BFP+) for BFP splicing reporter cells co-transfected with pD105, NC025, and one of either (1) pDL122, (2) pDL258, (3) pDL259, (4) pDL260, (5) pDL261, or (6) pDL262.

BRIEF DESCRIPTION OF THE SEQUENCE LISTING

Figure 1A:
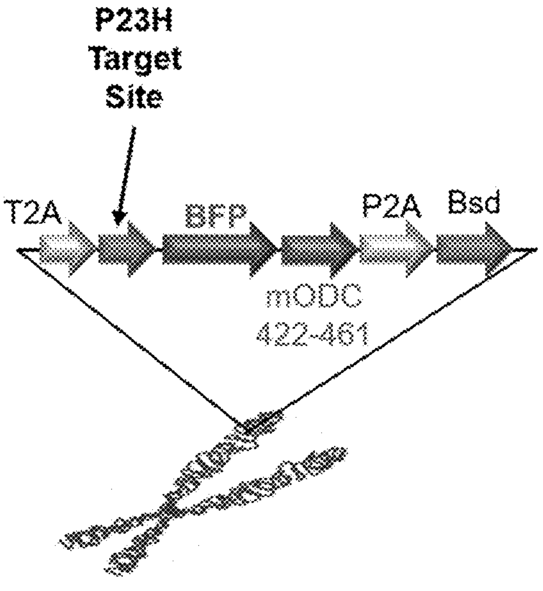
FIGS. 1A-1F show a reporter sequence comprising a P23H target site in an endogenous β-tubulin gene locus of human embryonic kidney (HEK) 293FT cells; a depiction of pSIA113; a depiction of pSIA122; and data (flow cytometry and western blot) generated using HEK 293FT reporter cells transfected with a RFP-expressing plasmid (NC026) and either pSIA113 or pSIA122.

SEQ ID NOs: 1 and 2 are sgRNA sequences that target the P23H allele of the human RHO gene.

SEQ ID NO: 3 is an H1 promoter sequence comprising 2 tetracycline operator (TetO) sites.

SEQ ID NO: 4 is a TetO site.

SEQ ID NOs: 5-8 are plasmid sequences comprising recombinant AAV vector sequences.

SEQ ID NOs: 9-11 are shRNA sequences which target SaCas9.

SEQ ID NO: 12 is a plasmid sequence comprising a recombinant AAV vector sequence.

SEQ ID NO: 13 is a plasmid sequence comprising a sequence encoding a tetracycline repressor (TetR) construct.

SEQ ID NOs: 14-16 are plasmid sequences comprising the shRNA sequences of SEQ ID NOs: 9-11.

SEQ ID NOs: 17-20 are plasmid sequences comprising recombinant AAV vector sequences.

SEQ ID NOs: 21-27 are sequences of oligonucleotide primers used during PCR.

SEQ ID NO: 28 is a sequence comprising a blue fluorescent protein (BFP) reporter construct.

SEQ ID NO: 29 is the sequence of the TetR construct of SEQ ID NO: 13.

SEQ ID NO: 30 is the spacer sequence of SEQ ID NO: 1.

SEQ ID NO: 31 is the DNA sequence of the DNA targeted by the spacer sequence of SEQ ID NO: 30.

SEQ ID NO: 32 is the DNA sequence of the DNA on the strand opposite the sequence of SEQ ID NO: 31.

SEQ ID NO: 33 is the spacer sequence of SEQ ID NO: 2.

SEQ ID NO: 34 is the DNA sequence of the DNA targeted by the spacer sequence of SEQ ID NO: 33.

SEQ ID NO: 35 is the DNA sequence of the DNA on the strand opposite the sequence of SEQ ID NO: 34.

SEQ ID NOs: 36-43 are plasmid sequences comprising recombinant AAV vector sequences.

SEQ ID NO: 44 is a sequence comprising a BFP reporter construct.

SEQ ID NO: 45 is a plasmid sequence comprising a recombinant AAV vector sequence.

SEQ ID NO: 46 is a sgRNA sequence that targets an exon 2 splice donor site in the BFP reporter construct of SEQ ID NO: 44.

SEQ ID NO: 47 is the spacer sequence of SEQ ID NO: 46.

SEQ ID NO: 48 is the DNA sequence of the DNA targeted by the spacer sequence of SEQ ID NO: 47.

SEQ ID NO: 49 is the DNA sequence of the DNA on the strand opposite the sequence of SEQ ID NO: 48.

SEQ ID NOs: 50-54 are plasmid sequences comprising sequence encoding shRNAs that target a sRGN gene transcript. One shRNA is encoded on each plasmid.

SEQ ID NOs: 55-59 are shRNAs sequences encoded by the plasmids of SEQ ID NOs: 50-54.

SEQ ID NO: 60 is a sRGN protein sequence.

SEQ ID NO: 61 is a sRGN nucleotide sequence.

SEQ ID NO: 62 is a TetR nucleotide sequence.

SEQ ID NO: 63 is a TetR protein sequence.

SEQ ID NO: 64 is a *S. aureus* Cas nuclease nucleotide sequence.

SEQ ID NO: 65 is a *S. aureus* Cas nuclease protein sequence.

SEQ ID NO: 66 is an AAV vector sequence from pSIA111 or pSIA121.

SEQ ID NO: 67 is an AAV vector sequence from pSIA142 or pSIA119.

SEQ ID NO: 68 is an AAV vector sequence from pSIA185-187 or pSIA036.

SEQ ID NO: 69 is an AAV vector sequence from pSIA188-190 or pSIA069.

The exemplifications set out in the accompanying sequence listing and description thereof illustrate certain examples, in one form, and such exemplifications are not to be construed as limiting the scope of the examples in any manner.

DETAILED DESCRIPTION

Self-inactivating viral vectors can be used to deliver and express CRISPR-related genes and proteins in order to effect desired changes in cells (e.g., gene editing or modulation of gene expression). After the desired changes in cells have been achieved, or at least partly achieved, further expression of CRISPR-related genes (e.g., a Cas nuclease gene and/or a gRNA gene) can be detrimental. Therefore, self-inactivating viral vectors can be advantageous because the viral vectors can inactivate the further expression of CRISPR-related genes after a period of time, thereby reducing the detrimental effects while still achieving desired changes in cells.

A self-inactivating viral vector system can be a 2-vector system or a 1-vector system. The 1-vector system can also be termed an all-in-one self-inactivating vector system. All-in-one self-inactivating vector systems can be advantageous because they comprise the Cas nuclease sequence, gRNA sequence, self-inactivation (SIN) sites and appropriate promoters to drive expression of the Cas nuclease and gRNA in the same vector instead of 2 vectors. However, for all-in-one self-inactivating viral vector systems, production of the viral vector systems can be challenging due to premature editing, DNA shuffling, and/or mutagenesis at SIN sites in the all-in-one self-inactivating viral vector DNA which is packaged in AAV capsids.

Applicants have discovered novel materials and methods for controlling gene editing. The materials and methods can control transcriptional expression of gRNAs and/or post-transcriptional expression of a Cas nuclease. The materials and methods can control transcriptional expression of gRNAs during AAV packaging, control post-transcriptional expression of a Cas nuclease during AAV packaging, and reduce mutagenesis (e.g., indels and/or deletions) at one or more SIN site in recombinant AAV vectors during packaging.

Novel Materials and Methods for Controlling Gene Editing

The novel materials and methods for controlling gene editing provided herein include the following:

(1) materials and methods that control transcriptional expression of gRNAs using a tetracycline operator/repressor system.

(2) materials and methods that control post-transcriptional expression of a Cas nuclease using a shRNA that is complementary to a Cas nuclease transcript.

(3) materials and methods that control both transcriptional expression of gRNAs using a tetracycline operator/repressor system and control post-transcriptional expression of Cas nuclease using a shRNA that is complementary to a Cas nuclease transcript.

CRISPR/Cas Systems that Control Transcriptional Expression of gRNAs Using a Tetracycline Operator/Repressor System Provided herein are CRISPR/Cas systems for controlling transcriptional expression of gRNAs using a tetracycline operator/repressor system. More specifically, provided herein are CRISPR/Cas systems for controlling transcriptional expression of gRNAs during AAV packaging using a tetracycline operator/repressor system.

Provided herein are CRISPR/Cas systems for reducing mutagenesis at one or more SIN site in a recombinant AAV vector using a tetracycline operator/repressor system. More specifically, provided herein are CRISPR/Cas systems for reducing mutagenesis at one or more SIN site in a recombinant AAV vector during AAV packaging using a tetracycline operator/repressor system.

The CRISPR/Cas system disclosed herein can comprise (1) a nuclease segment comprising a codon optimized nucleotide sequence that encodes a Cas nuclease or variant thereof; (2) a gRNA segment comprising a nucleotide sequence that encodes a gRNA or sgRNA; and (3) a promoter segment comprising a nucleotide sequence that encodes a first promoter comprising one or more tetracycline operator sequence. The gRNA segment can be operably linked to the promoter segment. The CRISPR/Cas system can further comprise a repressor segment comprising a nucleotide sequence that encodes a tetracycline repressor protein. The CRISPR/Cas system can further comprise one or more self-inactivating segments comprising a SIN site.

CRISPR/Cas Systems that Control Post-Transcriptional Expression of Cas Nuclease Using a shRNA that is Complementary to a Cas Nuclease Transcript Provided herein are CRISPR/Cas systems for controlling post-transcriptional expression of Cas nuclease using a shRNA that is complementary to a Cas nuclease transcript. More specifically, provided herein are CRISPR/Cas systems for controlling post-transcriptional expression of Cas nuclease during AAV packaging using a shRNA that is complementary to a Cas nuclease transcript.

Provided herein are CRISPR/Cas systems for reducing mutagenesis at one or more SIN site in a recombinant AAV vector using a shRNA that is complementary to a Cas nuclease transcript. More specifically, provided herein are CRISPR/Cas systems for reducing mutagenesis at one or more SIN site in a recombinant AAV vector during AAV packaging using a shRNA that is complementary to a Cas nuclease transcript.

The CRISPR/Cas system disclosed herein can comprise (1) a nuclease segment comprising a codon optimized nucleotide sequence that encodes a Cas nuclease or variant thereof; (2) a gRNA segment comprising a nucleotide sequence that encodes a gRNA or sgRNA; and (3) a shRNA segment comprising a nucleotide sequence that encodes a shRNA that comprises sequence that is complementary to a transcript from the nuclease segment. The CRISPR/Cas system can further comprise one or more self-inactivating segments comprising a SIN site.

CRISPR/Cas Systems that Control Transcriptional Expression of gRNAs and Control Post-Transcriptional Expression of Cas Nuclease Using a Tetracycline Operator/Repressor System and shRNA that is Complementary to a Cas Nuclease Transcript Provided herein are CRISPR/Cas systems for controlling transcriptional expression of gRNAs using a tetracycline operator/repressor system and controlling post-transcriptional expression of Cas nuclease using a shRNA that is complementary to a Cas nuclease transcript. More specifically, provided herein are CRISPR/Cas systems for controlling transcriptional expression of gRNAs using a tetracycline operator/repressor system and controlling post-transcriptional expression of Cas nuclease using a shRNA that is complementary to a Cas nuclease transcript during AAV packaging.

Provided herein are CRISPR/Cas systems for reducing mutagenesis at one or more SIN site in a recombinant AAV vector using a tetracycline operator/repressor system and a shRNA that is complementary to a Cas nuclease transcript. More specifically, provided herein are CRISPR/Cas systems for reducing mutagenesis at one or more SIN site in a recombinant AAV vector during AAV packaging using a tetracycline operator/repressor system and a shRNA that is complementary to a Cas nuclease transcript.

The CRISPR/Cas system disclosed herein can comprise (1) a nuclease segment comprising a codon optimized nucleotide sequence that encodes a Cas nuclease or variant thereof; (2) a gRNA segment comprising a nucleotide sequence that encodes a gRNA or sgRNA; (3) a promoter segment comprising a nucleotide sequence that encodes a first promoter comprising one or more tetracycline operator sequences; and (4) a shRNA segment comprising a nucleotide sequence that encodes a shRNA that comprises sequence that is complementary to a transcript from the nuclease segment. The gRNA segment is operably linked to the promoter segment. The CRISPR/Cas system can further comprise a repressor segment comprising a nucleotide sequence that encodes a tetracycline repressor protein. The CRISPR/Cas system can further comprise one or more self-inactivating segments comprising a SIN site.

Recombinant AAV Vectors that Control Transcriptional Expression of gRNAs Using a Tetracycline Operator/Repressor System Provided herein are recombinant AAV vectors for controlling transcriptional expression of gRNAs using a tetracycline operator/repressor system. More specifically, provided herein are recombinant AAV vectors for controlling transcriptional expression of gRNAs during AAV packaging using a tetracycline operator/repressor system.

Provided herein are recombinant AAV vectors for reducing mutagenesis at one or more SIN site in a recombinant AAV vector using a tetracycline operator/repressor system. More specifically, provided herein are recombinant AAV vectors for reducing mutagenesis at one or more SIN site in a recombinant AAV vector during AAV packaging using a tetracycline operator/repressor system.

The recombinant AAV vectors disclosed herein can comprise (1) a nuclease segment comprising a codon optimized nucleotide sequence that encodes a Cas nuclease or variant thereof; (2) a gRNA segment comprising a nucleotide sequence that encodes a gRNA or sgRNA; and (3) a promoter segment comprising a nucleotide sequence that encodes a promoter comprising one or more tetracycline operator sequence. The gRNA segment can be operably linked to the promoter segment. The recombinant AAV vectors can further comprise one or more self-inactivating segments comprising a SIN site. The recombinant AAV vectors can comprises a nucleic acid sequence having at least 85% sequence identity to SEQ ID NOs: 66-69. The recombinant AAV vectors can comprise a nucleic acid sequence having at least 85%, 86%, 87%, 88%, 89%, 90%, 91%, 92%, 93%, 94%, 95%, 96%, 97%, 98% or 99% sequence identity to SEQ ID NOs: 66-69. The recombinant AAV vectors can comprise SEQ ID NOs: 66-69.

Additional Recombinant AAV Vectors

Provided herein are recombinant AAV vectors prepared by any one of the methods of producing a recombinant AAV vector disclosed herein.

Nuclease Segment

The nuclease segment can comprise a codon optimized nucleotide sequence that encodes a Cas nuclease or variant thereof.

CRISPR/Cas loci define Class 1 and Class 2 CRISPR/Cas systems, having Types I to V or VI. See, e.g., Makarova et al., Nat Rev Microbiol, 13(11): 722-36 (2015); Shmakov et al., Molecular Cell, 60:385-397 (2015). Class 2 CRISPR/Cas systems have single protein effectors. Cas proteins of Types II, V, and VI may be single-protein, RNA-guided endonucleases, herein called "Class 2 Cas nucleases". The Cas nuclease can be a class 2 Cas nuclease.

The Cas nuclease can be selected from a group consisting of: *S. pyogenes* Cas nuclease, *S. aureus* Cas nuclease, *S. thermolphilus* Cas nuclease, *C. jejuni* Cas nuclease, *T. denticola* Cas nuclease, *N. meningitides* Cas nuclease, *S. lugdunensis* Cas nuclease, *S. hyicus* Cas nuclease, *S. microti* Cas nuclease, *S. pasteuri* Cas nuclease, and Cpf-1.

The Cas nuclease can be any one of the Cas orthologs from other bacterial strains including but not limited to, Cas proteins identified in *Acaryochloris marina* MBIC11017; *Acetohalobium arabaticum* DSM 5501; *Acidithiobacillus caldus; Acidithiobacillus ferrooxidans* ATCC 23270; *Alicyclobacillus acidocaldarius* LAA1; *Alicyclobacillus acidocaldarius* subsp. *acidocaldarius* DSM 446; *Allochromatium vinosum* DSM 180; *Ammonifex degensii* KC4; *Anabaena variabilis* ATCC 29413; *Arthrospira maxima* CS-328; *Arthrospira platensis* str. *Paraca; Arthrospira* sp. PCC 8005; *Bacillus pseudomycoides* DSM 12442; *Bacillus selenitireducens* MLS10; *Burkholderiales bacterium* 1_1_47; *Caldicelulosiruptor becscii* DSM 6725; *Candidatus Desulforudis audaxviator* MP104C; *Caldicellulosiruptor hydrothermalis*_108; *Clostridium* phage c-st; *Clostridium botulinum* A3 str. *Loch Maree; Clostridium botulinum* Ba4 str. 657; *Clostridium difficile* QCD-63q42; *Crocosphaera watsonii* WH 8501; *Cyanothece* sp. ATCC 51142; *Cyanothece* sp. CCY0110; *Cyanothece* sp. PCC 7424; *Cyanothece* sp. PCC 7822; *Exiguobacterium sibiricum* 255-15; *Finegoldia magna* ATCC 29328; *Ktedonobacter racemifer* DSM 44963; *Lactobacillus delbrueckii* subsp. *bulgaricus* PB2003/044-T3-4; *Lactobacillus salivarius* ATCC 11741; *Listeria innocua; Lyngbya* sp. PCC 8106; *Marinobacter* sp. ELB17; *Methanohalobium evestigatum* Z-7303; *Microcystis phage* Ma-LMM01; *Microcystis aeruginosa* NIES-843; *Microscilla marina* ATCC 23134; *Microcoleus chthonoplastes* PCC 7420; *Nitrosococcus halophilus* Nc4; *Nocardiopsis dassonvillei* subsp. *dassonvillei* DSM 43111; *Nodularia spumigena* CCY9414; *Nostoc* sp. PCC 7120; *Oscillatoria* sp. PCC 6506; *Pelotomaculum_thermopropionicum*_SI; *Petrotoga mobilis* SJ95; *Polaromonas naphthalenivorans* CJ2; *Polaromonas* sp. JS666; *Pseudoalteromonas haloplanktis* TAC125; *Streptomyces pristinaespiralis* ATCC 25486; *Streptomyces pristinaespiralis* ATCC 25486; *Streptomyces viridochromogenes* DSM 40736; *Streptosporangium roseum* DSM 43021; *Synechococcus* sp. PCC 7335; and *Thermosipho africanus* TCF52B (Chylinski et al., RNA Biol., 2013; 10(5): 726-737.

The Cas nuclease can be a a synthetic, RNA-Guided Nuclease (sRGN), such as any one of the sRGN disclosed in International Application No. PCT/US19/23044 (Publication No: WO/2019/183150), which is incorporated by reference in its entirety. The Cas nuclease can comprise a polypeptide sequence having at least 85%, 86%, 87%, 88%, 89%, 90%, 91%, 92%, 93%, 94%, 95%, 96%, 97%, 98%, or 99% sequence identity to SEQ ID NO: 60. The Cas nuclease can comprise SEQ ID NO: 60. A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, or mafft.cbrc.jp/alignment/software/. See, e.g., Altschul et al. (1990), J. Mol. Bioi. 215:403-10. Sequence alignments standard in the art are used according to the invention to determine amino acid residues in a Cas ortholog that "correspond to" amino acid residues in another Cas ortholog. The amino acid residues of Cas orthologs that correspond to amino acid residues of other Cas orthologs appear at the same position in alignments of the sequences.

A Cas nuclease can be codon-optimized for expression in the cell containing the target sequence. For example, if the intended target sequence is in a human cell, a human codon-optimized polynucleotide encoding Cas nuclease is contemplated for use for producing the Cas polypeptide.

The codon optimized nucleotide sequence that encodes a Cas nuclease or variant thereof can comprise one or more intron.

A nucleic acid sequence encoding a promoter can be operably linked to the codon optimized nucleotide sequence that encodes a Cas nuclease or variant thereof. The promoter can be a spatially-restricted promoter, bidirectional promoter, or an inducible promoter. The spatially-restricted promoter can be selected from a group consisting of: any tissue or cell type specific promoter, a hepatocyte-specific promoter, a neuron-specific promoter, an adipocyte-specific promoter, a cardiomyocyte-specific promoter, a skeletal muscle-specific promoter, lung progenitor cell specific promoter, a photoreceptor cell-specific promoter, and a retinal pigment epithelial (RPE) selective promoter.

A tissue specific promoter can be used to control transcription of Cas nuclease by directing the expression of Cas nuclease only in certain host cells. For example, the photoreceptor-specific promoter, GRK1, can direct transcription of a coding sequence in photoreceptor cells, but may not activate transcription of the same coding sequence at a similar level in non-photoreceptor cells. As a result, GRK1 promoters can be used in packaging cells, such as HEK 293T cells, to control transcription of Cas nuclease. This same approach can be used with other tissue-specific promoters.

A ubiquitously expressed promoter can also be used. A viral promoter can be used.

Although nomenclature is used herein to indicate the species of origin for a given Cas nuclease, it is understood that the Cas nuclease and/or the nucleic acid encoding the Cas nuclease can be modified compared to the sequence occurring in the species of origin. For example, "SpCas" indicates that the Cas gene/protein in question originated in *Streptococcus pyogenes* and was modified, such as by addition of a nuclear localization signal (NLS)(s) and/or the performance of codon optimization. For example, "SaCas" indicates that the Cas gene/protein in question originated in *Staphylococcus aureus* and was modified, such as by addition of NLS(s) and/or the performance of codon optimization.

gRNA Segment

The gRNA segment can comprise a nucleotide sequence that encodes a gRNA or sgRNA.

The gRNA segment can comprise a nucleotide sequence that encodes any gRNA or sgRNA that is complementary to a target sequence. A "target DNA" as used herein is a DNA polynucleotide that comprises a target sequence. "Target sequence" as used herein refers to a nucleic acid sequence present in a target DNA which can be edited by a Cas nuclease-gRNA complex directed thereto, provided sufficient conditions for binding exist. For example, the target sequence 5'-GAGCATATC-3' within a target DNA is targeted by the gRNA sequence 5'-GAGCAUAUC-3' (e.g., via binding of the opposite strand of the target DNA sequence 5'-GATATGCTC-3'). Suitable DNA/RNA binding conditions include physiological conditions normally present in a cell. Other suitable DNA/RNA binding conditions (e.g., conditions in a cell-free system) are known in the art; see, e.g., Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The target DNA can be a double-stranded DNA. The strand of the target DNA that is complementary to and hybridizes with the gRNA can be referred to as the "complementary strand" and the strand of the target DNA that is complementary to the "complementary strand" (and is therefore not complementary to the gRNA) can be referred to as the "noncomplementary strand" or "non-complementary strand."

The gRNA segment can comprise a nucleotide sequence that encodes a gRNA or sgRNA comprising a spacer sequence can be substantially complementary to a target sequence within the genomic DNA of a cell of a patient. By "complementary," it is meant that a nucleic acid (e.g. DNA) comprises a sequence of nucleotides that enables it to non-covalently bind, e.g.: form Watson-Crick base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C) [DNA, RNA]. By "substantially complementary," it is meant that a nucleic acid comprises a sequence where 1-10% or 1-20% of its sequence of nucleotides non-covalently bind to another nucleic acid in a sequence-specific, antiparallel, manner under the appropriate in vitro and/or in vivo conditions of temperature and solution ionic strength.

The gRNA segment can comprise a nucleotide sequence that encodes a gRNA or sgRNA that can be substantially complementary to a SIN site. The gRNA or sgRNA can be fully complementary to the nucleotide sequence of the SIN site except for at one base pair. The gRNA or sgRNA can be fully complementary to the nucleotide sequence of the SIN site except for at two base pairs.

The gRNA segment can comprise a nucleotide sequence that encodes a gRNA or sgRNA that can be substantially complementary to a SIN site and to a target sequence within the genomic DNA of a cell of a patient.

Promoter Segment

The promoter segment can comprise a nucleotide sequence that encodes a promoter comprising one or more tetracycline operator sequence. The gRNA segment can be operably linked to the promoter segment. The term "operably linked" means that the nucleotide sequence of interest (i.e., the gRNA segment comprising a nucleotide sequence that encodes a gRNA or sgRNA) is linked to regulatory sequence(s) (i.e., the promoter segment comprising a nucleotide sequence that encodes a first promoter comprising one or more tetracycline operator sequences) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, CA (1990).

For expressing gRNAs used in connection with Cas nucleases, various promoters such as RNA polymerase III promoters, including for example U6 and H1, can be advantageous. Descriptions of and parameters for enhancing the use of such promoters are known in art, and additional information and approaches are regularly being described; see, e.g., Ma, H. et al., *Molecular Therapy—Nucleic Acids* 3, e161 (2014) doi:10.1038/mtna.2014.12.

The promoter comprising one or more tetracycline operator sequences can be any RNA polymerase III promotor. The promoter can be selected from a group consisting of: H1 promoter, U6 promoter, 7SK promoter, and portions of any thereof.

The one or more tetracycline operator sequence can comprise a nucleic acid sequence having at least 85%, 86%, 87%, 88%, 89%, 90%, 91%, 92%, 93%, 94%, 95%, 96%, 97%, 98%, 99%, or 100% sequence identity to SEQ ID NO: 4. The one or more tetracycline operator sequence can comprise SEQ ID NO: 4. The one or more tetracycline operator sequences can be bound by a tetracycline repressor protein.

Repressor Segment

The repressor segment can comprise a nucleotide sequence that encodes a tetracycline repressor protein. The nucleotide sequence that encodes a tetracycline repressor protein can comprise a nucleic acid sequence having at least 85%, 86%, 87%, 88%, 89%, 90%, 91%, 92%, 93%, 94%, 95%, 96%, 97%, 98%, 99%, or 100% sequence identity to SEQ ID NO: 62. The nucleotide sequence that encodes a tetracycline repressor protein can comprise SEQ ID NO: 62. The tetracycline repressor protein can comprise an amino acid sequence having at least 85%, 86%, 87%, 88%, 89%, 90%, 91%, 92%, 93%, 94%, 95%, 96%, 97%, 98%, 99%, or 100% sequence identity to SEQ ID NO: 63. The tetracycline repressor protein can comprise SEQ ID NO: 63.

Binding of the tetracycline repressor protein to the one or more tetracycline operator sequences within the H1 promoter can prevent RNA polymerase from binding to the H1 promoter and thereby control transcriptional expression of gRNAs or sgRNAs.

Short-Hairpin RNA (shRNA) Segment shRNA is an artificial RNA molecule with a hairpin turn that can be used to silence (e.g., reduce) target gene expression via RNA interference (RNAi). Expression of shRNA in cells is typically accomplished by delivery of plasmids or through viral or bacterial vectors. shRNA is an advantageous mediator of RNAi in that it has a relatively low rate of degradation and turnover.

The shRNA segment can comprise a nucleotide sequence that encodes a shRNA that comprises sequence that is complementary to a transcript from the nuclease segment. The shRNA can comprise a sequence having at least 85% sequence identity to any one of SEQ ID NOs: 9-11 or 55-59. The shRNA can comprise a sequence having at least 85%, 86%, 87%, 88%, 89%, 90%, 91%, 92%, 93%, 94%, 95%, 96%, 97%, 98% or 99% sequence identity to any one of SEQ ID NOs: 9-11 or 55-59. The shRNA can comprise any one of SEQ ID NOs: 9-11 or 55-59.

Self-Inactivating (SIN) Segments

The SIN segments can comprise a SIN site. A "SIN site" as used herein is a site that comprises a target sequence and neighboring protospacer adjacent motif (PAM). For example, a SIN site can comprise 5'-$N_{17-21}$NRG-3' or 5'-$N_{19-24}$NNGRRT-3' wherein $N_{17-21}$ or $N_{19-24}$ represent a target sequence and NRG or NNGRRT represent PAMs for *S. pyogenes* Cas nuclease or *S. aureus* Cas nuclease, respectively. The spacer sequence of a gRNA or sgRNA can hybridize to the complementary strand of the target sequence of the SIN site.

One or more SIN segments can be located in at least one of: (i) at the 5' end of the codon optimized nucleotide sequence that encodes a Cas nuclease or variant thereof; (ii) at the 3' end of the codon optimized nucleotide sequence that encodes a Cas nuclease or variant thereof; and (iii) in an intron within the codon optimized nucleotide sequence that encodes a Cas nuclease or variant thereof.

One or more SIN segments can be located in: (i) at the 5' end of the codon optimized nucleotide sequence that encodes a Cas nuclease or variant thereof; and (ii) in an intron within the codon optimized nucleotide sequence that encodes a Cas nuclease or variant thereof.

The one or more SIN segments can be located within 1-2000 nucleotides, 1-1000 nucleotides, 1-500 nucleotides, 1-250 nucleotides, 1-200 nucleotides, 1-150 nucleotides, 1-100 nucleotides, 1-50 nucleotides, 1-25 nucleotides, 1-10 nucleotides, 1-5 nucleotides, or 1 nucleotide of the 5' end of the codon optimized nucleotide sequence that encodes a Cas nuclease or variant thereof.

The one or more SIN segments can be located within 1-2000 nucleotides, 1-1000 nucleotides, 1-500 nucleotides, 1-250 nucleotides, 1-200 nucleotides, 1-150 nucleotides, 1-100 nucleotides, 1-50 nucleotides, 1-25 nucleotides, 1-10 nucleotides, 1-5 nucleotides, or 1 nucleotide of the 3' end of the codon optimized nucleotide sequence that encodes a Cas nuclease or variant thereof.

One of the one or more SIN segments can be located upstream of the codon optimized nucleotide sequence that encodes a Cas nuclease or variant thereof and downstream of a NLS.

The PAM sequence in the SIN site can be selected from a group consisting of: NNGRRT, NRG, NAAAAN, NAAAAC, NNNNGHTT, YTN, NNNNACAC, NNVRYAC, NNNNVRYM, NNAAAAW, NNAGAAW, and NNGG. The PAM sequence in the SIN site can be any known PAM sequence located downstream from a target sequence and recognized by a Cas nuclease-sgRNA complex.

2-Vector System

The nuclease segment, the gRNA segment, and the promoter segment can be provided together in a first vector and the repressor segment can be provided in a second vector. The term "vector" refers to a nucleic acid molecule capable of transporting another nucleic acid to which it has been linked. One type of vector is a "plasmid", which refers to a circular double-stranded DNA loop into which additional nucleic acid segments can be ligated. Another type of vector is a viral vector; wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

The nuclease segment, the gRNA segment, the promoter segment, and the one or more SIN segments can be provided together in a first vector and the repressor segment can be provided in a second vector.

The nuclease segment and the gRNA segment can be provided together in a first vector and the shRNA segment can be provided in a second vector.

The nuclease segment, the gRNA segment, and the one or more SIN segments can be provided together in a first vector and the shRNA segment can be provided in a second vector.

The nuclease segment, the gRNA segment, and the promoter segment can be provided together in a first vector and the repressor segment and/or the shRNA segment can be provided in a second vector.

The nuclease segment, the gRNA segment, the promoter segment, and the one or more SIN segments can be provided together in a first vector and the repressor segment and/or the shRNA segment can be provided in a second vector.

The first vector and the second vector can be AAV vectors or plasmids. The AAV vectors can be AAV1 serotype vectors, AAV2 serotype vectors, AAV3 serotype vectors, AAV4 serotype vectors, AAV5 serotype vectors, AAV6 serotype vectors, AAV7 serotype vectors, AAV8 serotype vectors, AAV9 serotype vectors, or AAVrh8R serotype vectors.

1-Vector System (All-In-One Vector System)

The nuclease segment, the gRNA segment, the promoter segment, the one or more SIN segments, and the repressor segment can be provided in the same vector.

The nuclease segment, the gRNA segment, the one or more SIN segments, and the shRNA segment can be provided in the same vector.

The nuclease segment, the gRNA segment, the promoter segment, the one or more SIN segments, the repressor segment, and the shRNA segment can be provided in the same vector.

Pharmaceutical Compositions

Disclosed herein are pharmaceutical compositions comprising any one of the CRISPR/Cas systems disclosed herein.

Disclosed herein are pharmaceutical compositions comprising any one of the recombinant AAV vectors disclosed herein.

Packaging Cells

Disclosed herein are packaging cells comprising any one of the CRISPR/Cas systems disclosed herein.

"Packaging cells" as used herein are cells used to form virus particles or viral vectors capable of infecting a host cell. An example of a packaging cell can be a HEK 293T cells. The packaging cells can package one or more viral vector (e.g., based on one or more plasmid templates) comprising any one of the CRISPR/Cas systems disclosed herein into a viral vector particle. The viral vector can contain viral sequences required for packaging. Any missing viral functions can be supplied in trans by the packaging cell. For example, AAV vectors used in gene therapy typically only possess inverted terminal repeat (ITR) sequences from the AAV genome and the balance of the vector can comprise therapeutic sequences. The ITR sequences can be required for packaging into AAV capsids. The packaging cell can also contain a plasmid that encodes other AAV genes (e.g., rep and cap), but lacks ITR sequences. The plasmid that encodes rep and cap genes can not be packaged in significant amounts due to a lack of ITR sequences. The packaging cell can also be infected with adenovirus as a helper virus, which promotes replication of the AAV vector and expression of AAV genes from the plasmid that encodes rep and cap genes. The packaging cell can also be transfected with a helper plasmid encoding gene products of helper viruses, such as adenovirus, which promotes replication of the AAV vector and expression of AAV genes from the plasmid that encodes rep and cap genes.

Purification of AAV particles from a packaging cell involves growth of the packaging cells which produce the viral vectors, followed by collection of the viral vector particles from the cell supernatant and/or from the crude lysate. AAV can then be purified by methods known in the art including ion exchange chromatography (e.g. see U.S. Pat. Nos. 7,419,817 and 6,989,264), ion exchange chromatography and CsCl or iodixanol density centrifugation (e.g. PCT publication WO2011094198A10), immunoaffinity chromatography (e.g. WO2016128408) or purification using AVB Sepharose (e.g. GE Healthcare Life Sciences).

Genetically Modified Cells

"Genetically modified cell" refers to a cell that comprises at least one genetic modification introduced by genome editing (e.g., using a CRISPR/Cas nuclease system).

Disclosed herein are genetically modified cells comprising any one of the recombinant AAV vectors disclosed herein.

The genetically modified cells can be selected from a group consisting of: a eukaryotic cell, a somatic cell, a germ cell, a stem cell, an animal cell, a mammalian cell, a mouse cell, a non-human primate cell, and a human cell.

The term "genetic modification" refers to any change in the DNA genome (or RNA genome in some cases) of a cell, organism, virus, viral vector, or other biological agent.

Non-limiting examples of genetic modifications include an "insertion," a "deletion," a "substitution," "indels," a procedure such as a transfection or transformation where exogenous nucleic acid is added to a cell and/or organism, and cloning techniques.

"Insertion" refers to an addition of one or more nucleotides in a nucleic acid sequence. Insertions can range from small insertions of a few nucleotides to insertions of large segments such as a cDNA or a gene.

The term "deletion" refers to a loss or removal of one or more nucleotides in a nucleic acid sequence or a loss or removal of the function of a gene. In some cases, a deletion can include, for example, a loss of a few nucleotides, an exon, an intron, a gene segment, or the entire sequence of a gene. In some cases, deletion of a gene refers to the elimination or reduction of the function or expression of a gene or its gene product. This can result from not only a deletion of sequences within or near the gene, but also other events (e.g., insertion, nonsense mutation) that disrupt the expression of the gene.

"Substitution" refers to a replacement of one or more nucleotides in a nucleic acid sequence with an equal number of nucleotides.

"Indel" or "indels" refers to a series of insertions and/or deletions of nucleotides in a nucleic acid sequence. This can be caused by, for example, a double-stand break in a DNA molecule (e.g., one caused by gene editing nucleases) which is then repaired via a cell's endogenous DNA repair machinery. The double-strand break repair can cause the formation of indels.

Genetic modification of a nucleic acid sequence can result in a "recombinant" sequence. For example, the present disclosure provides "recombinant AAV vectors," which have been genetically modified to comprise elements disclosed herein.

Methods of Controlling Transcription of gRNAs During AAV Packaging

Disclosed herein are methods of controlling transcription of gRNAs during AAV packaging. The methods can comprise: contacting a packaging cell with any one of the disclosed CRISPR/Cas systems that control transcriptional expression of gRNAs using a tetracycline operator/repressor system. The methods can comprise: contacting a packaging cell with a nucleic acid encoding any one of the disclosed recombinant AAV vectors that control transcriptional expression of gRNAs using a tetracycline operator/repressor system; and contacting the packaging cell with at least one vector comprising a nucleic acid sequence encoding a tetracycline repressor.

Methods of Controlling Post-Transcriptional Expression of Cas Nuclease During AAV Packaging Disclosed herein are methods of controlling post-transcriptional expression of Cas nuclease during AAV packaging. The methods can comprise: contacting a packaging cell with any one of the disclosed CRISPR/Cas systems that control post-transcriptional expression of Cas nuclease during AAV packaging. The methods can comprise: contacting a packaging cell with a nucleic acid comprising a sequence encoding any one of the disclosed recombinant AAV vectors that control transcriptional expression of gRNAs using a tetracycline operator/repressor system; and contacting the packaging cell with at least one vector comprising nucleic acid sequence encoding a shRNA segment.

Methods of Controlling Transcription of gRNAs and Post-Transcriptional Expression of Cas Nuclease During AAV Packaging Disclosed herein are methods of controlling transcription of gRNAs and post-transcriptional expression of Cas nuclease during AAV packaging. The methods can comprise: contacting a packaging cell with any one of the disclosed CRISPR/Cas systems that control transcription of gRNAs and post-transcriptional expression of Cas nuclease during AAV packaging. The methods can comprise: contacting a packaging cell with a nucleic acid comprising a sequence encoding any one of the disclosed recombinant AAV vectors that control transcriptional expression of gRNAs using a tetracycline operator/repressor system; and contacting the packaging cell with a nucleic acid sequence encoding a tetracycline repressor segment and a shRNA segment.

Methods of Reducing Mutagenesis at One or More SIN Site in a Recombinant AAV Vector Disclosed herein are methods of reducing mutagenesis at one or more SIN site in a recombinant AAV vector.

The methods can comprise: contacting a packaging cell with any one of the disclosed CRISPR/Cas systems that control transcriptional expression of gRNAs using a tetracycline operator/repressor system during AAV packaging.

The methods can comprise: contacting a packaging cell with a nucleic acid comprising a sequence comprising any one of the disclosed recombinant AAV vectors that control transcriptional expression of gRNAs using a tetracycline operator/repressor system; and contacting the packaging cell with at least one vector comprising nucleic acid sequence encoding a tetracycline repressor.

The methods can comprise: contacting a packaging cell with any one of the disclosed CRISPR/Cas systems that control post-transcriptional expression of Cas nuclease during AAV packaging.

The methods can comprise: contacting a packaging cell with a nucleic acid comprising a sequence encoding any one of the disclosed recombinant AAV vectors that control transcriptional expression of gRNAs using a tetracycline operator/repressor system; and contacting the packaging cell with at least one vector comprising nucleic acid sequence encoding a shRNA segment.

The methods can comprise: contacting a packaging cell with any one of the disclosed CRISPR/Cas systems that control transcription of gRNAs and post-transcriptional expression of Cas nuclease during AAV packaging.

The methods can comprise: contacting a packaging cell with a nucleic acid comprising a sequence encoding any one of the disclosed recombinant AAV vectors that control transcriptional expression of gRNAs using a tetracycline operator/repressor system; and contacting the packaging cell with a nucleic acid sequence encoding a tetracycline repressor segment and a shRNA segment.

Methods of Producing a Recombinant AAV Vector

Disclosed herein are methods of producing a recombinant AAV vector.

The methods can comprise: introducing into a packaging cell: (i) a first vector comprising a repressor segment, wherein the repressor segment comprises a nucleotide sequence that encodes a tetracycline repressor protein; (ii) a nucleic acid comprising sequence encoding any one of the disclosed recombinant AAV vectors that control transcriptional expression of gRNAs using a tetracycline operator/repressor system; and (iii) one or more viral components for producing the recombinant AAV vector; culturing the packaging cell; and isolating the recombinant AAV vector comprising the nucleic acid from the packaging cell.

The methods can comprise: introducing into a packaging cell a nucleic acid comprising a sequence encoding any one of the disclosed recombinant AAV vectors that control transcriptional expression of gRNAs using a tetracycline operator/repressor system; introducing into the cell one or more viral components for producing the AAV; culturing the packaging cell; isolating the recombinant AAV vector comprising the nucleic acid from the packaging cell. In these methods, the packaging cell can express a tetracycline repressor protein.

The methods can comprise: introducing into a packaging cell: (i) a first vector comprising a shRNA segment comprising a nucleotide sequence that encodes a shRNA that comprises sequence that is complementary to a transcript from the nuclease segment; (ii) a nucleic acid comprising sequence encoding any one of the disclosed recombinant AAV vectors that control transcriptional expression of gRNAs using a tetracycline operator/repressor system; and (iii) one or more viral components for producing the recombinant AAV vector; culturing the packaging cell; isolating the recombinant AAV vector comprising the nucleic acid from the packaging cell.

The methods can comprise: introducing into a packaging cell a nucleic acid comprising a sequence encoding any one of the disclosed recombinant AAV vectors that control transcriptional expression of gRNAs using a tetracycline operator/repressor system; introducing into the cell one or more viral components for producing the AAV; culturing the packaging cell; isolating the recombinant AAV vector comprising the nucleic acid from the packaging cell. In these methods, the packaging cell can express a shRNA.

The methods can comprise: introducing into a packaging cell: (i) a first vector comprising a repressor segment, wherein the repressor segment comprises a nucleotide sequence that encodes a tetracycline repressor protein, (ii) a second vector comprising a shRNA segment comprising a nucleotide sequence that encodes a shRNA that comprises sequence that is complementary to a transcript from the nuclease segment, (iii) a nucleic acid comprising sequence encoding any one of the disclosed recombinant AAV vectors that control transcriptional expression of gRNAs using a tetracycline operator/repressor system, and (iv) one or more viral components for producing the recombinant AAV vector; culturing the packaging cell; and isolating the recombinant AAV vector comprising the nucleic acid of (iii) from the packaging cell.

The methods can comprise: introducing into a packaging cell a nucleic acid comprising a sequence encoding any one of the disclosed recombinant AAV vectors that control transcriptional expression of gRNAs using a tetracycline operator/repressor system; introducing into the packaging cell one or more viral components for producing the AAV; culturing the packaging cell; isolating the recombinant AAV vector comprising the nucleic acid from the packaging cell. In these methods, the packaging cells can express a a tetracycline repressor protein and shRNA.

The nucleic acid can further comprise one or more viral components. The one or more viral components can be introduced via separate vector other than the nucleic acid. The one or more viral components can be encoded in a cellular genome.

Guide RNA (gRNA) or Single-Molecule gRNA (sgRNA)

A gRNA can comprise a spacer sequence and a CRISPR repeat sequence. In Type II systems, the gRNA can also comprise a second RNA called a tracrRNA sequence. In the Type II gRNA, the CRISPR repeat sequence and the tracrRNA sequence hybridize to each other to form a duplex. In the Type V gRNA, the crRNA forms a duplex. In both systems, the duplex can bind a Cas nuclease, such that the gRNA and Cas nuclease form a complex.

A sgRNA in a Type II system can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the gRNA. The single-molecule guide linker can link the minimum CRISPR repeat and the minimum tracrRNA sequence to form a hairpin structure. The optional tracrRNA extension can comprise one or more hairpins.

As used herein, “gRNA” means a two-molecule gRNA as described above, a single-molecule gRNA (sgRNA) as described above, or means that either form of gRNA is suitable for the purpose described. As used herein, “sgRNA” means a single-molecule gRNA (sgRNA).

Spacer Sequence

The spacer sequence hybridizes to a sequence in a target sequence. The spacer sequence of a gRNA or sgRNA can interact with a target sequence in a sequence-specific manner via hybridization (i.e., base pairing). The nucleotide sequence of the spacer sequence can vary depending on the sequence of the target sequence. The spacer sequence can be designed to hybridize to a target sequence that is located 5' of a PAM of the Cas nuclease used in the system. The spacer sequence can perfectly match the target sequence or can have mismatches. Each Cas nuclease has a particular PAM sequence that it recognizes in a target sequence. For example, *S. pyogenes* recognizes in a target sequence a PAM that comprises the sequence 5'-NRG-3', where R comprises either A or G, where N is any nucleotide and N is immediately 3' of the target sequence targeted by the spacer sequence. For example, *S. aureus* Cas recognizes in a target sequence a PAM that comprises the sequence 5'-NNGRRT-3', where R comprises either A or G, where N is any nucleotide and N is immediately 3' of the target sequence targeted by the spacer sequence. *S. aureus* Cas can recognize in a target sequence a PAM that comprises the sequence 5'-NNGRRN-3', where R comprises either A or G, where N is any nucleotide and the N is immediately 3' of the target sequence targeted by the spacer sequence. For example, *C. jejuni* recognizes in a target sequence a PAM that comprises the sequence 5'-NNNNACA-3' or 5'-NNNNACAC-3', where N is any nucleotide and N is immediately 3' of the target sequence targeted by the spacer sequence. *C. jejuni* Cas can recognize in a target sequence a PAM that comprises the sequence 5'-NNNVRYM-3' or 5'-NNVRYAC-3', where V comprises either A, G or C, where R comprises either A or G, where Y comprises either C or T, where M comprises A or C, where N is any nucleotide and the N is immediately 3' of the target sequence targeted by the spacer sequence.

The target sequence can comprise 20 bases immediately 5' of the first nucleotide of the PAM. For example, in a sequence comprising 5'-NNNNNNNNNNNNNNNNNNNNNRG-3', the target sequence can comprise the sequence that corresponds to the Ns, wherein N is any nucleotide, and the underlined NRG sequence is the *S. pyogenes* PAM. The target sequence can comprise less than 20 nucleotides. The target sequence can comprise more than 20 nucleotides. The target sequence can comprise at least: 5, 10, 15, 16, 17, 18, 19, 20, 21, 22, 23, 24, 25, 30, 35 or more nucleotides. The target sequence can comprise at most: 5, 10, 15, 16, 17, 18, 19, 20, 21, 22, 23, 24, 25, 30, 35 or more nucleotides.

The spacer sequence that hybridizes to the target sequence can have a length of at least 15 nucleotides (nt), 16 nt, 17 nt, 18 nt, 19 nt, 20 nt, 21 nt, 22 nt, 23 nt, 24 nt, 25 nt, 26 nt, 27 nt, 28 nt, 29 nt, 303 nt, 313 nt, 323 nt, 33 nt, 34 nt, 35 nt. The gRNA or sgRNA can comprise a spacer sequence comprising 17 to 24 nucleotides. The gRNA or sgRNA can comprise a spacer sequence comprising 17 to 25 nt, 17 to 26 nt, 17 to 27 nt, 17 to 28 nt, 17 to 29 nt, 17 to 30 nt, 17 to 31 nt, 17 to 32 nt, 17 to 33 nt, 17 to 34 nt, or 17 to 35 nt.

The percent complementarity between the spacer sequence and the target sequence is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. The percent complementarity between the spacer sequence and the target sequence is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%.

The spacer sequence can be designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like.

Minimum CRISPR Repeat Sequence

A minimum CRISPR repeat sequence can be a sequence with at least about 30%, about 40%, about 50%, about 60%, about 65%, about 70%, about 75%, about 80%, about 85%, about 90%, about 95%, or 100% sequence identity to a reference CRISPR repeat sequence (e.g., crRNA from *S. pyogenes*).

A minimum CRISPR repeat sequence can comprise nucleotides that can hybridize to a minimum tracrRNA sequence in a cell. The minimum CRISPR repeat sequence and a minimum tracrRNA sequence can form a duplex, i.e. a base-paired double-stranded structure. Together, the minimum CRISPR repeat sequence and the minimum tracrRNA sequence can bind to Cas nuclease. At least a part of the minimum CRISPR repeat sequence can hybridize to the minimum tracrRNA sequence. At least a part of the minimum CRISPR repeat sequence can comprise at least about 30%, about 40%, about 50%, about 60%, about 65%, about 70%, about 75%, about 80%, about 85%, about 90%, about 95%, or 100% complementary to the minimum tracrRNA sequence. At least a part of the minimum CRISPR repeat sequence can comprise at most about 30%, about 40%, about 50%, about 60%, about 65%, about 70%, about 75%, about 80%, about 85%, about 90%, about 95%, or 100% complementary to the minimum tracrRNA sequence.

The minimum CRISPR repeat sequence can have a length from about 7 nucleotides to about 100 nucleotides. For example, the length of the minimum CRISPR repeat sequence is from about 7 nt to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. The minimum CRISPR repeat sequence can be approximately 9 nucleotides in length. The minimum CRISPR repeat sequence can be approximately 12 nucleotides in length.

The minimum CRISPR repeat sequence can be at least about 60% identical to a reference minimum CRISPR repeat sequence (e.g., wild-type crRNA from *S. pyogenes*) over a stretch of at least 6, 7, or 8 contiguous nucleotides. For example, the minimum CRISPR repeat sequence can be at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum CRISPR repeat sequence over a stretch of at least 6, 7, or 8 contiguous nucleotides.

Minimum tracrRNA Sequence

A minimum tracrRNA sequence can be a sequence with at least about 30%, about 40%, about 50%, about 60%, about 65%, about 70%, about 75%, about 80%, about 85%, about 90%, about 95%, or 100% sequence identity to a reference tracrRNA sequence (e.g., wild type tracrRNA from *S. pyogenes*).

A minimum tracrRNA sequence can comprise nucleotides that hybridize to a minimum CRISPR repeat sequence in a cell. A minimum tracrRNA sequence and a minimum CRISPR repeat sequence form a duplex, i.e. a base-paired double-stranded structure. Together, the minimum tracrRNA sequence and the minimum CRISPR repeat can bind to a Cas nuclease. At least a part of the minimum tracrRNA sequence can hybridize to the minimum CRISPR repeat sequence. The minimum tracrRNA sequence can be at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nt to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA nt 23-48 described in Jinek et al., *Science,* 337(6096):816-821 (2012).

The minimum tracrRNA sequence can be at least about 60% identical to a reference minimum tracrRNA (e.g., wild type, tracrRNA from *S. pyogenes*) sequence over a stretch of at least 6, 7, or 8 contiguous nucleotides. For example, the minimum tracrRNA sequence can be at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about 1, 2, 3, 4, 5, 6, 7, 8, 9, or 10 or more nucleotides. The duplex between the minimum CRISPR RNA and the minimum tracrRNA can comprise at most about 1, 2, 3, 4, 5, 6, 7, 8, 9, or 10 or more nucleotides.

The duplex can comprise a mismatch (i.e., the two strands of the duplex are not 100% complementary). The duplex can comprise at least about 1, 2, 3, 4, or 5 or mismatches. The duplex can comprise at most about 1, 2, 3, 4, or 5 or mismatches. The duplex can comprise no more than 2 mismatches.

3' tracrRNA Sequence

A 3' tracrRNA sequence can comprise a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from *S. pyogenes*).

The 3' tracrRNA sequence can have a length from about 6 nucleotides to about 100 nucleotides. For example, the 3' tracrRNA sequence can have a length from about 6 nt to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. The 3' tracrRNA sequence can have a length of approximately 14 nucleotides.

The 3' tracrRNA sequence can beat least about 60% identical to a reference 3' tracrRNA sequence (e.g., wild type 3' tracrRNA sequence from *S. pyogenes*) over a stretch of at least 6, 7, or 8 contiguous nucleotides. For example, the 3' tracrRNA sequence can be at least about 60% identical, about 65% identical, about 70% identical, about 75% identical, about 80% identical, about 85% identical, about 90% identical, about 95% identical, about 98% identical, about 99% identical, or 100% identical, to a reference 3' tracrRNA sequence (e.g., wild type 3' tracrRNA sequence from *S. pyogenes*) over a stretch of at least 6, 7, or 8 contiguous nucleotides.

The 3' tracrRNA sequence can comprise more than one duplexed region (e.g., hairpin, hybridized region). The 3' tracrRNA sequence can comprise two duplexed regions.

The 3' tracrRNA sequence can comprise a stem loop structure. The stem loop structure in the 3' tracrRNA can comprise at least 1, 2, 3, 4, 5, 6, 7, 8, 9, 10, 15 or 20 or more nucleotides. The stem loop structure in the 3' tracrRNA can comprise at most 1, 2, 3, 4, 5, 6, 7, 8, 9 or 10 or more nucleotides. The stem loop structure can comprise a functional moiety. For example, the stem loop structure can comprise an aptamer, a ribozyme, a protein-interacting hairpin, a CRISPR array, an intron, or an exon. The stem loop structure can comprise at least about 1, 2, 3, 4, or 5 or more functional moieties. The stem loop structure can comprise at most about 1, 2, 3, 4, or 5 or more functional moieties.

The hairpin in the 3' tracrRNA sequence can comprise a P-domain. The P-domain can comprise a double-stranded region in the hairpin.

tracrRNA Extension Sequence

A tracrRNA extension sequence can be provided whether the tracrRNA is in the context of single-molecule guides or double-molecule guides. The tracrRNA extension sequence can have a length from about 1 nucleotide to about 400 nucleotides. The tracrRNA extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, or 400 nucleotides. The tracrRNA extension sequence can have a length from about 20 to about 5000 or more nucleotides. The tracrRNA extension sequence can have a length of more than 1000 nucleotides. The tracrRNA extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. The tracrRNA extension sequence can have a length of less than 1000 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonuclease binding sequence). The functional moiety can comprise a transcriptional terminator segment (i.e., a transcription termination sequence). The functional moiety can have a total length from about 10 nt to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt. The functional moiety can function in a eukaryotic cell. The functional moiety can function in a prokaryotic cell. The functional moiety can function in both eukaryotic and prokaryotic cells.

Non-limiting examples of suitable tracrRNA extension functional moieties include a 3' poly-adenylated tail, a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like). The tracrRNA extension sequence can comprise a primer binding site or a molecular index (e.g., barcode sequence). The tracrRNA extension sequence can comprise one or more affinity tags.

Single-Molecule Guide Linker Sequence

The linker sequence of a single-molecule guide nucleic acid can have a length from about 3 nucleotides to about 100 nucleotides. In Jinek et al., supra, for example, a simple 4 nucleotide "tetraloop" (-GAAA-) was used, Science, 337 (6096):816-821 (2012). An illustrative linker has a length from about 3 nt to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about 100, 500, 1000, 1500, 2000, 2500, 3000, 3500, 4000, 4500, 5000, 5500, 6000, 6500, or 7000 or more nucleotides. The linker can be at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used, Science, 337 (6096):816-821 (2012), but numerous other sequences, including longer sequences can likewise be used.

The linker sequence can comprise a functional moiety. For example, the linker sequence can comprise one or more features, including an aptamer, a ribozyme, a protein-interacting hairpin, a protein binding site, a CRISPR array, an intron, or an exon. The linker sequence can comprise at least about 1, 2, 3, 4, or 5 or more functional moieties. The linker sequence can comprise at most about 1, 2, 3, 4, or 5 or more functional moieties.

Ribonucleoprotein Complex (RNP)

The gRNA or sgRNA can interact with at least one domain of the Cas nuclease to form a RNP complex and direct the RNP complex to the target sequence. The gRNA can interact with the Cas nuclease and the target sequence such that, once directed to the target sequence, the Cas nuclease is capable of cleaving the target sequence. By "cleavage" it is meant the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. A ribonucleoprotein complex comprising a gRNA and a Cas nuclease can be used for targeted double-stranded DNA cleavage.

AAV (Adeno Associated Virus)

A recombinant AAV vector can be used for delivering polynucleotides. Production of rAAV typically requires that the following components are present within a single packaging cell: a rAAV genome, AAV rep and cap genes separate from (i.e., not in) the rAAV genome, and helper virus functions. The AAV rep and cap genes can be from any AAV serotype for which recombinant virus can be derived, and can be from a different AAV serotype than the rAAV genome ITRs, including, but not limited to, AAV serotypes described herein. Production of pseudotyped rAAV is disclosed in, for example, international patent application publication number WO 01/83692.

AAV Serotypes

AAV particles packaging polynucleotides encoding compositions of the present disclosure, e.g., CRISPR/Cas systems or recombinant AAV vectors) can comprise or be derived from any natural or recombinant AAV serotype. According to the present disclosure, the AAV particles can utilize or be based on a serotype selected from any of the following serotypes, and variants thereof including but not limited to AAV1, AAV10, AAV106.1/hu.37, AAV11, AAV114.3/hu.40, AAV12, AAV127.2/hu.41, AAV127.5/hu.42, AAV128.1/hu.43, AAV128.3/hu.44, AAV130.4/hu.48, AAV145.1/hu.53, AAV145.5/hu.54, AAV145.6/hu.55, AAV16.12/hu.11, AAV16.3, AAV16.8/hu.10, AAV161.10/hu.60, AAV161.6/hu.61, AAV1-7/rh.48, AAV1-8/rh.49, AAV2, AAV2.5T, AAV2-15/rh.62, AAV223.1, AAV223.2, AAV223.4, AAV223.5, AAV223.6, AAV223.7, AAV2-3/rh.61, AAV24.1, AAV2-4/rh.50, AAV2-5/rh.51, AAV27.3, AAV29.3/bb.1, AAV29.5/bb.2, AAV2G9, AAV-2-pre-miRNA-101, AAV3, AAV3.1/hu.6, AAV3.1/hu.9, AAV3-11/rh.53, AAV3-3, AAV33.12/hu.17, AAV33.4/hu.15, AAV33.8/hu.16, AAV3-9/rh.52, AAV3a, AAV3b, AAV4, AAV4-19/rh.55, AAV42.12, AAV42-10, AAV42-11, AAV42-12, AAV42-13, AAV42-15, AAV42-1b, AAV42-2, AAV42-3a, AAV42-3b, AAV42-4, AAV42-5a, AAV42-5b, AAV42-6b, AAV42-8, AAV42-aa, AAV43-1, AAV43-12, AAV43-20, AAV43-21, AAV43-23, AAV43-25, AAV43-5, AAV4-4, AAV44.1, AAV44.2, AAV44.5, AAV46.2/hu.28, AAV46.6/hu.29, AAV4-8/r11.64, AAV4-8/rh.64, AAV4-9/rh.54, AAV5, AAV52.1/hu.20, AAV52/hu.19, AAV5-22/rh.58, AAV5-3/rh.57, AAV54.1/hu.21, AAV54.2/hu.22, AAV54.4R/hu.27, AAV54.5/hu.23, AAV54.7/hu.24, AAV58.2/hu.25, AAV6, AAV6.1, AAV6.1.2, AAV6.2, AAV7, AAV7.2, AAV7.3/hu.7, AAV8, AAV-8b, AAV-8h, AAV9, AAV9.11, AAV9.13, AAV9.16, AAV9.24, AAV9.45, AAV9.47, AAV9.61, AAV9.68, AAV9.84, AAV9.9, AAVA3.3, AAVA3.4, AAVA3.5, AAVA3.7, AAV-b, AAVC1, AAVC2, AAVC5, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAV-DJ, AAV-DJ8, AAVF3, AAVF5, AAV-h, AAVH-1/hu.1, AAVH2, AAVH-5/hu.3, AAVH6, AAVhE1.1, AAVhER1.14, AAVhEr1.16, AAVhEr1.18, AAVhER1.23, AAVhEr1.35, AAVhEr1.36, AAVhErL.5, AAVhEr1.7, AAVhEr1.8, AAVhEr2.16, AAVhEr2.29, AAVhEr2.30, AAVhEr2.31, AAVhEr2.36, AAVhEr2.4, AAVhEr3.1, AAVhu.1, AAVhu.10, AAVhu.11, AAVhu.11, AAVhu.12, AAVhu.13, AAVhu.14/9, AAVhu.15, AAVhu.16, AAVhu.17, AAVhu.18, AAVhu.19, AAVhu.2, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.3, AAVhu.31, AAVhu.32, AAVhu.34, AAVhu.35, AAVhu.37, AAVhu.39, AAVhu.4, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.5, AAVhu.51, AAVhu.52, AAVhu.53, AAVhu.54, AAVhu.55, AAVhu.56, AAVhu.57, AAVhu.58, AAVhu.6, AAVhu.60, AAVhu.61, AAVhu.63, AAVhu.64, AAVhu.66, AAVhu.67, AAVhu.7, AAVhu.8, AAVhu.9, AAVhu.t 19, AAVLG-10/rh.40, AAVLG-4/rh.38, AAVLG-9/hu.39, AAVLG-9/hu.39, AAV-LK01, AAV-LK02, AAVLK03, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK17, AAV-LK18, AAV-LK19, AAVN721-8/rh.43, AAV-PAEC, AAV-PAEC11, AAV-PAEC12, AAV-PAEC2, AAV-PAEC4, AAV-PAEC6, AAV-PAEC7, AAV-PAEC8, AAVpi.1, AAVpi.2, AAVpi.3, AAVrh.10, AAVrh.12, AAVrh.13, AAVrh.13R, AAVrh.14, AAVrh.17, AAVrh.18, AAVrh.19, AAVrh.2, AAVrh.20, AAVrh.21, AAVrh.22, AAVrh.23, AAVrh.24, AAVrh.25, AAVrh.2R, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.43, AAVrh.44, AAVrh.45, AAVrh.46, AAVrh.47, AAVrh.48, AAVrh.48, AAVrh.48.1, AAVrh.48.1.2, AAVrh.48.2, AAVrh.49, AAVrh.50, AAVrh.51, AAVrh.52, AAVrh.53, AAVrh.54, AAVrh.55, AAVrh.56, AAVrh.57, AAVrh.58, AAVrh.59, AAVrh.60, AAVrh.61, AAVrh.62, AAVrh.64, AAVrh.64R1, AAVrh.64R2, AAVrh.65, AAVrh.67, AAVrh.68, AAVrh.69, AAVrh.70, AAVrh.72, AAVrh.73, AAVrh.74, AAVrh.8, AAVrh.8R, AAVrh8R, AAVrh8R A586R mutant, AAVrh8R R533A mutant, BAAV, BNP61 AAV, BNP62 AAV, BNP63 AAV, bovine AAV, caprine AAV, Japanese AAV 10, true type AAV (ttAAV), UPENN AAV 10, AAV-LK16, AAAV, AAV Shuffle 100-1, AAV Shuffle 100-2, AAV Shuffle 100-3, AAV Shuffle 100-7, AAV Shuffle 10-2, AAV Shuffle 10-6, AAV Shuffle 10-8, AAV SM 100-10, AAV SM 100-3, AAV SM 10-1, AAV SM 10-2, and/or AAV SM 10-8.

The AAV serotype can be, or have, a mutation in the AAV9 sequence as described by N Pulicherla et al. (Molecular Therapy 19(6):1070-1078 (2011), such as but not limited to, AAV9.9, AAV9.11, AAV9.13, AAV9.16, AAV9.24, AAV9.45, AAV9.47, AAV9.61, AAV9.68, AAV9.84.

The AAV serotype can be, or have, a sequence as described in U.S. Pat. No. 6,156,303, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or derivatives thereof.

The serotype can be AAVDJ or a variant thereof, such as AAVDJ8 (or AAV-DJ8), as described by Grimm et al. (Journal of Virology 82(12): 5887-5911 (2008)). The amino acid sequence of AAVDJ8 can comprise two or more mutations in order to remove the heparin binding domain (HBD). As a non-limiting example, the AAV-DJ sequence described as SEQ ID NO: 1 in U.S. Pat. No. 7,588,772, can comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, can comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

The AAV serotype can be, or have, a sequence as described in International Publication No. WO2015121501, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present disclosure, AAV capsid serotype selection or use can be from a variety of species. In one example, the AAV can be an avian AAV (AAAV). The AAAV serotype can be, or have, a sequence as described in U.S. Pat. No. 9,238,800, such as, but not limited to, AAAV (SEQ ID NO: 1, 2, 4, 6, 8, 10, 12, and 14 of U.S. Pat. No. 9,238,800), or variants thereof.

In one example, the AAV can be a bovine AAV (BAAV). The BAAV serotype can be, or have, a sequence as described in U.S. Pat. No. 9,193,769, such as, but not limited to, BAAV (SEQ ID NO: 1 and 6 of U.S. Pat. No. 9,193,769), or variants thereof. The BAAV serotype can be or have a sequence as described in U.S. Pat. No. 7,427,396, such as, but not limited to, BAAV (SEQ ID NO: 5 and 6 of U.S. Pat. No. 7,427,396), or variants thereof.

In one example, the AAV can be a caprine AAV. The caprine AAV serotype can be, or have, a sequence as described in U.S. Pat. No. 7,427,396, such as, but not limited to, caprine AAV (SEQ ID NO: 3 of U.S. Pat. No. 7,427,396), or variants thereof.

The AAV can be engineered as a hybrid AAV from two or more parental serotypes. In one example, the AAV can be AAV2G9 which comprises sequences from AAV2 and AAV9. The AAV2G9 AAV serotype can be, or have, a sequence as described in United States Patent Publication No. US20160017005.

In one example, the AAV can be a serotype generated by the AAV9 capsid library with mutations in amino acids 390-627 (VP1 numbering) as described by Pulicherla et al. (*Molecular Therapy* 19(6):1070-1078 (2011). The serotype and corresponding nucleotide and amino acid substitutions can be, but is not limited to, AAV9.1 (G1594C; D532H), AAV6.2 (T1418A and T1436X; V473D and I479K), AAV9.3 (T1238A; F413Y), AAV9.4 (T1250C and A1617T;

F417S), AAV9.5 (A1235G, A1314T, A1642G, C1760T; Q412R, T548A, A587V), AAV9.6 (T1231A; F4111), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V606I), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T492I, H527N), AAV.59 (T1336C; Y446H), AAV9.61 (A1493T; N498I), AAV9.64 (C1531A, A1617T; L511I), AAV9.65 (C1335T, T1530C, C1568A; A523D), AAV9.68 (C1510A; P504T), AAV9.80 (G1441A; G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K5281), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In one example, the AAV can be a serotype comprising at least one AAV capsid CD8+ T-cell epitope. As a non-limiting example, the serotype can be AAV1, AAV2 or AAV8.

In one example, the AAV can be a variant, such as PHP.A or PHP.B as described in Deverman. 2016. Nature Biotechnology. 34(2): 204-209.

In one example, the AAV can be a serotype selected from any of those found in SEQ ID NOs: 4697-5265 and Table 5.

In one example, the AAV can be encoded by a sequence, fragment or variant as described in SEQ ID NOs: 4697-5265 and Table 5.

A method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line can then be infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

AAV vector serotypes can be matched to target cell types. For example, the following exemplary cell types can be transduced by the indicated AAV serotypes among others. See Table 1.

TABLE 1

Tissue/Cell Types and Serotypes

| Tissue/Cell Type | Serotype |
| --- | --- |
| Liver | AAV3, AA5, AAV8, AAV9 |
| Skeletal muscle | AAV1, AAV7, AAV6, AAV8, AAV9 |
| Central nervous system | AAV1, AAV4, AAV5, AAV8, AAV9 |
| RPE | AAV5, AAV4, AAV2, AAV8, AAV9, AAVrh8r |
| Photoreceptor cells | AAV5, AA8, AAV9, AAVrh8R |
| Lung | AAV9, AAV5 |
| Heart | AAV8 |
| Pancreas | AAV8 |
| Kidney | AAV2, AAV8 |

Materials and Methods of the Invention

Various aspects of the invention according to the present disclosure include, but are not limited to, the aspects listed in the following numbered clauses:

1. A CRISPR/Cas system comprising:
   a nuclease segment comprising a codon optimized nucleotide sequence that encodes a Cas nuclease or variant thereof;
   a guide RNA (gRNA) segment comprising a nucleotide sequence that encodes a gRNA or sgRNA; and
   a promoter segment comprising a nucleotide sequence that encodes a first promoter comprising one or more tetracycline operator sequence, wherein the gRNA segment is operably linked to the promoter segment.
2. The CRISPR/Cas system of clause 1, wherein the first promoter is selected from a group consisting of: H1 promoter, U6 promoter, 7SK promoter, and portions of any thereof.
3. The CRISPR/Cas system of clauses 1 or 2, wherein the one or more tetracycline operator sequence comprises a nucleic acid sequence having at least 85% sequence identity to SEQ ID NO: 4.
4. The CRISPR/Cas system of any one of clauses 1-3, wherein the one or more tetracycline operator sequence comprises SEQ ID NO: 4.
5. The CRISPR/Cas system of any one of clauses 1-4, further comprising:
   a repressor segment comprising a nucleotide sequence that encodes a tetracycline repressor protein.
6. The CRISPR/Cas system of clause 5, wherein the tetracycline repressor comprises a nucleic acid sequence having at least 85% sequence identity to SEQ ID NO: 62.

7. The CRISPR/Cas system of clause 5, wherein the tetracycline repressor comprises a nucleic acid sequence comprising SEQ ID NO: 62.
8. The CRISPR/Cas system of any one of clauses 1-7, wherein the one or more tetracycline operator sequence is capable of being bound by the tetracycline repressor protein.
9. The CRISPR/Cas system of any one of clauses 1-8, further comprising:
   one or more self-inactivating segments comprising a SIN site;
   wherein the gRNA or sgRNA is substantially complementary to the SIN site;
   wherein the gRNA or sgRNA is substantially complementary to a genomic target sequence within a cell of a patient.
10. The CRISPR/Cas system of clause 9, wherein the one or more self-inactivating segments are located in at least one of:
    (i) at the 5' end of the codon optimized nucleotide sequence that encodes a Cas nuclease or variant thereof;
    (ii) at the 3' end of the codon optimized nucleotide sequence that encodes a Cas nuclease or variant thereof; and
    (iii) in an intron within the codon optimized nucleotide sequence that encodes a Cas nuclease or variant thereof.
11. The CRISPR/Cas system of clause 9, wherein the one or more self-inactivating segments are located in:
    (i) at the 5' end of the codon optimized nucleotide sequence that encodes a Cas nuclease or variant thereof; and
    (ii) in an intron within the codon optimized nucleotide sequence that encodes a Cas nuclease or variant thereof.
12. The CRISPR/Cas system of any one of clauses 9-11, wherein one of the one or more self-inactivating segments are located upstream of the codon optimized nucleotide sequence that encodes a Cas nuclease or variant thereof and downstream of a NLS.
13. The CRISPR/Cas system of any one of clauses 9-11, wherein the SIN site comprises a PAM sequence.
14. The CRISPR/Cas system of clause 13, wherein the PAM sequence in the SIN site is selected from a group consisting of: NNGRRT, NRG, NAAAAN, NAAAAC, NNNNGHTT, YTN, NNNNACAC, NNVRYAC, NNNNVRYM, NNAAAAW, NNAGAAW, and NNGG.
15. The CRISPR/Cas system of any of clauses 1-14, wherein the gRNA or sgRNA is fully complementary to the nucleotide sequence of the SIN site except for at one base pair.
16. The CRISPR/Cas system of any of clauses 1-14, wherein the gRNA or sgRNA is fully complementary to the nucleotide sequence of the SIN site except for at two base pairs.
17. The CRISPR/Cas system of any one of clauses 1-16, wherein the Cas nuclease is a Class 2 Cas nuclease.
18. The CRISPR/Cas system of any one of clauses 1-17, wherein the Cas nuclease is selected from a group consisting of: *S. pyogenes* Cas, *S. aureus* Cas, *S. thermolphilus* Cas, *C. jejuni* Cas, *T. denticola* Cas, *N. meningitides* Cas, *S. lugdunensis* Cas, *S. hyicus* Cas, *S. microti* Cas, and *S. pasteuri* Cas.
19. The CRISPR/Cas system of any one of clauses 1-16, wherein the Cas nuclease is a sRGN.
20. The CRISPR/Cas system of clause 19, wherein the Cas nuclease comprises an amino acid sequence having at least 85% sequence identity to SEQ ID NO: 60.
21. The CRISPR/Cas system of any one of clauses 1-20, wherein a nucleic acid sequence encoding a second promoter is operably linked to the codon optimized nucleotide sequence that encodes a Cas nuclease or variant thereof.
22. The CRISPR/Cas system of clause 21, wherein the second promoter is a spatially-restricted promoter, bidirectional promoter, or an inducible promoter.
23. The CRISPR/Cas system of clause 22, wherein the spatially-restricted promoter is selected from a group consisting of: any tissue or cell type specific promoter, a hepatocyte-specific promoter, a neuron-specific promoter, an adipocyte-specific promoter, a cardiomyocyte-specific promoter, a skeletal muscle-specific promoter, lung progenitor cell specific promoter, a photoreceptor-specific promoter, and a RPE selective promoter.
24. The CRISPR/Cas system of any one of clauses 1-23, wherein the gRNA or sgRNA comprising a spacer sequence comprising 17 to 24 nucleotides.
25. The CRISPR/Cas system of any of clauses 1-25, wherein the nuclease segment, the gRNA segment, and the promoter segment are provided together in a first vector and the repressor segment is provided in a second vector.
26. The CRISPR/Cas system of any one of clauses 9-25, wherein the nuclease segment, the gRNA segment, the promoter segment, and the one or more self-inactivating segments are provided together in a first vector and the repressor segment is provided in a second vector.
27. The CRISPR/Cas system of any one of clauses 9-25, wherein the nuclease segment, the gRNA segment, the promoter segment, the one or more self-inactivating segments, and the repressor segment are provided in a vector.
28. The CRISPR/Cas system of any one of clauses 25-26, wherein the first vector and the second vector are AAV vectors or plasmids.
29. The CRISPR/Cas system of clause 28, wherein the AAV vectors are AAV2 serotype vectors, AAV5 serotype vectors, or AAV6 serotype vectors.
30. A pharmaceutical composition comprising the CRISPR/Cas system of any one of clauses 1-29.
31. A packaging cell comprising the CRISPR/Cas system of any one of clauses 1-29.
32. A method of controlling transcription of gRNAs during AAV packaging, the method comprising:
    contacting a packaging cell with the CRISPR/Cas system of any one of clauses 1-29.
33. A method of reducing mutagenesis at one or more SIN site in a recombinant AAV vector, the method comprising:
    contacting a packaging cell with the CRISPR/Cas system of any one of clauses 1-29.
34. A recombinant AAV vector comprising:
    a nuclease segment comprising a codon optimized nucleotide sequence that encodes a Cas nuclease or variant thereof;
    a gRNA segment comprising a nucleotide sequence that encodes a gRNA or sgRNA; and
    a promoter segment comprising a nucleotide sequence that encodes a first promoter comprising one or more tetracycline operator sequence, wherein the gRNA segment is operably linked to the promoter segment.

35. The recombinant AAV vector of clause 34, wherein the first promoter is selected from a group consisting of: H1 promoter, U6 promoter, 7SK promoter, and portions of any thereof.
36. The recombinant AAV vector of any one of clauses 34 or 35, wherein the one or more tetracycline operator sequence comprises a nucleic acid sequence having at least 85% sequence identity to SEQ ID NO: 4.
37. The recombinant AAV vector of any one of clauses 34-36, wherein the one or more tetracycline operator sequence comprises SEQ ID NO: 4.
38. The recombinant AAV vector of any one of clauses 34-37, wherein the one or more tetracycline operator sequences is capable of being bound by a tetracycline repressor.
39. The recombinant AAV vector of any one of clauses 34-38, further comprising: one or more self-inactivating segments comprising a SIN site; wherein the gRNA or sgRNA is substantially complementary to the SIN site; wherein the gRNA or sgRNA is substantially complementary to a genomic target sequence within a cell of a patient.
40. The recombinant AAV vector of clause 39, wherein the one or more self-inactivating segments are located in at least one of:
   (i) at the 5' end of the codon optimized nucleotide sequence that encodes a Cas nuclease or variant thereof;
   (ii) at the 3' end of the codon optimized nucleotide sequence that encodes a Cas nuclease or variant thereof; and
   (iii) in an intron within the codon optimized nucleotide sequence that encodes a Cas nuclease or variant thereof.
41. The recombinant AAV vector of clause 39, wherein the one or more self-inactivating segments are located in:
   (i) at the 5' end of the codon optimized nucleotide sequence that encodes a Cas nuclease or variant thereof; and
   (ii) in an intron within the codon optimized nucleotide sequence that encodes a Cas nuclease or variant thereof.
42. The recombinant AAV vector of any one of clauses 39-41, wherein one of the one or more self-inactivating segments are located upstream of the codon optimized nucleotide sequence that encodes a Cas nuclease or variant thereof and downstream of a NLS.
43. The recombinant AAV vector of any one of clauses 39-41, wherein the SIN site comprises a PAM sequence.
44. The recombinant AAV vector of clause 43, wherein the PAM sequence in the SIN site is selected from a group consisting of: NNGRRT, NRG, NAAAAN, NAAAAC, NNNNGHTT, YTN, NNNNACAC, NNVRYAC, NNNNVRYM, NNAAAAW, NNAGAAW, and NNGG.
45. The recombinant AAV vector of any one of clauses 34-44, wherein the gRNA or sgRNA is fully complementary to the nucleotide sequence of the SIN site except for at one base pair.
46. The recombinant AAV vector of any one of clauses 34-44, wherein the gRNA or sgRNA is fully complementary to the nucleotide sequence of the SIN site except for at two base pairs.
47. The recombinant AAV vector of any one of clauses 34-46, wherein the Cas nuclease is a Class 2 Cas nuclease.
48. The recombinant AAV vector of any one of clauses 34-47, wherein the Cas nuclease is selected from a group consisting of: *S. pyogenes* Cas, *S. aureus* Cas, *S. thermolphilus* Cas, *C. jejuni* Cas, *T. denticola* Cas, *N. meningitides* Cas, *S. lugdunensis* Cas, *S. hyicus* Cas, *S. microti* Cas, and *S. pasteuri* Cas.
49. The recombinant AAV vector of any one of clauses 34-46, wherein the Cas nuclease is a sRGN.
50. The recombinant AAV vector of clause 49, wherein the Cas nuclease comprises an amino acid sequence having at least 85% sequence identity to SEQ ID NO: 60.
51. The recombinant AAV vector of any one of clauses 34-50, wherein a nucleic acid sequence encoding a second promoter is operably linked to the codon optimized nucleotide sequence that encodes a Cas nuclease or variant thereof.
52. The recombinant AAV vector of clause 51, wherein the second promoter is a spatially-restricted promoter, bidirectional promoter, or an inducible promoter.
53. The recombinant AAV vector of clause 52, wherein the spatially-restricted promoter is selected from a group consisting of: any tissue or cell type specific promoter, a hepatocyte-specific promoter, a neuron-specific promoter, an adipocyte-specific promoter, a cardiomyocyte-specific promoter, a skeletal muscle-specific promoter, lung progenitor cell specific promoter, a photoreceptor-specific promoter, and a RPE selective promoter.
54. The recombinant AAV vector of any one of clauses 34-53, wherein the gRNA is a sgRNA.
55. The recombinant AAV vector of any one of clauses 34-54, wherein the gRNA or sgRNA comprising a spacer sequence comprising 17 to 24 nucleotides.
56. The recombinant AAV vector of any of clauses 34-55, wherein the nuclease segment, the gRNA segment, and the promoter segment are provided together in a vector.
57. The recombinant AAV vector of any of clauses 39-56, wherein the nuclease segment, the gRNA segment, the promoter segment, and the one or more self-inactivating segments are provided together in a vector.
58. The recombinant AAV vector of any one of clauses 34-57, wherein the recombinant AAV vector is a AAV2 serotype vector, AAV5 serotype vector, or AAV6 serotype vector.
59. The recombinant AAV vector of any one of clauses 34-58, wherein the recombinant AAV vector comprises a nucleic acid sequence having at least 85% sequence identity to any one of SEQ ID NOs: 66-69.
60. The recombinant AAV vector of any one of clauses 34-58, wherein the recombinant AAV vector comprises any one of SEQ ID NOs: 66-69.
61. A pharmaceutical composition comprising the recombinant AAV vector of any of clauses 34-60.
62. A genetically modified cell comprising the recombinant AAV vector of any of clauses 34-60.
63. The genetically modified cell of clause 62, wherein the genetically modified cell is selected from a group consisting of: a eukaryotic cell, a somatic cell, a germ cell, a stem cell, an animal cell, a mammalian cell, a mouse cell, a non-human primate cell, and a human cell.

64. A method of controlling transcription of gRNAs during AAV packaging, the method comprising:
contacting a packaging cell with a nucleic acid encoding the recombinant AAV vector of any one of clauses 34-60; and
contacting the packaging cell with at least one vector comprising nucleic acid sequence encoding a tetracycline repressor.
65. A method of reducing mutagenesis at one or more SIN site in a recombinant AAV vector, the method comprising:
contacting a packaging cell with nucleic acid encoding the recombinant AAV vector of any one of clauses 34-60; and
contacting the packaging cell with at least one vector comprising nucleic acid sequence encoding a tetracycline repressor.
66. The method of clause 65, wherein the packaging cell is a human cell.
67. A method of producing a recombinant AAV vector, the method comprising:
introducing into a packaging cell:
(i) a first vector comprising a repressor segment, wherein the repressor segment comprises a nucleotide sequence that encodes a tetracycline repressor protein;
(ii) a nucleic acid comprising sequence encoding the recombinant AAV vector of any one of clauses 34-60; and
(iii) one or more viral components for producing the recombinant AAV vector;
culturing the packaging cell; and
isolating the recombinant AAV vector comprising the nucleic acid from the packaging cell.
68. A method of producing a recombinant AAV vector, the method comprising:
introducing into a packaging cell a nucleic acid comprising a sequence encoding the recombinant AAV vector of any one of clauses 34-60;
introducing into the packaging cell one or more viral components for producing the AAV;
culturing the packaging cell; and
isolating the recombinant AAV vector comprising the nucleic acid from the packaging cell.
wherein the packaging cell expresses a tetracycline repressor protein.
69. The method of any one of clauses 67-68, wherein the one or more viral components are encoded by the nucleic acid.
70. The method of any one of clauses 67-68, wherein the one or more viral components are introduced via separate vector other than the nucleic acid.
71. The method of any one of clauses 67-78, wherein the one or more viral components are encoded in a cellular genome.
72. A CRISPR/Cas system comprising:
a nuclease segment comprising a codon optimized nucleotide sequence that encodes a Cas nuclease or variant thereof;
a gRNA segment comprising a nucleotide sequence that encodes a gRNA or sgRNA; and
a shRNA segment comprising a nucleotide sequence that encodes a shRNA that comprises sequence that is complementary to a transcript from the nuclease segment.
73. The CRISPR/Cas system of clause 72, wherein the shRNA comprises a sequence having at least 85% sequence identity to any one of SEQ ID NOs: 9-11 or 55-59.
74. The CRISPR/Cas system of clause 72, wherein the shRNA comprises any one of SEQ ID NOs: 9-11 or 55-59.
75. The CRISPR/Cas system of any one of clauses 72-74, further comprising:
one or more self-inactivating segments comprising a SIN site;
wherein the gRNA or sgRNA is substantially complementary to the SIN site;
wherein the gRNA or sgRNA is substantially complementary to a genomic target sequence within a cell of a patient.
76. The CRISPR/Cas system of clause 75, wherein the one or more self-inactivating segments are located in at least one of:
(i) at the 5' end of the codon optimized nucleotide sequence that encodes a Cas nuclease or variant thereof;
(ii) at the 3' end of the codon optimized nucleotide sequence that encodes a Cas nuclease or variant thereof; and
(iii) in an intron within the codon optimized nucleotide sequence that encodes a Cas nuclease or variant thereof.
77. The CRISPR/Cas system of clause 75, wherein the one or more self-inactivating segments are located in:
(i) at the 5' end of the codon optimized nucleotide sequence that encodes a Cas nuclease or variant thereof; and
(ii) in an intron within the codon optimized nucleotide sequence that encodes a Cas nuclease or variant thereof.
78. The CRISPR/Cas system of any one of clauses 75-77, wherein one of the one or more self-inactivating segments are located upstream of the codon optimized nucleotide sequence that encodes a Cas nuclease or variant thereof and downstream of a NLS.
79. The CRISPR/Cas system of any one of clauses 75-77, wherein the SIN site comprises a PAM sequence.
80. The CRISPR/Cas system of clause 79, wherein the PAM sequence in the SIN site is selected from a group consisting of: NNGRRT, NRG, NAAAAN, NAAAAC, NNNNGHTT, YTN, NNNNACAC, NNVRYAC, NNNNVRYM, NNAAAAW, NNAGAAW, and NNGG.
81. The CRISPR/Cas system of any of clauses 72-80, wherein the gRNA or sgRNA is fully complementary to the nucleotide sequence of the SIN site except for at one base pair.
82. The CRISPR/Cas system of any of clauses 72-80, wherein the gRNA or sgRNA is fully complementary to the nucleotide sequence of the SIN site except for at two base pairs.
83. The CRISPR/Cas system of any one of clauses 72-82, wherein the Cas nuclease is a Class 2 Cas nuclease.
84. The CRISPR/Cas system of any one of clauses 72-83, wherein the Cas nuclease is selected from a group consisting of: *S. pyogenes* Cas, *S. aureus* Cas, *S. thermolphilus* Cas, *C. jejuni* Cas, *T. denticola* Cas, *N. meningitides* Cas, *S. lugdunensis* Cas, *S. hyicus* Cas, *S. microti* Cas, and *S. pasteuri* Cas.
85. The CRISPR/Cas system of any one of clauses 72-82, wherein the Cas nuclease is a sRGN.

86. The CRISPR/Cas system of clause 85, wherein the Cas nuclease comprises an amino acid sequence having at least 85% sequence identity to SEQ ID NO: 60.
87. The CRISPR/Cas system of any one of clauses 72-86, wherein a nucleic acid sequence encoding a promoter is operably linked to the codon optimized nucleotide sequence that encodes a Cas nuclease or variant thereof.
88. The CRISPR/Cas system of clause 87, wherein the promoter is a spatially-restricted promoter, bidirectional promoter, or an inducible promoter.
89. The CRISPR/Cas system of clause 88, wherein the spatially-restricted promoter is selected from a group consisting of: any tissue or cell type specific promoter, a hepatocyte-specific promoter, a neuron-specific promoter, an adipocyte-specific promoter, a cardiomyocyte-specific promoter, a skeletal muscle-specific promoter, lung progenitor cell specific promoter, a photoreceptor-specific promoter, and a RPE selective promoter.
90. The CRISPR/Cas system of any one of clauses 72-89, wherein the gRNA is a sgRNA.
91. The CRISPR/Cas system of any one of clauses 72-90, wherein the gRNA or sgRNA comprising a spacer sequence comprising 17 to 24 nucleotides.
92. The CRISPR/Cas system of any of clauses 72-91, wherein the nuclease segment and the gRNA segment are provided together in a first vector and the shRNA segment is provided in a second vector.
93. The CRISPR/Cas system of any of clauses 75-91, wherein the nuclease segment, the gRNA segment, and the one or more self-inactivating segments are provided together in a first vector and the shRNA segment is provided in a second vector.
94. The CRISPR/Cas system of any of clauses 75-91, wherein the nuclease segment, the gRNA segment, the one or more self-inactivating segments, and the shRNA segment are provided in a vector.
95. The CRISPR/Cas system of any of clauses 92-93, wherein the first vector and the second vector are AAV vectors or plasmids.
96. The CRISPR/Cas system of clause 95, wherein the AAV vectors are AAV2 serotype vectors, AAV5 serotype vectors, or AAV6 serotype vectors.
97. A pharmaceutical composition comprising the CRISPR/Cas system of any of clauses 72-96.
98. A packaging cell comprising the CRISPR/Cas system of any of clauses 72-96.
99. A method of controlling post-transcriptional expression of Cas nuclease during AAV packaging, the method comprising:
 contacting a packaging cell with the CRISPR/Cas system of any one of clauses 72-96.
100. A method of reducing mutagenesis at one or more SIN site in a recombinant AAV vector, the method comprising: contacting a cell with the CRISPR/Cas system of any one of clauses 72-96.
101. The method of clauses 99 or 100, wherein the packaging cell is a human cell.
102. A method of controlling post-transcriptional expression of Cas nuclease during AAV packaging, the method comprising:
 contacting a packaging cell with a nucleic acid comprising a sequence encoding the recombinant AAV vector of any one of clauses 34-60; and
 contacting the packaging cell with at least one vector comprising nucleic acid sequence encoding a shRNA segment.
103. A method of producing a recombinant AAV vector, the method comprising:
 introducing into a packaging cell:
 (i) a first vector comprising a shRNA segment comprising a nucleotide sequence that encodes a shRNA that comprises sequence that is complementary to a transcript from the nuclease segment;
 (ii) a nucleic acid comprising sequence encoding the recombinant AAV vector of any one of clauses 34-60; and
 (iii) one or more viral components for producing the recombinant AAV vector;
 culturing the packaging cell; and
 isolating the recombinant AAV vector comprising the nucleic acid from the packaging cell.
104. A method of producing a recombinant AAV vector, the method comprising:
 introducing into a packaging cell a nucleic acid comprising sequence encoding the recombinant AAV vector of any one of clauses 34-60;
 introducing into the packaging cell one or more viral components for producing the AAV;
 culturing the packaging cell;
 isolating the recombinant AAV vector comprising the nucleic acid from the packaging cell;
 wherein the packaging cell expresses a shRNA.
105. The method of any one of clauses 103-104, wherein the one or more viral components are encoded by the nucleic acid.
106. The method of any one of clauses 103-104, wherein the one or more viral components are introduced via separate vector other than the nucleic acid.
107. The method of any one of clauses 103-104, wherein the one or more viral components are encoded in a cellular genome.
108. A CRISPR/Cas system comprising:
 a nuclease segment comprising a codon optimized nucleotide sequence that encodes a Cas nuclease or variant thereof;
 a gRNA segment comprising a nucleotide sequence that encodes a gRNA or sgRNA; a promoter segment comprising a nucleotide sequence that encodes a first promoter comprising one or more tetracycline operator sequences, wherein the gRNA segment is operably linked to the promoter segment; and
 a shRNA segment comprising a nucleotide sequence that encodes a shRNA that comprises sequence that is complementary to a transcript from the nuclease segment.
109. The CRISPR/Cas system of clause 108, wherein the first promoter is selected from a group consisting of: a H1 promoter, U6 promoter, 7SK promoter, and portions of any thereof.
110. The CRISPR/Cas system of clauses 108 or 109, wherein the one or more tetracycline operator sequence comprises a nucleic acid sequence having at least 85% sequence identity to SEQ ID NO: 4.
111. The CRISPR/Cas system of any one of clauses 108-109, wherein the one or more tetracycline operator sequence comprises SEQ ID NO: 4.
112. The CRISPR/Cas system of any one of clauses 108-111, further comprising: a repressor segment comprising a nucleotide sequence that encodes a tetracycline repressor protein.

113. The CRISPR/Cas system of clause 112, wherein the tetracycline repressor comprises a nucleic acid sequence having at least 85% sequence identity to SEQ ID NO: 62.

114. The CRISPR/Cas system of clause 112, wherein the tetracycline repressor comprises a nucleic acid sequence comprising SEQ ID NO: 62.

115. The CRISPR/Cas system of any one of clauses 108-114, wherein the one or more tetracycline operator sequences are capable of being bound by the tetracycline repressor protein.

116. The CRISPR/Cas system of any one of clauses 108-115, wherein the shRNA comprises sequence having at least 85% sequence identity to any one of SEQ ID NOs: 9-11 or 55-59.

117. The CRISPR/Cas system any one of clauses 108-116, wherein the shRNA comprises SEQ ID NOs: 9-11 or 55-59.

118. The CRISPR/Cas system of any one of clauses 108-117, further comprising:

one or more self-inactivating segments comprising a SIN site;

wherein the gRNA or sgRNA is substantially complementary to the SIN site;

wherein the gRNA or sgRNA is substantially complementary to a genomic target sequence within a cell of a patient.

119. The CRISPR/Cas system of clause 118, wherein the one or more self-inactivating segments are located in at least one of:

(i) at the 5' end of the codon optimized nucleotide sequence that encodes a Cas nuclease or variant thereof;

(ii) at the 3' end of the codon optimized nucleotide sequence that encodes a Cas nuclease or variant thereof; and (iii) in an intron within the codon optimized nucleotide sequence that encodes a Cas nuclease or variant thereof.

120. The CRISPR/Cas system of clause 118, wherein the one or more self-inactivating segments are located in:

(i) at the 5' end of the codon optimized nucleotide sequence that encodes a Cas nuclease or variant thereof; and (ii) in an intron within the codon optimized nucleotide sequence that encodes a Cas nuclease or variant thereof.

121. The CRISPR/Cas system of any one of clauses 118-120, wherein one of the one or more self-inactivating segments are located upstream of the codon optimized nucleotide sequence that encodes a Cas nuclease or variant thereof and downstream of a NLS.

122. The CRISPR/Cas system of any one of clauses 118-120, wherein the SIN site comprises a PAM sequence.

123. The CRISPR/Cas system of clause 122, wherein the PAM sequence in the SIN site is selected from a group consisting of: NNGRRT, NRG, NAAAAN, NAAAAC, NNNNGHTT, YTN, NNNNACAC, NNVRYAC, NNNNVRYM, NNAAAAW, NNAGAAW, and NNGG.

124. The CRISPR/Cas system of any of clauses 108-122, wherein the gRNA or sgRNA is fully complementary to the nucleotide sequence of the SIN site except for at one base pair.

125. The CRISPR/Cas system of any of clauses 108-122, wherein the gRNA or sgRNA is fully complementary to the nucleotide sequence of the SIN site except for at two base pairs.

126. The CRISPR/Cas system of any one of clauses 108-125, wherein the Cas nuclease is a Class 2 Cas nuclease.

127. The CRISPR/Cas system of any one of clauses 108-126, wherein the Cas nuclease is selected from a group consisting of: *S. pyogenes* Cas, *S. aureus* Cas, *S. thermolphilus* Cas, *C. jejuni* Cas, *T. denticola* Cas, *N. meningitides* Cas, *S. lugdunensis* Cas, *S. hyicus* Cas, *S. microti* Cas, and *S. pasteuri* Cas.

128. The CRISPR/Cas system of any one of clauses 108-125, wherein the Cas nuclease is a sRGN.

129. The CRISPR/Cas system of clause 128, wherein the Cas nuclease comprises an amino acid sequence having at least 85% sequence identity to SEQ ID NO: 60.

130. The CRISPR/Cas system of any one of clauses 108-129, wherein a nucleic acid sequence encoding a second promoter is operably linked to the codon optimized nucleotide sequence that encodes a Cas nuclease or variant thereof.

131. The CRISPR/Cas system of clause 130, wherein the second promoter is a spatially-restricted promoter, bidirectional promoter, or an inducible promoter.

132. The CRISPR/Cas system of clause 131, wherein the spatially-restricted promoter is selected from a group consisting of: any tissue or cell type specific promoter, a hepatocyte-specific promoter, a neuron-specific promoter, an adipocyte-specific promoter, a cardiomyocyte-specific promoter, a skeletal muscle-specific promoter, lung progenitor cell specific promoter, a photoreceptor-specific promoter, and a RPE selective promoter.

133. The CRISPR/Cas system of any one of clauses 108-132, wherein the gRNA is a sgRNA.

134. The CRISPR/Cas system of any one of clauses 108-133, wherein the gRNA or sgRNA comprising a spacer sequence comprising 17 to 24 nucleotides.

135. The CRISPR/Cas system of any one of clauses 108-134, wherein the nuclease segment, the gRNA segment, and the promoter segment are provided together in a first vector and the repressor segment and/or the shRNA segment is provided in a second vector.

136. The CRISPR/Cas system of any one of clauses 118-134, wherein the nuclease segment, the gRNA segment, the promoter segment, and the one or more self-inactivating segments are provided together in a first vector and the repressor segment and/or the shRNA segment is provided in a second vector.

137. The CRISPR/Cas system of any one of clauses 118-134, wherein the nuclease segment, the gRNA segment, the promoter segment, the one or more self-inactivating segments, the repressor segment, and the shRNA segment are provided in a vector.

138. The CRISPR/Cas system of any one of clauses 135-136, wherein the first vector and the second vector are AAV vectors or plasmids.

139. The CRISPR/Cas system of clause 138, wherein the AAV vectors are AAV2 serotype vectors, AAV5 serotype vectors, or AAV6 serotype vectors.

140. A pharmaceutical composition comprising the CRISPR/Cas system of any one of clauses 108-139.

141. A packaging cell comprising the CRISPR/Cas system of any one of clauses 108-139.

142. A method of controlling transcription of gRNAs and post-transcriptional expression of Cas nuclease during AAV packaging, the method comprising: contacting a packaging cell with the CRISPR/Cas system of any one of clauses 108-139.
143. A method of reducing mutagenesis at one or more SIN site in a recombinant AAV vector, the method comprising:
   contacting a cell with the CRISPR/Cas system of any one of clauses 108-139.
144. The method of any one of clauses 142 or 143, wherein the packaging cell is a human cell.
145. A method of controlling transcription of gRNAs and post-transcriptional expression of Cas nuclease during AAV packaging, the method comprising:
   contacting a packaging cell with a nucleic acid comprising sequence encoding the recombinant AAV vector of any one of clauses 34-60; and
   contacting the packaging cell with a nucleic acid sequence encoding a tetracycline repressor segment and a shRNA segment.
146. A method of producing a recombinant AAV vector, the method comprising:
   introducing into a packaging cell:
   (i) a first vector comprising a repressor segment, wherein the repressor segment comprises a nucleotide sequence that encodes a tetracycline repressor protein;
   (ii) a second vector comprising a shRNA segment comprising a nucleotide sequence that encodes a shRNA that comprises sequence that is complementary to a transcript from the nuclease segment;
   (iii) a nucleic acid comprising sequence encoding the recombinant AAV vector of any one of clauses 34-60; and
   (iv) one or more viral components for producing the recombinant AAV vector;
   culturing the packaging cell; and
   isolating the recombinant AAV vector comprising the nucleic acid of (iii) from the packaging cell.
147. A method of producing a recombinant AAV vector, the method comprising:
   introducing into packaging cell a nucleic acid comprising sequence encoding the recombinant AAV vector of any one of clauses 34-60;
   introducing into the packaging cell one or more viral components for producing the AAV;
   culturing the packaging cell; and
   isolating the recombinant AAV vector comprising the nucleic acid from the packaging cell;
   wherein the packaging cell expressing a tetracycline repressor protein and a shRNA.
148. The method of any one of clauses 146-147, wherein the nucleic acid further comprises one or more viral components.
149. The method of any one of clauses 146-147, wherein the one or more viral components are introduced via separate vector other than the nucleic acid.
150. The method of any one of clauses 146-147, wherein the one or more viral components are encoded in a cellular genome.
151. A recombinant AAV vector produced by any one of the methods of clauses 67-71, 103-107, or 146-150.

Definitions

In addition to the definitions previously set forth herein, the following definitions are relevant to the present disclosure:

The singular forms “a,” “an,” and “the” include plural references, unless the context clearly dictates otherwise.

Any numerical range recited in this specification describes all sub-ranges of the same numerical precision (i.e., having the same number of specified digits) subsumed within the recited range. For example, a recited range of “1.0 to 10.0” describes all sub-ranges between (and including) the recited minimum value of 1.0 and the recited maximum value of 10.0, such as, for example, “2.4 to 7.6,” even if the range of “2.4 to 7.6” is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with written description, sufficiency of description, and added matter requirements, including the requirements under 35 U.S.C. § 112(a) and Article 123(2) EPC. Also, unless expressly specified or otherwise required by context, all numerical parameters described in this specification (such as those expressing values, ranges, amounts, percentages, and the like) may be read as if prefaced by the word “about,” even if the word “about” does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameter.

Any patent, publication, or other disclosure material identified herein is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

The details of one or more aspects of the present disclosure are set forth in the accompanying examples below. Although any materials and methods similar or equivalent to those described herein can be used in the practice or testing of the present disclosure, specific examples of the materials and methods contemplated are now described. Other features, objects and advantages of the present disclosure will be apparent from the description. In the description examples, the singular forms also include the plural unless the context clearly dictates otherwise. Unless defined otherwise, all technical and scientific terms used herein have the same meaning as commonly understood by one of ordinary skill in the art to which this present disclosure belongs. In the case of conflict, the present description will control.

EXAMPLES

The present disclosure will be more fully understood by reference to the following examples, which provide illustrative, non-limiting aspects of the invention.

The examples describe the use of materials and methods for controlling gene editing. Gene editing can be controlled by controlling transcriptional expression of gRNAs and/or controlling post-transcriptional expression of a Cas nuclease, which can thereby reduce mutagenesis at one or more SIN site in a recombinant AAV vector during packaging. The defined control mechanisms represent a novel strategy for inhibiting mutagenesis at one or more SIN site in a recombinant AAV vector during packaging, as described and illustrated herein.

Example 1—Controlling Transcriptional Expression of gRNAs Using a Tetracycline Operator/Repressor System An experiment was conducted to determine whether on-target editing of a P23H target site is inhibited by controlling the transcription of gRNAs using a tetracycline operator/tetracycline repressor system.

Figure 1B:
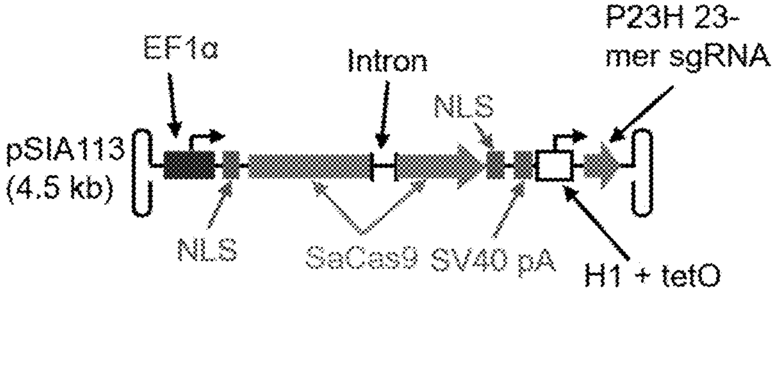
Figure 1C:
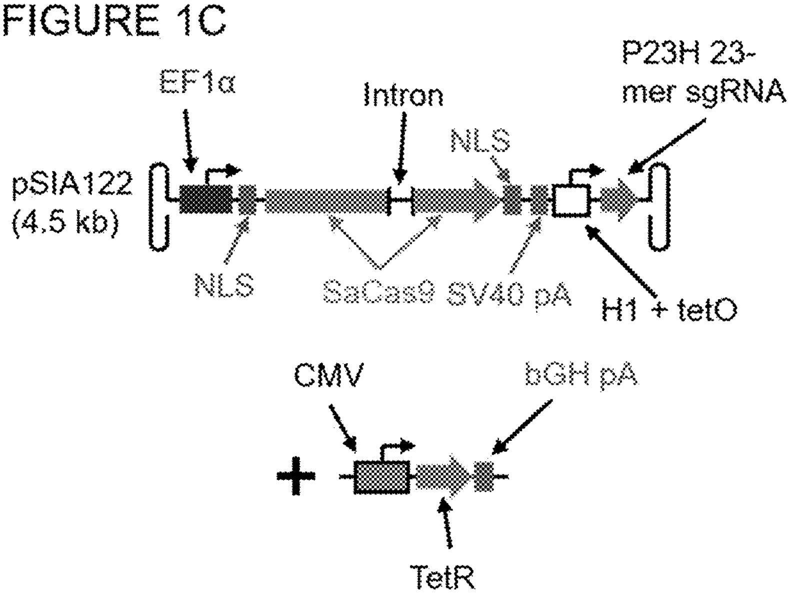

A reporter cell line was generated that contains a reporter construct comprising a P23H target site fused to a BFP coding sequence at the beta-tubulin gene locus of HEK 293FT cells (FIG. 1A).

pSIA113 (SEQ ID NO: 5), depicted in FIG. 1B, comprises a SaCas9 gene (SEQ ID NO: 64), a sequence that encodes a P23H 23-mer sgRNA (SEQ ID NO: 1), and an H1 promoter comprising two TetO sites (SEQ ID NO: 3) between two AAV ITRs. The P23H 23-mer sgRNA is a sgRNA comprising a spacer sequence (SEQ ID NO: 30) that targets the P23H target site on the reporter construct.

pSIA122 (SEQ ID NO: 6), depicted in FIG. 1C, comprises a SaCas9 gene (SEQ ID NO: 64), a sequence that encodes a P23H 23-mer sgRNA (SEQ ID NO: 1), an H1 promoter comprising two TetO sites (SEQ ID NO: 3) between two AAV ITRs, and a TetR (e.g., SEQ ID NO: 62). The tetracycline repressor is able to bind to the two TetO sites to repress transcription of the P23H 23-mer sgRNA gene.

The HEK 293FT reporter cell line was transfected with 1.25 μg pSIA113 and 1.25 μg red fluorescence (RFP)-expressing plasmid using Lipofectamine® 3000, available from Thermo Fisher Scientific, Massachusetts, US.

The HEK 293FT reporter cell line was separately transfected with 2.0 μg pSIA122 and 0.5 μg RFP-expressing plasmid using Lipofectamine® 3000.

At 2 and 5 days post-transfection, HEK 293FT reporter cells were dissociated from plates by incubation with trypsin-EDTA and analyzed for BFP and RFP by flow cytometry. A frame-shift induced by genome editing at the P23H target site of the HEK 293FT cell results in loss of BFP. This was analyzed at 5 days post-transfection.

BFP negative means that gene editing occurred at the P23H target site of these transfected HEK 293FT cells. RFP positive means that these transfected HEK 293FT cells contain a plasmid that encodes RFP and serves as a control for transfection efficiency. This was analyzed at 2 days post-transfection.

Figure 1D:
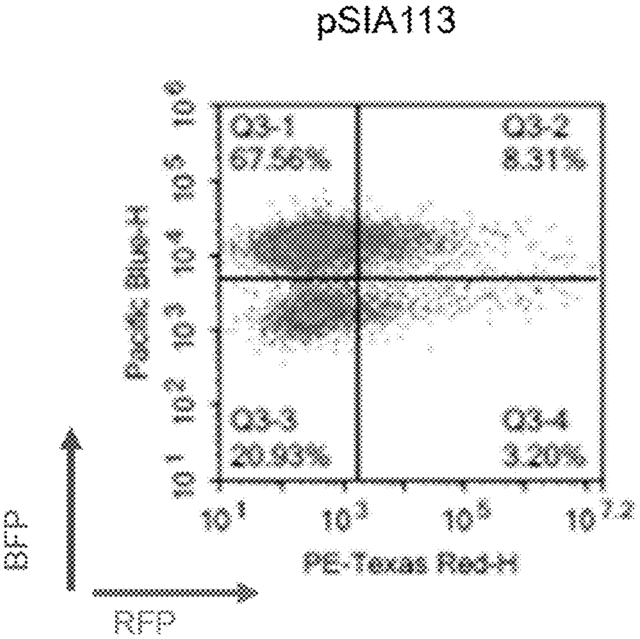

FIG. 1D shows that of the HEK 293FT reporter cells transfected with pSIA113, 20.93% of these cells had frame-shift mutations introduced at the P23H target site when P23H 23-mer sgRNA was used as the sgRNA.

Figure 1E:
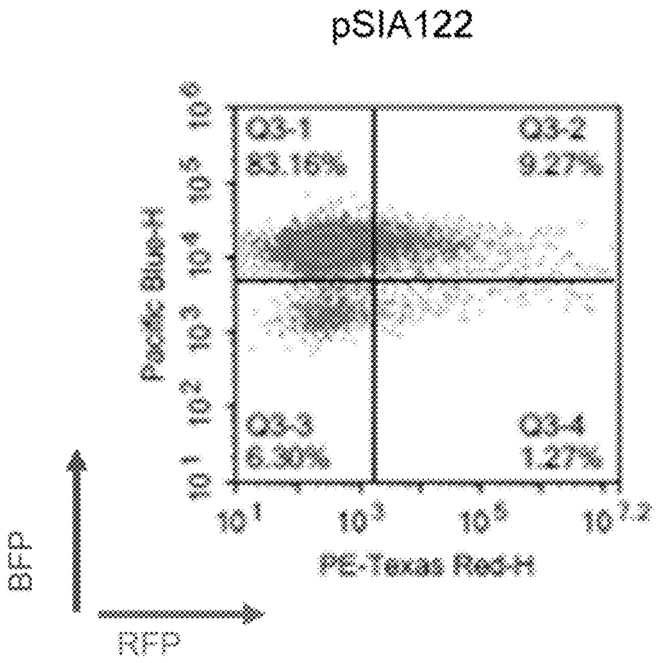

FIG. 1E shows that of the HEK 293FT reporter cells transfected with pSIA122, 6.30% of these cells had frame-shift mutations introduced at the P23H target site when P23H 23-mer sgRNA was used as the sgRNA.

The results in FIGS. 1D-1E demonstrate that overexpression of TetR can control gene editing through binding of TetR to the tetracycline operators, which inhibits transcriptional expression of gRNAs.

Figure 1F:
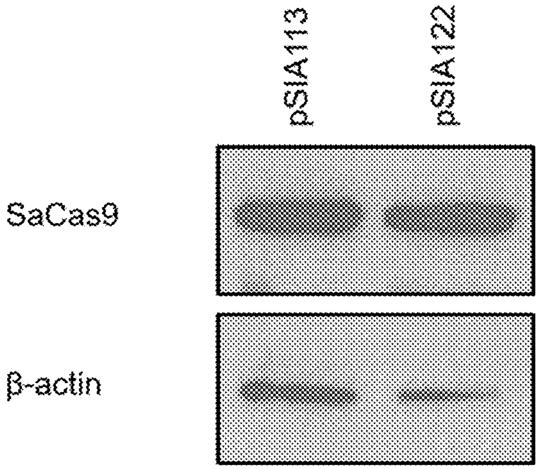

At 2 days post-transfection, HEK 293 FT reporter cells were dissociated from plates by incubation with trypsin-EDTA. Cells were lysed and protein isolated for western blot analysis. Levels of SaCas9 and j-actin were compared. SaCas9 levels in HEK 293FT reporter cells transfected with pSIA113 and SaCas9 levels in HEK 293FT reporter cells transfected with pSIA122 were similar (FIG. 1F) suggesting that expression of TetR did not affect the expression of SaCas9.

These data provide evidence that expression of TetR can control gene editing through binding of TetR to the tetracycline operators, which inhibits transcriptional expression of gRNAs. These data also provide evidence that the overexpression of TetR did not affect the expression of SaCas9. Overall, the data provide evidence that transcriptional control via repression of gRNA transcription is a possible method for inhibiting editing by CRISPR/Cas systems during recombinant AAV vector packaging.

Example 2—Gene Editing Comparison Between sgRNA Driven by a Human U6 Promoter and a H1 Promoter Comprising Two TetO Sites To determine how the TetO sites in the H1 promoter affect transcription of the gRNA gene, a second experiment was performed. A comparison was made to another exemplary PolIII promoter, U6, comprising no TetO sites.

Figure 2A:
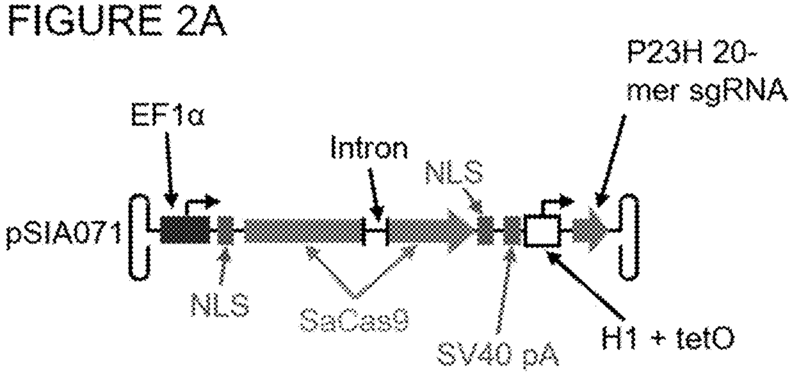
FIGS. 2A-2D show a depiction of pSIA071; a depiction of pSIA087; and data (flow cytometry and western blot) generated using HEK 293FT reporter cells transfected with NC026 and either pSIA071 or pSIA087.
Figure 2B:
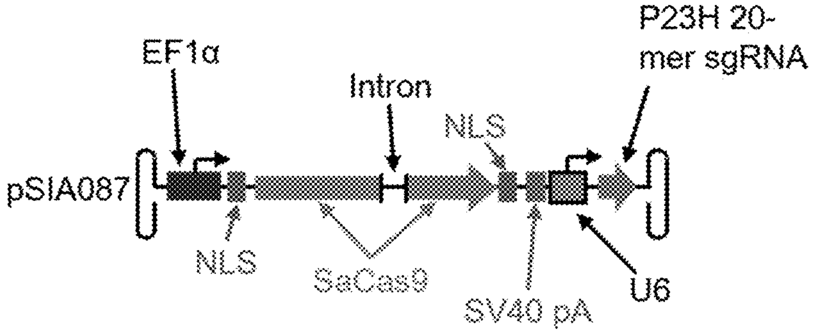

Using the reporter cell line of Example 1, cells were transfected with either pSIA071 or pSIA087. pSIA071 (SEQ ID NO: 7), depicted in FIG. 2A, comprises a SaCas9 gene (SEQ ID NO: 64), a sequence that encodes a P23H 20-mer sgRNA (SEQ ID NO: 2), and an H1 promoter comprising two TetO sites (SEQ ID NO: 3) between two AAV ITRs. The P23H 20-mer sgRNA is a sgRNA comprising a spacer sequence (SEQ ID NO: 33) that targets the P23H target site on the reporter construct.

pSIA087 (SEQ ID NO: 8), depicted in FIG. 2B, comprises a SaCas9 gene (SEQ ID NO: 64) and a sequence that encodes a P23H 20-mer sgRNA (SEQ ID NO: 2) driven by a U6 promoter between two AAV ITRs. No TetO sites are included in pSIA087 and no TetR gene or protein was included in either transfection. Thus, comparison of the relative gRNA promoter strength of each of the two constructs was possible.

The HEK 293FT reporter cell line was transfected with 2.0 μg of the pSIA071 plasmid, using Lipofectamine® 3000. The HEK 293FT reporter cell line was separately transfected with 2.0 μg of the pSIA087 plasmid using Lipofectamine® 3000. In both cases, the cells were also transfected with 0.5 μg of an RFP-expressing plasmid.

At 2 and 5 days post-transfection, HEK 293FT reporter cells were dissociated from plates by incubation with trypsin-EDTA and analyzed for BFP expression and RFP expression by flow cytometry. A frame-shift induced by genome editing at the P23H target site of the HEK 293FT cell results in loss of BFP. This was analyzed at 5 days post-transfection.

In BFP− cells, gene editing-mediated frame-shift occurred at the P23H target site of these transfected reporter cells. RFP+ cells contain a plasmid that encodes RFP. Transfection with the RFP plasmid allows for determination of whether or not cell populations were transfected at similar rates. This was analyzed at 2 days post-transfection.

Figure 2C:
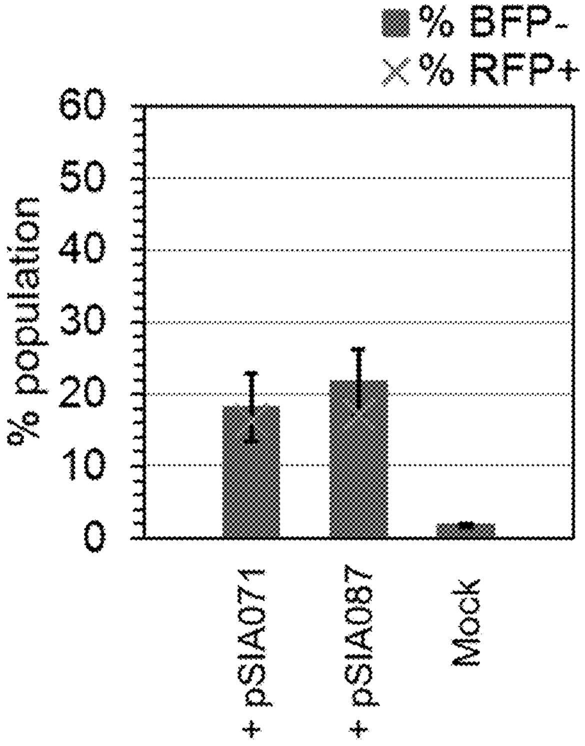

FIG. 2C shows that of the HEK 293FT reporter cells transfected with pSIA071, ~19% of these cells had frame-shift mutations introduced by the SaCas nuclease-sgRNA complex at the P23H target site. Of the HEK 293FT reporter cells transfected with pSIA087, ~21% of these cells had frame-shift mutations introduced by the SaCas nuclease-sgRNA complex at the P23H target site.

FIG. 2C also shows that of the HEK 293FT reporter cells transfected with pSIA071, ~16% of these cells expressed RFP. Of the HEK 293FT reporter cells transfected with pSIA087, ~18% of these cells expressed RFP.

Figure 2D:
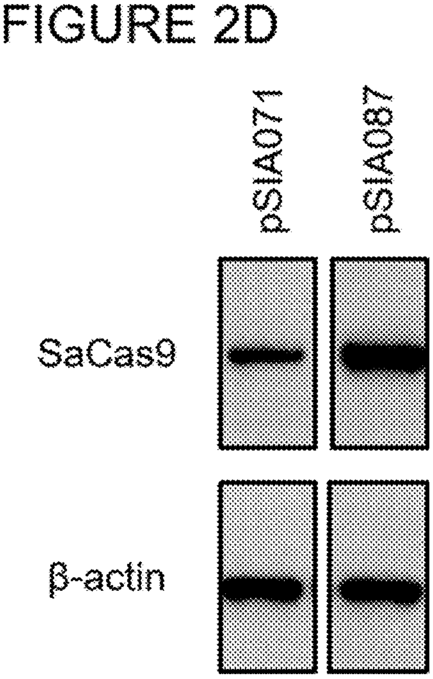

FIG. 2D shows an image of a western blot which was conducted using lysate from transfected cells harvested 2 days post-transfection. The blot was probed for SaCas9 and, as a loading control, β-actin. The left lane shows lysate from cells transfected with pSIA071, and the right lane shows lysate from cells transfected with pSIA087. SaCas9 is expressed at similar levels in both samples, indicating that the differences in the sgRNA promoters did not alter the expression of the SaCas9 gene.

Because the differences in editing efficiency were minimal (compare % BFP− in FIG. 2C), it is suggested that the strength of the two promoters (H1 variant containing 2 copies of TetO sites and U6) is similar and that, when un-occupied, the TetO sites of the H1 promoter do not negatively impact transcription. Furthermore, it is possible that other PolIII promoters, in addition to H1, such as U6, could be engineered to comprise one or more TetO sites, thereby achieving similar levels of transcriptional control of sgRNA genes during recombinant AAV vector production.

Example 3—Controlling Post-Transcriptional Expression of SaCas Nuclease Using a shRNAs To evaluate various shRNAs for their ability to inhibit translation of Cas nuclease gene transcripts, an experiment was performed. Comparisons were made between cell populations of the BFP reporter cell line from Example 1, which was transfected with a vector comprising SaCas9 and a sgRNA gene and another vector carrying either a shRNA gene or no shRNA gene.

Figure 3A:
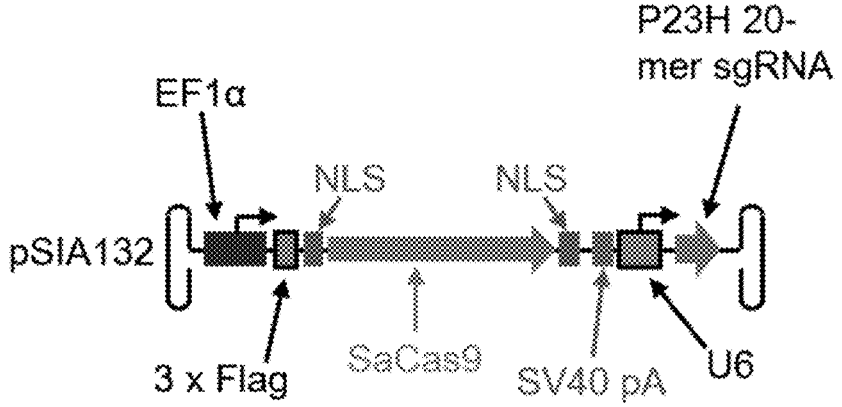
FIGS. 3A-3E show a depiction of pSIA132; a depiction of pDL122; a generalized depiction of pDL151-pDL153; and data (western blot and flow cytometry) generated using HEK 293FT reporter cells co-transfected with pSIA132, NC026, and either (1) pDL122, (2) pDL151, (3) pDL152; or (4) pDL153.
Figure 3B:
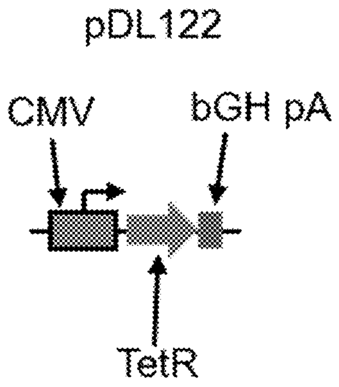
Figure 3C:
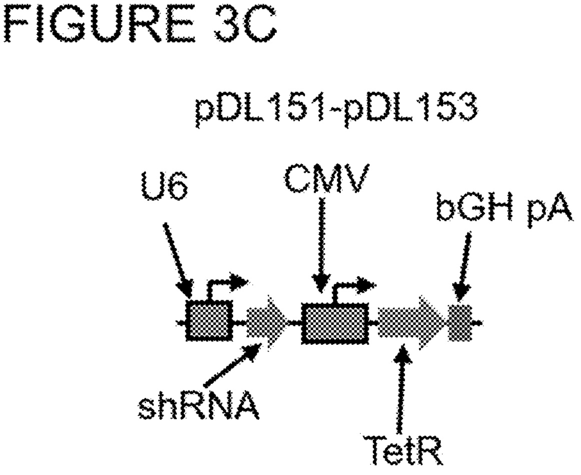

Cells were transfected with pSIA132 (SEQ ID NO: 12), depicted in FIG. 3A. pSIA132 is a plasmid comprising a SaCas9 gene (SEQ ID NO: 64) and a sequence that encodes a P23H 20-mer sgRNA (SEQ ID NO: 2), driven by a U6 promoter between two AAV ITRs. Cells were also transfected with one of 4 other plasmids: pDL122 (a negative control comprising no shRNA), pDL151, pDL152, or pDL153. pDL122 is depicted in FIG. 3B, and comprises a TetR gene. The TetR gene is not expected to affect the results of the experiment since no TetO sites are present on any of the constructs. A generalized view of pDL151, pDL152, and pDL153 is provided in FIG. 3C. Each of the three plasmids encodes a unique shRNA that is complementary to a portion of the SaCas9 transcript. pDL151 comprises a sequence encoding a shRNA comprising the sequence of SEQ ID NO: 9. pDL152 comprises a sequence encoding a shRNA comprising the sequence of SEQ ID NO: 10. pDL153 comprises a sequence encoding a shRNA comprising the sequence of SEQ ID NO: 11.

The HEK 293FT reporter cell line was transfected with 1.0 μg of the pSIA132 plasmid, using Lipofectamine® 3000. Additionally, the HEK 293FT reporter cell line was transfected with 1.0 μg of one of either pDL122, pDL151, pDL152, or pDL153 using Lipofectamine® 3000. In all cases, the cells were also transfected with 0.5 μg of an RFP-expressing plasmid.

Figure 3D:
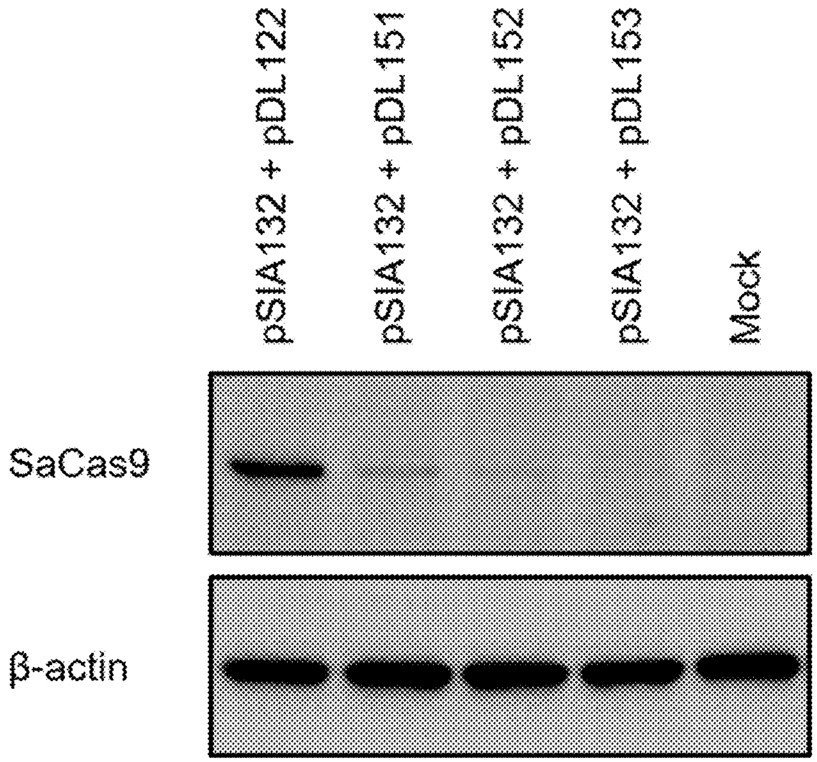

FIG. 3D shows an image of a western blot conducted using lysate from cells harvested 2 days post-transfection. Mock transfected cells (right-most lane) showed no SaCas9 signal above background. Cells transfected with pSIA132 and pDL122 showed strong expression of SaCas9, consistent with the absence of any shRNA reducing SaCas9 gene expression. Comparisons can be made between the cells transfected with pDL122 and those transfected with the shRNA-expressing plasmids. Cells transfected with pSIA132 and pDL151 showed decreased expression of SaCas9, consistent with the presence of a shRNA reducing SaCas9 gene expression. Cells transfected with pSIA132 and pDL152 showed decreased expression of SaCas9, consistent with the presence of a shRNA reducing SaCas9 gene expression. Cells transfected with pSIA132 and pDL153 showed decreased expression of SaCas9, consistent with the presence of a shRNA reducing SaCas9 gene expression.

Figure 3E:
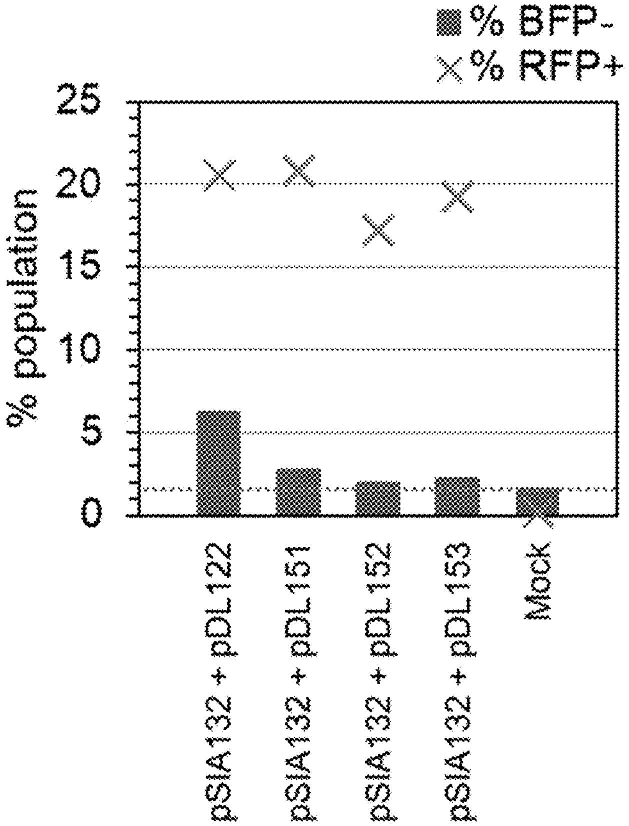

While FIG. 3D provides data on Cas nuclease expression, FIG. 3E provides data related to Cas nuclease editing activity, as directed by the P23H 20-mer sgRNA. 2 and 5 days post-transfection, cells were prepared for flow cytometry as described in Example 1. Mock transfected cells showed a baseline percentage of BFP− cells of ~1.5% at 5 days post-transfection. In contrast, cells transfected with pSIA132 and pDL122 showed an increase in the percentage of BFP− cells, with 6% of cells being negative for BFP expression. This increase is consistent with editing of the reporter construct in the absence of post-transcriptional control of SaCas9 expression by shRNAs. For cells transfected with pSIA132 and pDL151, ~3% of cells were negative for BFP expression. For cells transfected with pSIA132 and pDL152, ~2% of cells were negative for BFP expression. For cells transfected with pSIA132 and pDL153, ~2% of cells were negative for BFP expression. Between ~17% and ~21% of all transfected cells were positive for RFP at 2 days post-transfection, indicating that transfection efficiency was similar for all cells.

Taken together, FIGS. 3D and 3E provide evidence that expression of Cas nucleases can be controlled by shRNA expression and that this control can reduce editing by a Cas nuclease and a gRNA paired with the nuclease.

Example 4—Analysis of AAV Vectors Packaged in AAV2 or AAV5

To evaluate the ability to successfully package and prepare various recombinant AAV vectors, an experiment was performed. Specifically, accumulation of deletions in vector genomes was analyzed. Recombinant AAV vectors were prepared in packaging cells. Comparisons were made between recombinant AAV vectors comprising either SIN sites or no SIN sites and between vectors which were or were not packaged in packaging cells expressing TetR repressor protein.

One group of packaging cells was transfected with plasmid pSIA113 (SEQ ID NO: 5), depicted in FIG. 1B.

Figure 4A:
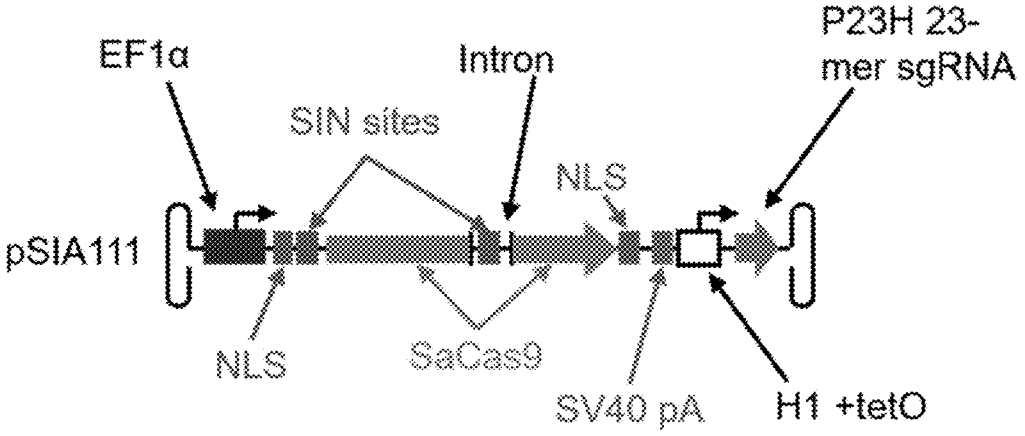
FIGS. 4A-4D show depictions of pSIA111, pSIA121, pSIA142, and pSIA119.

A second group of packaging cells was transfected with plasmid pSIA111 (SEQ ID NO: 17), depicted in FIG. 4A. pSIA111 comprises a SaCas9 gene (SEQ ID NO: 64), driven by an EF1α promoter and a sequence that encodes a P23H 23-mer sgRNA (SEQ ID NO: 1), driven by an H1 promoter comprising two TetO sites (SEQ ID NO: 3) between two AAV ITRs. The sequence between AAV ITRs of pSIA111 further comprises two SIN sites, with a first SIN site located between the NLS and the immediate 5' end of SaCas9 and a second SIN site located within the intron of SaCas9.

Figure 4B:
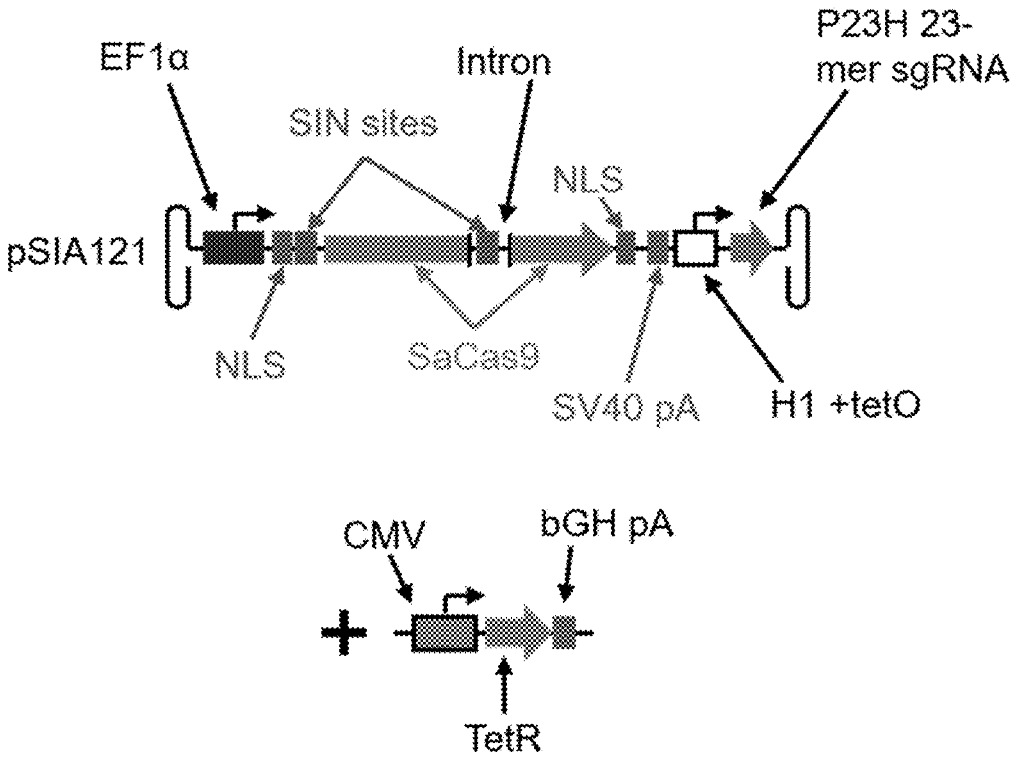

A third group of packaging cells was transfected with plasmid pSIA121 (SEQ ID NO: 18), depicted in FIG. 4B. pSIA121 is a plasmid comprising a SaCas9 gene (SEQ ID NO: 64), driven by an EF1α promoter and a sequence that encodes a P23H 23-mer sgRNA (SEQ ID NO: 1), driven by an H1 promoter comprising two TetO sites (SEQ ID NO: 3) between two AAV ITRs. The sequence between AAV ITRs of pSIA121 further comprises two SIN sites, with a first SIN site located between the NLS and the immediate 5' end of SaCas9 and a second SIN site located within the intron of SaCas9. pSIA121 further comprises a sequence encoding a TetR protein (e.g., SEQ ID NO: 62). The TetR sequence is located on a separate locus of the plasmid, compared to the sequence between the two AAV ITRs. The TetR gene, while expressed during packaging, is not included in recombinant AAV vectors prepared during packaging because the TetR gene is not located between the AAV inverted terminal repeats.

Figure 4C:
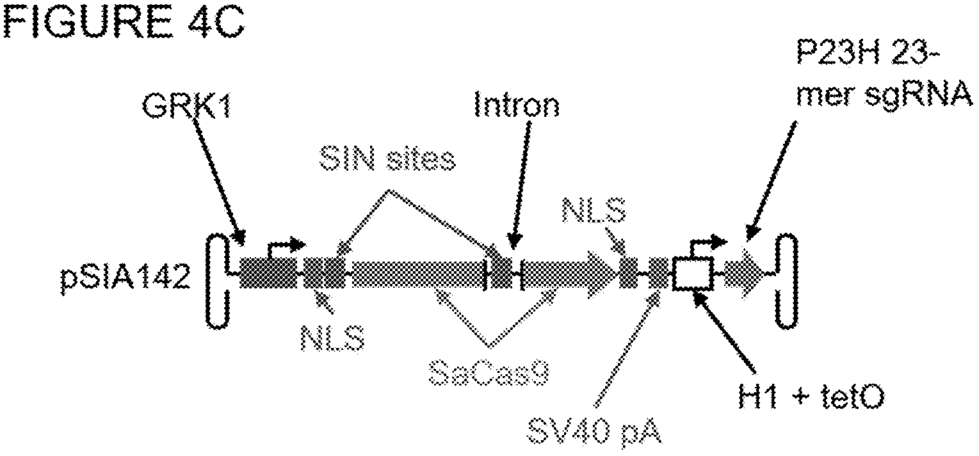

A fourth group of packaging cells was transfected with plasmid pSIA142 (SEQ ID NO: 19), depicted in FIG. 4C. pSIA142 is a plasmid comprising a SaCas9 gene (SEQ ID NO: 64), driven by a GRK1 promoter and a sequence that encodes a P23H 23-mer sgRNA (SEQ ID NO: 1), driven by an H1 promoter comprising two TetO sites (SEQ ID NO: 3) between two AAV ITRs. The sequence between AAV ITRs of pSIA142 further comprises two SIN sites, with a first SIN site located between the NLS and the immediate 5' end of SaCas9 and a second SIN site located within the intron of SaCas9.

Figure 4D:
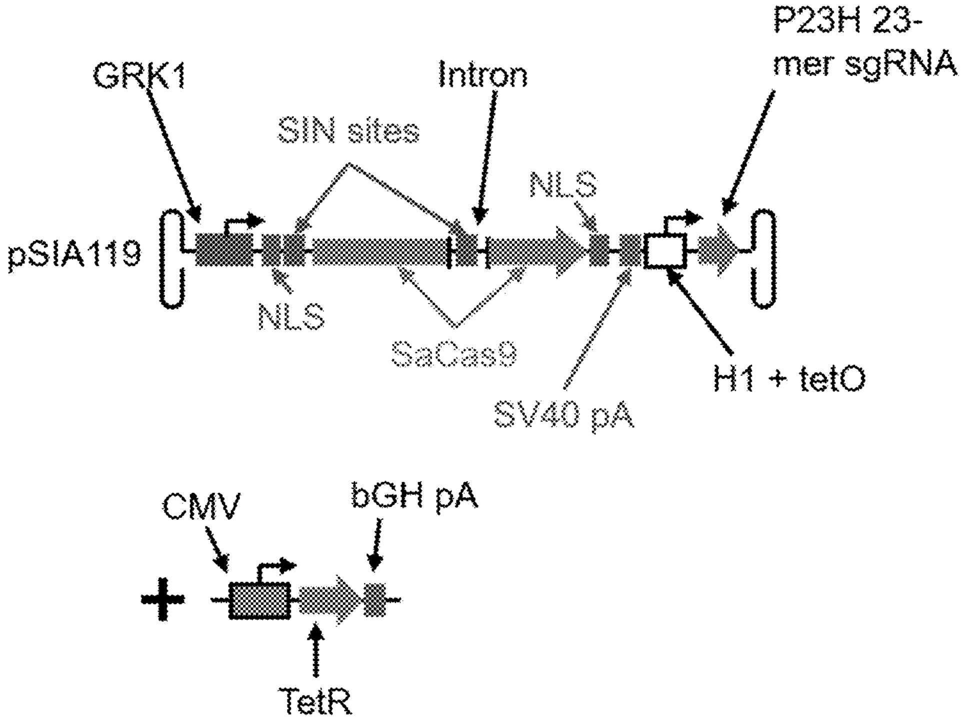

A fifth group of packaging cells was transfected with plasmid pSIA119 (SEQ ID NO: 20), depicted in FIG. 4D. pSIA119 is a plasmid comprising a SaCas9 gene (SEQ ID NO: 64), driven by a GRK1 promoter and a sequence that encodes a P23H 23-mer sgRNA (SEQ ID NO: 1), driven by an H1 promoter comprising two TetO sites (SEQ ID NO: 3) between two AAV ITRs. The sequence between AAV ITRs of pSIA119 further comprises two SIN sites, with a first SIN site located between the NLS and the immediate 5' end of SaCas9 and a second SIN site located within the intron of SaCas9. pSIA119 further comprises a sequence encoding a TetR protein (e.g., SEQ ID NO: 62). The TetR sequence is located on a separate locus of the plasmid, compared to the sequence between AAV ITRs. The TetR gene, while expressed during packaging, is not included in recombinant AAV vectors prepared during packaging because the TetR gene is not located between the AAV inverted terminal repeats.

Packaging was performed by a standard 'triple' transfection method. Packaging cells were transfected with one of the 5 plasmids (pSIA113, pSIA111, pSIA121, pSIA142, or pSIA119), and each of the 5 groups of packaging cells was also transfected with two other plasmids. One plasmid encodes AAV rep genes and AAV2 or AAV5 cap genes. The other plasmid encodes helper virus genes.

Figure 5:
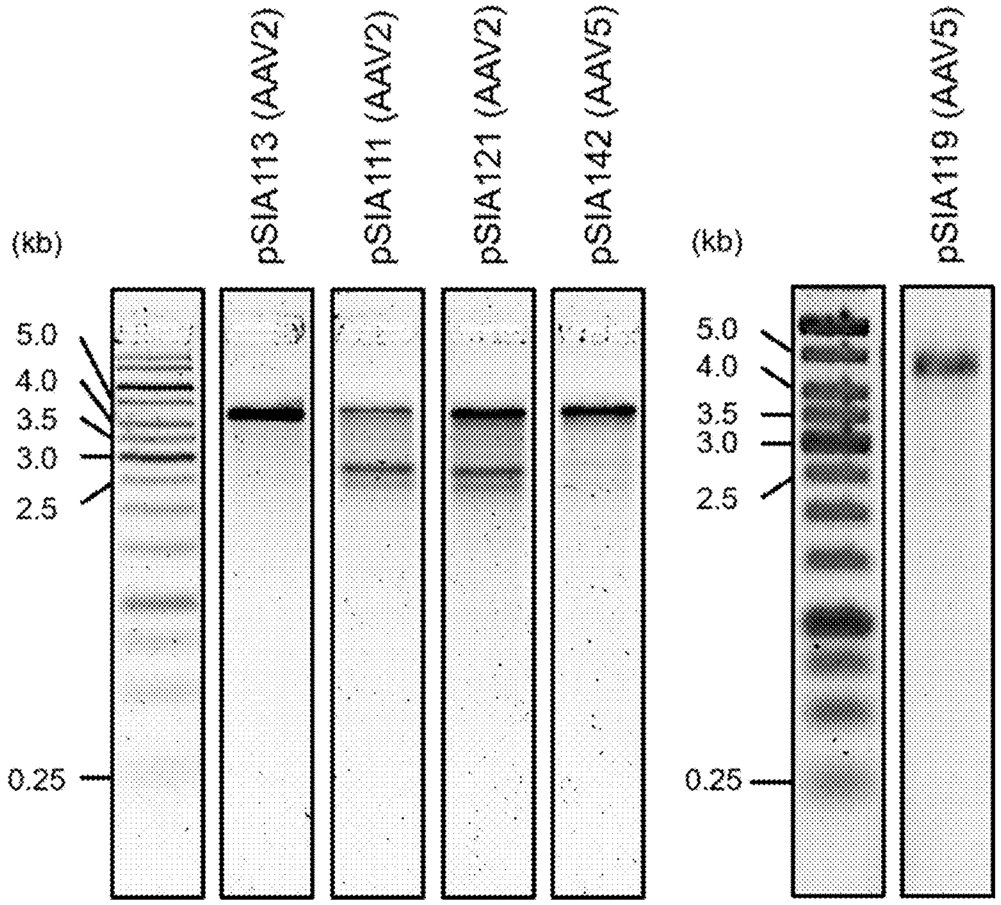
FIG. 5 shows an alkaline electrophoresis gel comparing AAV2 vectors packaged with either (1) pSIA113, (2) pSIA111, or (3) pSIA121 as the template for recombinant AAV vector production.

After packaging and recombinant AAV vector particle purification, genomic DNA was isolated from each sample and used for alkaline agarose gel electrophoresis (FIG. 5).

AAV serotype 2 vectors packaged with pSIA113 used as template showed a single band of the expected genome size. This was expected since no SIN sites are present on this vector, and thus it should not be targeted during packaging by the SaCas nuclease-sgRNA complex, even though the complex is expected to be expressed during packaging.

AAV serotype 2 vectors packaged with pSIA111 used as template showed multiple bands. This indicates that a portion of the genomes packaged in these cells sustained a deletion due to cutting by the SaCas nuclease-sgRNA complex at the two SIN sites in the viral vector genome. This cutting was expected since no TetR protein was supplied during packaging.

AAV serotype 2 vectors packaged with pSIA121 used as template showed multiple bands. This indicates that a portion of the genomes packaged in these cells sustained a deletion due to cutting by the SaCas nuclease-sgRNA complex at the two SIN sites in the viral vector genome. However, the full length band comprising intact genomes showed a stronger signal in the pSIA121 lane than in the pSIA111 lane, indicating that the TetR protein supplied during packaging was effective in reducing sgRNA expression and resultant cutting by the SaCas nuclease-sgRNA complex.

AAV serotype 5 vectors packaged with pSIA142 used as template showed multiple bands. This indicates that a portion of the genomes packaged in these cells sustained a deletion due to cutting by the SaCas nuclease-sgRNA complex at the two SIN sites in the viral vector genome. This cutting was expected since no TetR protein was supplied during packaging. It is noted that this viral vector carries a different promoter to drive expression of the SaCas9 gene, GRK1 compared to EF1α. The GRK1 promoter is active in photoreceptor cells but less active than the EF1α promoter in other cells such as the packaging cells used in this Example. Thus, fewer vector genomes with a deletion accumulated in vectors packaged with pSIA142, compared to vector packaged with pSIA111.

Finally, AAV serotype 5 vectors packaged with pSIA119 used as template showed only one visible band. This indicates that the combination of the photoreceptor cell-specific promoter driving SaCas9 expression and the TetR repressor protein decreasing transcription of the sgRNA worked synergistically to reduce vector genome deletion to a level low enough to escape detection by alkaline gel electrophoresis.

FIG. 5 provides evidence that editing activity leading to recombinant AAV vector genome deletion can be reduced during packaging of all-in-one vectors. This can be achieved by at least one of transcriptional control via a repressor of the sgRNA gene and transcriptional control of the Cas nuclease via a cell-type specific promoter.

Example 5—Analysis of AAV Vectors Packaged in AAV2 or AAV5

To further evaluate the accumulation of deletions in packaged AAV vectors, recombinant AAV vectors were prepared in packaging cells as described in Example 4. PCR was conducted to detect both full length vectors and vectors with deletion between two SIN sites. Comparisons were made between recombinant AAV vectors comprising SIN sites and those without SIN sites. Additionally vectors comprising a cell type-specific promoter driving SaCas9 expression were investigated. The viral vectors were packaged either with or without the presence of TetR protein.

Figure 6:
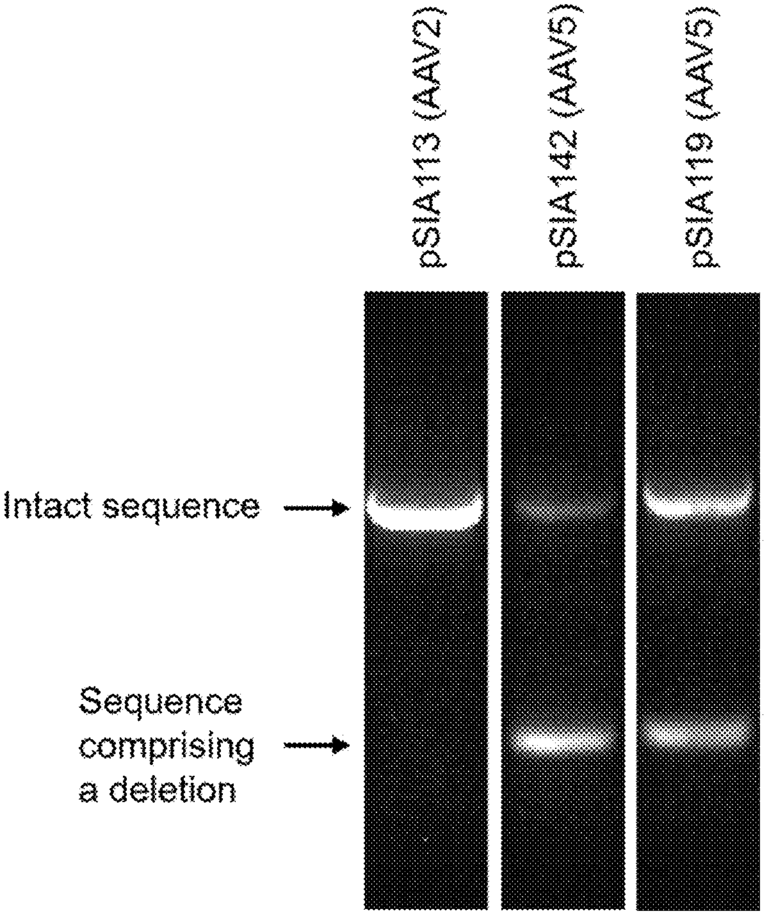
FIG. 6 shows images of a PCR analysis comparing AAV2 vector packaged with pSIA113 and AAV5 vectors packaged with either pSIA142 or pSIA119 as the template for recombinant AAV vector production.

After packaging and recombinant AAV vector particle purification, as described in Example 4, genomic DNA was isolated from each sample and used as a template for a PCR (FIG. 6). Two oligonucleotide primers (SEQ ID NOs: 21 and 22) were used to amplify a sequence comprising the DNA between the two SIN sites. Thus, a longer product would be made by genomic templates with no deletion and a shorter product would be made by genomic templates with a deletion due to cutting at both SIN sites by the SaCas nuclease-sgRNA complex.

FIG. 6 shows that recombinant AVV vector genomes produced from pSIA113 did not comprise any such deletion.

This is expected since this plasmid's AAV sequence does not comprise SIN sites. A portion of recombinant AVV vector genomes produced from either from pSIA142 or from pSIA119 did comprise a deletion. However, more intact genomes were produced when pSIA119 was used.

These results provide further evidence that both transcriptional control via a repressor of the sgRNA gene and transcriptional control of the Cas nuclease via a cell-type specific promoter can be successful strategies to control gene editing during packaging of viral vectors. Particularly, genomic deletion generation can be reduced by one or both of the strategies. A combination of these two strategies can be preferable.

Example 6—Analysis of AAV Vectors Packaged in AAV2 or AAV5

Examples 4 and 5 above relate to analysis of genomic deletions in recombinant AAV vector constructs during packaging and the use of materials and methods of the present disclosure to inhibit such deletions. In addition to deletions, unwanted expression of CRISPR/Cas-related genes during packaging can also cause indels at sites (e.g., SIN sites) on the vector genome. The present disclosure accordingly provides materials and methods to inhibit indel formation on recombinant AAV vectors during packaging, as well as to inhibit generation of genomic deletions.

To analyze the ability to inhibit indel formation on recombinant AAV vectors during packaging, recombinant AAV vectors were generated using either pSIA111, pSIA113, pSIA121, or pSIA142. Generation and packaging of the recombinant AAV vectors was performed similarly to the corresponding procedure described in Examples 4 and 5 above.

Genomic DNA was prepared from the recombinant AAV vectors and was used as a template in two separate PCRs.

In a first PCR, an oligonucleotide primer with the sequence of SEQ ID NO: 23 was used as a forward primer for genomes prepared from pSIA111, pSIA113 and pSIA121, and an oligonucleotide primer with the sequence of SEQ ID NO: 24 was used as a forward primer for genomes prepared from pSIA142. An oligonucleotide primer with the sequence of SEQ ID NO: 25 was used as a reverse primer for genomes prepared from all four plasmids. This PCR reaction amplified a region of each vector comprising the 5' SIN site of recombinant AAV vectors prepared from pSIA111, pSIA121, and pSIA142. Recombinant AAV vectors prepared from pSIA113 do not comprise a SIN site, but did produce an analogous PCR product.

In a second PCR, an oligonucleotide primer with the sequence of SEQ ID NO: 26 was used as a forward primer for genomes prepared from all four plasmids. An oligonucleotide primer with the sequence of SEQ ID NO: 27 was used as a reverse primer for genomes prepared from all four plasmids. This reaction amplified a region of each genome comprising the 3' SIN site of recombinant AAV vectors prepared from pSIA111, pSIA121, and pSIA142. Recombinant AAV vectors prepared from pSIA113 do not comprise a SIN site, but did produce an analogous PCR product.

Because indels, unlike the larger deletions examined in Examples 4 and 5, cannot be detected by only gel electrophoresis, both the first and second PCR products were then examined in a T7 Endonuclease I (T7EI) assay. In this assay the PCR products for each sample were denatured and allowed to re-anneal. After the re-annealing, and if indels were generated in the vector genomes used as PCR templates, a population of the re-annealed products would have contained mismatched and/or bulged bases, due to strands with indels pairing with either unaltered strands or strands containing different indels. Such mismatches and/or bulges are a substrate for the T7EI, which would cut the product at the indel site, generating two smaller bands on an agarose gel, relative to the intact re-annealed product.

Figure 7:
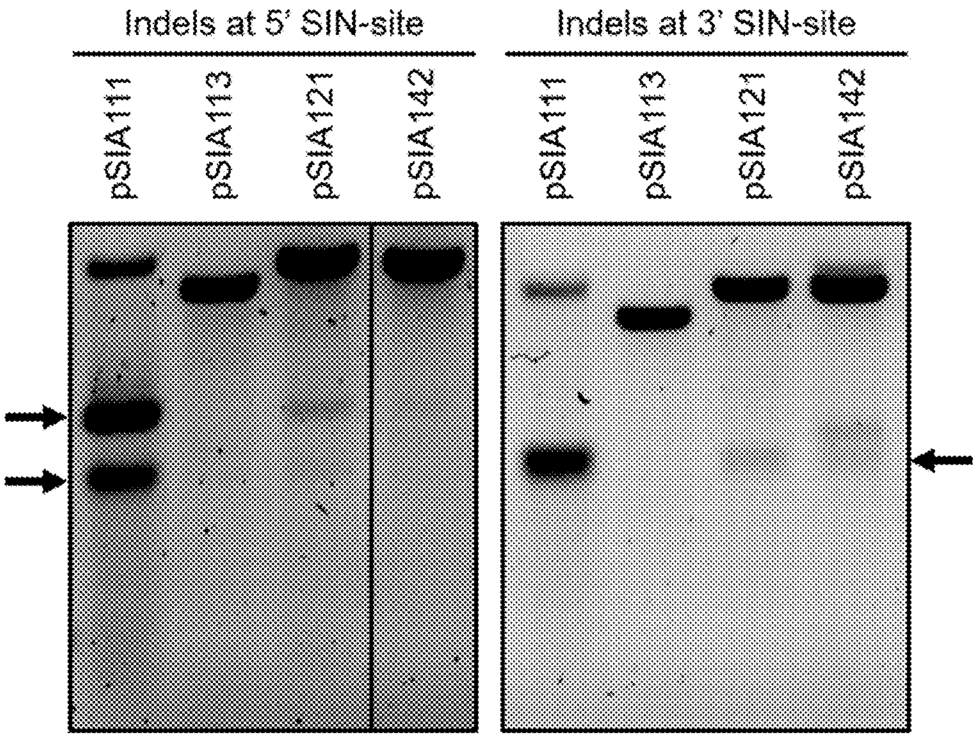
FIG. 7 shows T7E1 assay results comparing AAV2 vectors packaged with either (1) pSIA111, (2) pSIA113, or (3) pSIA121 as the template for recombinant AAV vector production and AAV5 vector packaged with pSIA142 as the template for recombinant AAV vector production.

Results from the T7EI assay are shown in FIG. 7. Referring to the assay using the 5'SIN site PCR product (left panel), PCR product from the vector prepared with the pSIA111 plasmid showed two smaller bands (marked by arrows), indicating that indels were present in this vector, consistent with the SIN sites in the vector and the absence of means for controlling transcription or translation of the SaCas9 gene or the sgRNA.

PCR product from the vector prepared with the pSIA113 plasmid did not show smaller bands, indicating that no indels were present in this vector, consistent with the absence of SIN sites in the vector.

PCR product from the vector prepared with the pSIA121 plasmid showed two smaller bands (marked by arrows), indicating that indels were present in this vector, consistent with the SIN sites in the vector. However, a smaller fraction of the vector contained indels, compared to that prepared from pSIA111. This difference further indicated that repression of transcription of the sgRNA via the TetR protein reduces indel formation via reduction of editing by the SaCas nuclease-sgRNA complex.

PCR product from the vector prepared with the pSIA142 plasmid showed two smaller bands (marked by arrows), indicating that indels were present in this vector, consistent with the SIN sites in the vector. However, a smaller fraction of the vector contained indels, compared to that prepared from pSIA111. This difference further indicated that limitation of transcription via the use of a cell-specific promoter driving expression of the SaCas nuclease gene reduces indel formation via reduction of editing by the Cas nuclease-sgRNA complex.

Referring to the assay using the 3' SIN site PCR product (right panel), PCR product from the vector prepared with the pSIA111 plasmid showed two smaller bands (marked by arrows), indicating that indels were present in these genomes, consistent with the SIN sites in the genome and the absence of means for controlling transcription or translation of the SaCas9 gene or the sgRNA.

PCR product from the vector prepared with the pSIA113 plasmid did not show smaller bands, indicating that no indels were present in this vector, consistent with the absence of SIN sites in the vector.

PCR product from the vector prepared with the pSIA121 plasmid showed two smaller bands (marked by arrows), indicating that indels were present in this vector, consistent with the SIN sites in the vector. However, a smaller fraction of the vector contained indels, compared to that prepared from pSIA111. This difference further indicated that repression of transcription of the sgRNA via the TetR protein reduces indel formation via reduction of editing by the SaCas nuclease-sgRNA complex.

PCR product from the vector prepared with the pSIA142 plasmid showed two smaller bands (marked by arrows), indicating that indels were present in this vector, consistent with the SIN sites in the vector. However, a smaller fraction of the genomes contained indels, compared to genomes prepared from pSIA111. This difference further indicated that limitation of transcription via the use of a cell-specific promoter driving expression of the SaCas nuclease gene reduces indel formation via reduction of editing by the SaCas nuclease-sgRNA complex.

These results provide evidence that at least one of transcriptional control via a repressor of the sgRNA gene and transcriptional control of the Cas nuclease via a cell-type specific promoter can be successful strategies to control gene editing during packaging of viral vectors. Particularly, indel generation can be reduced by one or both of the strategies. It is possible that a combination of these two strategies could be preferred.

Figure 8A:
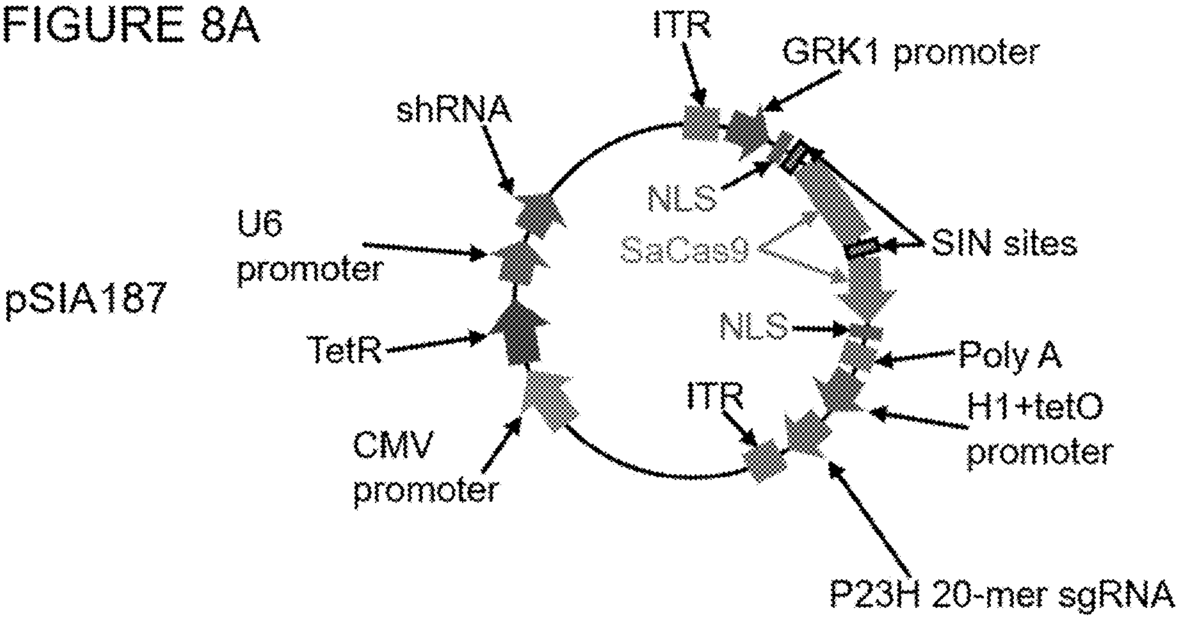
FIGS. 8A-B show a depiction of pSIA187 and PCR results comparing an AAV5 vectors packaged with either (1) pSIA185, (2) pSIA186, (3) pSIA187, or (4) pSIA036 as the template for recombinant AAV vector production.

Example 7—Controlling Both Transcriptional Expression of gRNAs and Post-Transcriptional Expression of SaCas9 Nuclease Using a Tetracycline Operator/Repressor System and shRNAs To analyze inhibition of genomic deletion in recombinant AAV vector genomes during packaging, recombinant AAV vectors were generated using either pSIA185, pSIA186, pSIA187, or pSIA036. In this experiment, both shRNA encoded on pDL153 (SEQ ID NO: 11) and the TetR protein were used to control expression of the Cas nuclease and the sgRNA, respectively. Generation and packaging of the AAV vectors was performed similarly to the corresponding procedure described in Example 4 above.

pSIA187 (SEQ ID NO: 38), depicted in FIG. 8A, is a plasmid comprising a SaCas9 gene (SEQ ID NO: 64) and a sequence that encodes a P23H 20-mer sgRNA (SEQ ID NO: 2), driven by an H1 promoter comprising two TetO sites (SEQ ID NO: 3) between two AAV ITRs. The sequence between AAV ITRs of pSIA187 further comprises two SIN sites, with a first SIN site located between the 5' NLS of SaCas9 and the immediate 5' end of SaCas9 and a second SIN site located within the intron of SaCas9. pSIA187 further comprises a sequence encoding a TetR protein (e.g., SEQ ID NO: 62) and a sequence encoding a shRNA (SEQ ID NO: 11) coded on pDL153. The TetR sequence and the shRNA sequence are located on a separate locus of the plasmid, compared to the sequence between AAV ITRs. The TetR gene and the shRNA gene, while expressed during packaging, are not included in recombinant AAV vectors prepared during packaging because the two genes are not located between the AAV inverted terminal repeats.

pSIA186 (SEQ ID NO: 37) is a plasmid similar to pSIA187, except that pSIA186 lacks the TetR gene cassette. pSIA185 (SEQ ID NO: 36) is a plasmid similar to pSIA187, except that pSIA185 lacks the shRNA gene cassette. pSIA036 (SEQ ID NO: 39) is a plasmid similar to pSIA187, except that pSIA036 lacks both the shRNA gene cassette and the TetR gene cassette.

Figure 8B:
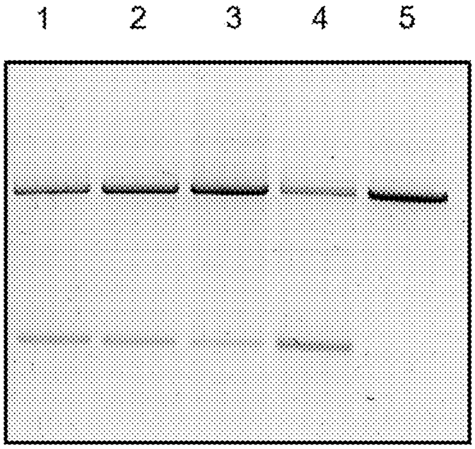

After packaging and recombinant AAV vector particle purification, as described in Example 4, genomic DNA was isolated from each sample and used as a template for a PCR (FIG. 8B). Two oligonucleotide primers (SEQ ID NOs: 21 and 22) were used to amplify a sequence comprising the DNA between the two SIN sites. Thus, a longer product would be made by vector templates with no deletion and a shorter product would be made by vector templates with a deletion due to cutting at both SIN sites by the SaCas nuclease-sgRNA complex.

FIG. 8B, lane 5, shows that PCR conducted using a plasmid, pSIA036, as PCR template yielded a single, full length product. This lane serves as a control confirming that a template with no deletion will only yield the single product shown. A portion of recombinant AAV vectors produced from any one of pSIA036, pSIA185, pSIA186, and pSIA187 did comprise a deletion. However, more intact vectors were produced when any one of pSIA185, pSIA186, and pSIA187 were used, compared to pSIA036. Additionally, when pSIA187 was used, an amount of the intact vector approaching that of the control (lane 5) were produced.

These results demonstrate that using at least one of a shRNA targeting the SaCas9 transcript and a TetR protein to control sgRNA transcription can reduce accumulation recombinant AAV vector genomic deletions during packaging. A combination of these two strategies can be preferred.

Figure 9A:
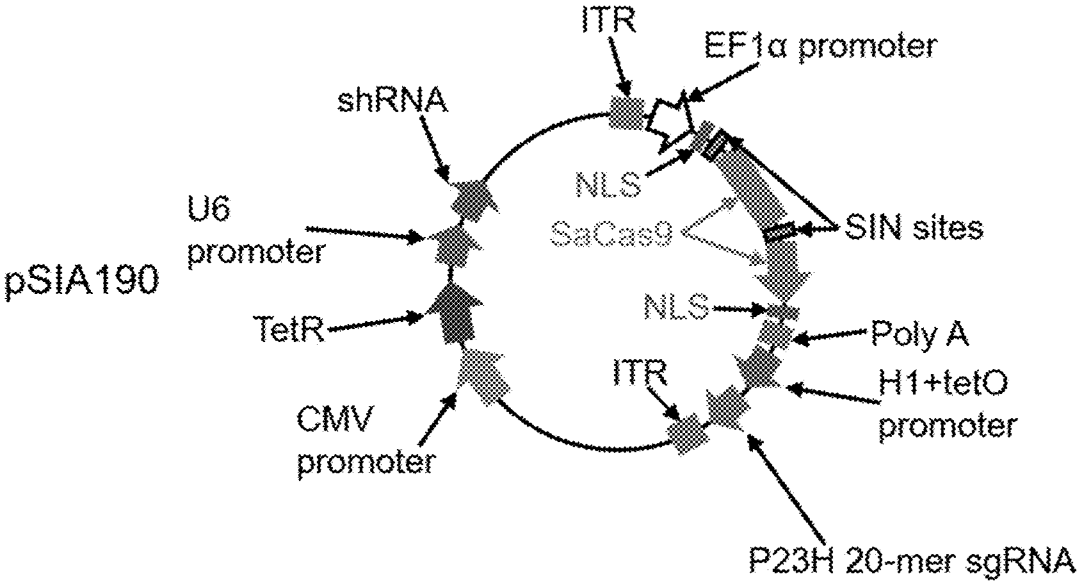
FIGS. 9A-9C show a depiction of pSIA190; an alkaline electrophoresis gel comparing AAV6 vectors packaged with either (1) pSIA069, (2) pSIA071, (3) pSIA188, (4) pSIA189, or (5) pSIA190 as the template for recombinant AAV vector production; and a bar graph showing the percentage of BFP− HEK 293FT reporter cells transduced with a recombinant AAV vector prepared with pSIA190.

Example 8—Controlling Both Transcriptional Expression of gRNAs and Post-Transcriptional Expression of SaCas9 Nuclease Using a Tetracycline Operator/Repressor System and shRNAs To further analyze inhibition of genomic deletion in recombinant AAV vector genomes during packaging, recombinant AAV vector genomes were generated using either pSIA190, pSIA189, pSIA188, pSIA071, or pSIA069. In this experiment, both shRNAs and the TetR protein were used to control expression of the Cas nuclease and the sgRNA, respectively. Generation and packaging of the genomes was performed similarly to the corresponding procedure described in Example 4 above.

pSIA190 (SEQ ID NO: 43), depicted in FIG. 9A, is a plasmid comprising a SaCas9 gene (SEQ ID NO: 64) and a sequence that encodes a P23H 20-mer sgRNA (SEQ ID NO: 2), driven by an H1 promoter comprising two TetO sites (SEQ ID NO: 3) between two AAV ITRs. The AAV sequence of pSIA190 further comprises two SIN sites, with a first SIN site located between the NLS and the immediate 5' end of SaCas9 and a second SIN site located within the intron of SaCas9. pSIA190 further comprises a sequence encoding a TetR protein (e.g., SEQ ID NO: 62) and a sequence encoding a shRNA (SEQ ID NO: 11) coded on pDL153. The TetR sequence and the shRNA sequence are located on a separate locus of the plasmid, compared to the sequence between AAV ITRs. The TetR gene and the shRNA gene, while expressed during packaging, are not included in recombinant AAV vectors prepared during packaging because the two genes are not located between the AAV inverted terminal repeats.

pSIA189 (SEQ ID NO: 42) is a plasmid similar to pSIA190, except that pSIA189 lacks the TetR gene cassette. pSIA188 (SEQ ID NO: 41) is a plasmid similar to pSIA190, except that pSIA188 lacks the shRNA gene cassette. pSIA069 (SEQ ID NO: 40) is a plasmid similar to pSIA190, except that pSIA069 lacks both the shRNA gene cassette and the TetR gene cassette. pSIA071 (SEQ ID NO: 7) is a plasmid similar to pSIA190, except that pSIA071 lacks both the shRNA gene cassette and the TetR gene cassette and also lacks the two SIN sites.

After packaging and recombinant AAV vector particle purification, as described in Example 4, vector DNA was isolated from each sample and analyzed by alkaline agarose gel electrophoresis. A band of approximately 4.5 kb corresponds to AAV vectors with no deletion and shorter bands correspond to AAV vectors with a deletion due to cutting at both SIN sites by the SaCas nuclease-sgRNA complex.

Figure 9B:
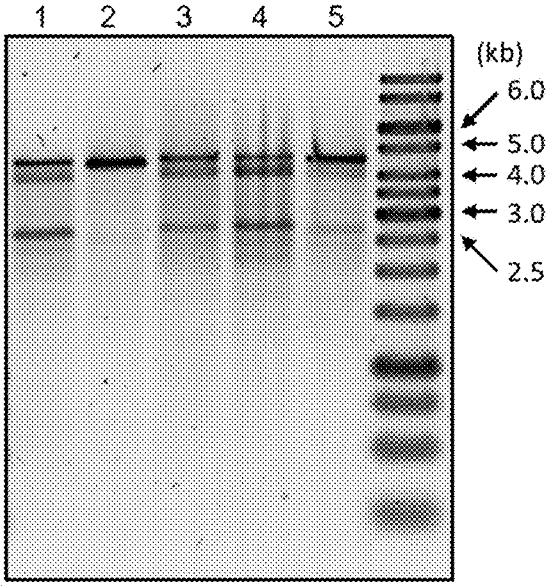

FIG. 9B, lane 2, shows that a single sequence of the expected size was packaged in the recombinant AAV vector from pSIA071. This lane serves as a control confirming that a template with no SIN sites will only yield a full length vector. A portion of recombinant AAV vectors produced from any one of pSIA069, pSIA188, pSIA189, and pSIA190 did comprise a deletion, as indicated by the accumulation of shorter (lower) bands in the gel. However, more intact vectors were produced when any one of pSIA188, pSIA189, and pSIA190 were used, compared to pSIA069. Additionally, when pSIA190 was used, an amount of intact genomes approaching that of the control (lane 2) were produced.

Figure 9C:
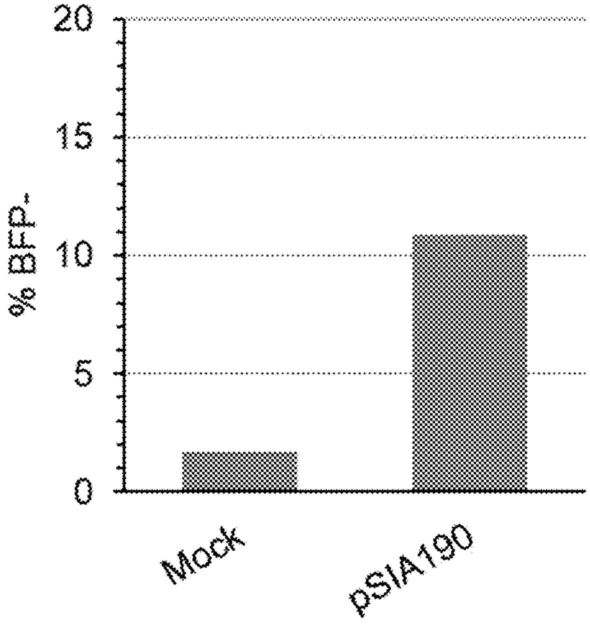

FIG. 9C shows results from a BFP reporter cell assay similar to the one conducted in Example 1. However, a recombinant AAV vector (serotype 6) produced from pSIA190 was used to transduce the reporter cell line at 1,000,000 viral vectors per cell, rather than transfection with a plasmid. Mock transduced cells showed a background level loss of BFP fluorescence~1.5%. In contrast, about 11% of cells transduced with the recombinant AAV vector produced from pSIA190 showed loss of BFP fluorescence, indicating that many of the all-in-one SIN viral vectors were able to introduce frame-shift mutations in the P23H target site that was positioned upstream of the BFP gene.

These results demonstrate that using at least one of a shRNA targeting the SaCas9 transcript and a TetR protein to control sgRNA transcription can reduce accumulation of deletion on a recombinant AAV vector during packaging. A combination of these two strategies can be preferred. These results further suggest that functional all-in-one SIN viral vectors can be produced using the materials and methods disclosed herein.

Example 9—Controlling Post-Transcriptional Expression of sRGN Cas Nuclease (Gib11Spa1) Using a shRNAs To investigate inhibition of expression of sRGN expression during recombinant AAV vector packaging, an experiment was conducted. In this experiment, a BFP reporter cell assay was used to investigate sRGN expression from a plasmid when controlled by shRNAs encoded on a second plasmid.

Figure 10A:
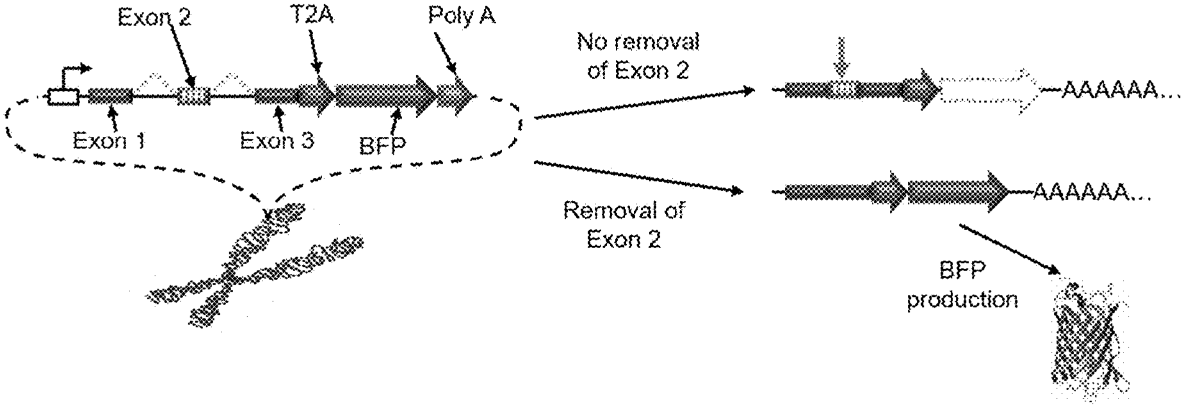
FIGS. 10A-10F show a depiction of a BFP splicing reporter sequence integrated in Jump-In™ Grip Tite™ HEK 293 cells; a depiction of pD105; a generalized depiction of pDL258, pDL259, pDL260, pDL261, and pDL262; a depiction of a transfection control, NC026; and flow cytometry results (ratio of GFP to RFP and % BFP+) for BFP splicing reporter cells co-transfected with pD105, NC025, and one of either (1) pDL122, (2) pDL258, (3) pDL259, (4) pDL260, (5) pDL261, or (6) pDL262.

FIG. 10A shows a diagram of the reporter construct (SEQ ID NO: 44) used in this experiment. The reporter cell line was generated from Jump-In™ GripTite™ HEK293 cells, available from Thermo Fisher Scientific, Massachusetts, US. The reporter construct will produce a nonfunctional transcript from the BFP locus if Exon 2 is unedited by the sRGN. If editing at the splice donor site of Exon 2 does occur, Exon 2 will be spliced out of the transcript and a functional protein product will be produced, resulting in T2A cleavage and production of free BFP.

Figure 10B:
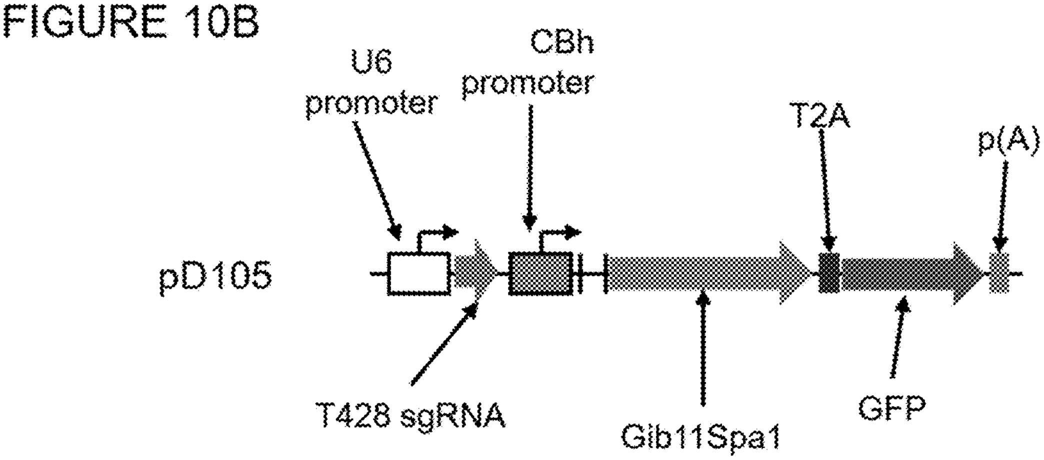

FIG. 10B shows a diagram of pD105, which is a plasmid that comprises a Gib11Spa1 sRGN gene sequence that encodes Gib11Spa1 sRGN protein sequence (SEQ ID NO: 60) and a T428 sgRNA gene (SEQ ID NO: 46). GFP is also produced from the sRGN gene. The GFP protein is separated from the sRGN protein by a T2A self-cleaving peptide.

Figure 10C:
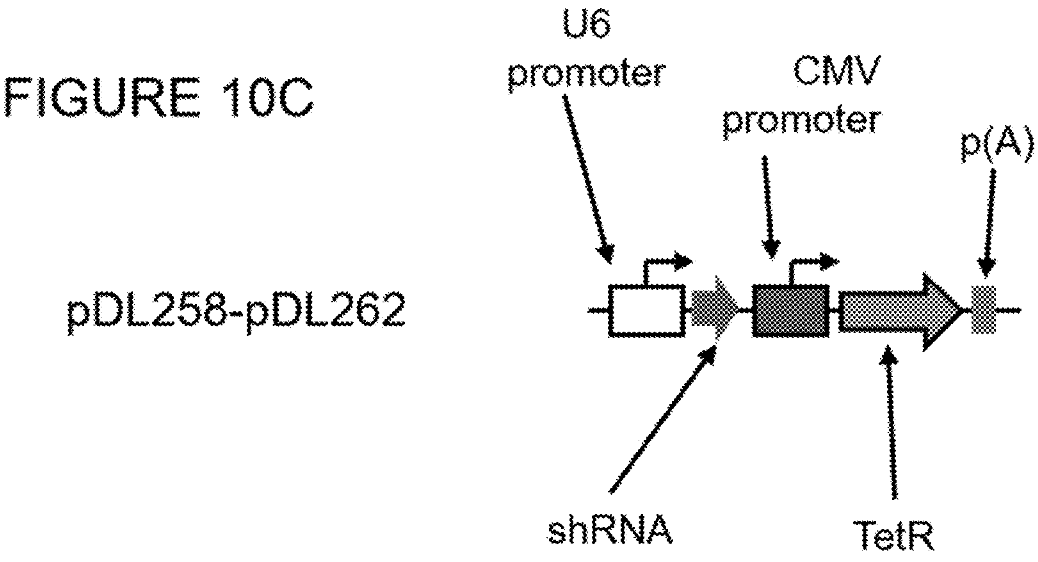

FIG. 10C shows a generalized diagram of plasmids used to express various shRNAs that target Gib11Spa1 transcripts. Each shRNA is driven by a U6 promoter. Additionally, a CMV promoter drives expression of a TetR protein, but none of the promoters in this example comprise a TetO site, so this aspect of the plasmids is not relevant in the Example.

pDL258 (SEQ ID NO: 50) comprises a shRNA comprising the sequence of SEQ ID NO: 55. pDL259 (SEQ ID NO: 51) comprises a shRNA comprising the sequence of SEQ ID NO: 56. pDL260 (SEQ ID NO: 52) comprises a shRNA comprising the sequence of SEQ ID NO: 57. pDL261 (SEQ ID NO: 53) comprises a shRNA comprising the sequence of SEQ ID NO: 58. pDL262 (SEQ ID NO: 54) comprises a shRNA comprising the sequence of SEQ ID NO: 59.

Figure 10D:
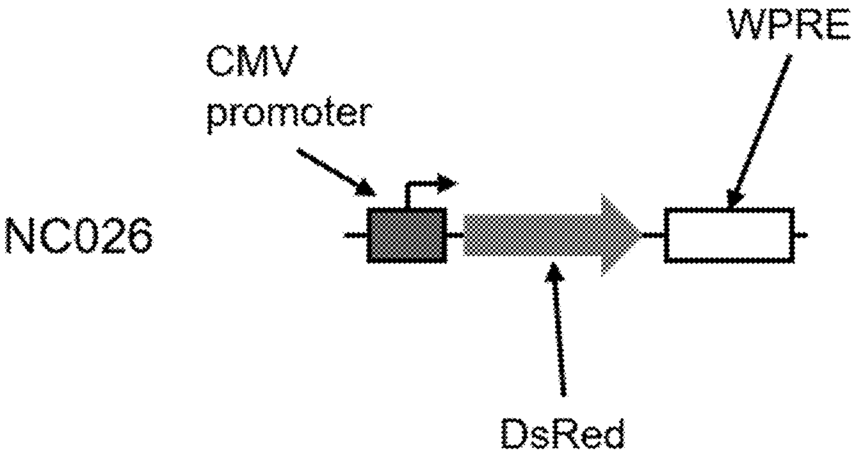

FIG. 10D shows a diagram of a plasmid (NC026) expressing an RFP gene, which was used as a transfection control. The RFP gene is regulated by the CMV promoter and the woodchuck hepatitis virus posttranscriptional regulatory element (WPRE), which increases translation of the RFP transcript.

Figure 10E:
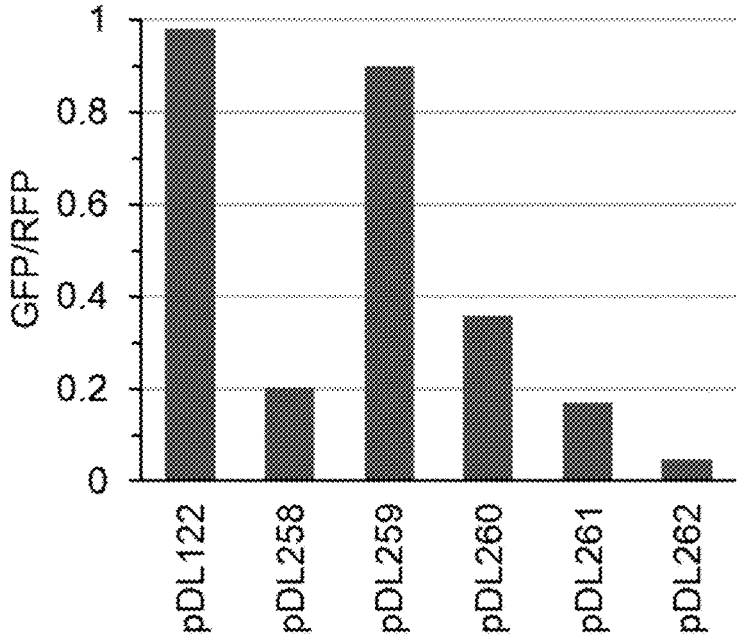

FIG. 10E shows results of a BFP reporter cell assay. Flow cytometry was conducted similarly to Example 1. All cells were transfected with NC026 and pD105. Thus, all samples show some GFP and RFP signal. Cells additionally transfected with pDL122, which is a negative control comprising no shRNA gene (SEQ ID NO: 13), showed nearly equal numbers of GFP-expressing and RFP-expressing cells, indicating that the sRGN and GFP were expressed relatively strongly at the protein level.

Cells additionally transfected with pDL258, which expresses a first shRNA gene, showed that GFP-expressing cells were only ~20% of the RFP-expressing cells, indicating that the sRGN and GFP were expressed relatively weakly at the protein level.

Cells additionally transfected with pDL259, which expresses a second shRNA gene, showed that GFP-expressing cells were ~90% of RFP-expressing cells, indicating that the sRGN and GFP were expressed only slightly less at the protein level.

Cells additionally transfected with pDL260, which expresses a third shRNA gene, showed that GFP-expressing cells were only ~35% of RFP-expressing cells, indicating that the sRGN and GFP were expressed relatively weakly at the protein level.

Cells additionally transfected with pDL261, which expresses a fourth shRNA gene, showed that GFP-expressing cells were only ~15% of the RFP-expressing cells, indicating that the sRGN and GFP were expressed relatively weakly at the protein level.

Cells additionally transfected with pDL262, which expresses a fifth shRNA gene, showed the GFP-expressing cells were only ~5% of RFP-expressing cells, indicating that the sRGN and GFP were expressed relatively weakly at the protein level.

Figure 10F:
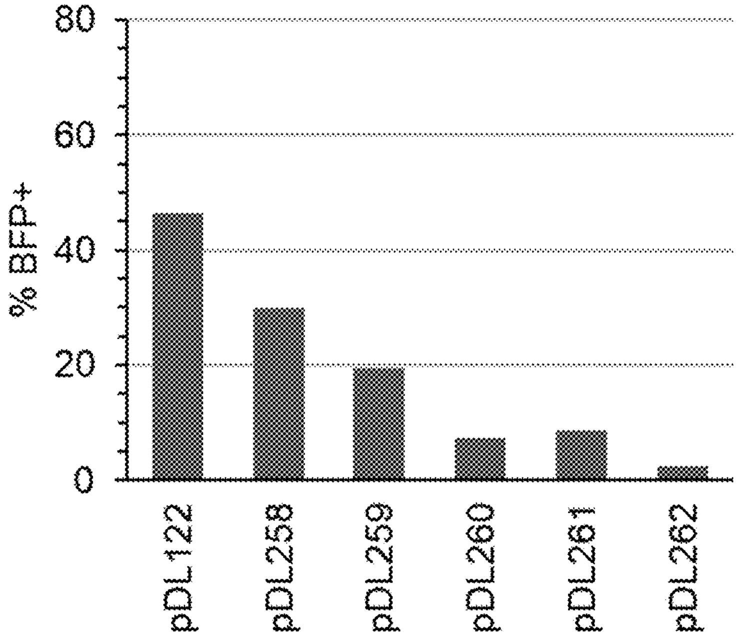

FIG. 10F shows additional results of the BFP reporter cell assay. ~45% of cells additionally transfected with pDL122 were positive for BFP, indicating a baseline for BFP expression levels resulting from relatively uncontrolled editing by the sRGN-sgRNA complex at the BFP locus.

~30% of cells additionally transfected with pDL258 were positive for BFP, indicating a reduction from the baseline for BFP expression levels resulting from relatively reduced editing by the sRGN-sgRNA complex at the BFP locus. Thus, the shRNA encoded on pDL258 appears to have reduced sRGN expression.

~20% of cells additionally transfected with pDL259 were positive for BFP, indicating a reduction from the baseline for BFP expression levels resulting from relatively reduced editing by the sRGN-sgRNA complex at the BFP locus. Thus, the shRNA encoded on pDL259 appears to have reduced sRGN expression.

~10% of cells additionally transfected with pDL260 were positive for BFP, indicating a reduction from the baseline for BFP expression levels resulting from relatively reduced editing by the sRGN-sgRNA complex at the BFP locus. Thus, the shRNA encoded on pDL260 appears to have reduced sRGN expression.

~10% of cells additionally transfected with pDL261 were positive for BFP, indicating a reduction from the baseline for BFP expression levels resulting from relatively reduced editing by the sRGN-sgRNA complex at the BFP locus. Thus, the shRNA encoded on pDL261 appears to have reduced sRGN expression.

~5% of cells additionally transfected with pDL262 were positive for BFP, indicating a reduction from the baseline for BFP expression levels resulting from relatively reduced editing by the sRGN-sgRNA complex at the BFP locus. Thus, the shRNA encoded on pDL262 appears to have reduced sRGN expression.

These results provide evidence that sRGN gene expression can be regulated at the post-transcriptional level by shRNA expression, thereby reducing editing by the sRGN gene.

NOTE REGARDING ILLUSTRATIVE EXAMPLES

While the present disclosure provides descriptions of various specific aspects for the purpose of illustrating various examples of the present disclosure and/or its potential applications, it is understood that variations and modifications will occur to those skilled in the art. Accordingly, the invention or inventions described herein should be understood to be at least as broad as they are claimed, and not as more narrowly defined by particular illustrative examples provided herein.

What is claimed is:

1. A CRISPR/Cas system comprising:

a nuclease segment comprising a codon optimized nucleotide sequence that encodes a Cas9 nuclease or variant thereof, wherein the Cas9 nuclease comprises an amino acid sequence having at least 90% sequence identity to SEQ ID NO: 60;

a guide RNA (gRNA) segment comprising a nucleotide sequence that encodes a gRNA or sgRNA;

a promoter segment comprising a nucleotide sequence that encodes a promoter comprising one or more tetracycline operator sequence, wherein the gRNA segment is operably linked to the promoter segment; and/or a short-hairpin RNA (shRNA) segment comprising a nucleotide sequence that encodes a shRNA that comprises sequence that is complementary to a transcript from the nuclease segment;

wherein the Cas9 nuclease comprising an amino acid sequence having at least 90% sequence identity to SEQ ID NO: 60 introduces a double stranded break at a site in a nucleic acid complementary to the gRNA segment.

2. The CRISPR/Cas system of claim 1, wherein the promoter is selected from a group consisting of: H1 promoter, U6 promoter, 7SK promoter, and portions of any thereof.

3. The CRISPR/Cas system of claim 1, wherein the one or more tetracycline operator sequence comprises a nucleic acid sequence having at least 85% sequence identity to SEQ ID NO: 4, or comprises SEQ ID NO: 4.

4. The CRISPR/Cas system of claim 1, further comprising:

a repressor segment comprising a nucleotide sequence that encodes a tetracycline repressor protein.

5. The CRISPR/Cas system of claim 4, wherein the tetracycline repressor comprises a nucleic acid sequence having at least 85% sequence identity to SEQ ID NO: 62, or comprises SEQ ID NO: 62.

6. The CRISPR/Cas system of claim 1, wherein the one or more tetracycline operator sequence is capable of being bound by the tetracycline repressor protein.

7. The CRISPR/Cas system of claim 1, further comprising:

one or more self-inactivating segments comprising a SIN site;

wherein the gRNA or sgRNA is substantially complementary to the SIN site;

wherein the gRNA or sgRNA is substantially complementary to a genomic target sequence within a cell of a patient.

8. The CRISPR/Cas system of claim 7, wherein the one or more self-inactivating segments are located in at least one of:

(i) at the 5' end of the codon optimized nucleotide sequence that encodes the Cas9 nuclease or variant thereof;

(ii) at the 3' end of the codon optimized nucleotide sequence that encodes the Cas9 nuclease or variant thereof; and (iii) in an intron within the codon optimized nucleotide sequence that encodes the Cas9 nuclease or variant thereof.

9. The CRISPR/Cas system of claim 7, wherein one of the one or more self-inactivating segments are located upstream of the codon optimized nucleotide sequence that encodes the Cas9 nuclease or variant thereof and downstream of a nuclear localization signal (NLS).

10. The CRISPR/Cas system of claim 7, wherein the SIN site comprises a protospacer adjacent motif (PAM) sequence.

11. The CRISPR/Cas system of claim 10, wherein the PAM sequence in the SIN site is NNGG.

12. The CRISPR/Cas system of claim 1, wherein the gRNA or sgRNA is fully complementary to the nucleotide sequence of the SIN site except for at one base pair or except for at two base pairs.

13. The CRISPR/Cas system of claim 1, further comprising a nucleic acid sequence encoding a promoter that is operably linked to the codon optimized nucleotide sequence that encodes the Cas9 nuclease or variant thereof.

14. The CRISPR/Cas system of claim 13, wherein the promoter is a spatially-restricted promoter, bidirectional promoter, or an inducible promoter.

15. The CRISPR/Cas system of claim 14, wherein the spatially-restricted promoter is selected from a group consisting of: a hepatocyte-specific promoter, a neuron-specific promoter, an adipocyte-specific promoter, a cardiomyocyte-specific promoter, a skeletal muscle-specific promoter, lung progenitor cell specific promoter, a photoreceptor-specific promoter, and a retinal pigment epithelial (RPE) selective promoter.

16. The CRISPR/Cas system of claim 1, wherein the gRNA or sgRNA comprises a spacer sequence comprising 17 to 24 nucleotides.

17. The CRISPR/Cas system of claim 1, wherein (i) the nuclease segment is provided in a first vector, and the gRNA segment and the promoter segment are provided together in a second vector or (ii) the nuclease segment and the gRNA segment are provided together in a first vector and the shRNA segment is provided in a second vector.

18. The CRISPR/Cas system of claim 4, wherein (i) the nuclease segment, the gRNA segment, and the promoter segment are provided together in a first vector and the repressor segment is provided in a second vector, (ii) the nuclease segment is provided in a first vector, the gRNA segment and the promoter segment are provided together in a second vector, and the repressor segment and/or the shRNA segment is provided in a third vector; or the nuclease segment, the gRNA segment, and the promoter segment are provided together in a first vector and the repressor segment and/or the shRNA segment is provided in a second vector.

19. The CRISPR/Cas system of claim 7, wherein (i) the nuclease segment, the gRNA segment, the promoter segment, and the one or more self-inactivating segments are provided together in a first vector and the repressor segment is provided in a second vector, (ii) the nuclease segment, the gRNA segment, the promoter segment, the one or more self-inactivating segments, and the repressor segment are provided in a vector;

(iv) the nuclease segment, the gRNA segment, and the one or more self-inactivating segments are provided together in a first vector and the shRNA segment is provided in a second vector; or (v) the nuclease segment, the gRNA segment, the one or more self-inactivating segments, and the shRNA segment are provided in a vector.

20. The CRISPR/Cas system of claim 17, wherein the first vector and the second vector are AAV vectors or plasmids.

21. The CRISPR/Cas system of claim 20, wherein the AAV vectors are AAV2 serotype vectors, AAV5 serotype vectors, or AAV6 serotype vectors.

22. A pharmaceutical composition comprising the CRISPR/Cas system of claim 1.

23. A packaging cell comprising the CRISPR/Cas system of claim 1.

24. A recombinant AAV vector comprising:

a nuclease segment comprising a codon optimized nucleotide sequence that encodes a Cas9 nuclease or variant thereof; wherein the Cas9 nuclease comprises an amino acid sequence having at least 90% sequence identity to SEQ ID NO: 60, wherein the Cas9 nuclease comprising an amino acid sequence having at least 90% sequence identity to SEQ ID NO: 60 introduces a double stranded break at a site in a nucleic acid complementary to the gRNA segment;

a gRNA segment comprising a nucleotide sequence that encodes a gRNA or sgRNA; and a promoter segment comprising a nucleotide sequence that encodes a first promoter comprising one or more tetracycline operator sequence, wherein the gRNA segment is operably linked to the promoter segment.

25. The recombinant AAV vector of claim 24, wherein the recombinant AAV vector comprises a nucleic acid sequence having at least 85% sequence identity to any one of SEQ ID NOs: 66-69.

26. A pharmaceutical composition comprising the recombinant AAV vector of claim 24.

27. An isolated genetically modified cell comprising the recombinant AAV vector of claim 24.

28. The CRISPR/Cas system of claim 1, wherein the shRNA comprises a sequence having at least 85% sequence identity to any one of SEQ ID NOs 55¬59, or the shRNA comprises any one of SEQ ID NOs: 9-11.

* * * * *